(12) United States Patent
Hassanein et al.

(10) Patent No.: US 9,301,519 B2
(45) Date of Patent: *Apr. 5, 2016

(54) SYSTEMS AND METHODS FOR EX-VIVO ORGAN CARE

(75) Inventors: Waleed Hassanein, Andover, MA (US); Richard Bringham, North Andover, MA (US); Giovanni Cecere, Sudbury, MA (US); Ahmed Elbetanony, North Andover, MA (US); Robert Fishman, Somerville, MA (US); Larry Goff, Andover, MA (US); Tamer Khayal, North Andover, MA (US); Stanley Kyi, Andover, MA (US); Scott Newell, Ipswich, MA (US); Burt Ochs, Andover, MA (US); Dennis Sousa, Stoughton, MA (US); Ronald Taylor, Chester, NH (US); Jonathan Rourke, Belmont, MA (US); Hossam Algamil, Scranton, PA (US); David Carpenter, Jaffrey, NH (US); Robert Havner, Lynnfield, MA (US); Dmitri Menn, Marblehead, MA (US)

(73) Assignee: TRANSMEDICS, INC., Andover, MA (US)

(*) Notice: Subject to any disclaimer, the term of this patent is extended or adjusted under 35 U.S.C. 154(b) by 1304 days.

This patent is subject to a terminal disclaimer.

(21) Appl. No.: 11/246,013

(22) Filed: Oct. 7, 2005
(Under 37 CFR 1.47)

(65) Prior Publication Data
US 2006/0154357 A1    Jul. 13, 2006

Related U.S. Application Data

(60) Provisional application No. 60/616,835, filed on Oct. 7, 2004, provisional application No. 60/694,971, filed on Jun. 28, 2005, provisional application No. 60/725,168, filed on Oct. 6, 2005.

(51) Int. Cl.
*A01N 1/02* (2006.01)

(52) U.S. Cl.
CPC ............. *A01N 1/02* (2013.01); *A01N 1/0247* (2013.01)

(58) Field of Classification Search
CPC ..... A01N 1/02; A01N 1/0247; A01N 1/0273; A01N 1/0205; A01N 1/0263
USPC ............................................. 435/1.2, 284.1
See application file for complete search history.

(56) References Cited

U.S. PATENT DOCUMENTS 3,253,595 A   5/1966 Murphy et al.
3,388,803 A   6/1968 Scott
(Continued)

FOREIGN PATENT DOCUMENTS

CN    1232723 A    10/1999
DE    42 01 259    7/1993
(Continued)

OTHER PUBLICATIONS

"2002 Design & Engineering Awards, Portable Organ Preservation System," *Science* (2002).
(Continued)

*Primary Examiner* — Michael Hobbs
(74) *Attorney, Agent, or Firm* — Wilmer Cutler Pickering Hale and Dorr LLP

(57) ABSTRACT

The invention provides, in various embodiments, systems, devices and methods relating to ex-vivo organ care. In certain embodiments, the invention relates to maintaining an organ ex-vivo at near-physiologic conditions.

65 Claims, 66 Drawing Sheets

(56) References Cited

U.S. PATENT DOCUMENTS

| | | | |
|---|---|---|---|
| 3,406,531 A | 10/1968 | Swenson et al. | |
| 3,468,136 A | 9/1969 | Swenson et al. | |
| 3,537,956 A | 11/1970 | Falcone | |
| 3,545,221 A | 12/1970 | Swenson et al. | |
| 3,545,605 A | 12/1970 | Robins | |
| 3,587,567 A | 6/1971 | Schiff | |
| 3,607,646 A | 9/1971 | de Roissart | |
| 3,632,473 A | 1/1972 | Belzer et al. | |
| 3,639,084 A | 2/1972 | Goldhaber | |
| 3,654,085 A | 4/1972 | Norr et al. | |
| 3,738,914 A | 6/1973 | Thorne et al. | |
| 3,772,153 A | 11/1973 | De Roissart | |
| 3,777,507 A | 12/1973 | Burton et al. | |
| 3,843,455 A | 10/1974 | Bier | |
| 3,851,646 A | 12/1974 | Sarns | |
| 3,881,990 A | 5/1975 | Burton et al. | |
| 3,995,444 A | 12/1976 | Clark et al. | |
| 4,186,565 A | 2/1980 | Toledo-Pereyra | |
| 4,231,354 A | 11/1980 | Kurtz et al. | |
| 4,415,556 A | 11/1983 | Bretschneider | |
| 4,598,697 A | 7/1986 | Numazawa et al. | |
| 4,605,644 A | 8/1986 | Foker | |
| 4,666,425 A | 5/1987 | Fleming | |
| 4,719,201 A | 1/1988 | Foker | |
| 4,723,939 A | 2/1988 | Anaise | |
| 4,745,759 A | 5/1988 | Bauer et al. | |
| 4,759,371 A * | 7/1988 | Franetzki | 600/373 |
| 4,847,470 A | 7/1989 | Bakke | |
| 4,920,044 A | 4/1990 | Bretan, Jr. | |
| 5,051,352 A | 9/1991 | Martindale et al. | |
| 5,066,578 A | 11/1991 | Wikman-Coffelt | |
| 5,141,847 A | 8/1992 | Sugimachi et al. | |
| 5,145,771 A | 9/1992 | Lemasters et al. | |
| 5,157,930 A | 10/1992 | McGhee et al. | |
| 5,200,398 A | 4/1993 | Strasberg et al. | |
| 5,217,860 A | 6/1993 | Fahy et al. | |
| 5,285,657 A | 2/1994 | Bacchi et al. | |
| 5,306,711 A | 4/1994 | Andrews | |
| 5,326,706 A * | 7/1994 | Yland et al. | 435/1.2 |
| 5,338,662 A | 8/1994 | Sadri | |
| 5,356,593 A * | 10/1994 | Heiberger et al. | 422/45 |
| 5,356,771 A | 10/1994 | O'Dell | |
| 5,362,622 A | 11/1994 | O'Dell et al. | |
| 5,370,989 A | 12/1994 | Stern et al. | |
| 5,381,510 A | 1/1995 | Ford et al. | |
| 5,385,821 A | 1/1995 | O'Dell et al. | |
| 5,395,314 A | 3/1995 | Klatz et al. | |
| 5,405,742 A | 4/1995 | Taylor | |
| 5,407,669 A | 4/1995 | Lindstrom et al. | |
| 5,407,793 A | 4/1995 | Del Nido et al. | |
| 5,472,876 A | 12/1995 | Fahy | |
| 5,473,791 A | 12/1995 | Holcomb et al. | |
| 5,494,822 A | 2/1996 | Sadri | |
| 5,498,427 A | 3/1996 | Menasche | |
| 5,505,709 A | 4/1996 | Funderburk et al. | |
| 5,514,536 A | 5/1996 | Taylor | |
| 5,552,267 A | 9/1996 | Stern et al. | |
| 5,554,123 A | 9/1996 | Herskowitz | |
| 5,554,497 A | 9/1996 | Raymond | |
| 5,571,801 A | 11/1996 | Segall et al. | |
| 5,584,804 A | 12/1996 | Klatz et al. | |
| 5,586,438 A | 12/1996 | Fahy | |
| 5,588,816 A | 12/1996 | Abbott et al. | |
| 5,599,173 A | 2/1997 | Chen et al. | |
| 5,599,659 A | 2/1997 | Brasile et al. | |
| 5,613,944 A | 3/1997 | Segall et al. | |
| 5,643,712 A | 7/1997 | Brasile | |
| 5,656,420 A | 8/1997 | Chien | |
| 5,679,565 A | 10/1997 | Mullen et al. | |
| 5,693,462 A | 12/1997 | Raymond | |
| 5,698,536 A | 12/1997 | Segall et al. | |
| 5,699,793 A | 12/1997 | Brasile | |
| 5,702,881 A | 12/1997 | Brasile et al. | |
| 5,716,378 A | 2/1998 | Minten | |
| 5,723,281 A | 3/1998 | Segall et al. | |
| 5,733,894 A | 3/1998 | Segall et al. | |
| 5,747,071 A | 5/1998 | Segall et al. | |
| 5,752,929 A | 5/1998 | Klatz et al. | |
| 5,770,149 A | 6/1998 | Raible | |
| 5,776,063 A | 7/1998 | Dittrich et al. | |
| 5,786,136 A | 7/1998 | Mayer | |
| 5,787,544 A | 8/1998 | Meade | |
| 5,807,737 A | 9/1998 | Schill et al. | |
| 5,823,799 A * | 10/1998 | Tor et al. | 439/79 |
| 5,843,024 A | 12/1998 | Brasile | |
| 5,856,081 A | 1/1999 | Fahy | |
| 5,882,328 A | 3/1999 | Levy et al. | |
| 5,965,433 A | 10/1999 | Gardetto et al. | |
| 5,998,240 A | 12/1999 | Hamilton et al. | |
| 6,024,698 A | 2/2000 | Brasile | |
| 6,034,109 A | 3/2000 | Ramasamy et al. | |
| 6,042,550 A | 3/2000 | Haryadi et al. | |
| 6,046,046 A | 4/2000 | Hassanein | |
| 6,050,987 A | 4/2000 | Rosenbaum | |
| 6,100,082 A | 8/2000 | Hassanein | |
| 6,110,139 A | 8/2000 | Loubser | |
| 6,110,504 A | 8/2000 | Segall et al. | |
| 6,144,444 A | 11/2000 | Haworth et al. | |
| 6,168,877 B1 * | 1/2001 | Pedicini et al. | 429/27 |
| 6,365,338 B1 | 4/2002 | Bull et al. | |
| 6,375,611 B1 | 4/2002 | Voss et al. | |
| 6,375,613 B1 | 4/2002 | Brasile | |
| 6,389,308 B1 | 5/2002 | Shusterman | |
| 6,475,716 B1 | 11/2002 | Seki | |
| 6,490,880 B1 | 12/2002 | Walsh | |
| 6,492,103 B1 | 12/2002 | Taylor | |
| 6,492,745 B1 | 12/2002 | Colley, III et al. | |
| 6,524,785 B1 | 2/2003 | Cozzone et al. | |
| 6,569,615 B1 | 5/2003 | Thatte et al. | |
| 6,582,953 B2 | 6/2003 | Brasile | |
| 6,600,941 B1 | 7/2003 | Khuri | |
| 6,609,987 B1 | 8/2003 | Beardmore | |
| 6,631,830 B2 | 10/2003 | Ma et al. | |
| 6,642,045 B1 | 11/2003 | Brasile | |
| 6,673,594 B1 | 1/2004 | Owen et al. | |
| 6,696,238 B2 | 2/2004 | Murphy et al. | |
| 6,783,328 B2 | 8/2004 | Lucke et al. | |
| 6,792,309 B1 | 9/2004 | Noren | |
| 6,794,124 B2 | 9/2004 | Steen | |
| 6,811,965 B2 | 11/2004 | Vodovotz et al. | |
| 6,878,339 B2 | 4/2005 | Akiyama et al. | |
| 6,925,324 B2 | 8/2005 | Shusterman | |
| 6,953,655 B1 | 10/2005 | Hassanein et al. | |
| 6,974,436 B1 | 12/2005 | Aboul-Hosn et al. | |
| 7,001,354 B2 | 2/2006 | Suzuki et al. | |
| 7,008,380 B1 | 3/2006 | Rees et al. | |
| 7,238,165 B2 * | 7/2007 | Vincent et al. | 604/6.11 |
| 7,316,666 B1 | 1/2008 | Entenman et al. | |
| 7,452,711 B2 | 11/2008 | Daykin | |
| 7,572,622 B2 | 8/2009 | Hassanein et al. | |
| 7,651,835 B2 | 1/2010 | Hassanein et al. | |
| 8,304,181 B2 | 11/2012 | Hassanein et al. | |
| 8,409,846 B2 | 4/2013 | Hassanein et al. | |
| 8,420,380 B2 | 4/2013 | Fishman et al. | |
| 8,465,970 B2 | 6/2013 | Hassanein et al. | |
| 8,535,934 B2 | 9/2013 | Hassanein et al. | |
| 8,585,380 B2 | 11/2013 | Hassanein et al. | |
| 2001/0003652 A1 | 6/2001 | Freeman | |
| 2002/0012988 A1 | 1/2002 | Brasile | |
| 2002/0102720 A1 | 8/2002 | Steen | |
| 2002/0132220 A1 | 9/2002 | Berens et al. | |
| 2002/0151950 A1 | 10/2002 | Okuzumi | |
| 2002/0164795 A1 | 11/2002 | Gen | |
| 2002/0177117 A1 | 11/2002 | Wolf, Jr. | |
| 2003/0011604 A1 | 1/2003 | Capers | |
| 2003/0040665 A1 | 2/2003 | Khuri et al. | |
| 2003/0050689 A1 | 3/2003 | Matson | |
| 2003/0053998 A1 | 3/2003 | Daemen et al. | |
| 2003/0073227 A1 | 4/2003 | Hull et al. | |
| 2003/0074760 A1 | 4/2003 | Keller | |
| 2003/0086830 A1 | 5/2003 | Haywood et al. | |
| 2003/0111604 A1 * | 6/2003 | Quek | 250/338.1 |
| 2003/0135152 A1 * | 7/2003 | Kollar et al. | 604/35 |
| 2003/0147466 A1 * | 8/2003 | Liang | 375/240.12 |

(56) References Cited

U.S. PATENT DOCUMENTS

| | | |
|---|---|---|
| 2004/0015042 A1 | 1/2004 | Vincent et al. |
| 2004/0018966 A1 | 1/2004 | Segall et al. |
| 2004/0029096 A1 | 2/2004 | Steen |
| 2004/0038192 A1 | 2/2004 | Brasile |
| 2004/0058432 A1 | 3/2004 | Owen et al. |
| 2004/0082057 A1 | 4/2004 | Alford et al. |
| 2004/0086578 A1 | 5/2004 | Segall et al. |
| 2004/0102415 A1 | 5/2004 | Thatte et al. |
| 2004/0102678 A1 | 5/2004 | Haindl |
| 2004/0106958 A1 | 6/2004 | Mathis et al. |
| 2004/0110800 A1 | 6/2004 | Bril et al. |
| 2004/0115689 A1 | 6/2004 | Augello et al. |
| 2004/0138542 A1 | 7/2004 | Khuri et al. |
| 2004/0168341 A1 | 9/2004 | Petersen et al. |
| 2004/0170950 A1* | 9/2004 | Prien ............................ 435/1.2 |
| 2004/0171138 A1 | 9/2004 | Hassanein et al. |
| 2004/0202993 A1 | 10/2004 | Poo et al. |
| 2004/0224298 A1 | 11/2004 | Brassil et al. |
| 2004/0235142 A1 | 11/2004 | Schein et al. |
| 2004/0236170 A1 | 11/2004 | Kim |
| 2004/0248281 A1 | 12/2004 | Wright et al. |
| 2005/0010118 A1 | 1/2005 | Toyoda et al. |
| 2005/0019917 A1 | 1/2005 | Toledo-Pereyra et al. |
| 2005/0142532 A1 | 6/2005 | Poo et al. |
| 2005/0153271 A1 | 7/2005 | Wenrich |
| 2005/0170019 A1 | 8/2005 | Roth |
| 2005/0182349 A1 | 8/2005 | Linde et al. |
| 2005/0187469 A1 | 8/2005 | Phillips |
| 2006/0039870 A1 | 2/2006 | Turner |
| 2006/0074470 A1 | 4/2006 | Bartels et al. |
| 2006/0121438 A1 | 6/2006 | Toledo-Pereyra et al. |
| 2006/0124130 A1 | 6/2006 | Bonassa |
| 2006/0134073 A1 | 6/2006 | Naka et al. |
| 2006/0154357 A1 | 7/2006 | Hassanein et al. |
| 2006/0154359 A1 | 7/2006 | Hassanein et al. |
| 2006/0160204 A1 | 7/2006 | Hassanein et al. |
| 2006/0292544 A1 | 12/2006 | Hassanein et al. |
| 2007/0196461 A1 | 8/2007 | Weers |
| 2008/0017194 A1 | 1/2008 | Hassanein et al. |
| 2008/0234768 A1 | 9/2008 | Hassanein et al. |
| 2009/0142830 A1 | 6/2009 | Yamashiro et al. |
| 2009/0143417 A1 | 6/2009 | Smith et al. |
| 2009/0197240 A1 | 8/2009 | Fishman et al. |
| 2009/0197292 A1 | 8/2009 | Fishman et al. |
| 2009/0197324 A1 | 8/2009 | Fishman et al. |
| 2009/0197325 A1 | 8/2009 | Fishman et al. |
| 2009/0215022 A1 | 8/2009 | Page et al. |
| 2009/0312724 A1 | 12/2009 | Pipkin et al. |
| 2011/0136096 A1 | 6/2011 | Hassanein et al. |
| 2011/0190572 A1 | 8/2011 | Brophy et al. |
| 2013/0011823 A1 | 1/2013 | Hassanein et al. |
| 2013/0078710 A1 | 3/2013 | Hassanein et al. |
| 2013/0157248 A1 | 6/2013 | Fishman et al. |
| 2013/0295552 A1 | 11/2013 | Hassanein et al. |

FOREIGN PATENT DOCUMENTS

| | | |
|---|---|---|
| DE | 4201259 A1 | 7/1993 |
| DE | 10121159 A1 | 11/2002 |
| EP | 0 347 923 | 12/1989 |
| EP | 0 376 763 | 7/1990 |
| JP | 04-099701 A | 3/1992 |
| JP | 2001061956 A | 3/2001 |
| JP | 2004513889 A | 5/2004 |
| JP | 2004525290 A | 8/2004 |
| WO | WO-88/05261 | 7/1988 |
| WO | WO-95/31897 | 11/1995 |
| WO | WO-96/18293 | 6/1996 |
| WO | WO-96/29865 | 10/1996 |
| WO | WO-97/46091 | 12/1997 |
| WO | WO-99/15011 | 4/1999 |
| WO | WO-0060936 A1 | 10/2000 |
| WO | WO-2004026031 A2 | 4/2004 |
| WO | WO-2006042138 A2 | 4/2006 |
| WO | WO-2008106724 A1 | 9/2008 |

OTHER PUBLICATIONS

Ahmad et al., "A Pathophysiologic Study of the Kidney Tubule to Optimize Organ Preservation Solutions," *Kidney Int.* 66(1):77-90 (2004).

Ananthaswamy "Machine Keeps Organs Alive for Longer," New Scientist.com (2001).

Bando et al. Oxygenated Perfluorocarbon, Recombinant Human Superoxide Dismutase, and Catalase Ameliorate Free Radical Induced Myocardial Injucy During Heart Preservation and Transplantation. *J Thorac Cardiovasc Surg.* 96:930-8(Dec. 1988).

Belzer, "Formula for Belzer MPS Solution," *University of Wisconsin-Madison Organ Preservation* (internet reference) (2003).

Benichou et al. Canine and Human Liver Preservation for 6 to 18 Hr by Cold Infusion. *Transplantation.* 24(6):407-411(Dec. 1977).

Birkett et al., "The fatty-acid content and drug binding characteristics of commercial albumin preparations" *Clin. Chem. Acta,* 85:253-258 (1978).

Blanchard et al. Techniques for Perfusion and Storage of Heterotopic Heart Transplants in Mice. *Microsurgery.* 6:169-174(1985).

Boggi et al., "Pancreas preservation with University of Wisconsin and Celsior solutions," *Transplant Proc.* 36(3):563-5 (2004).

Boggi et al., "Pancreas preservation with University of Wisconsin and Celsior solutions: a single-center, prospective, randomized pilot study;" *Transplantation* 27:77(8):1186-90 (2004).

Burt et al., "Myocardial Function After Preservation for 24 Hours," *Jour. Thorac. and Cardiovascular Surg.* 92(2):238-46 (1986).

Brasile et al., "Organ Preservation Without Extreme Hypothermia Using an Oxygen Supplemented Perfusate," *Art. Cells. Blood Subs. and Immob. Biotech.* 22(4):1463-68 (1994).

Canelo R, et al.; "Experience with Hystidine Tryptophan Ketoglutarate Versus University Wisconsin Preservation Solutions in Transplantation," *Int Surg.* 88(3):145-51 (2003).

"CELSIOR Cold Storage Solution," *Sangstat Medical Corporation* (internet reference) (1999).

Chambers et al., "Long-Term Preservation of the Heart: The Effect of Infusion Pressure During Continuous Hypothermic Cardioplegia," *Jour. of Heart and Lung Transp.* 11(4):665-75 (1992).

Chen et al., "Development of New Organ Preservation Solutions in Kyoto University," *Yonsei Medical Journal* 46(6):1107-40 (2004).

Chien et al., "A Simple Technique for Multiorgan Preservation," *Jour. of Thor. and Card. Surg.* 95(1):55-61 (1988).

Chien et al., "Functional Studies of the Heart During a 24-Hour Preservation Using a New Autoperfusion Preparation," *The Journal of Heart and Lung Transplantation* 10(3):401-8 (1991).

Cimino, Adria "Doctor Develops Device to Preserve Donated Organs," *Mass High Tech* (2001).

Christophi et al. "A Comparison of Standard and Rapid Infusion Methods of Liver Preservation During Multi-Organ Procurement," *Aust. N. Z. J. Surg.* 61(9):692-94 (1991).

Collins, BH "Organ Transplantation: What Is the State of the Art'?," *Ann Surg.* 238(6 Suppl):S72-89 (2003).

Cronin et al., "Liver Transplantation at the University of Chicago," *Clin Transpl.* 231-8 (1999).

Daemen et al., "Short-Term Outcome of Kidney Transplants From Non-Heart-Beating Donors After Preservation by Machine Perfusion," *Transpl Int.* 9(Suppl 1):S76-S80 (1996).

Den Butter et al.; "Comparison of Solutions for Preservation of the Rabbit Liver as Tested by Isolated Perfusion," *Transpl. Int.* 8(6):466-71 (1995).

Denham et al., "Twenty-Four Hour Canine Renal Preservation by Pulsatile Perfusion, Hypothermic Storage, and Combinations of the Two Methods," *Transplant Proc.* 9(3):1553-56 (1977).

Dobrian et al., "In vitro formation of oxidatively-modified and reassembled human low-density lipoproteins," *Biochimica et Biophysica Acta (BBA)* 1169:12-24 (1993).

Eiseman et al., "A Disposable Liver Perfusion Chamber," *Surgery* 6:1163-66 (1966).

(56) References Cited

OTHER PUBLICATIONS

Fabregas, Luis "UPMC Tests Machine to Aid Heart Transplants," *Pittsburg Tribune-Review* (2002).
Faggian et al., "Donor Organ Preservation in High-Risk Cardiac Transplantation," *Transplant Proc.* 36:617-19 (2004).
Fehrenberg et al., "Protective Effects of B2 Preservation Solution in Comparison to a Standard Solution (Histidine-Tryptophan-Ketoglutarate/Bretschneider) in a Model of Isolated Autologous Hemoperfused Porcine Kidney," *Nephron Physiol.* 96:52-58 (2004).
Fourcade et al., "A New Method of Kidney Preservation with Collins' Solution," *Biomed.* 21(7):308-11 (1974).
Fraser et al., "Evaluation of Current Organ Preservation Methods for Heart-Lung Transplantation," *Transplant. Proc.* 20(1 Suppl 1):987-90 (1988).
Guarrera et al., "Pulsatile Machine Perfusion with Vasosol Solution Improves Early Graft Function After Cadaveric Renal Transplantation," *Transplantation* 77(8):1264-68 (2004).
Hachida et al. Abstract "Efficacy of Myocardial Preservation using HTK Solution in Continuous 120 Min Cross-Clamping Method—a Comparative Study with GIK Method," *Nippon Kyobu Geka Gakkai Zasshi* 41(9):1495-1501 (1993).
Hassanein et al., "A Novel Approach for 12-Hour Donor Heart Preservation. Presented at the 70th Scientific Session of the American Heart Association. Abstract was published in Circulation," 1997.
Hassanein et al., "Continuous Perfusion of Donor Hearts in the Beating State Extends Preservation Time and Improves Recovery of Function," *The Journal of Thoracic and Cardiovascular Surgery* 821-30 (1998).
"Heart Kept Beating Outside Body," *Associated Press*, CNN.com (2001).
Heil et al., "A Controlled Comparison of Kidney Preservation by Two Methods: Machine Perfusion and Cold Storage," *Transplant. Proc.* 19(1):2046 (1987).
"History of Transplantation and Organ Preservation," *Barr Laboratories, Inc.* (internet reference) (2004).
"Human Heart Beats on its own Outside Body," *USA Today* (2001).
"Human Heart Kept Alive Outside Body for First Time in Study of Portable Organ Preservation System™ at University of Pittsburgh Medical Center," *UPMC, McGowan Institute for Regenerative Medicine* (2001).
Imber et al.; "Advantages of Normothermic Perfusion Over Cold Storage in Liver Preservation," *Transplantation* 73(5):701-09 (2002).
Janssen et al., "UW is Superior to Celsior and HTK in the Protection of Human Liver Endothelial Cells Against Preservation Injury," *Liver Transpl.* 10(12):1514-23 (2004).
Kawamura et al., "Long-Term Preservation of Canine Pancreas by a New Simple Cold Storage Method Using Perfluorochemical—The Two-Layer Cold Storage Method (Euro-Collins' Solution/Perfluorochemical)," *Kobe J med Sci.* 38(2):135-45 (1992).
Kelly "Current Strategies in Lung Preservation," *J. Lab Clin. Med.* 136:427-40 (2000).
Keshavjee et al., "A Method for Safe Twelve-Hour Pulmonary Preservation," *J. Thorac Cardiovasc Surg.* 98:529-34 (1989).
Kioka et al., "Twenty-Four-Hour Isolated Heart Preservation by Perfusion method With Oxygenated Solution Containing Perfluorochemicals and Albumin," *J. Heart Transplant.* 5:437-43 (1986).
Kozaki et al., "Usefulness of a Combination of Machine Perfusion and Pentoxifylline for Porcine Liver Transplantation From Non-Heart-Beating Donors With Prolonged Hypotension," *Transplant Proc.* 29:3476-77 (1997).
Kuroda et al., "A New, Simple Method for Cold Storage of the Pancreas Using Perfluorochemical," *Transplantation* 46(3):457-60 (1988).
Lawrence "Machine Preserves Organs Outside Body," *Chicago Sun Times* (2001).
Li et al., "Insulin in University of Wisconsin Solution Exacerbates the Ischemic Injury and Decreases the Graft Survival Rate in Rat Liver Transplantation," *Transplantation.* 15:76(1):44-49 (2003).
Li et al., "Insulin in UW Solution Exacerbates Hepatic Ischemia/Reperfusion Injury by Energy Depletion Through the IRS-2/SREBP-1C Pathway," *Liver Transpl.* 10(9):1173-82 (2004).
Liu et al., "Annexin V Assay-proven Anti-apoptotic Effect of Ascorbic Acid 2-glucoside after Cold Ischemia/Reperfusion Injury in Rat Liver Transplantation," *Acta Med. Okayama* 57(5):209-16 (2003).
"Machine Keeps Human Kidney Alive for 24-Hours," www.worldhealth.net, Aug. 25, 2001.
"Machine May Be Organ Transplant Breakthrough," *USA Today* (2001).
Moisiuk et al., "Histidine-Tryptophan-Ketoglutarate Versus Euro-Collins for Preservation of Kidneys From Non-Heart-Beating Donors," *Transplant Proc.* 28(1):202 (19996).
Moller-Pedersen et al.; "Evaluation of Potential Organ Culture Media for Eye Banking Using Human Donor Corneas," *Br J Ophthamol.* 85(9):1075-79 (2001).
Morimoto et al., a Simple Method for Extended Heart-Lung Preservation by Autoperfusion. *Trans Am Soc Artif Intern Organs.* 30:320-24 (1984).
"New Discovery in Organ Transplantation," *MSNBC* (2001).
Innovations-report "New Organ Preservation Solution Easier to Use" (internet reference) (2003).
Nicholson et al.; "A Comparison of Renal Preservation by Cold Storage and Machine Perfusion Using a Porcine Autotransplant Model," *Transplantation* 78(3):333-37 (2004).
Opelz et al., "Advantage of Cold Storage Over Machine Perfusion for Preservation of Cadaver Kidneys" *Transplantation.* 33(1):64-68 (1982).
Opelz et al., "Comparative Analysis of Kidney Preservation Methods. Collaborative Transplant Study," *Transplant Proc.* 28(1):87-90 (1996).
Petrovsky et al., Justification and Application of a New Method for Transorganic Oxygen Preservation of the Kidneys. *Vestn Akad Med Nauk SSSR.* (2):69-82(1989).
Ploeg et al. Successful 72-Hour Cold Storage of Dog Kidneys With UW Solution. *Transplantation* 46(2):191-96 (1988).
Pokorny et al., "Histidine-Tryptophan-Ketoglutarate Solution for Organ Preservation in Human Liver Transplantation—a Prospective Multi-Centre Observation Study," *Transpl Int.* 17(5):256-60 (2004).
Potdar et al.; "Initial Experience Using Histidine-Tryptophan-Ketoglutarate Solution in Clinical Pancreas Transplantation," *Clin. Transplant.* 18(6):661-65 (2004).
Pozniak "Keeping Hearts Alive; Doctors Develop a High-Tech System to Salvage Donated Organs," *ABC News.com* (2001).
Reddy et al., "Preservation of Porcine Non-Heart Beating Donor Livers by Sequential Cold Storage and Warm Perfusion," *Transplantation* 77(9):1328-32 (2004).
Rossi "Portable Organ Preservation System™ Keeps Human Heart Alive Outside Body," *PITT Campaign Chronicle* (2001).
Schmid et al., "The Use of Myocytes As a Model for Developing Successful Heart Preservation Solutions," *Transplantation* 52(1):20-6 (Jul. 1991).
Schon et at; "Liver Transplantation After Organ Preservation with Normothermic Extracorporeal Perfusion," *Ann Surg.* 233(1):114-23 (2001).
Segel et al., "Recovery of Sheep Hearts After Perfusion Preservation or Static Storage With Crystalloid Media," *The Journal of Heart and Lung Transplantation* 17:211-21 (1998).
Shimokawa et al., "A New Lung Preservation Method of Topical Cooling by Ambient Cold Air Combined with High-Frequency Oscillation: An Experimental Study," *Transplant. Proc.* 26(4):2364-66 (1994).
Shimokawa et al., "A New Lung Preservation Method of Topical Cooling by Ambient Cold Air: an Experimental Study," Transplant. Proc. 23 (1 Pt 1):653-54 (1991).
Southard "The Right Solution for Organ Preservation" *Business Briefings: Global Surgery*, 79-84 (2004).
Stubenitsky et al, "Kidney Preservation in the Next Millenium," *Transpl. Int.* 12:83-91 (1999).
Tang et al., "Warm Ischemia Lung Protection with Pinacidil: an ATP Regulated Potassium Channel Opener," *Ann Thorac Surg.* 76:385-9 (2003).

(56) References Cited

OTHER PUBLICATIONS

"The Nation Warm-Storage Device May Aid Organ Transplants," *Dow Jones Publications Library* (2001).
Turpin et al., "Perifusion of Isolated Rat Adipose Cells," *The Journal of Clinical Investigation*, 60:442-448 (1977).
"ViaSpan (Belzer UW) Cold Storage Solution," *Barr Laboratiories, Inc.* (2002).
"Warm-Storage for Donor Organs," Univ. of Chicago Magazine (2001).
Watanabe et al., "Effects of free fatty acids on the binding of bovine and human serum albumin with steroid hormones" *Biochimica et Biophysica Acta (BBA)*, 1289:385-96 (1996).
Zhengquang et al., "A Study on the Preservation of Rat Kidney with HX-III Solution," *WCUMS* 31(3):347-49 (2000).
Wicomb et al., "Cardiac Transplantation Following Storage of the Donor Heart by a Portable Hypothermic Perfusion System," *The Annals of Thoracic Surgery* 37(3):243-48 (1984).
Wicomb et al., "Orthotopic Transplantation of the Baboon Heart After 20 to 24 Hours Preservation by Continuous Hypothermic Perfusion With an Oxygenated Hyperosmolar Solution," *The Journal of Thoracic and Cardiovascular Surgery* 83(1):133-40 (1982).
Yland et al., "New Pulsatile Perfusion Method for Non-Heart-Beating Cadaveric Donor Organs: A Preliminary Report," *Transplantation Proceedings* 25(6):3087-90 (1993).
Zhang et al., "Research Progress on Preservation of Severed Limbs," *Chinese Journal of Reparative and Reconstructive Surgery* 14(3):189-192 (2000).
Chien et al. Canine Lung Transplantation After More Than Twenty-four Hours of Normothermic Preservation. J. Heart Lung Transplant. 16:3340-51 (1997).
Menasche et al. Improved Recovery of Heart Transplants With a Specific Kit of Preservation Solutions. J. Thorac. Cardiovasc. Surg. 105(2):353-63 (1993).
Vinten-Johansen et al. Reduction in Surgical Ischemic-Reperfusion Injury With Adenosine and Nitric Oxide Therapy. Ann. Thorac. Surg. 60(3):852-57 (1995).
Lasley et al. Protective Effects of Adenosine in the Reversibly Injured Heart. Ann. Thorac. Surg. 60(3):843-46 (1995).
Calhoon et al. Twelve-Hour Canine Heart Preservation With a Simple, Portable Hypothermic Organ Perfusion Device. Ann. Thorac. Surg. 62:91-3 (1996).
Rao et al. Donor Blood Perfusion Improves Myocardial Recovery After Heart Transplantation. J. Heart Lung Transplant. 16(6):667-73 (1997).
Pearl et al. Loss of endothelium-dependent vasodilatation and nitric oxide release after myocardial protection with University of Wisconsin solution. J. Thorac. Cardiovasc. Surg. 107(1):257-64 (1994).
Lefer, A.M. Attenuation of Myocardial Ischemia-Reperfusion Injury With Nitric Oxide Replacement Therapy. Ann. Thorac. Surg. 60(3):847-51 (1995).
Hartman, J. C. The Role of Bradykinin and Nitric Oxide in the Cardioprotective Action of ACE Inhibitors. Ann. Thor. Surg. 60:789-92 (1995).
Rinder et al. Blockade of C5a and C5b-9 Generation Inhibits Leukocyte and Platelet Activation during Extracorporeal Circulation. J. Clin. Invest. 96:3(1564-72). 1995.
Aoki, M. et al. Anti-CD18 Attenuates Deleterious Effects of Cardiopulmonary Bypass and Hypothermic Circulatory Arrest in Piglets. J. Card. Surg. 10:407-17 (1995).
Rosenkranz, E.R. Substrate Enhancement of Cardioplegic Solution: Experimental Studies and Clinical Evaluation. Ann. Thorac. Surg. 60:797-800 (1995).
Engelman et al. Influence of Steroids on Complement and Cytokine Generation After Cardiopulmonary Bypass. Ann. Thorac. Surg. 60(3):801-04 (1995).
Boyle, Jr. et al. Ischemia-Reperfusion Injury. Ann. Thorac. Surg. 64:524-30 (1997).
Li, G. et al. Functional Recovery in Rabbit Heart after Preservation with a Blood Cardioplegic Solution and Perfusion. J. Herat Lung Transplant. 12(2)263-70 (1993).

Seccombe et al. Coronary Artery Endothelial Function After Myocardial Ischemia and Reperfusion. Ann. Thorac. Surg. 60(3):778-88 (1995).
Mankad et al. Endothelial dysfunction caused by University of Wisconsin preservation solution in the rat heart. J. Thorac. Cardiovasc. Surg. 104(6):1618-24 (1992).
Sunamori et al. Relative Advantages of Nondepolarizing Solution to Depolarizing University of Wisconsin Solution in Donor Heart Preservation. Transplant. Proc. 25(1):1613-17 (1993).
Pinsky et al. Restoration of the cAMP Second Messenger Pathway Enhances Cardiac Preservation for Transplantation in a Heterotopic Rat Model. J. Clin. Invest. 92(6):2944-3002 (1993).
Richens et al. Clinical Study of Crystalloid Cardioplegia vs Aspartate-Enriched Cardioplegia Plus Warm Reperfusion for Donor Heart Preservation. Transplant. Proc. 24(1):1608-10 (1993).
Finn et al. Effects of Inhibition of Complement Activation Using Recombinant Soluble Complement Receptor 1 on Neutrophil CD11B/CD18 and L-Selectin Expression and Release of Interleukin-8 and Elastase in Simulated Cardiopulmonary Bypass. J. Thorac. Cardiovasc. Surg. 111(2):451-49 (1996).
Wicomb et al. 24-Hour Rabbit Heart Storage with UW Solution. Transplantation. 48(1):6-9 (1989).
Menasche et al. Experimental evaluation of Celsior®, a new heart preservation solution. Eur. J. Cardiothor. Surg. 8:207-13 (1994).
Ferrera et al. Comparison of Different Techniques of Hypothermic Pig Heart Preservation. Ann. Thorac. Surg 57(5):1233-39 (1994).
Gundry et al. Successful Transplantation of Hearts Harvested 30 Minutes After Death From Exsanguination. Ann. Thorac. Surg. 53(5):772-75 (1992).
Demertzis et al. University of Wisconsin Versus St. Thomas' Hospital Solution for Human Donor Heart Preservation. Ann. Thorac. Surg. 55:1131-7 (1993).
Schwalb et al. New Solution for Prolonged Myocardial Preservation for Transplantation. J. Heart Lung Transplant. 17(2):222-29 (1998).
Drexler et al. Effect of L-Arginine on Coronary Endothelial Function in Cardiac Transplant Recipients. Circulation.89(4):1615-23 (1994).
Sato, H. et al. Supplemental L-Arginine During Cardioplegic Arrest and Reperfusion Avoids Regional Postischemic Injury. J. Thorac. Cardiovasc. Surg. 110(2):302-14 (1995).
Matsuno et al. The Effect of Machine Perfusion Preservation Versus Cold Storage on the Function of Kidneys from Non-Heart-Beating Donors. Transplantation. 57(2):293-94 (1994).
Tesi et al. Pulsatile Kidney Perfusion for Preservation and Evaluation: Use of High-Risk Kidney Donors to Expand the Donor Pool. Transplant. Proc. 25(6):3099-100 (1993).
Shirakura et al. Multiorgan Procurement from Non-Heart-Beating Donors by use of Osaka University Cocktail, Osaka Rinse Solution, and the Portable Cardiopulmonary Bypass Machine. Transplant. Proc. 25(6):3093-94 (1993).
Matsuno et al. Effectiveness of Machine Perfusion Preservation as a Viability Determination Method for Kidneys Procured from Non-Heart-Beating Donors. Transplant. Proc. 26(4):2421-22 (1994).
Habazettl et al. Improvement in Functional Recovery of the Isolated Guinea Pig Heart After Hyperkalemic Reperfusion with Adenosine. J. Thorac. Cardiovasc. Surg. 111(1):74-84 (1996).
Menasche, P. The inflammatory response to cardiopulmonary bypass and its impact on postoperative myocardial function. Curr. Opin. Cardiology. 10:597-604 (1995).
Segel et al. Posttransplantation Function of Hearts Preserved with Fluorochemical Emulsion. J. Heart Lung Transplant. 13(4):669-80 (1994).
Birkett et al. The Fatty Acid Content and Drug Binding Characteristics of Commercial Albumin Preparations. Clin. Chem. Acta. 85:253-58 (1978).
The Merck Index, 11th ed. Entry 4353 (pp. 699-700) (1989).
"http://dictionary.reference.com/browse/synchrony," Random House Unabridged Dictionary (2006).
Merriam-Webster Dictionary. Definition of Examine. www.m-w.com/dictionary/examine. Printed on Feb. 9, 2011. 1 page.
Barinov, et al. "Hormonal-metabolic disturbances during biological preservation of the heart," Fiziol. ZH., (Kiev), 29(3):293-299 (1983) (7 pages)—Russian Language.

(56) References Cited

OTHER PUBLICATIONS

Brandes et al. "Influence of high molecular dextrans on lung function in an ex Vivo porcine lung model," J. Of Surgical Research, 101:2, 225-231 (Dec. 2001) (7 pages).
File History for U.S. Appl. No. 60/616,835, filed Oct. 7, 2004. 82 pages.
File History for U.S. Appl. No. 60/694,971, filed Jun. 28, 2005. 280 pages.
File History for U.S. Appl. No. 60/725,168 filed Oct. 6, 2005. 699 pages.
Grynberg et al. "Fatty acid oxidation in the heart," Journal of Cardiovascular Pharmacology, 28(Suppl. 1):S11-S17 (1996) (8 pages).
Hardesty et al. Original Communications, "Autoperfusion of the heart and lungs for preservation during distant procurement," J. Thorac. Cardiovasc. Surg., 93:11-18 (1987) (8 pages).
Hülsmann et al. "Loss of cardiac contractility and severe morphologic changes by acutely lowering the pH of the perfusion medium: protection by fatty acids," Bragen 20256, Biochimica et Biophysica Acta., 1033:214-218 (1990) (5 pages).
Imber et al. "Advantages of Normothermic Perfusion Over Cold Storage in Liver Preservation," Transplantation, 73(5):701-09 (2002) (9 pages).
Macchiarini et al. "Ex vivo lung model of pig-to-human hyperacute xenograft rejection," J. Of Thoracic and Cardiovascular Surgery, 114:3, 315-325 (Sep. 1997) (9 pages).
PCT/US07/009652 International search report mailed Apr. 18, 2008 (7 pages).
PCT/US09/032619 International search report mailed Jun. 4, 2009 (4 pages).
PCT/US98/19912 International search report mailed May 3, 1999 (4 pages).
Probst et al. "Carbohydrate and fatty acid metabolism of cultured adult cardiac myocytes," Am. J. Physiol. 250 (Heart, Circ. Physiol. 19):H853-H860 (1986) (8 pages).
Voiglio et al. "Rat multiple organ blocks: microsurgical technique of removal for ex vivo aerobic organ preservation using a fluorocarbon emulsion," Microsurgery 20: 109-115 (2000) (7 pages).
Wright et al. "A porcine ex vivo paracorporeal model of lung transplantation," Laboratory Animals, 34: 56-62 (2000) (7 pages).
Katz, Robert et al. "Physics, Chapter 9: Hydrodynamics (Fluids in Motion)." Hydrodynamics. University of Nebraska—Lincoln. Pap143. No Month Listed 1958. 18 pages.
European Search Report for European Patent Application No. 08795820.3 mailed Apr. 17, 2014. 6 pages.
European Search Report for European Patent Application No. 09707471.0 mailed May 27, 2014. 7 pages.
Featherstone et al. "Comparison of Phosphodiesterase Inhibitors of Differing Isoenzyme Selectivity Added to St. Thomas' Hospital Cardioplegic Solution Used for Hypothermic Preservation of Rat Lungs." Am. J. Respir. Crit. Care Med. Mar. 2000. 162(3):850-856.
International Search Report and Written Opinion for International Application No. PCT/US12/33626 mailed Sep. 20, 2012. 12 pages.
Johnson, Kerry et al: "POPS: Portable Organ Preservation System." UPMC Health System and TransMedics, Inc. Tribune Review (no. date) 1 page.
No Author Listed. "CUSTODIOL HTK Solution for Multi-Organ Protection." Saudi Center for Organ Transplantation. Date Unknown. 2 pages.
No Author Listed. "Custodiol HTK." Physicians' Desk Reference. 57th Edition, Thomson PDR. ISBN:1-56363-445-7. No Month Listed—2003. 3 pages.
No Author Listed. "Soltran Kidney Perfusion Fluid." Baxter. No Month Listed—2001-2004. 1 page.
No Author Listed. "The Comprehensive Resource for Physicians, Drug and Illness Information." VIASPAN DuPont Pharma Cold Storage Solution. Date Unknown. 3 pages.
No Author Listed. "UW Solution Composition." Date Unknown. 1 page.
PCT/US08/61454 International search report mailed Dec. 5, 2008 (3 pages).
"Celsior, Cold Storage Solution." Sangstat Medical Corporation and Fresenius Kabi France. (No date). 5 pages.
SOLU-MEDROL, Drug Details, U.S. Food and Drug Administration, Center for Drug Evaluation and Research, "Drugs@FDA—Drug Details" (Accessible online at http://www.accessdata.fda.gov/scripts/cder/drugsatfda/index.cfm?fuseaction=Search.DrugDetails) (1 page). Date not provided.
SOLU-MEDROL, Label and Approval History, U.S. Food and Drug Administration, Center for Drug Evaluation and Research, "Drugs@FDA—Label and Approval History," (Available online at http://www.accessdata.fda.gov/scripts/cder/drugsatfda/index.cfm?fuseaction=Search.Label_ApprovalHistory#apphist) (3 pages). Date not provided.
Aitchison, J. Douglas et al. "Nitric Oxide During Perfusion Improves Posttransplantation Function of Non-Heart-Beating Donor Lungs." Transplantation. Jun. 27, 2003. vol. 75, No. 12, pp. 1960-1964. (5 pages).
European Search Report for European Patent Application No. 12770852.7 mailed Sep. 23, 2014. (8 pages).
Odagiri, Shigetoh et al. "New Pulsatile Pump Using Pulsatile Assist Device-Hemodynamic Comparison of Pulsatile V-A Bypass (VABP), Pulsatile Left Hear ByPass (LHBP) and Constant Flow Left Heart Bypass (LHB)." Journal of Japan Surgical Society 83(6):515-523, Jun. 1982—English Abstract (12 pages).
Ota et al. "Artificial Organ-Current State and Future of Substitution of Functions." No Month Listed 1983. pp. 150-151 (4 pages)—Japanese Language.
Steen, Stig et al. "Transplantation of Lungs from Non-Heart-Beating Donors After Functional Assessment Ex Vivo." The Annals of Thoracic Surgery. Elsevier Inc. No Month Listed 2003. vol. 76, pp. 244-252. (11 pages).
Poston et al., "Optimizing Donor Heart Outcome After Prolonged Storage with Endothelial Function Analysis and Continuous Perfusion," The Annals of Thoracic Surgery, vol. 78, No. 4, Oct. 2004 (pp. 1362-1370).

\* cited by examiner

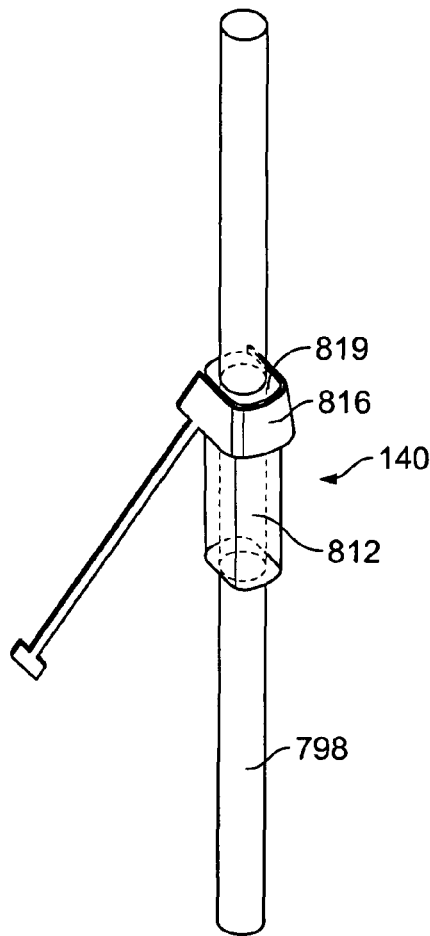
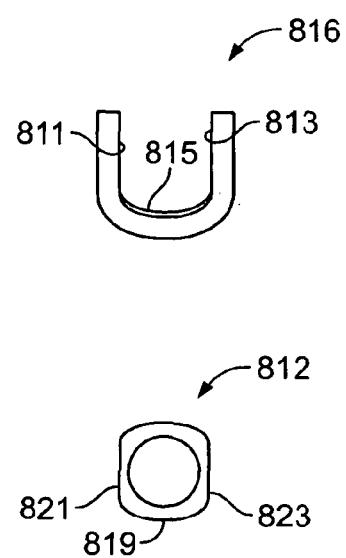
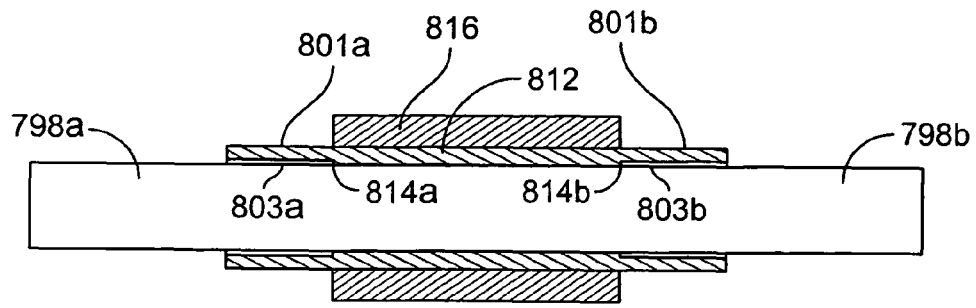
FIG. 28A
FIG. 28C
FIG. 28B

SYSTEMS AND METHODS FOR EX-VIVO ORGAN CARE

REFERENCE TO RELATED APPLICATIONS

This application claims the benefit of U.S. Provisional Patent Application Ser. No. 60/616,835, filed on Oct. 7, 2004; U.S. Provisional Patent Application Ser. No. 60/694,971, filed on Jun. 28, 2005; and U.S. Provisional Patent Application Ser. No. 60/725,168, filed on Oct. 6, 2005, and entitled Systems and Methods for Ex-Vivo Organ Care. The specifications of each of the foregoing are incorporated by reference herein in their entirety.

FIELD OF THE INVENTION

The invention generally relates to systems, methods, and devices for ex-vivo organ care. More particularly, in various embodiments, the invention relates to caring for an organ ex-vivo at physiologic or near-physiologic conditions.

BACKGROUND OF THE INVENTION

Current organ preservation techniques typically involve hypothermic storage of the organ in a chemical perfusate solution on ice. In the case of a heart, it is typically arrested, and cooled with the storage/cardioplegic solution in a hypothermic, non-functioning state. These techniques utilize a variety of cardioplegic solutions, none of which sufficiently protect the heart from myocardial damage resulting from ischemia. Such injuries are particularly undesirable when an organ, such as a heart, is intended to be transplanted from a donor into a recipient. In addition to myocardial damage resulting from ischemia, reperfusion of a heart may exacerbate the myocardial injury and may cause coronary vascular endothelial and smooth muscle injury, which may lead to coronary vasomotor dysfunction.

Using conventional approaches, such injuries increase as a function of the length of time an organ is maintained ex-vivo. For example, in the case of a heart, typically it may be maintained ex-vivo for only a few hours before it becomes unusable for transplantation. This relatively brief time period limits the number of recipients who can be reached from a given donor site, thereby restricting the recipient pool for a harvested heart. Even within the few hour time limit, the heart may nevertheless be significantly damaged. A significant issue is that there may not be any apparent indication of the damage. Because of this, less-than-optimal organs may be transplanted, resulting in post-transplant organ dysfunction or other injuries. Thus, it would be desirable to develop techniques that can extend the time during which an organ can be preserved in a healthy state ex-vivo. Such techniques would reduce the risk of transplantation failure and enlarge potential donor and recipient pools.

Effective preservation of an ex-vivo organ would also provide numerous other benefits. For instance, prolonged ex-vivo preservation would permit more careful monitoring and functional testing of the harvested organ. This would in turn allow earlier detection and potential repair of defects in the harvested organ, further reducing the likelihood of transplantation failure. The ability to perform simple repairs on the organ would also allow many organs with minor defects to be saved, whereas current transplantation techniques require them to be discarded.

In addition, more effective matching between the organ and a particular recipient may be achieved, further reducing the likelihood of eventual organ rejection. Current transplantation techniques rely mainly on matching donor and recipient blood types, which by itself is a relatively unreliable indicator of whether or not the organ will be rejected by the recipient. A more preferred test for organ compatibility is a Human Leukocyte Antigen (HLA) matching test, but current cold ischemic organ preservation approaches preclude the use of this test, which can often require 12 hours or more to complete.

Prolonged and reliable ex-vivo organ care would also provide benefits outside the context of organ transplantation. For example, a patient's body, as a whole, can typically tolerate much lower levels of chemo-, bio- and radiation therapy than many particular organs. An ex-vivo organ care system would permit an organ to be removed from the body and treated in isolation, reducing the risk of damage to other parts of the body.

In view of the foregoing, improved systems, methods, and devices for caring for an organ ex-vivo are needed.

SUMMARY OF THE INVENTION

The invention addresses the deficiencies in the prior art by, in various embodiments, providing improved systems, methods and devices relating to portable ex-vivo organ care. More particularly, according to various aspects, the invention provides systems, methods and devices relating to portable ex-vivo heart care. According to one advancement, the heart care system of the invention maintains the heart in a beating state at, or near, normal physiological conditions. To this end, the system circulates an oxygenated, nutrient enriched perfusion fluid to the heart at or near physiological temperature, pressure and flow rate. According to one implementation, the system employs a blood product-based perfusion fluid to more accurately mimic normal physiologic conditions. In alternative embodiments, the system uses a synthetic blood-substitute solution, while in other embodiments, the solution may contain a blood product in combination with a blood substitute product.

According to another advancement, the system of the invention can maintain a harvested heart in two modes of operation; a normal aortic flow mode (also referred to as "normal flow mode"), and a retrograde aortic flow mode (also referred to as a "retrograde flow mode"). Generally, in the normal flow mode, the system circulates the perfusion fluid to the heart in the same manner as blood would circulate in the human body. More particularly, the perfusion fluid enters the heart via the left atrium and is flowed away from the heart via the right and left ventricles. In normal flow mode, the system pumps the perfusion fluid to the heart at a rate of between about 1 liter/min and about 5 liters/minute. This mode is useful, for example, for performing functional testing to verify that the heart is defect free, both prior and subsequent to transportation to a donor location. Alternatively, in retrograde flow mode, the system flows the perfusion fluid into the heart via the aorta, through the coronary sinus, and then out of the heart via the right ventricle. In this mode of operation, the system reduces the flow rate of the perfusion fluid to between about 300 milliliters/min and about 1 liter/min. The inventors have found that the retrograde flow path, along with the reduced flow rate, reduces damage to the heart during extended periods of ex-vivo care. Thus, according to one feature of the invention, the heart is transported to a donor site in retrograde flow mode.

According to various aspects, the systems and/or devices of the invention include, and/or the methods of the invention employ, one or more of: an organ chamber assembly for containing a heart during ex-vivo care; a reservoir for containing and optionally, defoaming and/or filtering a volume of perfusion fluid; a perfusion fluid pump for pumping/circulating perfusion fluid to and from the harvested heart; a heater assembly for maintaining the temperature of the perfusion fluid at or near physiological temperatures; a flow mode selector valve for switching between normal and retrograde flow modes; an oxygenator for re-oxygenating the perfusion fluid subsequent to it being expelled by the heart; a nutritional subsystem for replenishing nutrients in the perfusion fluid as they are metabolized by the heart and for providing preservatives to the perfusion fluid to reduce, for example, ischemia and/or other reperfusion related injuries to the heart; a sensor subsystem for monitoring, for example, temperature, pressure, flow rate and/or oxygenation of the perfusion fluid, and/or electrical signals from the heart and/or the various components employed to maintain suitable flow conditions to and from the heart; an operator interface for assisting an operator in monitoring system operation and/or the condition of the heart, and/or for enabling the operator to set various operating parameters; a power subsystem for providing fault tolerant power to the organ care system; and a control subsystem for controlling operation of the organ care system.

Operationally, in one practice, a heart is harvested from a donor and affixed to the organ chamber assembly by a process of cannulation. The perfusion fluid pump pumps perfusion fluid from a reservoir to the heater assembly. The heater assembly heats the perfusion fluid to or near a normal physiological temperature. According to one embodiment, the heater assembly heats the perfusion fluid to between about 32° C. and about 37° C. From the heater assembly, the perfusion fluid flows to the flow mode selector valve. Initially, the flow mode selector valve is positioned for retrograde flow mode to direct the perfusion fluid from the heater assembly to a first interface on the organ chamber assembly. Also referred to as an aorta interface or the left ventricle interface, the first interface is cannulated to vascular tissue of the left ventricle (e.g., an aorta stub) via a conduit located within the organ chamber assembly. The heart then pumps the perfusion fluid out of the heart through the right ventricle via a second interface on the organ chamber assembly. The second interface, also referred to as a pulmonary artery interface or right ventricle interface, is cannulated to vascular tissue of the right ventricle (e.g., a pulmonary artery stub) via a conduit located within the organ chamber assembly. In retrograde flow mode, fluid is not pumped into or out of the left side of the heart other than in the form of a small trickle of perfusion fluid, which is delivered to moisten the left atrium. In response to the flow mode selector valve being in the normal flow mode position, it directs the perfusion fluid into the left atrium of the heart via a third interface on the organ chamber assembly. The third interface, also referred to as a pulmonary vein interface or left atrium interface, is cannulated to the vascular tissue of the left atrium (e.g., a pulmonary vein stub) via a conduit located within the organ chamber assembly. The heart then expels the perfusion fluid through the left ventricle via the aorta interface, and through the right ventricle via the pulmonary artery interface.

In both modes of operation, from the pulmonary artery interface, the perfusion fluid flows into the oxygenator. The oxygenator receives oxygen from an external or onboard gas source and applies gas (e.g., oxygen) to the perfusion fluid prior to returning it to the reservoir. The system may include one or more oxygen saturation sensors to measure the oxygen saturation level of the perfusion fluid to ensure that the perfusion fluid is maintained at physiological oxygen levels. In the embodiments where the perfusion fluid is blood-product based, it contains red blood cells (i.e., oxygen carrying cells). Optionally, the oxygen sensors also provide a hematocrit measurement of the concentration of red blood cells in the perfusion fluid.

In both normal and retrograde flow modes, the nutritional subsystem infuses the perfusion fluid with a supply of maintenance solutions as the perfusion fluid flows through the system, and in some embodiments, while it is in the reservoir. According to one feature, the maintenance solutions include nutrients, such as glucose. According to another feature, the maintenance solutions include a supply of therapeutics and/or preservatives (e.g., cardio stimulants, insulin, amino acids, etc.) for reducing ischemia and/or other reperfusion related injuries to the heart.

According to another practice, the perfusion fluid includes blood removed from the donor through a process of exsanguination during harvesting of the heart. Initially, the blood from the donor is loaded into the reservoir and the cannulation locations in the organ chamber assembly are bypassed with a bypass conduit to enable normal mode flow of perfusion fluid through the system without a heart being present. Prior to cannulating the harvested heart, the system may be primed by circulating the exsanguinated donor blood through the system to heat, oxygenate and/or filter it. Nutrients, preservatives, and/or other therapeutics may also be provided during priming via the infusion pump of the nutritional subsystem. During priming, various parameters may also be initialized and calibrated via the operator interface during priming. Once primed and running appropriately, the pump flow is reduced or cycled off, the bypass conduit is removed from the organ chamber assembly, and the heart is cannulated into the organ chamber assembly. The pump flow is then restored or increased, as the case may be. According to one feature, the operator interface may be plugged into the system via a hard wired connection, or may be unplugged and used to wirelessly communicate with the system of the invention.

According to one feature, the system includes a plurality of compliance chambers. The compliance chambers are essentially small inline fluid accumulators with flexible, resilient walls for simulating the human body's vascular compliance by aiding the system in more accurately mimicking blood flow in the human body, for example, by providing flow back-pressure and/or by filtering/reducing fluid pressure spikes due, for example, to flow rate changes. In one configuration, compliance chambers are located on either side of the flow mode selector valve and on the output of the perfusion fluid pump. According to one feature, a compliance chamber is located next to a clamp used for regulating back pressure seen by the aorta during normal flow mode operation.

According to one implementation, the sensor subsystem includes an electrocardiogram (ECG) sensor for monitoring electrical signals from the heart. According to one embodiment, the control subsystem synchronizes the pumping of the perfusion fluid to the heart with the ECG signals. According to one feature, the ECG signals include an r-wave, and the control subsystem uses the r-wave to synchronize the fluid pumping with a diastolic state of the heart. According to another feature, the control subsystem adjusts pump stroke volume and/or pump rate in dependence on the ECG signals. For example, in one embodiment, the control subsystem reduces the pump stroke volume as heart rate increases in order to maintain blood flow. In another embodiment, the system reduces the pump stroke volume in response to detecting an irregular heart rate. In both cases, the result is to reduce fluid volume pumped to the heart, which in turn reduces the likelihood of causing damage to the heart. In various embodiments, the sensors include perfusion fluid flow rate and/or flow pressure sensors, which provide feedback for controlling the perfusion fluid pump. According to one embodiment, to more accurately simulate normal circulation through the body, the pump of the system is a pulsatile pump.

According to one aspect of the invention, the organ chamber assembly includes a plurality of improved features. More particularly, in one configuration, the organ chamber assembly of the invention includes a housing, an outer lid and an intermediate lid. The housing includes a bottom and one or more walls for containing the organ. The intermediate lid covers an opening to the housing for substantially enclosing the organ within the housing, and includes a frame and a flexible membrane suspended within the frame. The flexible membrane, preferably, is transparent but may be opaque, translucent, or substantially transparent. According to one feature, the flexible membrane includes sufficient excess membrane material to contact an organ contained within the chamber. This feature enables a medical operator to touch/examine the organ indirectly through the membrane while still maintaining sterility of the system and the organ. The outer lid opens and closes over the intermediate lid independently from the intermediate lid. Preferably, the outer lid is rigid enough to protect the organ from physical contact, indirect or direct.

According to one implementation, the intermediate lid is hinged to the housing. The intermediate lid may also include a latch for securing the intermediate lid closed over the opening of the organ chamber. The outer lid may be similarly hinged and latched. In some configurations, gaskets are provided for forming a fluid seal between the intermediate lid frame and the one or more organ chamber walls, and/or for forming a fluid seal between the periphery of the outer lid and the frame of the intermediate lid.

Optionally, the organ chamber assembly includes a pad or a sac assembly sized and shaped for interfitting within a bottom of the housing. Preferably, the pad assembly includes a pad formed from a material resilient enough to cushion the organ from mechanical vibrations and shocks during transport. In the case of the organ chamber assembly being configured to receive a heart, according to one feature, the pad of the invention includes a mechanism for receiving at least one electrode. The mechanism may include, without limitation, one or more slots, indentations, protrusions, through apertures, partially through apertures, hooks, eyelets, snaps, adhesive patches, or the like. According to one advantage, the mechanism allows for adjustable placement of the at least one electrode on or in the pad to accommodate differently sized and shaped hearts. According to one embodiment, the pad includes a through-aperture through which an electrical lead of the at least one electrode may pass.

According to one embodiment, the pad assembly includes at least one electrode adjustably positioned at a location on or in the pad in such a way as to facilitate contact with a heart placed on the pad in the organ chamber assembly. According to one configuration, the at least one electrode rests on the surface of the pad and is held in place by the weight of the heart. In another configuration, the at least one electrode is glued to the surface of the pad. The at least one electrode includes one or more sensors for monitoring one or more electrical signals from the heart. It may also include one or more defibrillator contacts for providing an electrical signal to the heart. One advantage of the pad/electrode configuration of the invention is that it does not require the at least one electrode to be permanently or temporarily sutured or otherwise mechanically connected to the heart. Instead, electrical connection is made by placing the heart on the one or more electrodes. In one configuration, the at least one electrode includes an integrated sensor and defibrillation contact that allows the user to monitor electrical signals from the heart and provide an electrical signal to the heart through a common electrical interface connection to the organ chamber assembly. According to another feature, the common electrical interface includes one or more electrical ports on the organ chamber assembly for transferring electrical signals between the at least one electrode within the chamber and instrumentation located external to the housing. By way of example, the ports may provide the ECG signals to an external processor and/or display, and/or may provide defibrillation power to the electrodes.

Optionally, the organ chamber housing also includes a base for angling the housing for optimal heart function. According to one feature, the base maintains a heart contained within the organ chamber at an angle of between about 30° and about 60° relative to horizontal.

According to another aspect, the perfusion fluid heater assembly of the invention includes a plurality of improved features relating to providing a compact, solid state mechanism for heating the perfusion fluid. Some features of the heater assembly make it particularly suitable for heating blood-product based embodiments of the perfusion fluid. In one embodiment, the heater assembly of the invention includes an inlet, an outlet, a flow channel, first and second flow channel plates and a first heater. The flow channel is formed between the first and second flow channel plates. The inlet flows the perfusion fluid into the flow channel and the outlet flows the perfusion fluid out of the heater. The first and second flow channel plates have substantially bioinert perfusion fluid contacting surfaces for providing direct contact with the perfusion fluid flowing through the channel. The perfusion fluid contacting surfaces may be formed, for example, from a treatment or coating on a substrate or may be the substrate surface itself. The first heater is thermally coupled to the first flow channel plate for heating the first flow channel plate. In one configuration, the first heater is located on a nonperfusion fluid contacting side of the first flow channel plate. According to a further embodiment, the heater assembly of the invention also includes a second heater thermally coupled to the second flow channel plate for heating the second flow channel plate to provide a more uniform temperature distribution in the flow channel.

According to one configuration, the heater assembly includes a first heater plate disposed between the first heater and the first flow channel plate for thermally coupling heat from the first heater to the first flow channel plate. According to one feature, the first heater plate is formed from a material, such as aluminum, that conducts and distributes heat from the heater relatively uniformly. The uniformly distributed heat of the heater plate is then coupled to the first channel plate, which preferably is formed from a bioinert material, such as titanium, which does not necessarily provide sufficiently uniform heat distribution if put in direct contact with the heater. The heater assembly may also include a second heater plate disposed between the second heater and the second flow channel plate for coupling heat from the second heater to the second flow channel plate.

According to one embodiment, the first and/or second heaters of the invention are resistive heaters. In one configuration, they each include a resistive heating element formed on a polyimide substrate. According to a further configuration, the resistive heating elements have a resistance of about 5 ohms. In other configurations, the resistance of the heating elements ranges from about 3 ohms to about 10 ohms.

Optionally, the heater assembly of the invention includes one or more temperature sensors. For example, the heater assembly may include a temperature sensor at its outlet for reporting the temperature of the perfusion fluid exiting the heater to the control subsystem. The signal from this sensor may be employed in a feedback loop to control drive signals to the first and second heaters to control the temperature of the heater plates. Additionally, to ensure that the perfusion fluid contacting surfaces of the heater plates do not reach a temperature that might damage the perfusion fluid, the heater assembly may also include temperature sensors for reporting the temperature of the first and/or second heaters to the control subsystem. The signals from these sensors may also be employed in a feedback loop to further control the drive signals to the first and/or second heaters to limit the maximum temperature of the heater plates. According to a variation of this embodiment, the heater assembly may include temperature sensors for reporting the temperature of the first and/or second heaters to the control subsystem.

To provide improved contact between the first and/or second heaters and their respective heater plates, and also between the first and/or second heater plates and their respective flow channel plates, the heater assembly may also include first and second resilient pads disposed on the respective heaters for maintaining the first heater in contact with the first heater plate and the second heater in contact with the second heater plate in response to compressive force. The compressive force may be provided, for example, by way of one or more heater assembly housing components. According to one feature, the heater assembly includes housing components formed from a polycarbonate, and weighs less than about 5 lb, while in other embodiments the heater assembly may weigh less than about 4 lb, less than about 3 lb, less than about 2 lb, or even less than about 1 lb. According to another feature, the heater assembly is about 6.75 inches long, about 2.75 inches wide, and about 2.5 inches thick, all exclusive of inlet and outlet ports and temperature sensor assemblies. According to another feature, the heater assembly is a single use disposable assembly.

According to one embodiment, in operation, the heater assembly uses between about 1 Watt and about 200 Watts of power. According to a further embodiment, the heater assembly of the invention is sized and shaped to transition about 2.5 liters of perfusion fluid flowing through the channel at a rate of between about 300 mil/min and about 5 L/min from a temperature of less than about 30° C. to a temperature of about 37° C. in less than about 25 minutes, less than about 20 minutes, less than about 15 minutes or even less than about 10 minutes, without causing substantial hemolysis to the blood cells or denaturation of any proteins that may be contained in the perfusion fluid.

According to a further embodiment, the power subsystem of the invention provides a fault tolerant battery arrangement. More particularly, a plurality of batteries are interlocked such that all of them may not be removed from the system at any particular time while the system is operating to maintain an organ. According to one feature, the power subsystem can switch between external power and onboard battery backup, without interruption of system operation. According to another feature, the power subsystem automatically allocates externally supplied power between powering the system, charging the batteries, and charging internal batteries of the wireless operator interface.

According to another aspect, the invention segments various subsystems and components of the portable organ care system into two modules; a portable multiple use module and a single use disposable module. According to one segmentation, the system of the invention generally assigns perfusion fluid contacting (and thus, blood product contacting in embodiments employing a blood product perfusion fluid) components to the disposable module, and non perfusion-fluid-contacting (and thus, non-blood product contacting components) to the multiple use module. However, the disposable unit may also include non-blood contacting components. According to one feature, the perfusion-fluid contacting components may be coated or bonded with heparin or other anticoagulant or biocompatible material to reduce the inflammatory response that may otherwise arise when the perfusion fluid contacts the surfaces of the components. Heparin may also be added to the maintenance solutions for circulation within the system.

In one embodiment, the portable multiple use module includes a portable housing constructed on a portable chassis, and the single use disposable module includes a disposable chassis. To reduce weight, in one configuration, the single use module chassis is formed from molded plastic such as polycarbonate, and the multiple use module chassis is formed from molded materials such as polycarbonate or carbon fiber composites. According to one feature, the single use chassis unloaded with components weighs less than about 12 pounds and the loaded single use module weighs less than about 18 pounds. According to another feature, the multiple use housing and chassis unloaded with components weighs less than about 50 pounds, and when loaded with a multiple use module, batteries, gas, maintenance solutions, perfusion fluid and a heart, weighs about 85 pounds or less. According to another advantage, the system of the invention including both single and multiple use modules, exclusive of any perfusion, nutrient, preservative or other fluids, batteries and oxygen supply, weighs less than about 65 pounds.

The single use disposable chassis is sized and shaped for interlocking with the portable chassis of the multiple use module for electrical, mechanical, gas and fluid interoperation with the multiple use module. According to one feature, the multiple and single use modules communicate with each other via an optical interface, which comes into optical alignment automatically upon the single use disposable module being installed into the portable multiple use module. According to another feature, the portable multiple use module provides power to the single use disposable module via spring loaded connections, which also automatically connect upon the single use disposable module being installed into the portable multiple use module. According to one feature, the optical interface and spring loaded connections ensure that connection between the single and multiple modules is not lost due to jostling, for example, during transport over rough terrain.

In various embodiments, the organ chamber assembly and the pump interface assembly both mount to the disposable chassis. The pump interface assembly is aligned to receive a pumping force from the pump driver of the perfusion fluid pump, and the interface assembly then translates the pumping force to the perfusion fluid to circulate the perfusion fluid to the organ chamber assembly. According to one embodiment, the perfusion fluid pump is a pulsatile pump and the pump interface assembly includes a housing, a first deformable membrane, a fluid inlet, and a fluid outlet. The housing of the pump interface assembly includes an interior side and an exterior side. The first deformable membrane mounts in fluid tight interconnection with the interior side of the housing to form a chamber between an interior side of the first deformable membrane and the interior side of the housing. The fluid inlet receives perfusion fluid, for example, from the reservoir, and provides the fluid into the chamber in response to the pump driver moving in a direction away from the interior side of the housing, and thus deforming the first deformable membrane in the same direction. The outlet expels the perfusion fluid out of the chamber, for example, to the heater assembly, in response to the pump driver moving in a direction toward the interior side of the housing.

According to one configuration, the pump interface assembly includes a bracket for fitting over a periphery of the first deformable membrane to form the fluid tight seal between the periphery of the interior side of the deformable membrane and a periphery of the interior side of the housing. According to a further configuration, the pump interface assembly includes a gasket for providing a fluid tight seal between the perfusion fluid pump driver and the pump interface housing.

According to one implementation, the system also includes a flow valve positioned on the input to the fluid inlet. The flow valve includes a ball valve assembly oriented to open and pass the perfusion fluid into the chamber through the bidirectional fluid inlet in response to the pump driver moving in the direction away from the interior side of the housing, and oriented to close and stop perfusion fluid passing back out of the chamber through the fluid inlet in response to the pump driver moving in the direction toward the interior surface of the housing. In a further implementation, the fluid outlet also includes a ball valve assembly oriented to close in response to the pump driver moving in the direction away from the interior surface of the housing, and to open to expel the organ perfusion fluid through the fluid outlet in response to the pump driver moving in the direction toward the interior side of the housing.

Optionally, the perfusion fluid pump rigidly mounts to the portable multiple use chassis, the pump interface assembly rigidly mounts to the disposable single use chassis, and the system includes features for automatically forming a fluid tight seal between the perfusion pump driver and the pump interface assembly in response to the single use disposable module being interfitted with the portable multiple use module. More particularly, the pump interface assembly may include one or more projections out of the exterior side of the interface assembly housing, sized and shaped for engaging with and abutting one or more surfaces on the portable multiple-use module to force/draw the interior side of the pump interface assembly housing in a direction toward the pump driver of the perfusion pump.

According to one feature, the pump interface assembly includes a second deformable membrane mounted adjacent to the first deformable membrane for providing a fault tolerant seal in case the first deformable membrane tears. According to another feature, the pump interface assembly is formed at least in part from a polycarbonate or other molded plastic material, to reduce the weight of the single use disposable module.

In one embodiment, the perfusion fluid reservoir mounts to the single use disposable chassis and is in fluid communication with the organ chamber. According to a further embodiment, the flow mode selector valve mounts to the disposable chassis. In other embodiments, the solid state perfusion heater of the invention mounts to the disposable chassis. The oxygenator is preferably provided with the multiple-use module, but in certain embodiments may alternatively be part of the disposable module. The oxygen source feeding the oxygenator may be included on the multiple use portable chassis, may be part of the multiple-use module, or may be external to the system.

In one configuration, the various sensors associated with the heater assembly, the oxygenator and/or the perfusion fluid pump are included on the disposable single use module. However, this need not be the case, for example, with regard to non-perfusion fluid contacting sensors. According to one embodiment, the single use disposable module employs an oxygen sensor including in-line cuvette through which the perfusion fluid passes, an optical source for directing light at the perfusion fluid passing through the cuvette, and an optical sensor for measuring an optical quality of the perfusion fluid passing through the cuvette. Preferably, the in-line cuvette seamlessly or substantially seamlessly attaches to a perfusion fluid flow conduit to reduce turbulence in the perfusion fluid and provide one or more accurate measurements. The seamless or substantially seamless configuration also reduces damage to any blood based components of the perfusion fluid.

According to a further configuration, the disposable single-use module includes the above-mentioned plurality of inline compliance chambers located, for example, at the outlet of the perfusion fluid pump, and on either side of the mode select valve between the organ chamber and the mode select valve. In a further embodiment, the disposable single-use module includes a plurality of ports for sampling fluids from the organ chamber assembly. According to one feature, the ports are interlocked such that sampling fluid from a first of the plurality of ports prohibits simultaneously sampling fluids from a second port of the plurality. This safety feature reduces the likelihood of mixing fluid samples and inadvertently opening the ports. In one embodiment, the organ chamber assembly includes ports for fluid interconnection with one or more of the pulmonary artery, aorta, and left atrium interfaces.

In another aspect, the invention is directed to a method of preserving a heart ex-vivo. The method includes placing a heart in a protective chamber of a portable organ care system, pumping a perfusion fluid to the heart, the perfusion fluid being at a temperature of between about 25° C. and about 37° C., and at a volume of between about 200 ml/min and about 5 L/min, monitoring one or more physiologic characteristics of the heart while it is beating in the protective chamber, and adjusting a pumping characteristic based at least in part on the electrical characteristics to preserve the heart ex vivo.

According to another aspect, the invention is directed to a method of preserving a heart ex vivo, the method including the steps of placing a heart on one or more electrodes in a protective chamber of a portable organ care system, pumping a perfusion fluid to the heart, the perfusion fluid being at a temperature of between about 25° C. and about 37° C., and at a volume of between about 200 ml/min and about 5 L/min, and monitoring electrical signals from the electrodes while pumping the perfusion fluid to the heart to preserve the heart ex vivo.

In a further aspect, the invention is directed to a method of transporting a heart ex vivo, including the steps of placing a heart for transplantation in a protective chamber of a portable organ care system, pumping a perfusion fluid into the heart via an aorta of the heart, providing a flow of the perfusion fluid away from the heart via a right ventricle of the heart, and transporting the heart in the portable organ care system from a donor site to a recipient site while pumping the perfusion fluid into the heart via the aorta and providing the flow of the perfusion fluid away from the heart via the right ventricle.

According to an additional aspect, the invention is directed to a method of evaluating a heart for transplantation, including the steps of placing a heart in a protective chamber of a portable organ care system, pumping a perfusion fluid into the heart via a left ventricle of the heart, providing a flow of the perfusion fluid away from the heart via a right ventricle of the heart, transporting the heart via the portable organ care system from a donor site to a recipient site while pumping the perfusion fluid into the heart via the left ventricle and providing the flow of the perfusion fluid away from the heart via the right ventricle; prior to transplanting the heart into a recipient, operating a flow control external to the protective chamber to alter a flow of the perfusion fluid such that the perfusion fluid is pumped into the heart via a left atrium of the heart and is flowed away from the heart via the right ventricle and the left ventricle of the heart; and performing an evaluation of the heart. In certain embodiments the evaluation includes performing an HLA test on the heart while the perfusion fluid is pumping.

In another aspect, the invention is directed to a method of providing therapy to a heart. The method includes placing a heart in a protective chamber of a portable organ care system, pumping a perfusion fluid into the heart via a left ventricle of the heart, providing a flow of the perfusion fluid away from the heart via a right ventricle of the heart, operating a flow control external to the protective chamber to alter a flow of the perfusion fluid such that the perfusion fluid is pumped into the heart via a left atrium of the heart and is flowed away from the heart via the right ventricle and the left ventricle of the heart, and administering a therapeutic treatment to the heart. The treatments may include, for example, administering one or more of immunosuppressive treatment, chemotherapy, gene therapy and irradiation therapy to the heart.

According to another aspect, the invention is directed to a method of transplanting a heart. The method includes arresting a heart of a donor, explanting the heart from the donor, transferring the heart to an organ care system, and pumping a perfusion fluid to the heart in less than 30 minutes after explanting the heart from the donor (so as to reduce the heart's explantation cold ischemia time), the perfusion fluid being at a temperature of between about 32° C. and about 37° C. In certain embodiments the heart is brought to a temperature of between about 35° C. and about 37° C. in less than 10 minutes after transferring the heart to the organ care system.

These and other features and advantages of the invention are described in further detail below with regard to illustrative embodiments of the invention.

BRIEF DESCRIPTION OF THE DRAWINGS

The following figures depict illustrative embodiments of the invention in which like reference numerals refer to like elements. These depicted embodiments may not be drawn to scale and are to be understood as illustrative of the invention and not as limiting, the scope of the invention instead being defined by the appended claims.

FIGS. 28A-28C show various views of an exemplary hematocrit and oxygen saturation sensor of the type employed in the illustrative single use disposable module of FIGS. 19A-19C.

ILLUSTRATIVE DESCRIPTION

Figure 1:
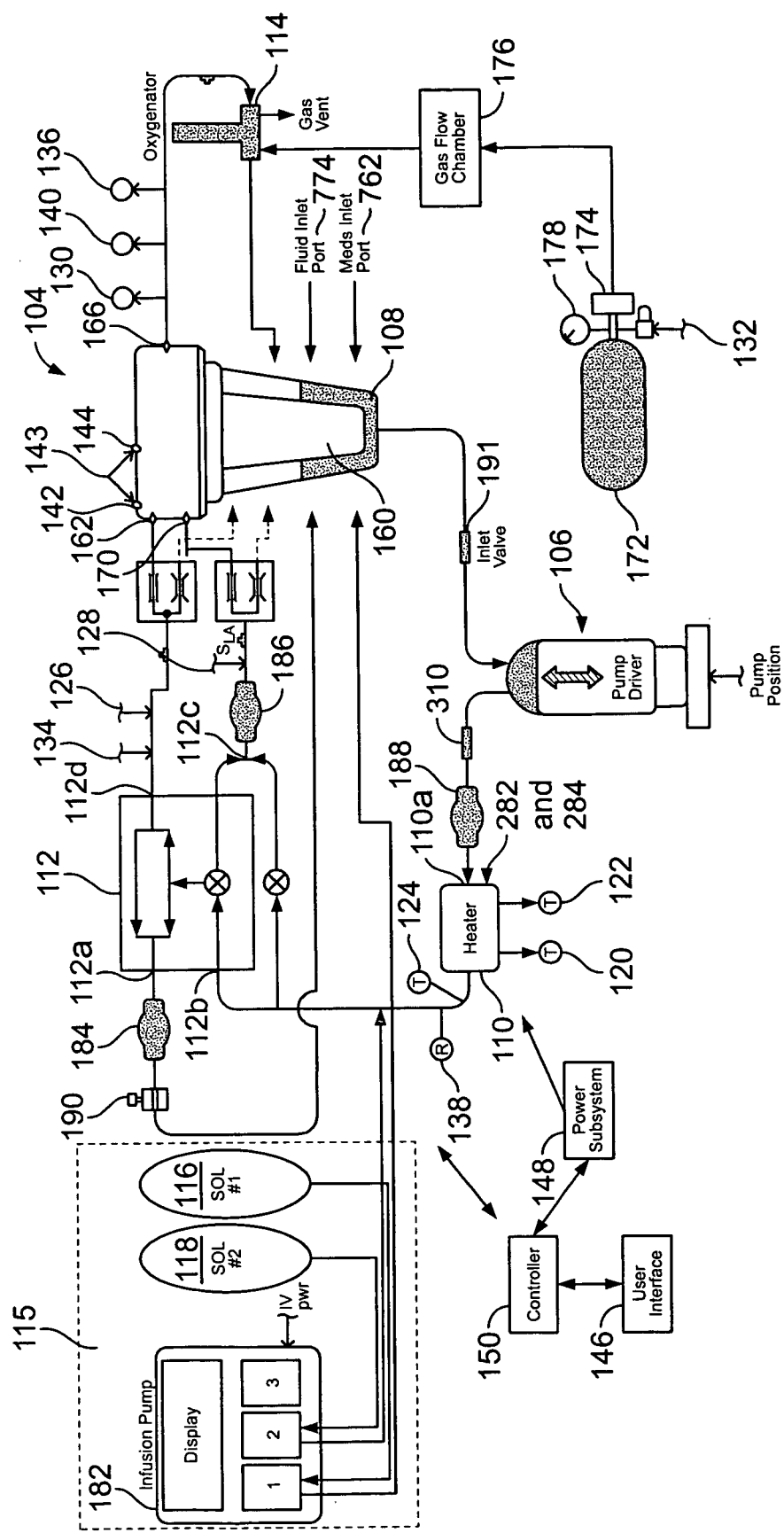
FIG. 1 is a schematic diagram of a portable organ care system according to an illustrative embodiment of the invention.

As described above in summary, the invention generally provides improved approaches to ex-vivo organ care. More particularly, in various embodiments, the invention is directed to improved systems, methods and devices relating to maintaining an organ in an ex-vivo portable environment. According to one improvement, the organ preservation system of the invention maintains a heart beating at or near normal physiological conditions. To this end, the system circulates an oxygenated, nutrient enriched perfusion fluid to the heart at near physiological temperature, pressure and flow rate. According to one implementation, the system employs a perfusion fluid solution that more accurately mimics normal physiologic conditions. In one embodiment, the perfusion fluid is blood-product based. In alternative embodiments, the solution is synthetic blood substitute based. In other embodiments the solution may contain a blood product in combination with a blood substitute product.

According to various illustrative embodiments, the improvements of the invention enable an organ, such as a heart, to be maintained ex-vivo for extended periods of time, for example, exceeding 3, 4, 5, 6, 8, 10, 12, 14, 16, 18, 20, 22, 24 or more hours. Such extended ex-vivo maintenance times expand the pool of potential recipients for donor organs, making geographical distance between donors and recipients less important. Extended ex-vivo maintenance times of the invention also provide the time needed for better genetic and HLA matching between donor organs and organ recipients, increasing the likelihood of a favorable outcome. The ability to maintain the organ in a near physiologic functioning condition also enables a clinician to evaluate the organ's function ex-vivo, further increasing the likelihood of transplantation success. In some instances, the extended maintenance time enables medical operators to perform repairs on donor organs with minor defects. According to another advantage, the increased ex-vivo organ maintenance times of the invention enable an organ to be removed from a patient, treated in isolation ex-vivo, and then put back into the body of a patient. Such treatment may include, without limitation, surgical treatments, chemo-, bio-, gene and/or radiation therapies.

The illustrative systems, methods and devices of the invention are described below in the following order. First, the components of an illustrative organ care system 100 are described. Second, illustrative operation of the system 100 is discussed. Third, a subset of the components of the system 100 are described in further detail. Fourth, illustrative control systems and methods for the system 100 are discussed. Fifth, an illustrative user interface is described. Sixth, mechanical features of the system 100 are discussed in further detail with regard to an exemplary implementation. Seventh, exemplary methods for employing the system 100 during an organ harvest, transport, and transplantation procedure are described. Eighth, illustrative perfusion, nutritional and preservative solutions suitable for use with the system 100 are presented.

Figure 2:
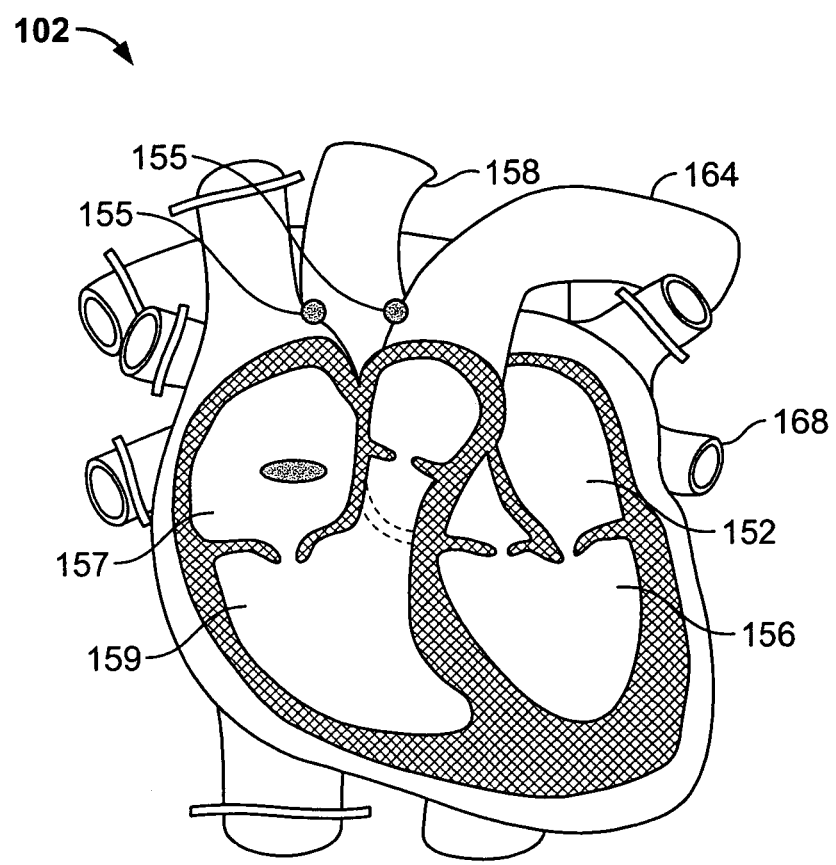
FIG. 2 is a diagram depicting a harvested heart.

Turning to the illustrative embodiments, FIG. 1 depicts a schematic diagram of a portable organ care system 100 according to an illustrative embodiment of the invention. FIG. 2 shows a conceptual drawing of a heart 102, which may be preserved/maintained ex-vivo by the organ care system 100 of the invention. Referring to FIGS. 1 and 2, the illustrative system 100 includes an organ chamber assembly 104 for containing the heart 102 during ex-vivo maintenance, a reservoir 160 for holding, defoaming and filtering the perfusion fluid 108, portal 774 for loading perfusion fluid 108 into the reservoir 160 and a portal 762 for applying therapeutics to the fluid 108 contained in the reservoir 160, a perfusion fluid pump 106 for pumping/circulating perfusion fluid 108 to and from the harvested heart 102; a heater assembly 110 for maintaining the temperature of the perfusion fluid 108 at or near physiological temperatures; a flow mode selector valve 112 for switching between normal and retrograde aortic flow modes (also referred to as "normal flow mode" and "retrograde flow mode," respectively); an oxygenator 114 for re-oxygenating the perfusion fluid 108 subsequent to it being expelled by the heart 102; a nutritional subsystem 115 for replenishing nutrients 116 in the perfusion fluid 108 as they are metabolized by the heart 102 and for providing additional preservatives 118 to the perfusion fluid to reduce, for example, ischemia and/or other re-perfusion related injuries to the heart 102. The illustrative system 100 also includes a plurality of sensors, including without limitation: temperature sensors 120, 122 and 124; pressure sensors 126, 128, 130 and 132; perfusion flow rate sensors 134, 136 and 138; a perfusion fluid oxygenation sensor 140; and sensor electrodes 142 and 144, and defibrillation source 143. The system 100 further includes: various components employed for maintaining suitable flow conditions to and from the heart 102; an operator interface 146 for assisting an operator in monitoring operation of the system 100, and the condition of the heart 102, and for enabling the operator to select various operating parameters; a power subsystem 148 for providing fault tolerant power to the system 100; and a controller 150 for controlling operation of the organ care system 100.

Figure 3:
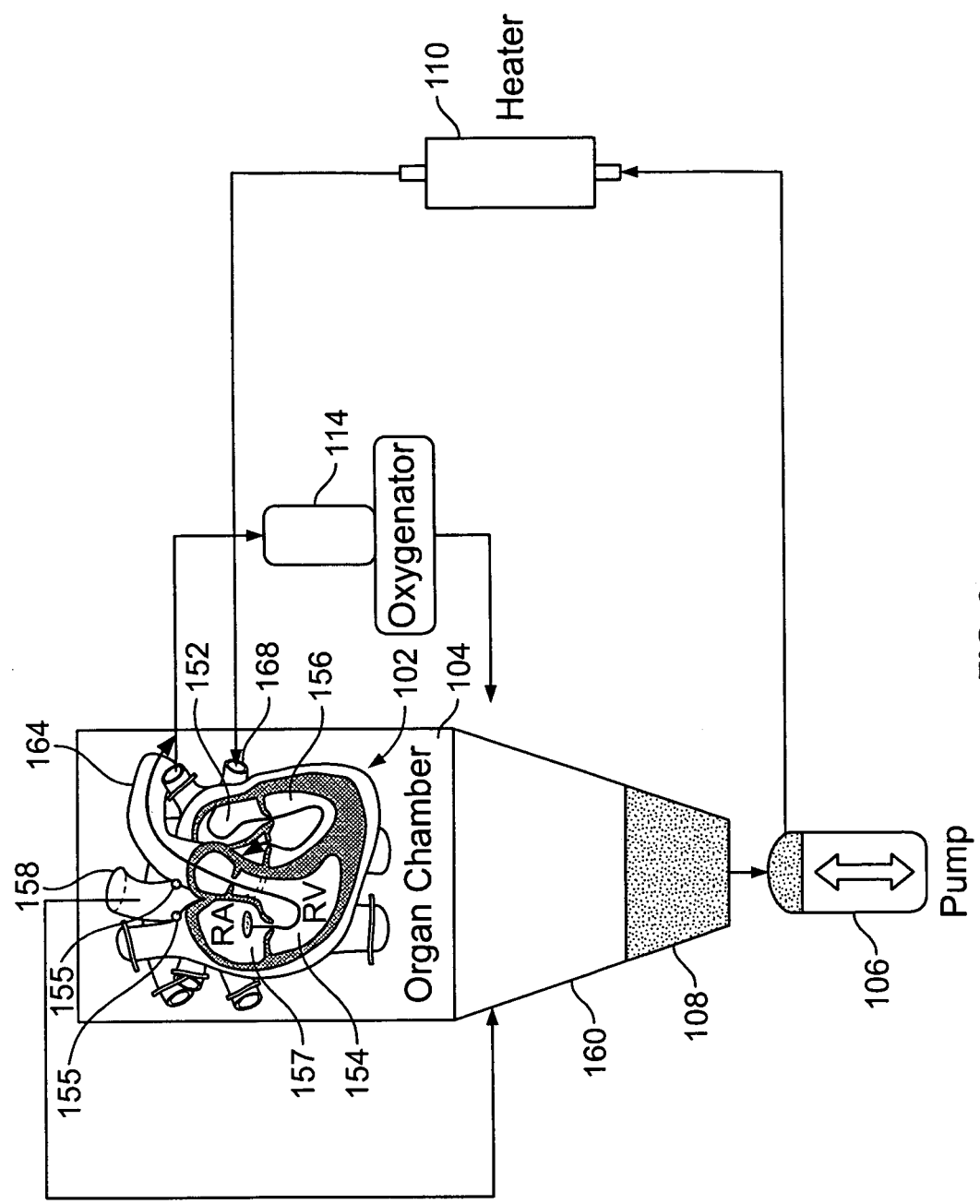
FIG. 3 is a conceptual diagram depicting the harvested heart of FIG. 2 interconnected with the organ care system of FIG. 1 in a normal flow mode configuration according to an illustrative embodiment of the invention.
Figure 4:
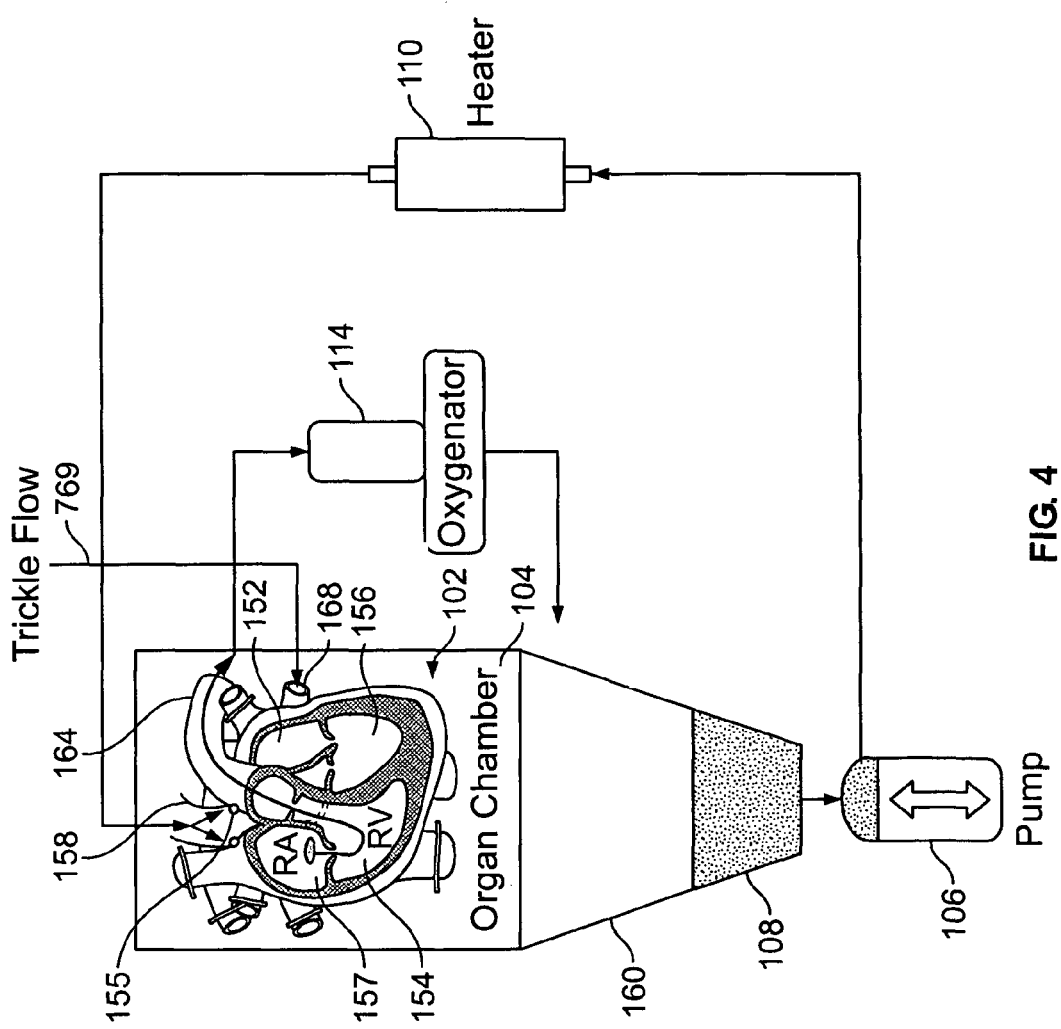
FIG. 4 is a conceptual diagram depicting the harvested heart of FIG. 2 interconnected with the organ care system of FIG. 1 in a retrograde flow mode configuration according to an illustrative embodiment of the invention.

Referring also to FIGS. 3 and 4, according to the illustrative embodiment, the system 100 can maintain the heart 102 in two modes of operation—a normal flow mode, shown in FIG. 3, and a retrograde flow mode shown in FIG. 4. Generally, in the normal flow mode of FIG. 3, the system 100 circulates the perfusion fluid 108 to the heart 102 in the same manner as blood would circulate in the human body. More particularly, referring to FIGS. 1-3, the perfusion fluid enters the left atrium 152 of the heart 102 via the pulmonary vein 168. The perfusion fluid 108 is flowed away from the right ventricle 154 via the pulmonary artery 164 and away from the left 156 ventricle via the aorta 158. In normal flow mode, the system 100 pumps the perfusion fluid to the heart 102 at a near physiological rate of between about 1 liter/min and about 5 liters/minute. This mode is useful, for example, for performing functional testing to verify that the heart 102 is defect free, both prior and subsequent to transportation to a donor location.

Alternatively, in retrograde flow mode, shown in FIG. 4, the system 100 flows the perfusion fluid 108 into the heart 102 via the aorta 158, through the coronary sinus 155 and other coronary vasculature of the heart, and out of the right ventricle 154 of the heart 102 via the pulmonary artery 164. As discussed in further detail below with regard to FIGS. 24A and 24B, the system 100 also provides a trickle flow 769 to the left atrium 152 through trickle valve 768. The trickle flow is provided in an amount sufficient to moisten the left atrium 152 and left ventricle 156. In certain applications the trickle flow is less than about 5 ml/min, less than about 1 ml/min, or less than about 0.1 ml/min. In this mode of operation, the system 100 reduces the flow rate of the perfusion fluid 108 to between about 300 milliliters/minute and about 1 liter/minute. The inventors have found that the retrograde flow path of FIG. 4, along with the reduced flow rate, reduces damage to the heart 102 during extended periods of ex-vivo maintenance. Thus, according to one feature of the invention, the heart 102 is transported to a donor site in retrograde flow mode.

Having briefly described the normal and retrograde flow modes, the system 100 will next be described in further detail operationally. Referring once again to FIGS. 1-4, in one practice, the heart 102 is harvested from a donor and cannulated into the organ chamber assembly 104. The perfusion fluid 108 is prepared for use within system 100 by being loaded into the reservoir 160 via portal 774 and, optionally, being treated with therapeutics via portal 762. The pump 106 pumps the loaded perfusion fluid 108 from a reservoir 160 to the heater assembly 110. The heater assembly 110 heats the perfusion fluid 108 to or near a normal physiological temperature. According to one embodiment, the heater assembly 110 heats the perfusion fluid to between about 32° C. and about 37° C. The heater assembly 110 has an internal flow channel with a cross-sectional flow area that is approximately equal to the inside cross-sectional area of fluid conduits that carry the perfusion fluid 108 into and/or away from the heater assembly 110, so as to minimize disturbance of fluid flow. From the heater assembly 110, the perfusion fluid 108 flows to the flow mode selector valve 112.

Figure 5A:
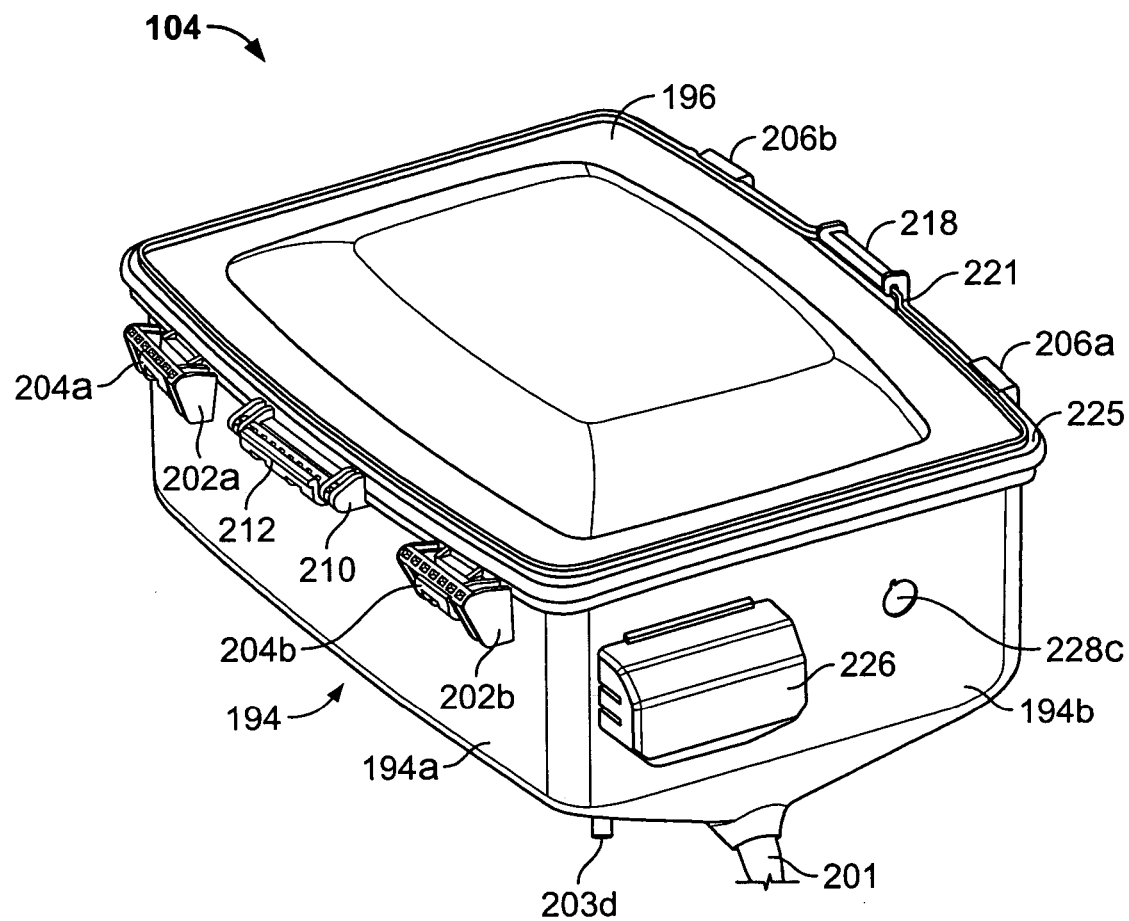
FIGS. 5A-5F show various views of an organ chamber assembly of the type employed in the organ care system of FIG. 1 according to an illustrative embodiment of the invention.
Figure 5B:
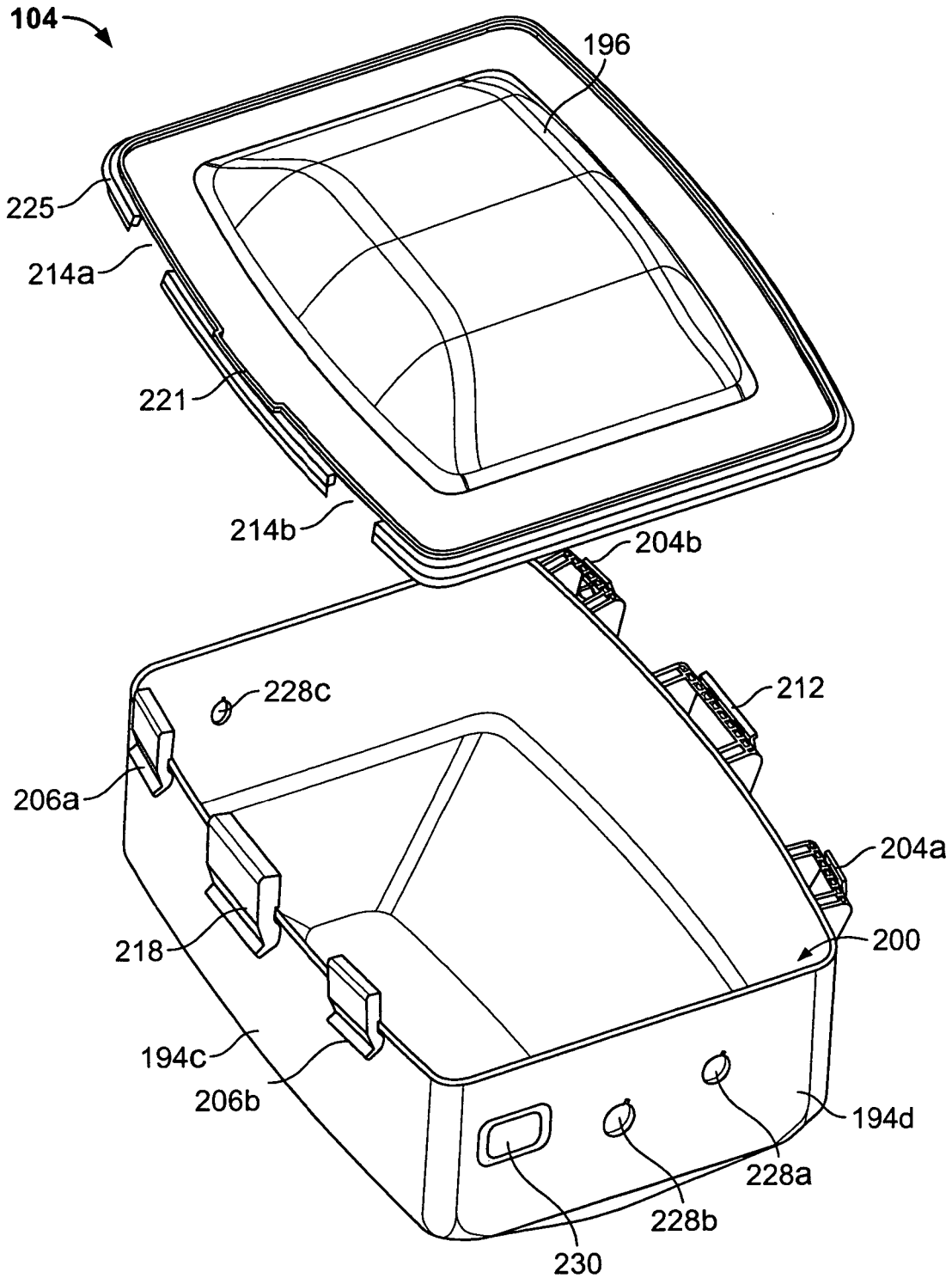

Initially, the flow mode selector valve 112 is positioned in retrograde mode to direct the perfusion fluid 108 from the heater assembly 110 into the organ chamber assembly 104 via a first interface 162. Also referred to as an aorta interface or left ventricle interface, the interface 162 includes cannulation to vascular tissue of the left ventricle via an aperture 228b located on the organ chamber assembly 104 (as shown in FIGS. 5A-5B). As the heart 102 warms, it begins to beat which causes the heart 102 to pump the perfusion fluid 108 through the coronary vasculature 155 and out of the heart 102 through the right ventricle 154 via a second interface 166. The second interface 166, also referred to as a pulmonary artery interface or a right ventricle interface, includes cannulation to vascular tissue of the right ventricle via an aperture 228c located on the organ chamber assembly 104 (as shown in FIGS. 5A-5B). As mentioned above, in retrograde flow mode, fluid is not actively pumped into or out of the left side of the heart, except for a relatively small trickle 769 of perfusion fluid, which is delivered to moisten the left atrium 152 and left ventricle 156, as described below in reference to FIGS. 24A-24E.

In response to the flow mode selector valve 112 being placed in the normal mode position, it directs the perfusion fluid 108 into the left atrium 152 of the heart 102 via a third interface 170. The third interface 170, also referred to as a pulmonary vein interface or left atrium interface, includes cannulation to vascular tissue of the left atrium 152 via an aperture 228a located on the organ chamber assembly 104 (as shown in FIGS. 5A-5B). The heart 102 then expels the perfusion fluid 108 through the left ventricle 156 via the aorta interface 162 and through the right ventricle 154 via the pulmonary artery interface 166.

Each of the interfaces 162, 166 and 170 may be cannulated to the heart 102 by pulling vascular tissue (e.g., an aorta stub) over the end of the interface, then tying or otherwise securing the tissue to the interface. The vascular tissue is preferably a short segment of a blood vessel (e.g., an aorta stub 158) that remains connected to the heart 102 after the heart 102 is severed and explanted from the donor. For example, the aorta interface 162 is cannulated to a small segment of the severed aorta 158 which has been formed by severing the aorta 158 in a location down-stream from the coronary sinus 155. In certain applications, the short vessel segments may be about 5 to about 10 inches in length or longer. The segments may also be shorter than about 5 inches. The segments may be about 2 to about 4 inches in length, or about 1 to about 2 inches in length; in other applications the segments may be less than about ½ inch, or less than about ¼ inch.

Alternatively, the cannulation may occur by affixing the interface directly to the applicable atrium or ventricle, as may be preferred in applications where the heart 102 is prepared for explantation by severing an entire blood vessel without leaving any stub portion of the vessel connected to the heart 102. For example, a left atrium 152 cannulation can be formed by inserting the interface 170 directly into the left atrium 152 and clamping the interface 170 in place, without the need to tie to any pulmonary vein 168 tissue.

With continued reference to FIG. 1, in both flow modes the perfusion fluid 108 flows from the pulmonary artery interface 166 into the oxygenator 114. The oxygenator 114 receives gas from an external or onboard source 172 through a gas regulator 174 and a gas flow chamber 176, which can be a pulse-width modulated solenoid valve that controls gas flow, or any other gas control device that allows for precise control of gas flow rate. A gas pressure gauge 178 provides a visual indication of how full the gas supply 172 is. The transducer 132 provides similar information to the controller 150. The controller 150 can regulate automatically the gas flow into the oxygenator 114 in dependence, for example, on the perfusion fluid oxygen content measured at the sensor 140. According to various illustrative embodiments, the oxygenator 114 is a standard membrane oxygenator, such as the Liliput 2 manufactured by Dideco, a division of Sorin Biomedical, or the MINIMAX PLUS™ manufactured by Medtronic, Inc. In the illustrative embodiment, the gas includes an oxygen and carbon dioxide mixture. An exemplary composition of such a mixture contains about 85% $O_2$, about 1% $CO_2$, with the balance being $N_2$. Subsequent to re-oxygenation, the oxygenator 114 returns the perfusion fluid 108 to the reservoir 160. According to the illustrative embodiment, the sensor 140 measures the amount of light absorbed or reflected by the perfusion fluid 108 when applied at a multi-wavelength to provide an optical-based measurement of oxygen saturation. Since the perfusion fluid 108 is blood product based in certain embodiments, it may contain red blood cells (i.e., oxygen carrying cells). Accordingly, the sensor 140 also provides a signal 145 indicative of a hematocrit measurement of the perfusion fluid 108. In alternative embodiments the solution 108 is formed of a synthetic blood substitute, while in other embodiments, the solution 108 may contain a blood product in combination with a blood substitute product.

Also, in both flow modes, the nutritional subsystem 115, including a supply of maintenance solutions 116/118 and an infusion pump 182, infuses the perfusion fluid 108 with nutrients 116, such as glucose, as the perfusion 108 solution flows through the system 100, and in some embodiments, while it is in the reservoir 160. The maintenance solutions 116/118 also include a supply of therapeutics and preservatives 118 for reducing ischemia and other re-perfusion related injuries to the heart 102.

Both normal and retrograde flow modes are described in further detail below with reference to FIGS. 24A-26B.

According to the illustrative embodiment, the system 100 is primed prior to introducing an organ into the organ chamber assembly 104. During priming, a priming solution (described below) is inserted into the organ chamber 160 and pumped through the system 100. In one exemplar application, the priming occurs for a period of between about 5 and about 20 minutes. The cannulation interfaces 162, 166 and 170 in the organ chamber assembly 104 are bypassed to enable normal mode flow of perfusion fluid 108 through the system 100, without the donor heart 102 being present. Blood (or a synthetic blood substitute) is then loaded into the reservoir 160. The blood may be the blood exsanguinated from the donor during harvesting of the heart 102 or obtained from typed and cross-matched banked blood. The system 100 then circulates the blood (or blood substitute) through the system 100 to heat, oxygenate, and filter it. Nutrients, preservatives and/or other therapeutics are provided via the infusion pump 182 of the nutritional subsystem 115. Various parameters may also be initialized and calibrated via the operator interface 146 during priming. Once the system 100 is running appropriately, the pump rate can be decreased or brought to zero, and the heart 102 can be cannulated into the organ chamber assembly 104. The pump rate can then be increased. Priming of the system 100 is described in further detail below with reference to the flow diagram of FIG. 29A.

As shown in FIG. 1, the system 100 also includes a plurality of compliance chambers 184, 186 and 188. The compliance chambers 184, 186 and 188 are essentially small inline fluid accumulators with flexible, resilient walls designed to simulate the human body's vascular compliance by aiding the system in more accurately mimicking blood flow in the human body, for example, by providing flow back-pressure and/or by filtering/reducing fluid pressure spikes due, for example, to flow rate changes and/or the pumping of the pump 106. According to the illustrative embodiment, the compliance chamber 184 is located between an output 112a of the mode valve 112 and the reservoir 160 and operates in combination with an adjustable clamp 190 during normal flow mode to provide back pressure to the aorta 158 to cause perfusion fluid to flow into the coronary sinus 155 to feed the heart 102. In the illustrative embodiment, the fluid back-pressure provided to the aorta 158 is between about 55 mmHg and about 85 mmHg, which is within an acceptable near-physiologic range of mean aortic blood pressure (which is typically between about 80 mmHg and about 100 mmHg). The back pressure to the aorta 158 aids the system 100 in simulating normal physiologic conditions. The compliance chamber 186 is located between an output 112b of the mode valve 112 and the pulmonary vein cannulation interface 170 of the organ chamber assembly 104. The primary function of the compliance chamber 186 is to provide back-pressure to the left atrium 152 and to smooth pressure/flow spikes caused from the pumping action of the perfusion fluid pump 106, which delivers blood to the heart without causing substantial fluid pressure spikes. In the illustrative embodiment, the fluid back-pressure provided to the left atrium 152 is between about 0 mmHg to about 14 mmHg, which is approximately the same as the left atrial pressure under normal physiologic conditions. The compliance chamber 188 is located between an output of a one way valve 310 and an inlet 110a of the heater 110. The primary function of the compliance chamber 188 is also to smooth pressure/flow spikes caused by the pumping action of the perfusion fluid pump 106 and to provide fluid back-pressure to the pulmonary artery 164. In the illustrative embodiment, the fluid back-pressure provided to the pulmonary artery 164 is between about 0 mmHg and about 25 mmHg, which is within an acceptable near-physiologic range of mean arterial blood pressure (between about 0 mmHg and about 12 mmHg).

The compliance chambers 184, 186 and 188 provide the benefits described above through their size and shape and the materials used in their design. The chambers 184, 186 and 188 are sized to contain about 20 ml to about 100 ml of fluid 108, and they are shaped in an oval configuration to allow them to receive fluid 108 and expand to dampen pressure spikes and to provide back-pressure to the heart 102. In certain applications, the material used for the chambers 184, 186 and 188 includes at least one flexible membrane, selected so that the chambers have a Shore A durametric hardness (ASTM D2240 00) of about 10 (more flexible) to about 60 (less flexible), with certain preferred embodiments having a hardness of between about 30 (+/− about 8) and about 50 (+/− about 8). In the illustrative embodiment, the compliance chamber 184 has a Shore A hardness of about 50 (+/− about 8) and the compliance chamber 186 has a Shore A hardness of about 30 (+/− about 8). In the illustrative embodiment, the compliance chamber 188 has a dual-layered configuration, with an inner chamber having a Shore A hardness of about 50 (+/− about 8) and an outer sleeve having a Shore A hardness of about 30 (+/− about 8). Alternatively, the inner chamber can have a lower hardness (e.g., about 30, +/− about 8) and outer sleeve can have a higher hardness (e.g., about 50, +/− about 8)).

Figure 5C:
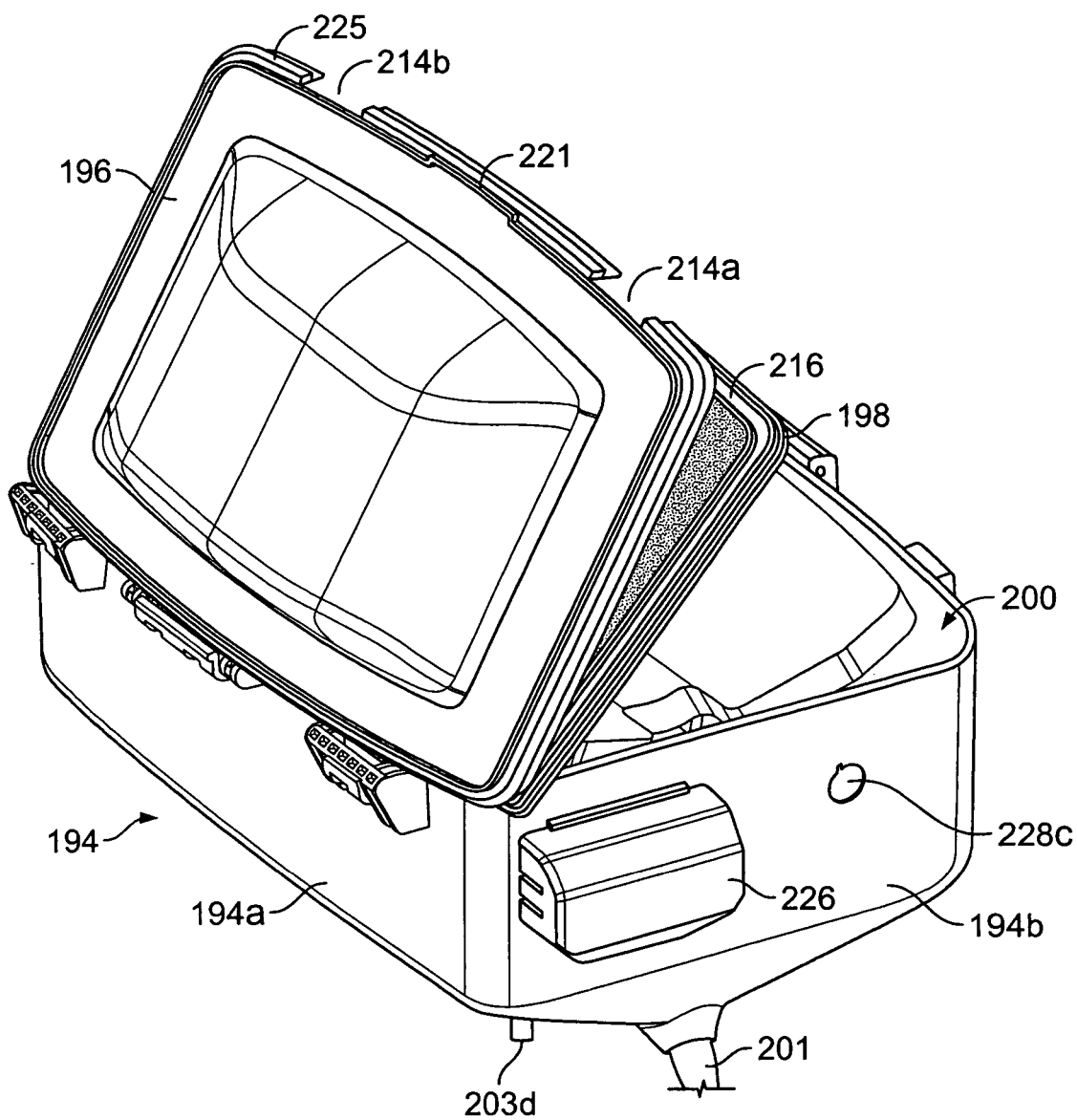

Having provided an operational overview of the system 100, the organ chamber assembly 104, the perfusion heater assembly 110, and a pump head interface assembly 192 for interfacing with the pump 106 are next described in further detail. FIGS. 5A-5F depict various views of the illustrative organ chamber assembly 104 of FIG. 1. As shown most clearly in FIGS. 5A-5D, the organ chamber assembly 104 includes a housing 194, a outer lid 196 and an intermediate lid 198. The housing includes a bottom 194e and one or more walls 194a-194d for containing the heart 102. The intermediate lid 198 covers an opening 200 to the housing 194 for substantially enclosing the heart 102 within the housing 194. As most clearly shown in FIGS. 5E and 5F, the intermediate lid 198 includes a frame 198a and a flexible membrane 198b suspended within the frame 198a. The flexible membrane 198b, preferably, is transparent but may be opaque, translucent, or substantially transparent. According to one feature, the flexible membrane includes sufficient excess membrane material to contact the heart 102 when contained within the housing 195. This feature enables a medical operator to touch/examine the heart 102 indirectly through the membrane 198b, or apply an ultrasound probe to the heart 102 through the membrane 198b, while maintaining sterility of the housing 195. The membrane 198b may be made, for example, from any suitable flexible polymer plastic, for example polyurethane. The membrane 198b may also have integrated electrically conductive pads/contacts 199a and 199b through which electrical activity of the heart may be sensed via electrodes such as the electrodes 142 and 144, and/or for through which defibrillation or pacing signals may be delivered, as described more fully below. Alternatively, the contacts 199a and 199b may be electrodes including all or a portion of the functionality of the electrodes 142 and 144. As shown in FIG. 5C, the outer lid 196 opens and closes over the intermediate lid 198 independently from the intermediate lid 198. Preferably, the outer lid 196 is rigid enough to protect the heart 102 from physical contact, indirect or indirect. The outer lid 196 and the chamber 194 may also be made from any suitable polymer plastic, for example polycarbonate.

Figure 5D:
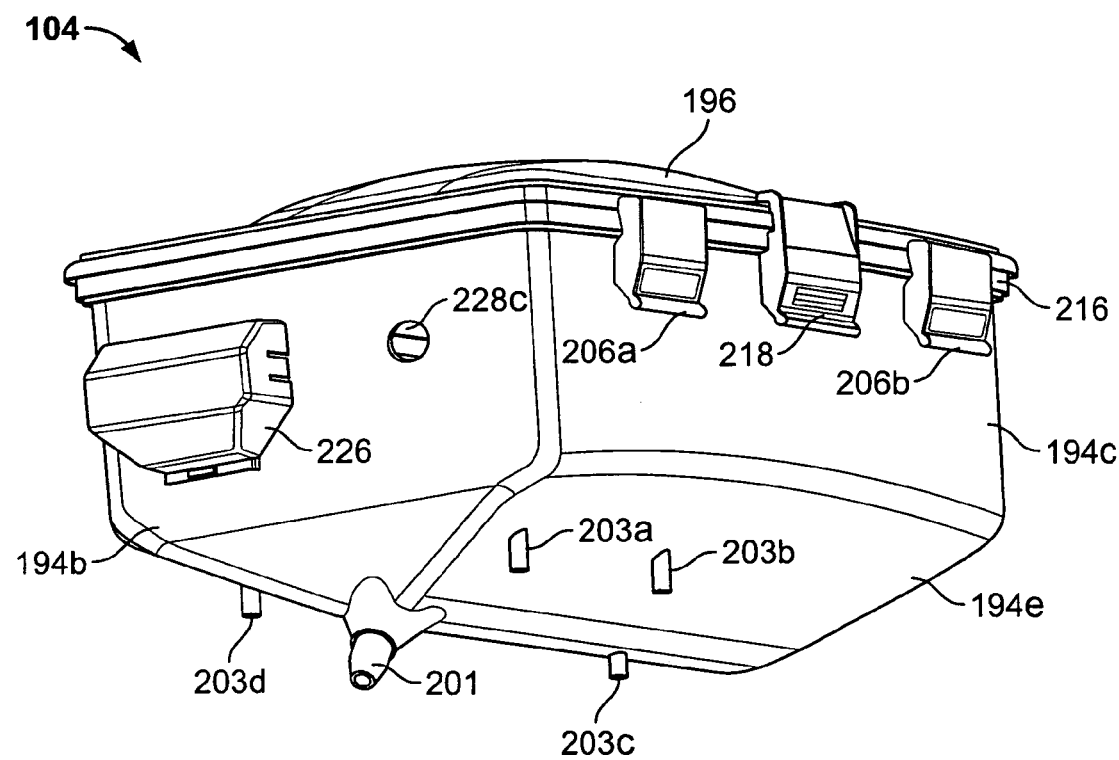
Figure 5E:
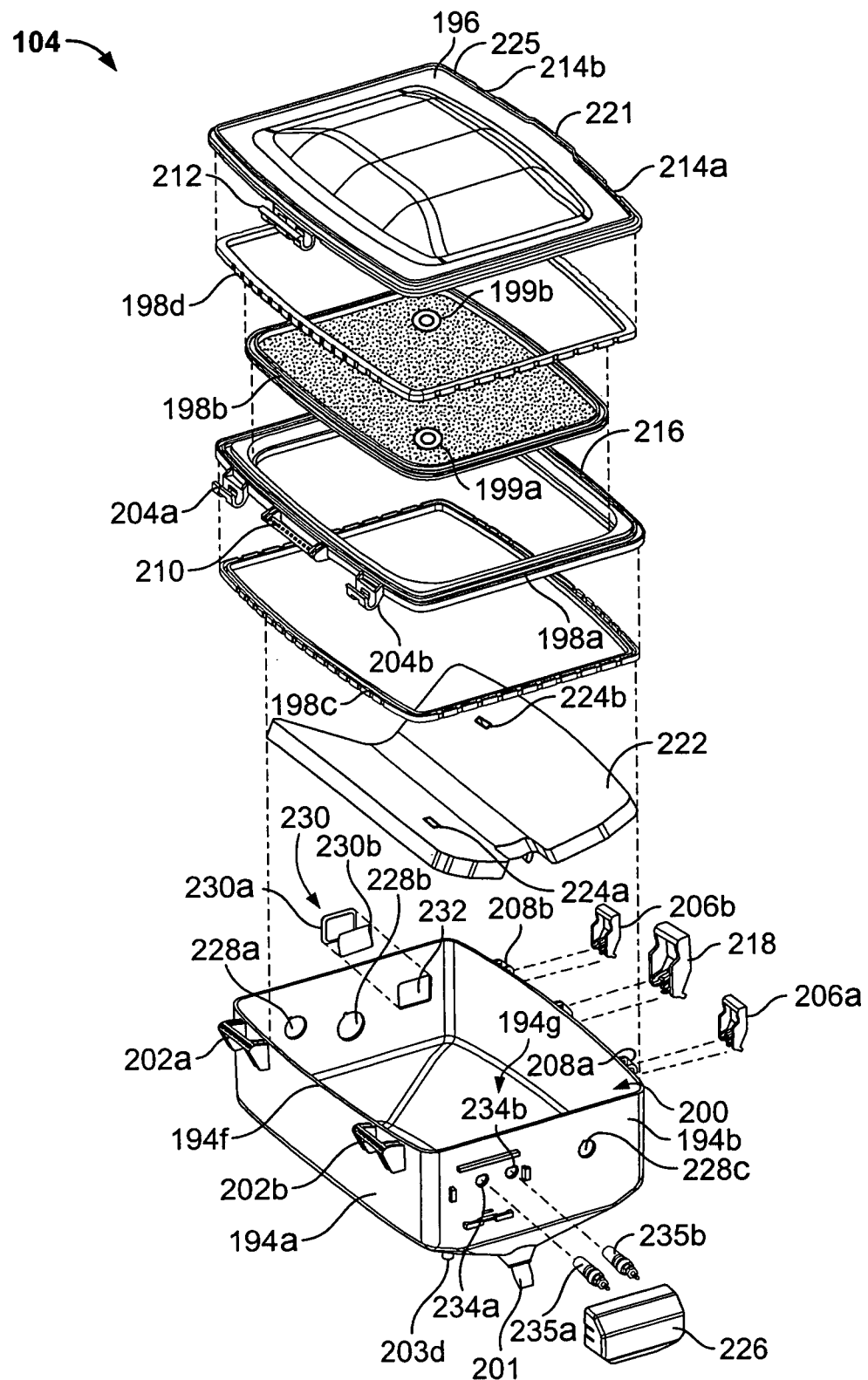
Figure 5F:
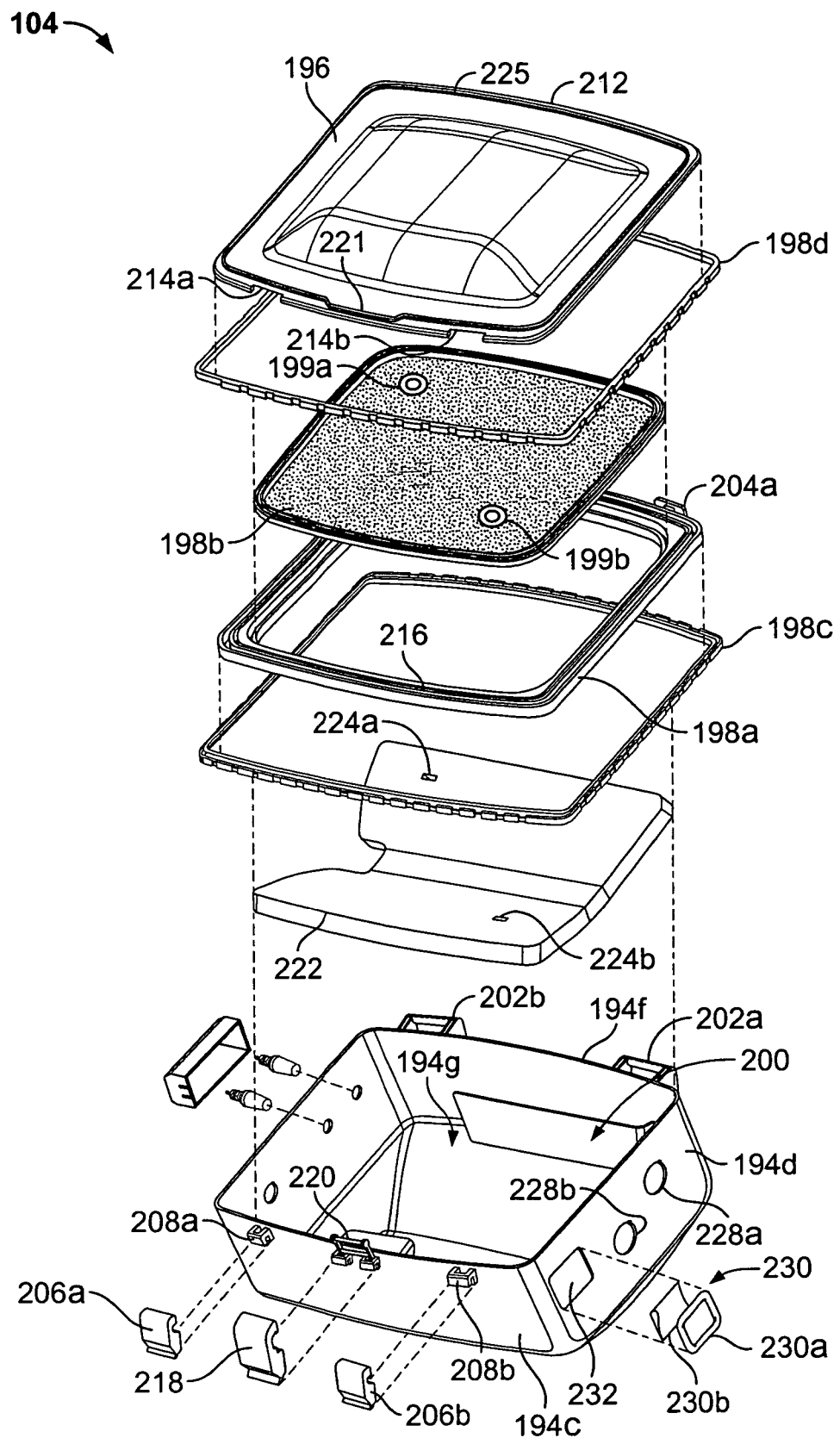

According to one implementation, the housing 194 includes two hinge sections 202a and 202b, and the intermediate lid frame 198a includes two corresponding mating hinge sections 204a and 204b, respectively. The hinge sections 202a and 202b on the housing 194 interfit with the hinge sections 204a and 204b on the intermediate lid frame 198a to enable the intermediate lid 198 to open and close relative to the opening 200 of the housing 194. As shown most clearly in FIGS. 5D and 5F, the organ chamber assembly 104 also includes two latches 206a and 206b for securing the intermediate lid 198 closed over the opening 200. As shown in FIGS. 5E and 5F, the latches 206a and 206b rotatably snap fit onto latch hinge section 208a and 208b, respectively, on the wall 194c of the housing 194. As shown most clearly in FIGS. 5A and 5E, the intermediate lid frame 198a also includes a hinge section 210. The hinge section 210 rotatably snap fits with a mating hinge section 212 on the outer lid 196 to enable the outer lid 196 to open without opening the intermediate lid 198. As shown best in FIGS. 5B, 5D and 5F, the outer lid 196 also includes two cutouts 214a and 214b for enabling the latches 206a and 206b to clamp down on the edge 216 of the intermediate lid frame 198a. As shown in FIGS. 5B, 5D and 5F, the organ chamber assembly 104 also includes a latch 218, which rotatably snap fits onto a hinge part 220 on the wall 194c of the housing 194. In operation, the latch 218 engages a tab 221 on the edge 225 of the outer lid 196 to secure the outer lid 196 closed over the intermediate lid 198.

As shown most clearly in FIGS. 5E and 5F, the intermediate lid also includes two gaskets 198c and 198d. The gasket 198d interfits between a periphery of the intermediate lid frame 198a and a periphery of the outer lid 196 to form a fluid seal between the intermediate lid 198 and the outer lid 196 when the outer lid 196 is closed. The gasket 198c interfits between an outer rim 194f of the housing 194 and the intermediate lid frame 198a to form a fluid seal between the intermediate lid 198 and the periphery 194f of the housing 194 when the intermediate lid 198 is closed.

Optionally, the organ chamber assembly 104 includes a pad 222 or a sac assembly sized and shaped for interfitting over an inner bottom surface 194g of the housing 194. Preferably, the pad 222 is formed from a material resilient enough to cushion the heart 102 from mechanical vibrations and shocks during transport, for example a closed-cell foam. According to one feature, the pad 222 includes a mechanism for adjustably positioning a pair of electrodes, such as the electrodes 142 and 144 of FIG. 1. According to the illustrative embodiment, the mechanism includes two through-apertures 224a and 224b for passing electrical leads from the under side of the pad 222 to corresponding electrodes 142 and 144 on the heart-contacting surface of the pad. Passing the electrical leads through the pad 222 to the electrodes 142 and 144 enables the electrodes 142 and 144 to be adjustably positioned within the pad 222 to accommodate variously sized hearts. In other embodiments, the mechanism may include, without limitation, one or more differently oriented slots, indentations, protrusions, through apertures, partially through apertures, hooks, eyelets, adhesive patches, or the like. In certain embodiments, the pad 222 may be configured with one or more sleeve-like structures that allow an electrode to be inserted within the pad 222, thus providing a membrane-like surface of the pad 222 positioned between the electrode and the heart 102.

In some illustrative embodiments, the pad 222 is configured as a pad assembly, with the assembly including one or more electrodes, such as the electrodes 142 and 144, adjustably located in or on the pad 222. According to one advantage, the pad/electrode configuration of the invention facilitates contact between the electrodes and the heart 102 placed on the pad 222, without temporarily or permanently suturing or otherwise mechanically connecting the electrodes to the heart 102. The weight of the heart 102 itself can also help stabilize the electrodes during transport. According to the illustrative embodiment, the electrodes 142 and 144 include one or more sensors for monitoring one or more electrical signals from the heart and/or defibrillators for providing an electrical signal to the heart. As shown in FIGS. 1 and 5C, the organ chamber assembly 104 includes electrical interface connections 235a-235b, which mount into the apertures 234a-234b, respectively, in the wall 194b of the housing 194. A cover 226 is provided for protecting the electrical interface connections 235a-235b when not being used.

Figure 15:
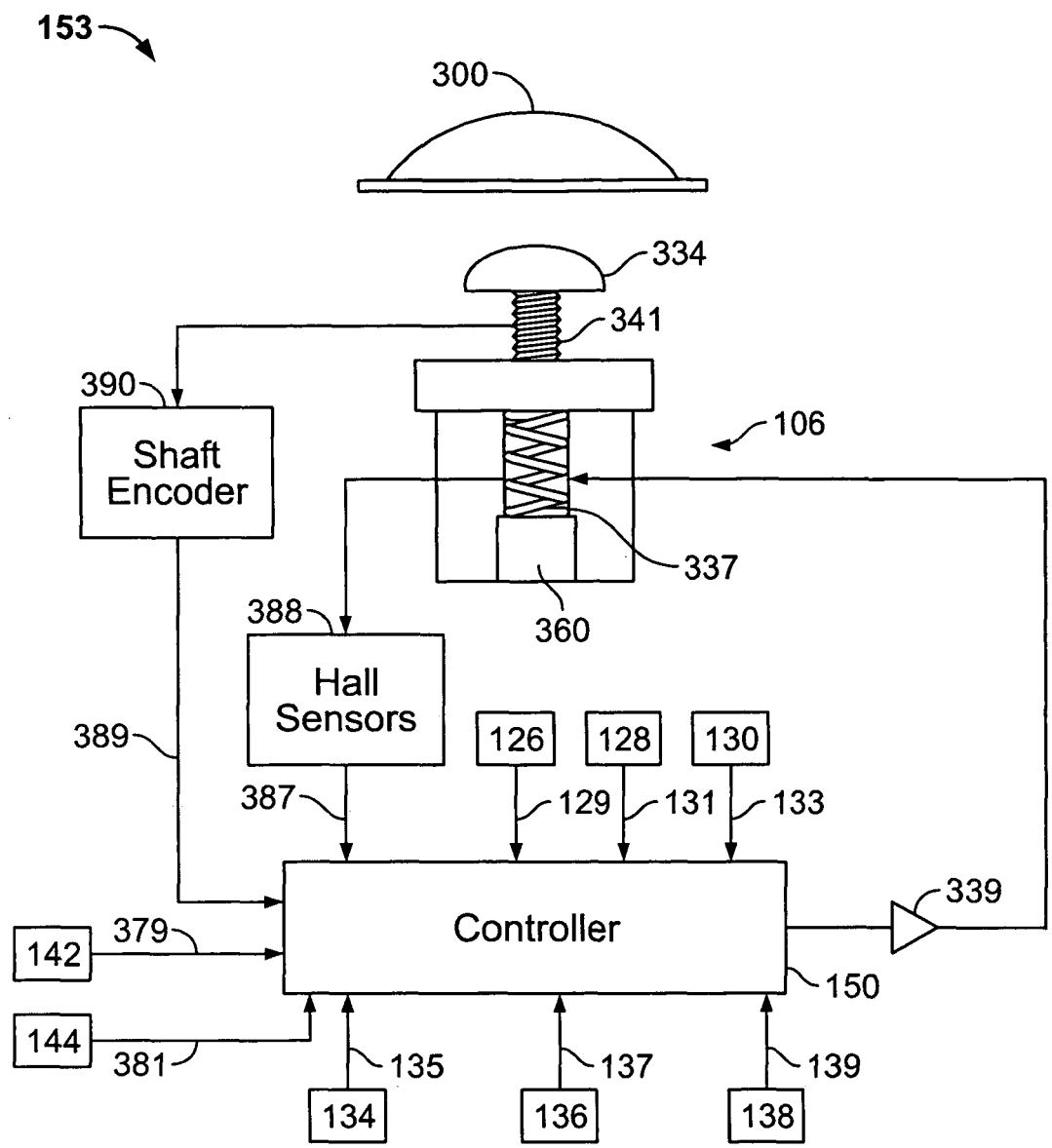
FIG. 15 is a block diagram of an exemplary pumping control subsystem of the type that may be employed for controlling operation of a perfusion fluid pump assembly in the illustrative organ care system of FIG. 1.

As described below in further detail with reference to FIG. 15, the interface connections 235a and 235b couple electrical signals, such as ECG signals, from the electrodes 142 and 144 out of the housing 194, for example, to the controller 194 and/or the operator interface 146. As described in further detail below with reference to FIG. 22A, the interface connections 235a and 235b may also couple to a defibrillation source, which may be either provided by external instrumentation or through circuitry within the system 100, and which can send a defibrillation or pacing signal 143 through electrodes 142 and 144 to the heart 102.

As shown most clearly in FIGS. 5E and 5F, the organ chamber assembly 104 includes a resealable membrane interface 230, which mounts in an interface aperture 232. The interface 230 includes a frame 230a and a resealable polymer membrane 230b mounted in the frame 230a. The membrane 230b may be made of silicone or any other suitable polymer. In operation, the interface 230 is used to provide pacing leads, when necessary, to the heart 102, without having to open the chamber lids 196 and 198. The membrane 230b seals around the pacing leads to maintain a closed environment around the heart 102. The membrane 230b also reseals in response to removing the pacing leads.

As shown in FIGS. 5A and 5B, the organ chamber assembly 104 includes apertures 228a-228c for receiving the aorta interface 162, the pulmonary artery interface 166 and the pulmonary vein interface 170, described above with reference to FIGS. 1-4, and below with reference to FIGS. 24A-28C. As shown in FIG. 5D, the organ chamber assembly 104 also includes a drain 201 for draining perfusion fluid 108 out of the housing 194 back into the reservoir 160, and mounting receptacles 203A-203d for mounting the organ chamber assembly 104 onto the single use module (shown at 634 in FIG. 19A).

Figure 6A:
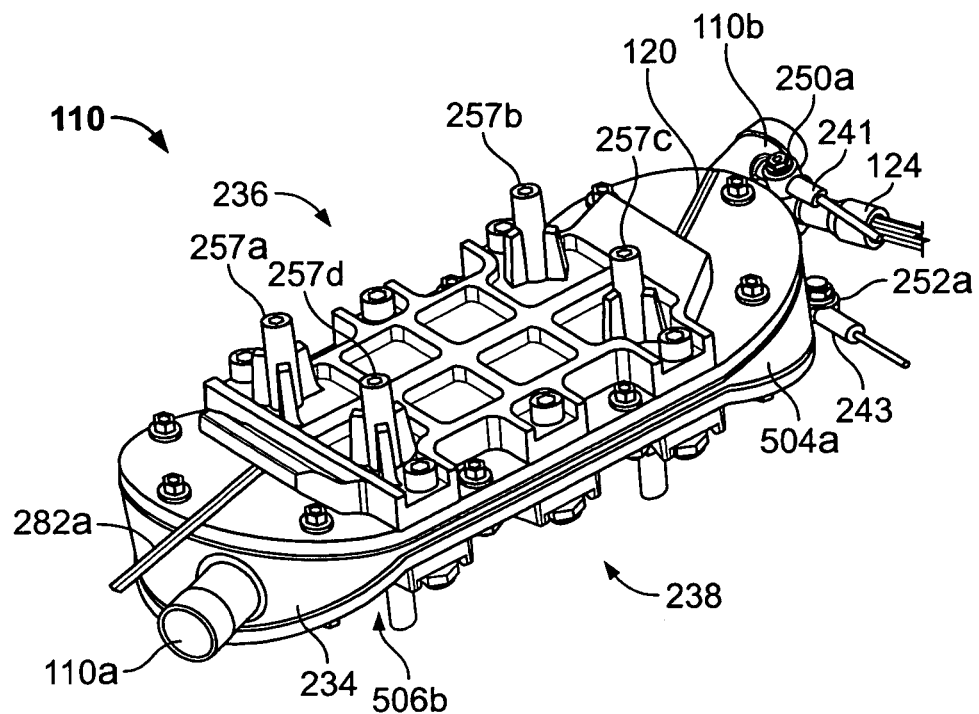
FIGS. 6A-6F show various views of a perfusion heater assembly of the type employed in the organ care system of FIG. 1 according to an illustrative embodiment of the invention.
Figure 6B:
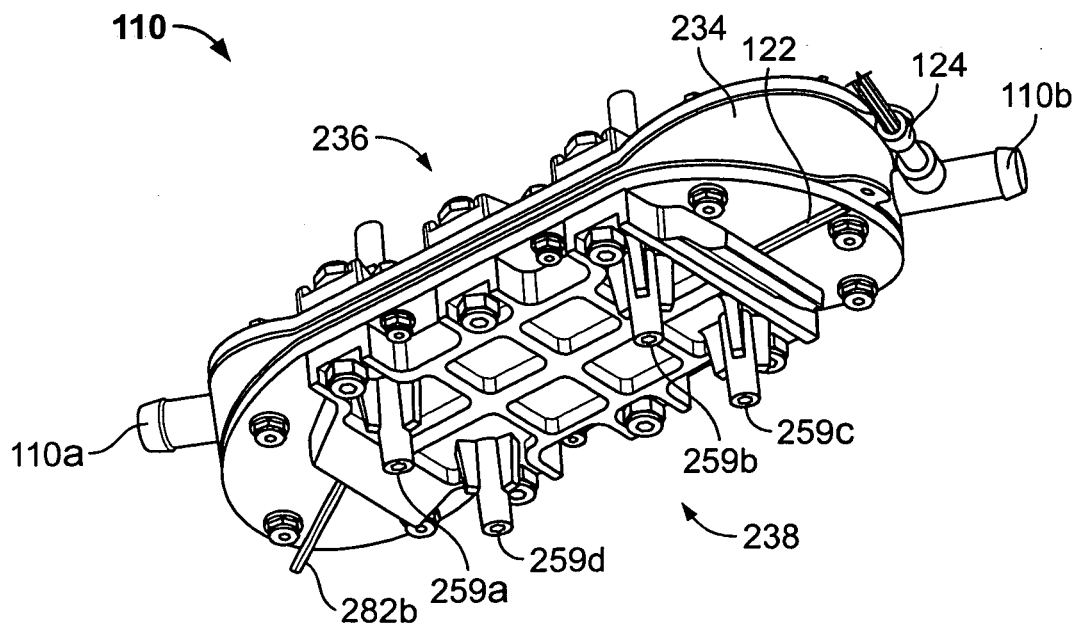
Figure 6C:
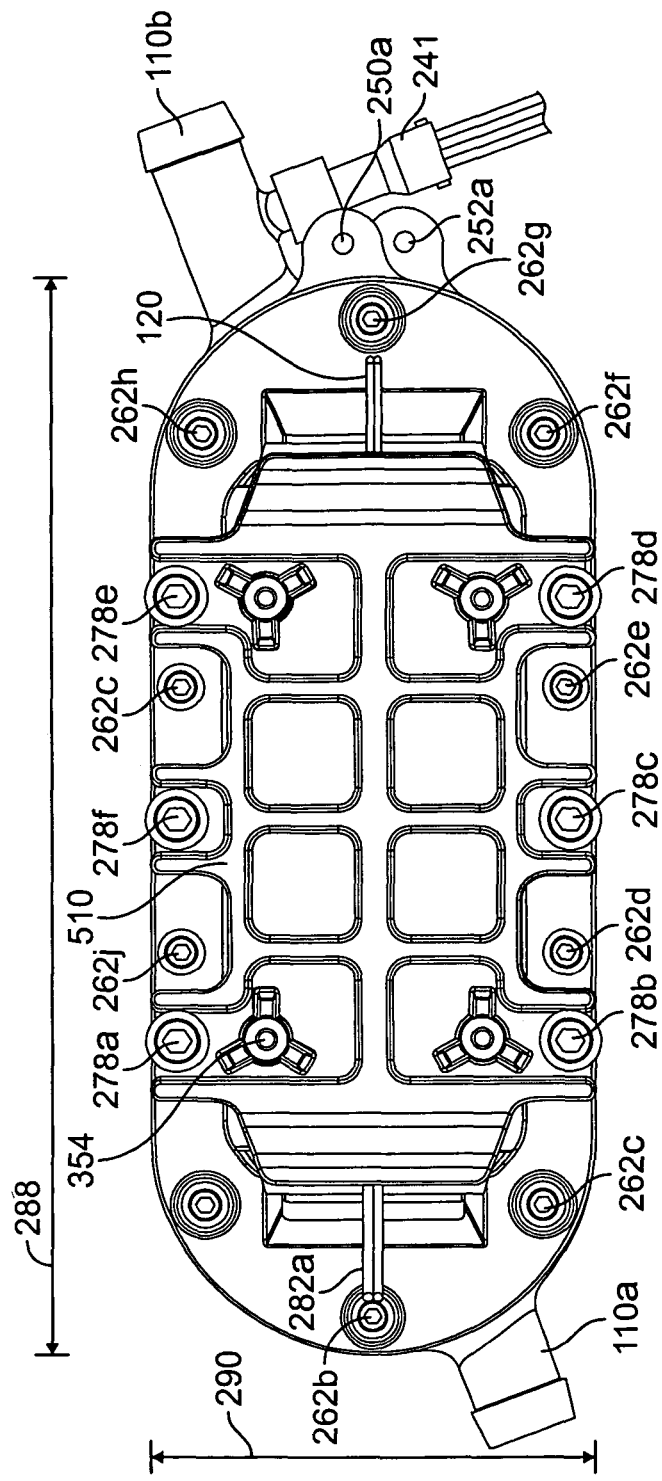

FIGS. 6A-6F depict various views of the perfusion fluid heater assembly 110 of FIG. 1. As shown in FIGS. 6A and 6B, the heater assembly 110 includes a housing 234 having an inlet 110*a* and an outlet 110*b*. As shown in both the longitudinal cross-sectional view of FIG. 6D and the lateral cross-sectional view of FIG. 6E, the heater assembly 110 includes a flow channel 240 extending between the inlet 110*a* and the outlet 110*b*. The heater assembly 110 may be conceptualized as having upper 236 and lower 238 symmetrical halves. Accordingly, only the upper half is shown in an exploded view in FIG. 6F.

Figure 6D:
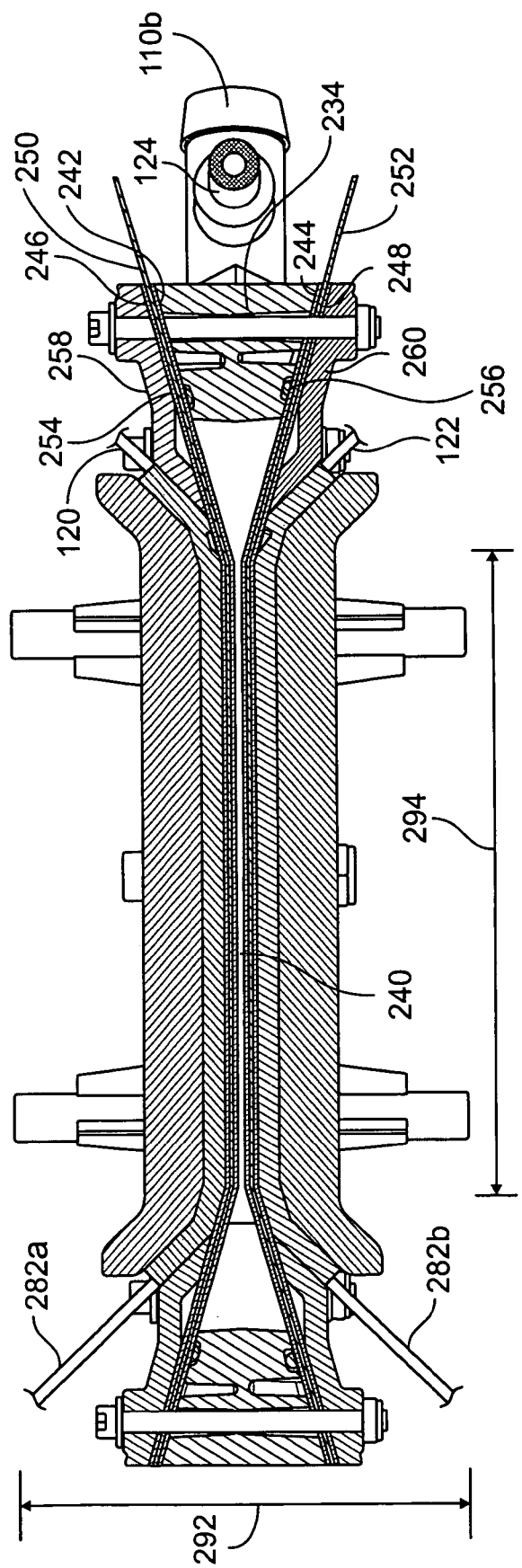
Figure 6E:
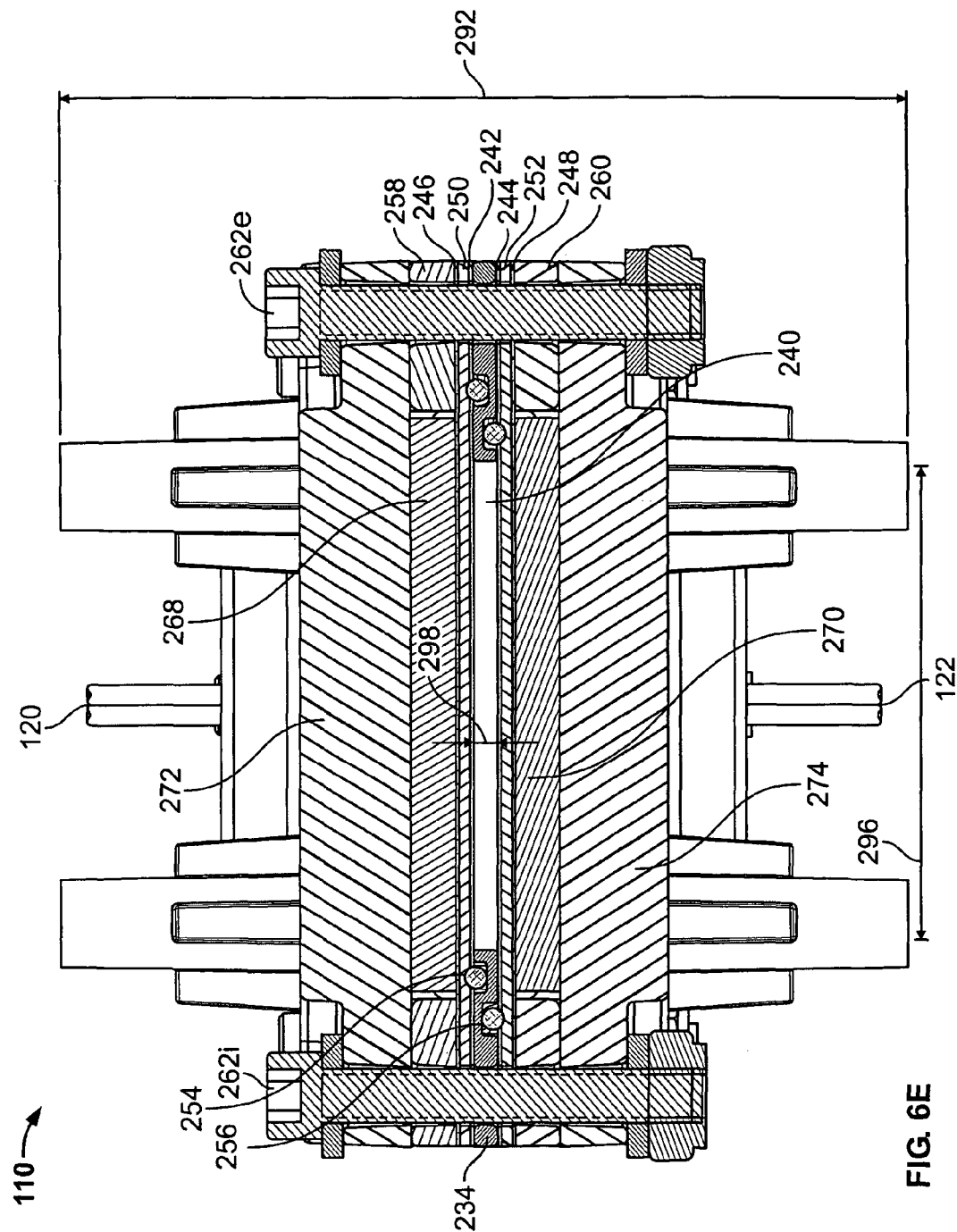
Figure 6F:
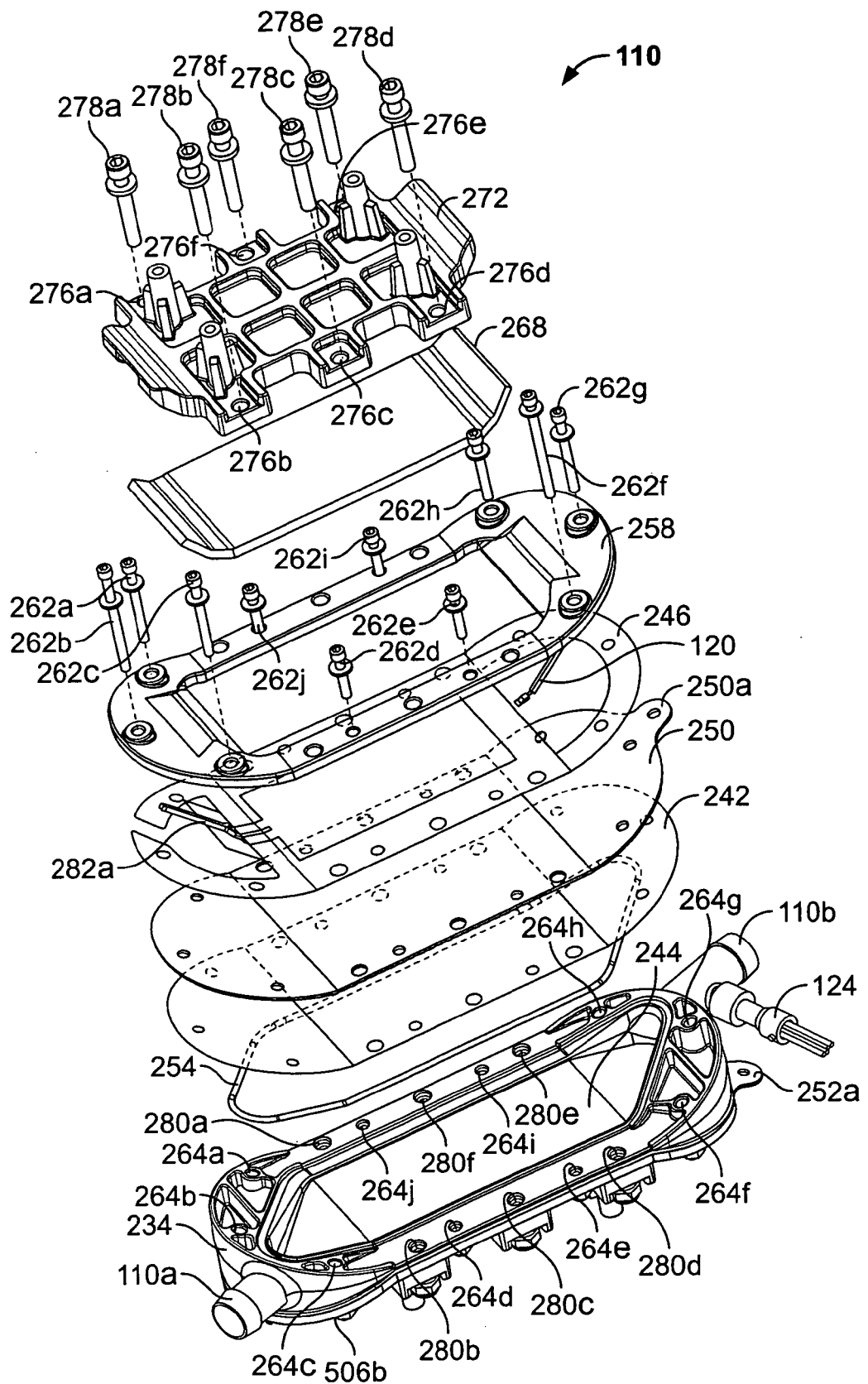

Referring now to FIGS. 6D-6F, the flow channel 240 is formed between first 242 and second 244 flow channel plates. The inlet 110*a* flows the perfusion fluid into the flow channel 240 and the outlet 110*b* flows the perfusion fluid out of the heater 110. The first 242 and second 244 flow channel plates have substantially bioinert perfusion fluid 108 contacting surfaces (which may contain a blood-product in certain embodiments) for providing direct contact with the perfusion fluid flowing through the channel 240. The fluid contacting surfaces may be formed from a treatment or coating on the plate or may be the plate surface itself. The heater assembly 110 includes first and second electric heaters 246 and 248, respectively. The first heater 246 is located adjacent to and couples heat to a first heater plate 250. The first heater plate 250, in turn, couples the heat to the first flow channel plate 242. Similarly, the second heater 248 is located adjacent to and couples heat to a second heater plate 252. The second heater plate 252 couples the heat to the second flow channel plate 244. According to the illustrative embodiment, the first 250 and second 252 heater plates are formed from a material, such as aluminum, that conducts and distributes heat from the first 246 and second 248 electric heaters, respectively, relatively uniformly. The uniform heat distribution of the heater plates 250 and 252 enables the flow channel plates to be formed from a bioinert material, such as titanium, reducing concern regarding its heat distribution characteristic.

Referring particularly to FIGS. 6E and 6F, the heater assembly 110 also includes O-rings 254 and 256 for fluid sealing respective flow channel plates 242 and 244 to the housing 234 to form the flow channel 240.

The heater assembly 110 further includes first assembly brackets 258 and 260. The assembly bracket 258 mounts on the top side 236 of the heater assembly 110 over a periphery of the electric heater 246 to sandwich the heater 246, the heater plate 250 and the flow channel plate 242 between the assembly bracket 258 and the housing 234. The bolts 262*a*-262*j* fit through corresponding through holes in the bracket 258, electric heater 246, heater plate 250 and flow channel plate 242, and thread into corresponding nuts 264*a*-264*j* to affix all of those components to the housing 234. The assembly bracket 260 mounts on the bottom side 238 of the heater assembly 110 in a similar fashion to affix the heater 248, the heater plate 252 and the flow channel plate 244 to the housing 234. A resilient pad 268 interfits within a periphery of the bracket 258. Similarly, a resilient pad 270 interfits within a periphery of the bracket 260. A bracket 272 fits over the pad 268. The bolts 278*a*-278*f* interfit through the holes 276*a*-276*f*, respectively, in the bracket 272 and thread into the nuts 280*a*-280*f* to compress the resilient pad 268 against the heater 246 to provide a more efficient heat transfer to the heater plate 250. The resilient pad 270 is compressed against the heater 248 in a similar fashion by the bracket 274.

As mentioned with respect to FIG. 1, and as also shown in FIG. 6A, the illustrative heater assembly 110 includes temperature sensors 120 and 122 and dual-sensor 124. The dual sensor 124 in practice includes a dual thermistor sensor for providing fault tolerance, measures the temperature of the perfusion fluid 108 exiting the heater assembly 110, and provides these temperatures to the controller 150. As described in further detail below with respect to the heating subsystem 149 of FIG. 13, the signals from the sensors 120, 122 and 124 may be employed in a feedback loop to control drive signals to the first 246 and/or second 248 heaters to control the temperature of the heaters 256 and 248. Additionally, to ensure that heater plates 250 and 252 and, therefore, the blood contacting surfaces 242 and 244 of the heater plates 250 and 252 do not reach a temperature that might damage the perfusion fluid, the illustrative heater assembly 110 also includes temperature sensors/lead wires 120 and 122 for monitoring the temperature of the heaters 246 and 248, respectively, and providing these temperatures to the controller 150. In practice, the sensors attached to sensors/lead wires 120 and 122 are RTD (resistance temperature device) based. As also discussed in further detail with respect to FIG. 13, the signals from the sensors attached to sensors/lead wires 120 and 122 may be employed in a feedback loop to further control the drive signals to the first 246 and/or second 248 heaters to limit the maximum temperature of the heater plates 250 and 252. As a fault protection, there are sensors for each of the heaters 246 and 248, so that if one should fail, the system can continue to operate with the temperature at the other sensor.

Figure 7:
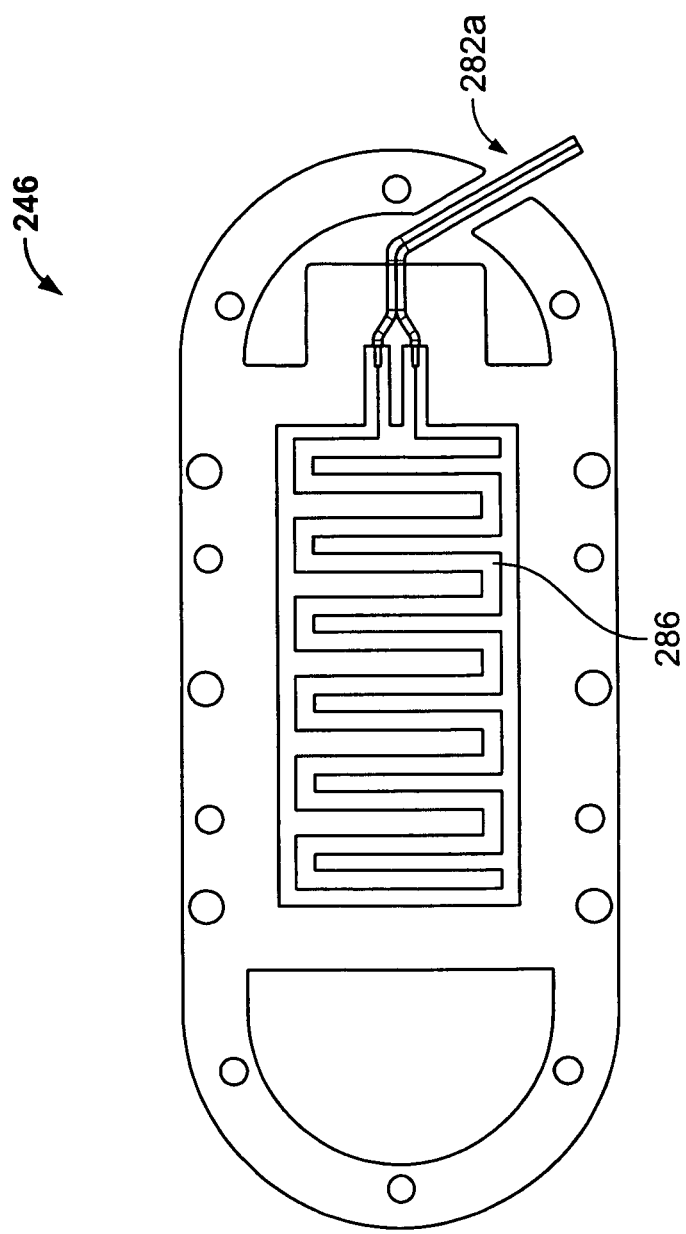
FIG. 7 shows a more detailed view of an exemplary resistive heater element of the type employed in the heater assembly of FIGS. 6A-6F.

As described in further detail below with respect to FIG. 13, the heater 246 of the heater assembly 110 receives from the controller 150 drive signals 281*a* and 281*b* (collectively 281) onto corresponding drive lead 282*a*. Similarly, the heater 248 receives from the controller 150 drive signals 283*a* and 283*b* (collectively 283) onto drive lead 282*b*. The drive signals 281 and 283 control the current to, and thus the heat generated by, the respective heaters 246 and 248. More particularly, as shown in FIG. 7, the drive leads 282*a* includes a high and a low pair, which connect across a resistive element 286 of the heater 246. The greater the current provided through the resistive element 286, the hotter the resistive element 286 gets. The heater 248 operates in the same fashion with regard to the drive lead 282*b*. According to the illustrative embodiments, the element 286 has a resistance of about 5 ohms. However, in other illustrative embodiments, the element may have a resistance of between about 3 ohms and about 10 ohms. As discussed in more detail below with regard to FIGS. 11 and 13, the heaters 246 and 248 may be controlled independently by the processor 150.

According to the illustrative embodiment, the heater assembly 110 housing components are formed from a molded plastic, for example, polycarbonate, and weighs less than about one pound. More particularly, the housing 234 and the brackets 258, 260, 272 and 274 are all formed from a molded plastic, for example, polycarbonate. According to another feature, the heater assembly is a single use disposable assembly.

In operation, the illustrative heater assembly 110 uses between about 1 Watt and about 200 Watts of power, and is sized and shaped to transition perfusion fluid 108 flowing through the channel 240 at a rate of between about 300 ml/min and about 5 L/min from a temperature of less than about 30° C. to a temperature of at least about 37° C. in less than about 30 minutes, less than about 25 minutes, less than about 20 minutes, less than about 15 minutes or even less than about 10 minutes, without substantially causing hemolysis of cells, or denaturing proteins or otherwise damaging any blood product portions of the perfusion fluid.

According to one feature, the heater assembly 110 includes housing components, such as the housing 234 and the brackets 258, 260, 272 and 274, that are formed from a polycarbonate and weighs less than about 5 lb. In other embodiments, the heater assembly may weigh less than about 4 lb, less than about 3 lb, less than about 2 lb, or even less than about 1 lb. In the illustrative embodiment, the heater assembly 110 has a length 288 of about 6.6 inches, not including the inlet 110a and outlet 110b ports, and a width 290 of about 2.7 inches. The heater assembly 110 has a height 292 of about 2.6 inches. The flow channel 240 of the heater assembly 110 has a nominal width 296 of about 1.5 inches, a nominal length 294 of about 3.5 inches, and a nominal height 298 of about 0.070 inches. The height 298 and width 296 are selected to provide for uniform heating of the perfusion fluid 108 as it passes through the channel 240. The height 298 and width 296 are also selected to provide a cross-sectional area within the channel 240 that is approximately equal to the inside cross-sectional area of fluid conduits that carry the perfusion fluid 108 into and/or away from the heater assembly 110. In one configuration, the height 298 and width 296 are selected to provide a cross-sectional area within the channel 240 that is approximately equal to the inside cross-sectional area of the inlet fluid conduit 792 (shown below with reference to FIG. 25C) and/or substantially equal to the inside cross-sectional area of the outlet fluid conduit 794 (shown below with reference to FIG. 24E).

Figure 20A:
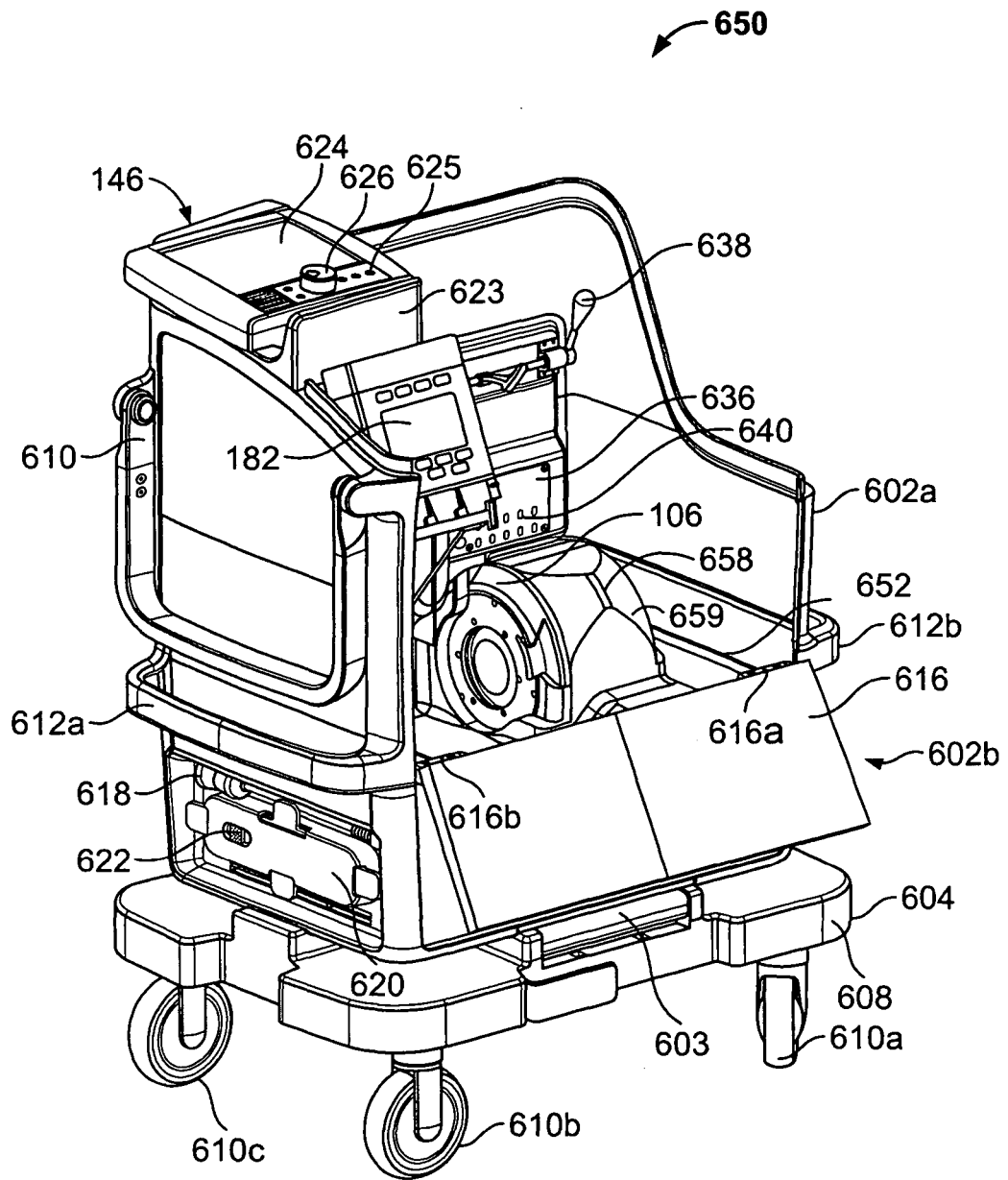
FIG. 20A is a front perspective view of the system of FIGS. 18A and 18B with the top removed, the front panel open and the single use disposable module removed according to an illustrative embodiment of the invention.

Projections 257a-257d and 259a-259d are included in the heater assembly 110 and are used to receive a heat-activated adhesive for binding the heating assembly to the multiple-use unit 650 (referenced in FIG. 20A).

Figure 8A:
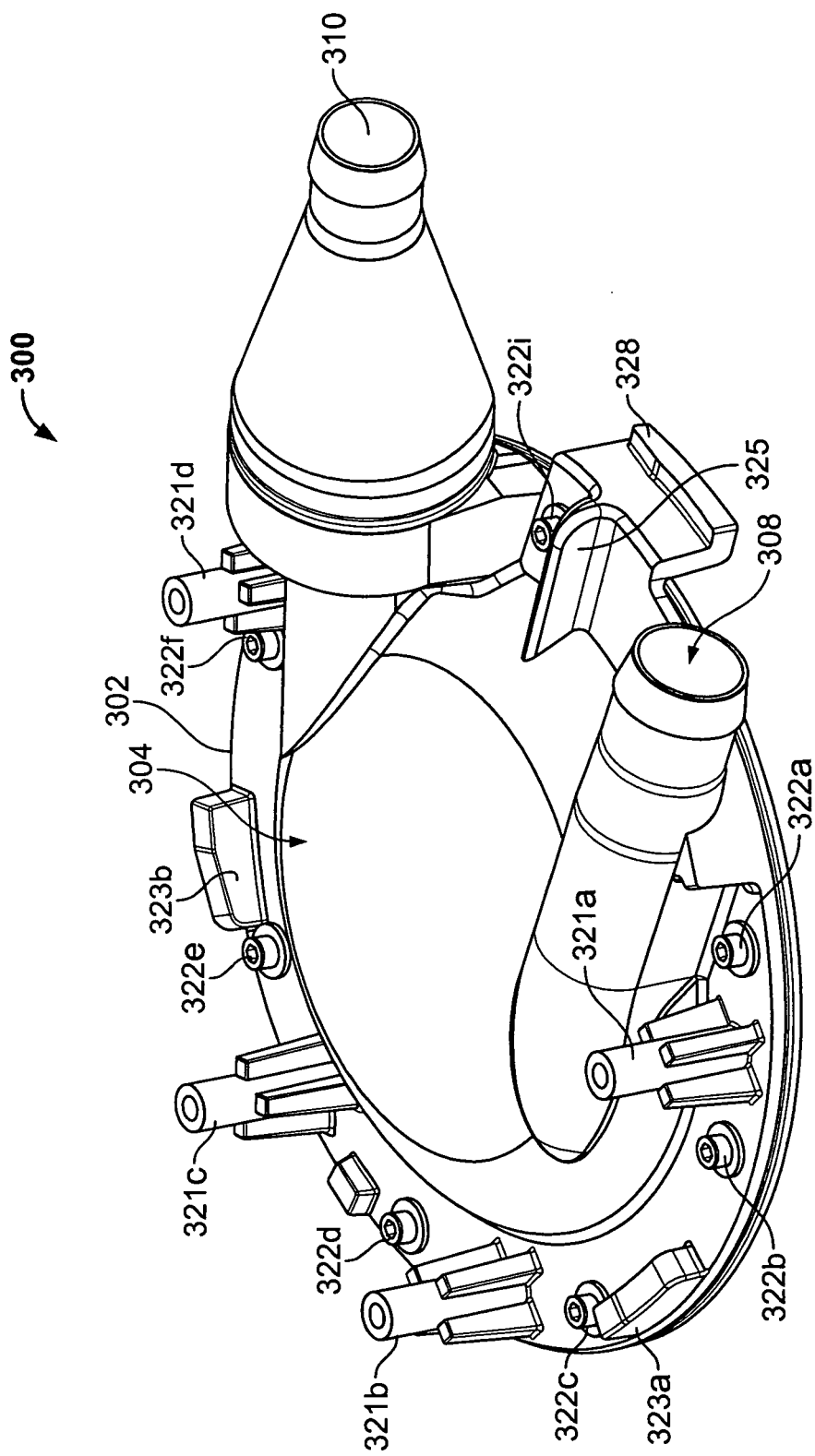
FIGS. 8A-8C show various views of a perfusion fluid pump interface assembly according to an illustrative embodiment of the invention.
Figure 8B:
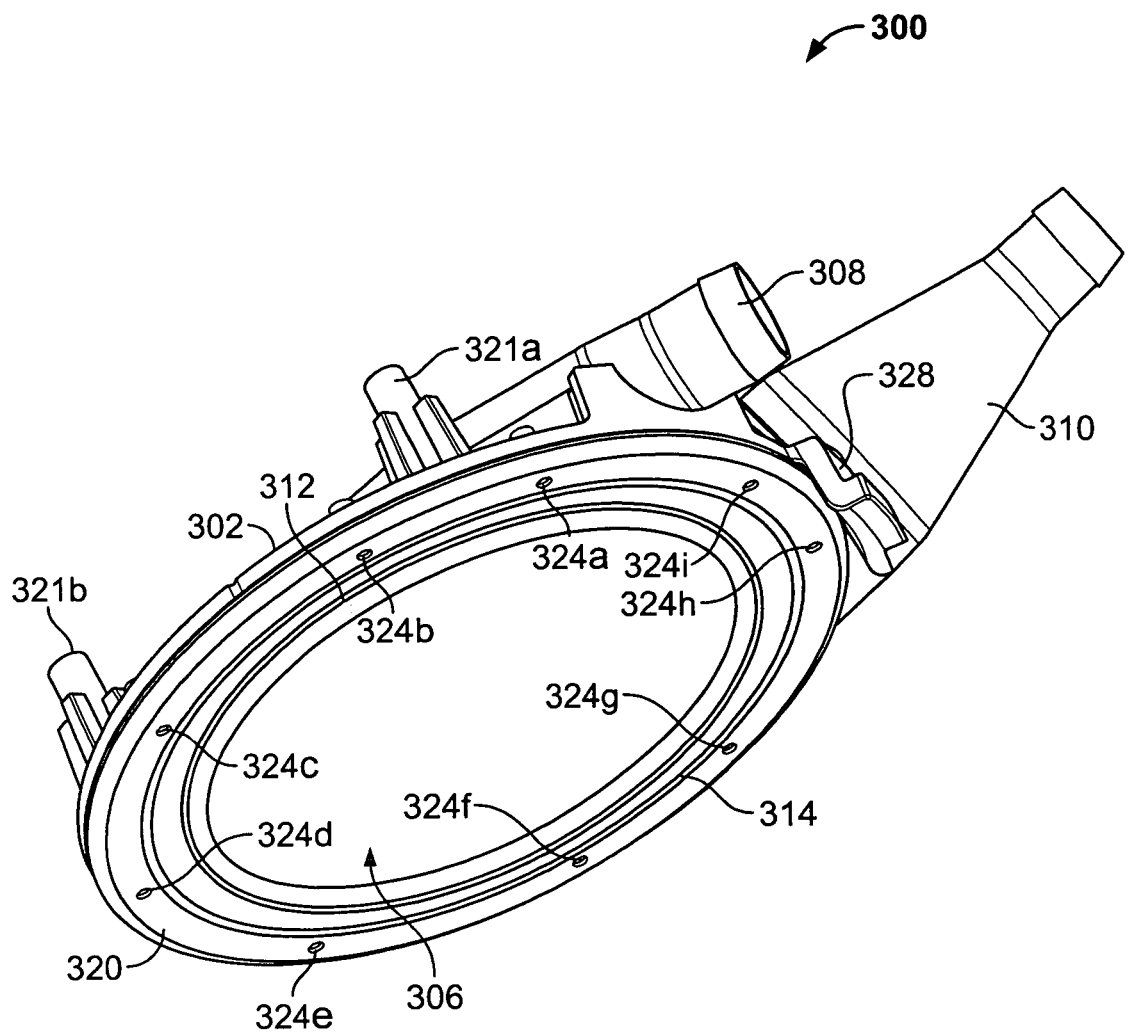
Figure 8C:
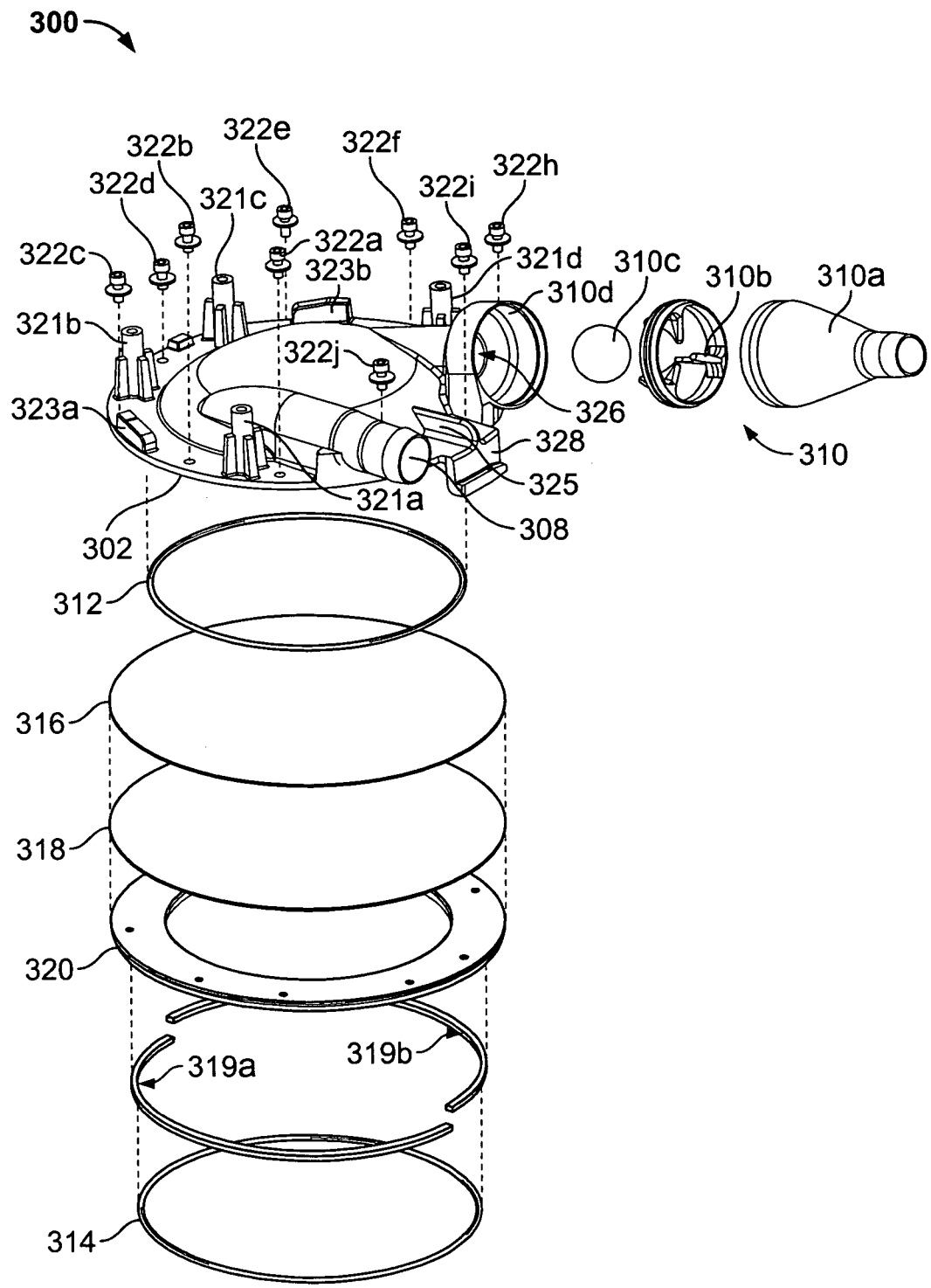
Figure 9:
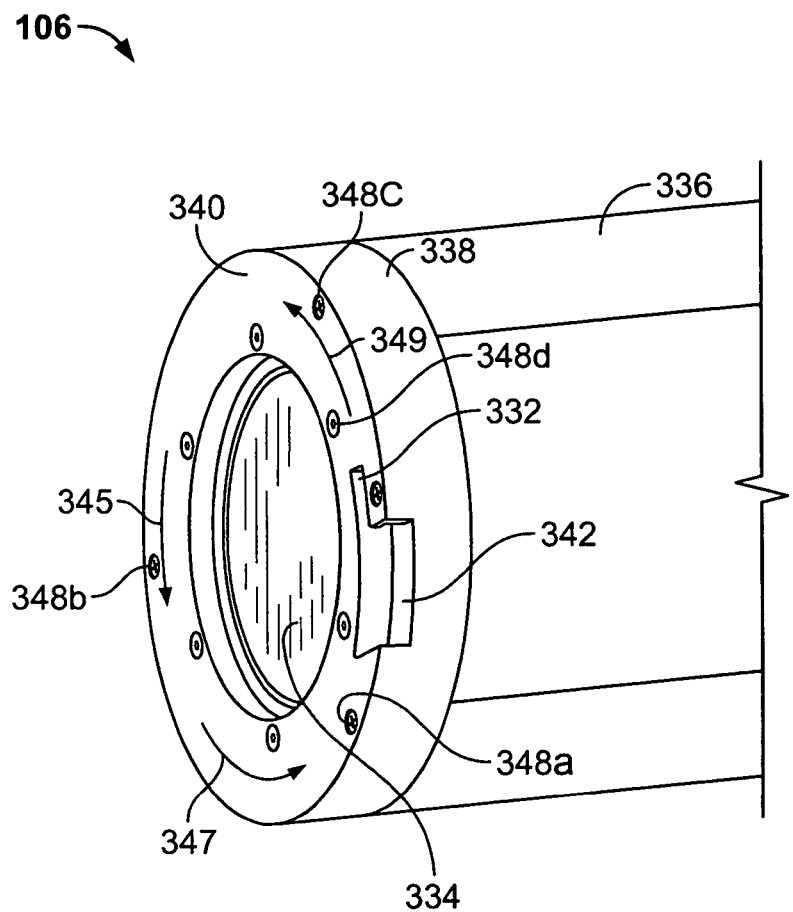
FIG. 9 shows a perspective view of a pump driver side of a perfusion fluid pump assembly of the type depicted in FIG. 1, along with a bracket for mounting with the perfusion pump interface assembly.
Figure 10:
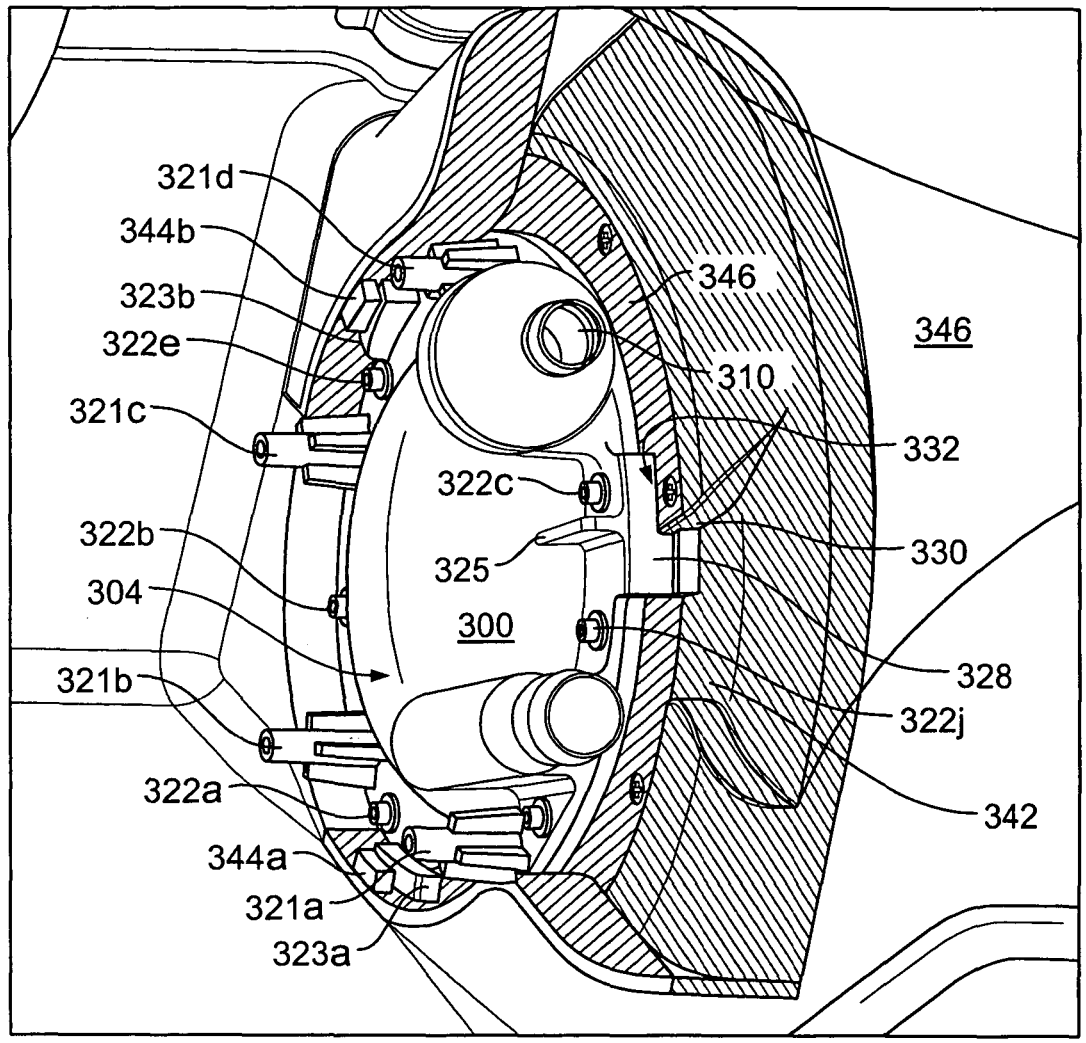
FIG. 10 shows a side view of the perfusion fluid pump interface assembly of FIGS. 8A-8C mated with the pump driver side of the perfusion fluid pump assembly of FIG. 9.

FIGS. 8A-8C show various views of a pump interface assembly 300 according to an illustrative embodiment of the invention. FIG. 9 shows a perspective view of a pump-driver end of the perfusion fluid pump assembly 106 of FIG. 1, and FIG. 10 shows the pump interface assembly 300 mated with the pump-driver end of the perfusion fluid pump assembly 106, according to an illustrative embodiment of the invention. Referring to FIGS. 8A-10, the pump interface assembly 300 includes a housing 302 having an outer side 304 and an inner side 306. The interface assembly 300 includes an inlet 308 and an outlet 310. As shown most clearly in the bottom view of FIG. 8B and the exploded view of FIG. 8C, the pump interface assembly 300 also includes inner 312 and outer 314 O-ring seals, two deformable membranes 316 and 318, a doughnut-shaped bracket 320, and half-rings 319a and 319b that fit between the o-ring 314 and the bracket 320. The half-rings 319a and 319b may be made of foam, plastic, or other suitable material.

The inner O-ring 312 fits into an annular track along a periphery of the inner side 306. The first deformable membrane 316 mounts over the inner O-ring 312 in fluid tight interconnection with the inner side 306 of the housing 302 to form a chamber between an interior side of the first deformable membrane 316 and the inner side 306 of the housing 302. A second deformable membrane 318 fits on top of the first deformable membrane 316 to provide fault tolerance in the event that the first deformable membrane 316 rips or tears. Illustratively, the deformable membranes 316 and 318 are formed from a thin polyurethane film (about 0.002 inches thick). However, any suitable material of any suitable thickness may be employed. Referring to FIGS. 8A and 8B, the bracket 320 mounts over the second deformable membrane 318 and the rings 319a and 319b and affixes to the housing 302 along a periphery of the inner side 306. Threaded fasteners 322a-322i attach the bracket 320 to the housing 302 by way of respective threaded apertures 324a-324i in the bracket 320. As shown in FIG. 8B, the outer O-ring 314 interfits into an annular groove in the bracket 320 for providing fluid tight seal with the pump assembly 106. Prior to inserting O-ring 314 into the annular groove in bracket 320, the half-rings 319a and 319b are placed in the groove. The O-ring 314 is then compressed and positioned within the annular groove in bracket 320. After being positioned within the annular groove, the O-ring 314 expands within the groove to secure itself and the half-rings 319a and 319b in place.

The pump interface assembly 300 also includes heat stake points 321a-321c, which project from its outer side 304. As described in further detail below with reference to FIGS. 21A-21C and 24A-24C, the points 321a-321c receive a hot glue to heat-stake the pump interface assembly 300 to a C-shaped bracket 656 of the single use disposable module chassis 635.

As shown in FIG. 8C, the fluid outlet 310 includes an outlet housing 310a, an outlet fitting 310b, a flow regulator ball 310c and an outlet port 310d. The ball 310c is sized to fit within the outlet port 310d but not to pass through an inner aperture 326 of the outlet 310. The fitting 310b is bonded to the outlet port 310d (e.g., via epoxy or another adhesive) to capture the ball 310c between the inner aperture 326 and the fitting 310b. The outlet housing 310a is similarly bonded onto the fitting 310b.

In operation, the pump interface assembly 300 is aligned to receive a pumping force from a pump driver 334 of the perfusion fluid pump assembly 106 and translate the pumping force to the perfusion fluid 108, thereby circulating the perfusion fluid 108 to the organ chamber assembly 104. According to the illustrative embodiment, the perfusion fluid pump assembly 106 includes a pulsatile pump having a driver 334 (described in further detail below with regard to FIG. 9), which contacts the membrane 318. The fluid inlet 308 draws perfusion fluid 108, for example, from the reservoir 160, and provides the fluid into the chamber formed between the inner membrane 316 and the inner side 306 of the housing 302 in response to the pump driver moving in a direction away from the deformable membranes 316 and 318, thus deforming the membranes 316 and 318 in the same direction. As the pump driver moves away from the deformable membranes 316 and 318, the pressure head of the fluid 108 inside the reservoir 160 causes the perfusion fluid 108 to flow from the reservoir 160 into the pump assembly 106. In this respect, the pump assembly 106, the inlet valve 191 and the reservoir 160 are oriented to provide a gravity feed of perfusion fluid 108 into the pump assembly 106. At the same time, the flow regulator ball 310c is drawn into the aperture 326 to prevent perfusion fluid 108 from also being drawn into the chamber through the outlet 310. It should be noted that the outlet valve 310 and the inlet valve 191 are one way valves in the illustrated embodiment, but in alternative embodiments the valves 310 and/or 191 are two-way valves. In response to the pump driver 334 moving in a direction toward the deformable membranes 316 and 318, the flow regulator ball 310c moves toward the fitting 310b to open the inner aperture 326, which enables the outlet 310 to expel perfusion fluid 108 out of the chamber formed between the inner side 306 of the housing 302 and the inner side of the deformable membrane 316. A separate one-way inlet valve 191, shown between the reservoir 160 and the inlet 308 in FIG. 1, stops any perfusion fluid from being expelled out of the inlet 308 and flowing back into the reservoir 160.

As discussed in further detail below with respect to FIGS. 18A-27B, in certain embodiments the organ care system 100 mechanically divides into a disposable single-use unit (shown at 634 in FIGS. 19A-19C and 24A-25C) and a non-disposable multi-use unit (shown at 650 in FIG. 20A). In such embodiments, the pump assembly 106 rigidly mounts to the multiple use module 650, and the pump interface assembly 300 rigidly mounts to the disposable single use module 634. The pump assembly 106 and the pump interface assembly 300 have corresponding interlocking connections, which mate together to form a fluid tight seal between the two assemblies 106 and 300.

More particularly, as shown in the perspective view of FIG. 9, the perfusion fluid pump assembly 106 includes a pump driver housing 338 having a top surface 340, and a pump driver 334 housed within a cylinder 336 of the housing 338 The pump driver housing 338 also includes a docking port 342, which includes a slot 332 sized and shaped for mating with a flange 328 projecting from the pump interface assembly 300. As shown in FIG. 10, the top surface 340 of the pump driver housing 338 mounts to a bracket 346 on the non-disposable multiple use module unit 650. The bracket 346 includes features 344a and 344b for abutting the tapered projections 323a and 323b, respectively, of the pump interface assembly 300. The bracket 346 also includes a cutout 330 sized and shaped for aligning with the docking port 342 and the slot 332 on the pump driver housing 338.

Operationally, the seal between the pump interface assembly 300 and the fluid pump assembly 106 is formed in two steps, illustrated with reference to FIGS. 9 and 10. In a first step, the flange 328 is positioned within the docking port 342, while the tapered projections 323a and 323b are positioned on the clockwise side next to corresponding features 344a and 344b on the bracket 346. In a second step, as shown by the arrows 345, 347 and 349 in FIG. 9, the pump interface assembly 300 and the fluid pump assembly 106 are rotated in opposite directions (e.g., rotating the pump interface assembly 300 in a counter clockwise direction while holding the pump assembly 106 fixed) to slide the flange 328 into the slot 332 of the docking port 342. At the same time, the tapered projections 323a and 323b slide under the bracket features 344a and 344b, respectively, engaging inner surfaces of the bracket features 344a and 344b with tapered outer surfaces of the tapered projections 323a and 323b to draw the inner side 306 of the pump interface assembly 300 toward the pump driver 334 and to interlock the flange 328 with the docking ports 342, and the tapered projections 323a and 323b with the bracket features 344a and 344b to form the fluid tight seal between the two assemblies 300 and 106.

Figure 11:
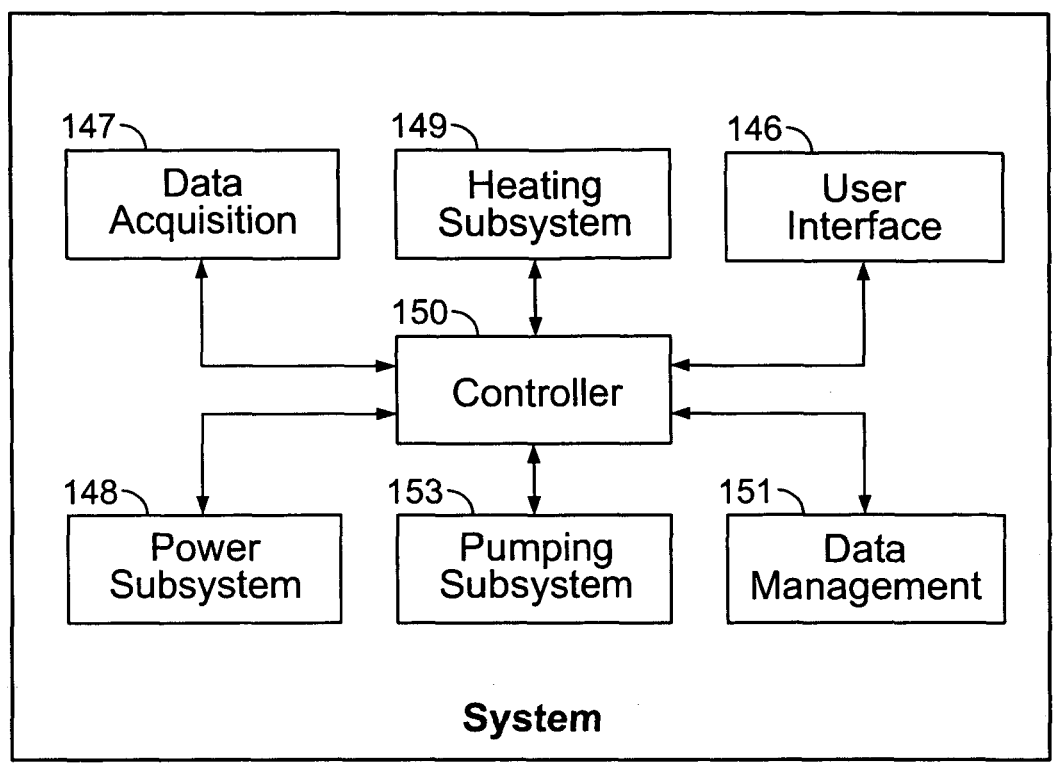
FIG. 11 depicts a block diagram of an illustrative control scheme for controlling operation of the organ care system of FIG. 1.
Figure 12:
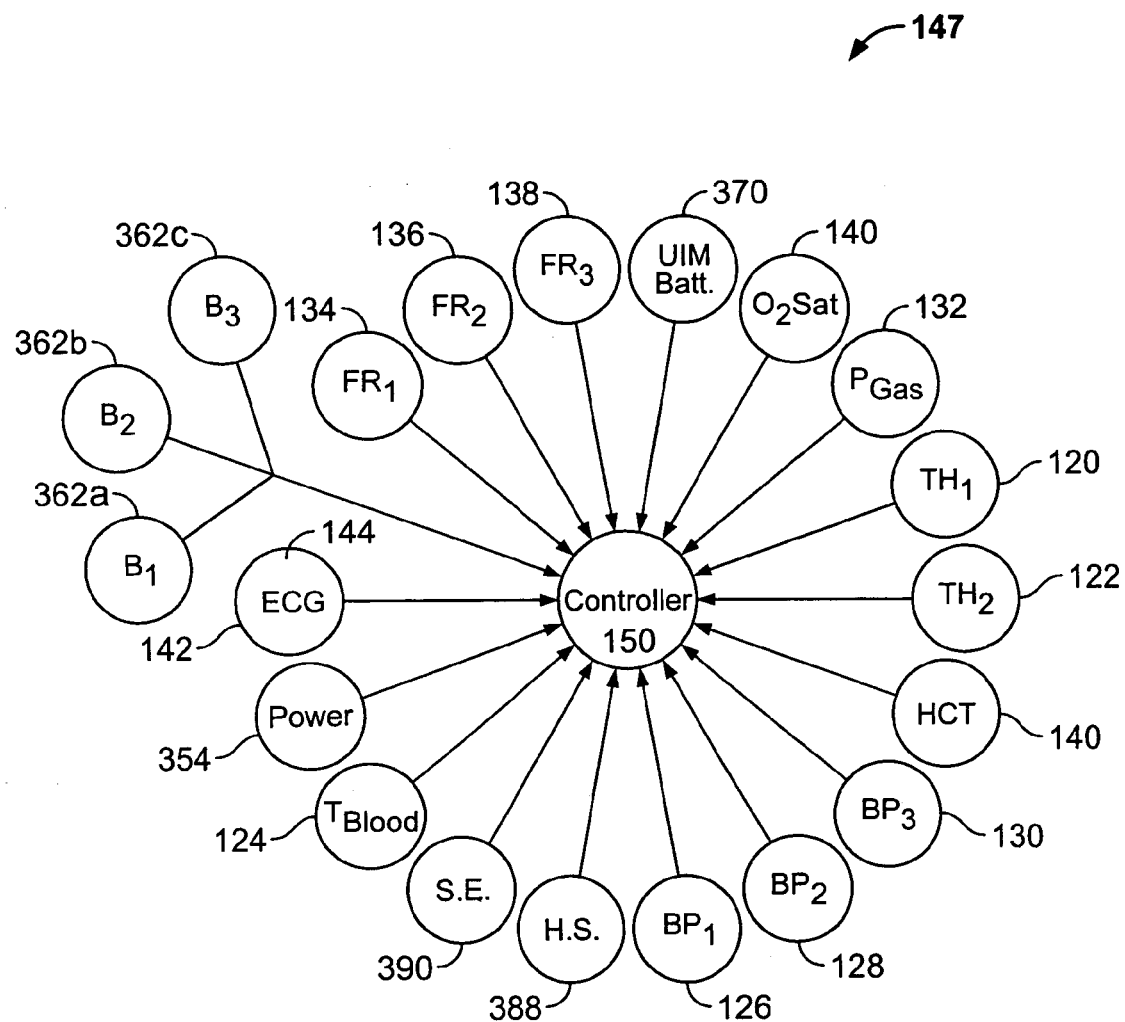
FIG. 12 is a block diagram of an exemplary data acquisition subsystem of the type that may be employed with an the illustrative organ care system of FIG. 1.

Having described the illustrative organ care system 100 from a system, operational and component point of view, illustrative control systems and methods for achieving operation of the system 100 are next discussed. More particularly, FIG. 11 depicts a block diagram of an illustrative control scheme for the system 100. As described above with reference to FIG. 1, the system 100 includes a controller 150 for controlling operation of the system 100. As shown, the controller 150 connects interoperationally with the following six subsystems: an operator interface 146 for assisting an operator in monitoring and controlling the system 100 and in monitoring the condition of the heart 102; a data acquisition subsystem 147 having various sensors for obtaining data relating to the heart 102 and to the system 100, and for conveying the data to the controller 150; a power management subsystem 148 for providing fault tolerant power to the system 100; a heating subsystem 149 for providing controlled energy to the heater 110 for warming the perfusion fluid 108; a data management subsystem 151 for storing and maintaining data relating to operation of the system 100 and with respect to the heart 102; and a pumping subsystem 153 for controlling the pumping of the perfusion fluid 108 through the system 100. It should be noted that although the system 100 is described conceptually with reference to a single controller 150, the control of the system 100 may be distributed in a plurality of controllers or processors. For example, any or all of the described subsystems may include a dedicated processor/controller. Optionally, the dedicated processors/controllers of the various subsystems may communicate with and via a central controller/processor.

FIGS. 12-17J illustrate the interoperation of the various subsystems of FIG. 11. Referring first to the block diagram of FIG. 12, the data acquisition subsystem 147 includes sensors for obtaining information pertaining to how the system 100 and the heart 102 is functioning, and for communicating that information to the controller 150 for processing and use by the system 100. As described with respect to FIG. 1, the sensors of subsystem 147 include, without limitation: temperature sensors 120, 122 and 124; pressure sensors 126, 128, and 130; flow rate sensors 134, 136 and 138; the oxygenation/hematocrit sensor 140; and electrodes 142 and 144. The data acquisition subsystem 147 also includes: a set of Hall sensors 388 and a shaft encoder 390 from the perfusion pump assembly 106; battery sensors 362a-362c for sensing whether the batteries 352a-352c, respectively, are sufficiently charged; an external power available sensor 354 for sensing whether external AC power is available; an operator interface module battery sensor 370 for sensing a state of charge of the operator interface module battery; and a gas pressure sensor 132 for sensing gas flow from the gas flow chamber 176. How the system 100 uses the information from the data acquisition subsystem 147 will now be described with regard to the heating 149, power management 148, pumping 153, data management 151, and operator interface 146 subsystems, shown in further detail in FIGS. 13-17J, respectively.

Figure 13:
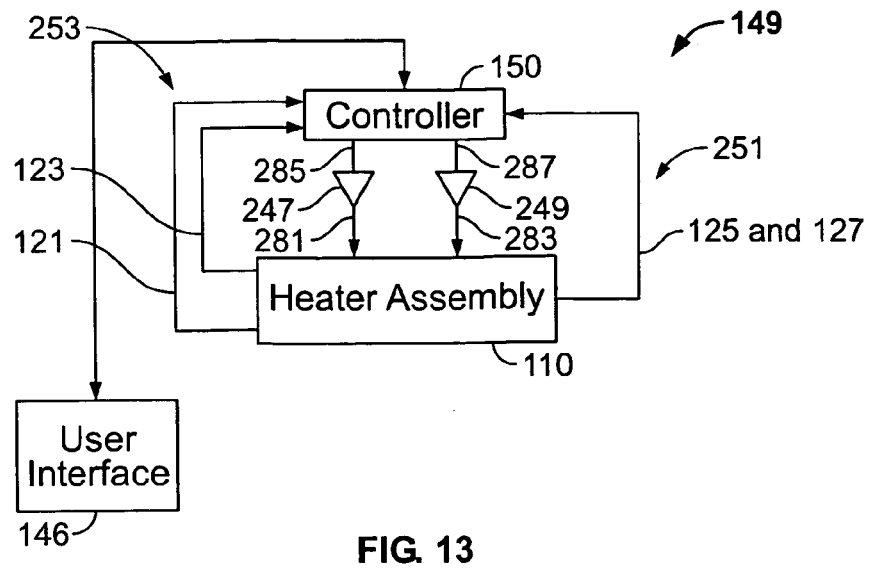
FIG. 13 is a block diagram of an exemplary heating control subsystem of the type that may be employed for maintaining perfusion fluid temperature in the illustrative organ care system of FIG. 1.

The heating subsystem 149 is depicted in the block diagram of FIG. 13. With continued reference also to FIG. 1, the heating subsystem 149 controls the temperature of the perfusion fluid 108 within the system 100 through a dual feedback loop approach. In the first loop 251 (the perfusion fluid temperature loop), the perfusion fluid temperature thermistor sensor 124 provides two (fault tolerant) signals 125 and 127 to the controller 150. The signals 125 and 127 are indicative of the temperature of the perfusion fluid 108 as it exits the heater assembly 110. The controller 150 regulates the drive signals 285 and 287 to the drivers 247 and 249, respectively. The drivers 247 and 249 convert corresponding digital level signals 285 and 287 from the controller 150 to heater drive signals 281 and 283, respectively, having sufficient current levels to drive the first 246 and second 248 heaters to heat the perfusion fluid 108 to within an operator selected temperature range. In response to the controller 150 detecting that the perfusion fluid temperatures 125 and 127 are below the operator-selected temperature range, it sets the drive signals 281 and 283 to the first 246 and second 248 heaters, respectively, to a sufficient level to continue to heat the perfusion fluid 108. Conversely, in response to the controller 150 detecting that the perfusion fluid temperatures 125 and 127 are above the operator-selected temperature range, it decreases the drive signals 281 and 283 to the first 246 and second 248 heaters, respectively. In response to detecting that the temperature of the perfusion fluid 108 is within the operator-selected temperature range, the controller 150 maintains the drive signals 281 and 283 at constant or substantially constant levels.

Preferably, the controller 150 varies the drive signals 281 and 283 in substantially the same manner. However, this need not be the case. For example, each heater 246 and 248 may respond differently to a particular current or voltage level drive signal. In such a case, the controller 150 may drive each heater 246 and 248 at a slightly different level to obtain the same temperature from each. According to one feature, the heaters 246 and 248 each have an associated calibration factor, which the controller 150 stores and employs when determining the level of a particular drive signal to provide to a particular heater to achieve a particular temperature result. In certain configurations, the controller 150 sets one of the thermistors in dual sensor 124 as the default thermistor, and will use the temperature reading from the default thermistor in instances where the thermistors give two different temperature readings. In certain configurations, where the temperature readings are within a pre-defined range, the controller 150 uses the higher of the two readings. The drivers 247 and 249 apply the heater drive signals 281 and 283 to corresponding drive leads 282a and 282b on the heater assembly 110.

In the second loop 253 (the heater temperature loop), the heater temperature sensors 120 and 122 provide signals 121 and 123, indicative of the temperatures of the heaters 246 and 248, respectively, to the controller 150. According to the illustrated embodiment, a temperature ceiling is established for the heaters 246 and 248 (e.g., by default or by operator selection), above which the temperatures of the heaters 246 and 248 are not allowed to rise. As the temperatures of the heaters 246 and 248 rise and approach the temperature ceiling, the sensors 121 and 123 indicate the same to the controller 150, which then lowers the drive signals 281 and 283 to the heaters 246 and 248 to reduce or stop the supply of power to the heaters 246 and 248. Thus, while a low temperature signal 125 or 127 from the perfusion fluid temperature sensor 124 can cause the controller 150 to increase power to the heaters 246 and 248, the heater temperature sensors 120 and 122 ensure that the heaters 246 and 248 are not driven to a degree that would cause their respective heater plates 250 and 252 to become hot enough to damage the perfusion fluid 108. According to various illustrative embodiments, the controller 150 is set to maintain the perfusion fluid temperature at between about 32° C. and about 37° C., or between about 34° C. and about 36° C. According to a further illustrative embodiment, the controller 150 is set to limit the maximum temperature of the heater plates 250 and 252 to less than about 38° C., 39° C., 40° C., 41° C., or 42° C.

As can be seen, the second loop 253 is configured to override the first loop 251, if necessary, such that temperature readings from temperature sensors 120 and 122 indicating that the heaters 246 and 248 are approaching the maximum allowable temperature override the effect of any low temperature signal from the perfusion fluid temperature sensor 124. In this respect, the subsystem 149 ensures that the temperature of the heater plates 250 and 252 do not rise above the maximum allowable temperature, even if the temperature of the perfusion fluid 108 has not reached the operator-selected temperature value. This override feature is particularly important during failure situations. For example, if the perfusion fluid temperature sensors 124 both fail, the second loop 253 stops the heater assembly 110 from overheating and damaging the perfusion fluid 108 by switching control exclusively to the heater temperature sensors 120 and 122 and dropping the temperature set point to a lower value. According to one feature, the controller 150 takes into account two time constants assigned to the delays associated with the temperature measurements from the heaters 246 and 248 and perfusion fluid 108 to optimize the dynamic response of the temperature controls.

Figure 14:
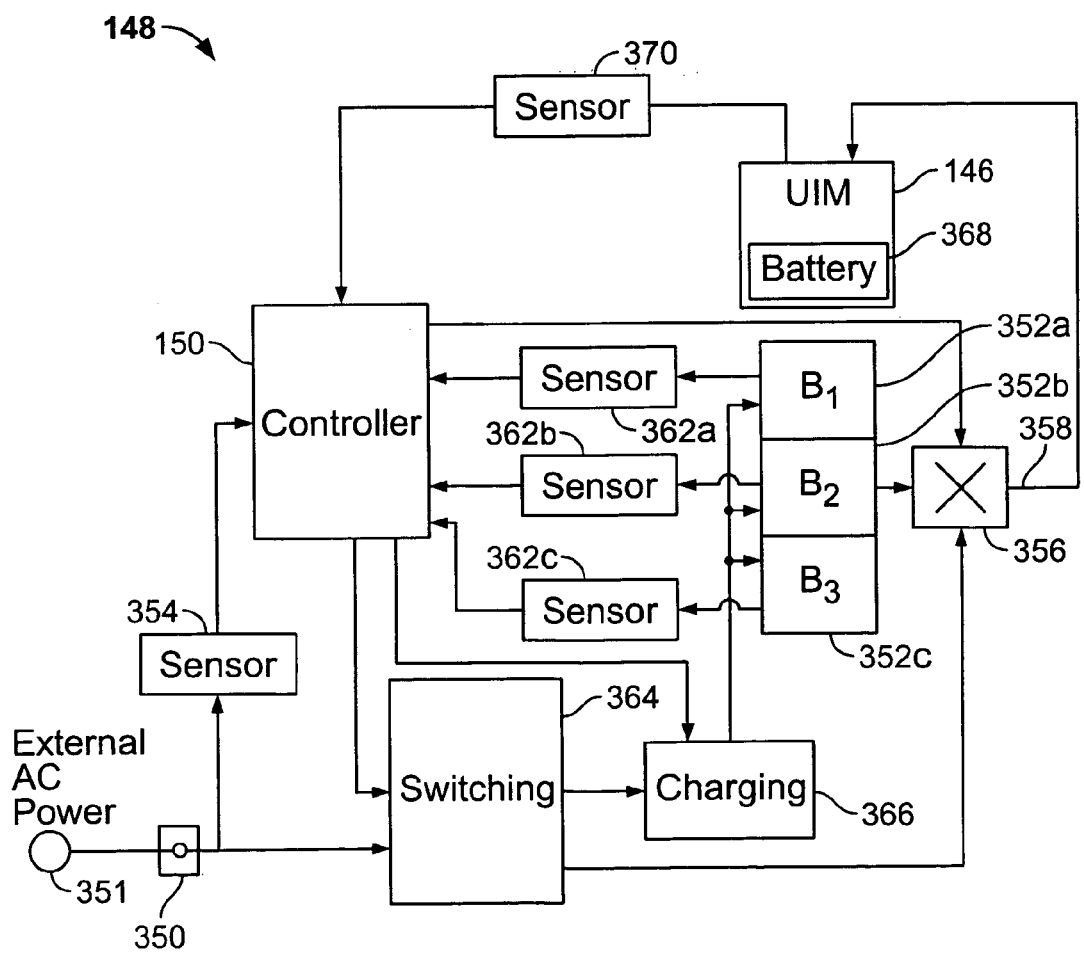
FIG. 14 is a block diagram of an exemplary power management subsystem of the type that may be employed in the illustrative organ care system of FIG. 1.

FIG. 14 depicts a block diagram of the power management system 148 for providing fault tolerant power to the system 100. As shown, the system 100 may be powered by one of four sources—by an external AC source 351 (e.g., 60 Hz, 120 VAC in North America or 50 Hz, 230 VAC in Europe) or by any of three independent batteries 352a-352c. The controller 150 receives data from an AC line voltage availability sensor 354, which indicates whether the AC voltage 351 is available for use by the system 100. In response to the controller 150 detecting that the AC voltage 351 is not available, the controller 150 signals the power switching circuitry 356 to provide system power high 358 from one of the batteries 352a-352c. The controller 150 determines from the battery charge sensors 362a-362c which of the available batteries 352a-352c is most fully charged, and then switches that battery into operation by way of the switching network 356.

Alternatively, in response to the controller 150 detecting that the external AC voltage 351 is available, it determines whether to use the available AC voltage 351 (e.g., subsequent to rectification) for providing system power 358 and for providing power to the user interface module 146, for charging one or more of the batteries 352a-352c, and/or for charging the internal battery 368 of user interface module 146, which also has its own internal charger and charging controller. To use the available AC voltage 351, the controller 150 draws the AC voltage 351 into the power supply 350 by signaling through the switching system 364. The power supply 350 receives the AC voltage 351 and converts it to a DC current for providing power to the system 100. The power supply 350 is universal and can handle any line frequencies or line voltages commonly used throughout the world. According to the illustrative embodiment, in response to a low battery indication from one or more of the battery sensors 362a-362c, the controller 150 also directs power via the switching network 364 and the charging circuit 366 to the appropriate battery. In response to the controller 150 receiving a low battery signal from the sensor 370, it also or alternatively directs a charging voltage 367 to the user interface battery 368. According to another feature, the power management subsystem 148 selects batteries to power the system 100 in order of least-charged first, preserving the most charged batteries. If the battery that is currently being used to power the system 100 is removed by the user, the power management subsystem 148 automatically switches over to the next least-charged battery to continue powering the system 100.

According to another feature, the power management subsystem 148 also employs a lock-out mechanism to prevent more than one of the batteries 352a-352c from being removed from the system 100 at a given time. If one battery is removed, the other two are mechanically locked into position within the system 100. In this respect, the system 148 provides a level of fault tolerance to help ensure that a source of power 358 is always available to the system 100.

Figure 16:
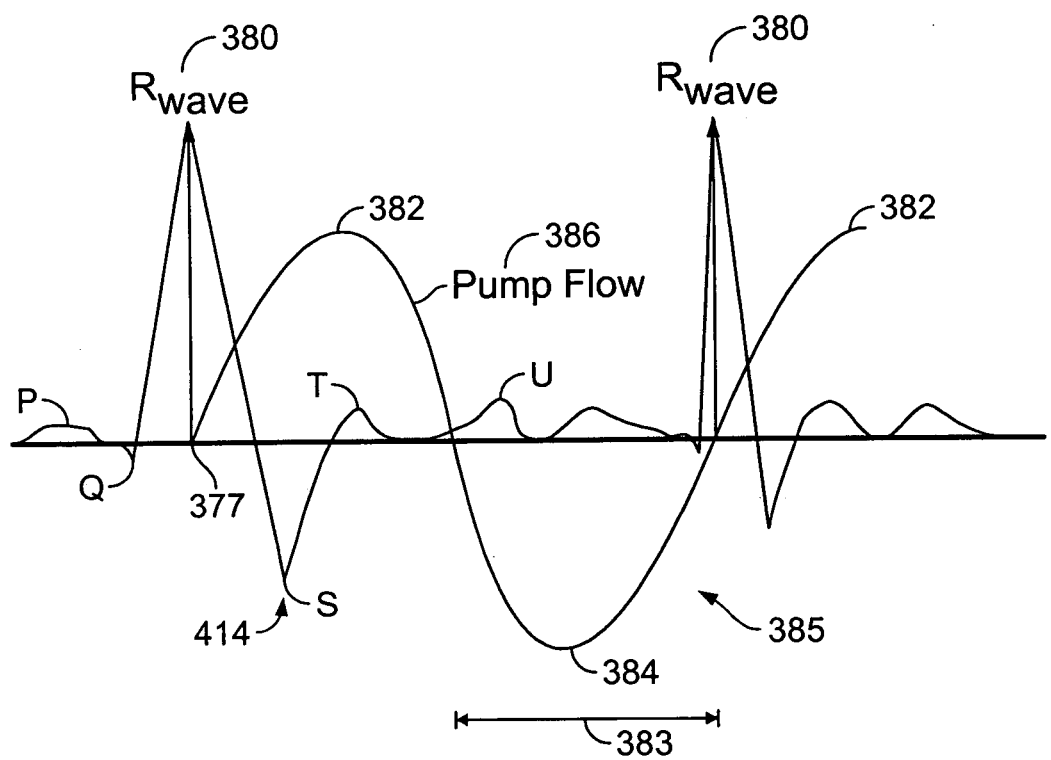
FIG. 16 is a graph depicting an r-wave with which the pumping control subsystem of FIG. 15 synchronizes according to an illustrative embodiment of the invention.

The pumping subsystem 153 of FIG. 11 will now be described in further detail with reference to FIGS. 15 and 16. More particularly, FIG. 15 is a conceptual block diagram depicting the illustrative pumping subsystem 153, and FIG. 16 shows an exemplary ECG 414 of a heart 102 synchronized with an exemplary wave 385 depicting pumping output by the subsystem 153. The ECG 414 shown in FIG. 16 has P, Q, R, S, T, and U peaks. The pumping subsystem 153 includes the perfusion fluid pump 106 interoperationally connected to the pump interface assembly 300, as described in more detail above with reference to FIGS. 8A-10. As shown in FIG. 15, the controller 150 operates the pumping subsystem 153 by sending a drive signal 339 to a brushless three-phase pump motor 360 using Hall Sensor feedback. The drive signal 339 causes the pump motor shaft 337 to rotate, thereby causing the pump screw 341 to move the pump driver 334 up and/or down. According to the illustrative embodiment, the drive signal 339 is controlled to change a rotational direction and rotational velocity of the motor shaft 337 to cause the pump driver 334 to move up and down cyclically. This cyclical motion pumps the perfusion fluid 108 through the system 100.

In operation, the controller 150 receives a first signal 387 from the Hall sensors 388 positioned integrally within the pump motor shaft 337 to indicate the position of the pump motor shaft 337 for purposes of commutating the motor winding currents. The controller 150 receives a second higher resolution signal 389 from a shaft encoder sensor 390 indicating a precise rotational position of the pump screw 341. From the current motor commutation phase position 387 and the current rotational position 389, the controller 150 calculates the appropriate drive signal 339 (both magnitude and polarity) to cause the necessary rotational change in the motor shaft 337 to cause the appropriate vertical position change in the pump screw 341 to achieve the desired pumping action. By varying the magnitude of the drive signal 339, the controller 150 can vary the pumping rate (i.e., how often the pumping cycle repeats) and by varying the rotational direction changes, the controller 150 can vary the pumping stroke volume (e.g., by varying how far the pump driver 334 moves during a cycle). Generally speaking, the cyclical pumping rate regulates the pulsatile rate at which the perfusion fluid 108 is provided to the heart 102, while (for a given rate) the pumping stroke regulates the volume of perfusion fluid 108 provided to the heart 102.

Both the rate and stroke volume affect the flow rate, and indirectly the pressure, of the perfusion fluid 108 to and from the heart 102. As mentioned with regard to FIG. 1, the system includes three flow rate sensors 134, 136 and 138, and three pressure sensors 126, 128 and 130. As shown in FIG. 15, the sensors 134, 136, and 138 provide corresponding flow rate signals 135, 137 and 139 to the controller 150. Similarly, the sensors 126, 128 and 130 provide corresponding pressure signals 129, 131 and 133 to the controller 150. The controller 150 employs all of these signals in feedback to ensure that the commands that it is providing to the perfusion pump 106 have the desired effect on the system 100. In some instances, and as discussed below in further detail with reference to FIGS. 17A-17J, the controller 150 may generate various alarms in response to a signal indicating that a particular flow rate or fluid pressure is outside an acceptable range. Additionally, employing multiple sensors enables the controller 150 to distinguish between a mechanical issue (e.g., a conduit blockage) with the system 100 and a biological issue with the heart 102.

According to one feature of the invention, the pumping system 153 may be configured to control the position of the pump driver 334 during each moment of the pumping cycle to allow for finely tuned pumping rate and volumetric profiles. This in turn enables the pumping system 153 to supply perfusion fluid 108 to the heart with any desired pulsatile pattern. According to one illustrative embodiment, the rotational position of the shaft 337 is sensed by the shaft encoder 390 and adjusted by the controller 150 at least about 100 increments per revolution. In another illustrative embodiment, the rotational position of the shaft 337 is sensed by the shaft encoder 390 and adjusted by the controller 150 at least about 1000 increments per revolution. According to a further illustrative embodiment, the rotational position of the shaft 337 is sensed by the shaft encoder 390 and adjusted by the controller 150 at least about 2000 increments per revolution. The vertical position of the pump screw 341 and thus the pump driver 334 is calibrated initially to a zero or a ground position, corresponding to a reference position of the pump screw 341.

According to the illustrative embodiment, the positional precision of the pumping subsystem 153 enables the controller 150 to precisely regulate the pumping of the perfusion fluid 108 through the heart 102. This process of synchronizing the pulsatile flow of the perfusion fluid to the heart's natural rate is referred to herein as "r-wave synchronization," which is described with continued reference to FIGS. 2, 15, and 16. A normally functioning heart has a two-phase pumping cycle—diastole and systole. During the diastolic phase, also known as the "resting phase," the heart's atria 157 and 152 contract, causing valves to open between the atria 157 and 152 and the ventricles 154 and 156 to allow blood to flow into and load the ventricles 154 and 156. During the systolic phase, the loaded ventricles eject the blood, and the atria 157 and 152 are opened and fill with blood. The cyclical expansion and contraction of the heart 102 during this process can be represented by graphing the heart's ventricular ECG wave form, shown at 414 in FIG. 16. FIG. 16 depicts the ECG waveform 414 synchronized with an exemplary wave 385 representative of a pumping output by the subsystem 153.

The pumping subsystem 153 is configured to provide the maximum output at a time that will result in delivery of fluid 108 to the heart 102 at the most beneficial time. In the illustrated embodiment, in retrograde mode, the pumping subsystem 153 is configured to pump fluid 108 toward the heart 102 so that the maximum pump output 382 occurs during the diastolic phase of the heart, which begins after the S peak shown in FIG. 16 and is when the left ventricle 156 has finished ejecting perfusion fluid 108 through the aorta 158. Timing the pump output in this manner allows the user to maximize the injection of perfusion fluid 108 through the aorta 158 and into the coronary sinus 155. The timed pumping is accomplished by starting the pumping at point 377 on wave 385, which is a point prior to point 382 and corresponds to the peak of the heart's r-wave pulse 380 and the middle of ventricular systole. The point 377 is selected to account for time-delay between the time a signal is provided from the controller 150 to start pumping the fluid and the time of actual delivery of the pumped fluid 108 to the heart 102. In another example, during normal flow mode where the left side of the heart fills and ejects perfusion fluid (as described in more detail with reference to FIG. 24A), the controller 150 synchronizes the pumping subsystem 153 to start pumping at a fixed period of time after the r-wave 380, so as to match the natural filling cycle of the left atrium 152. The synchronization may be adjusted and fine-tuned by the operator through a pre-programmed routine in the operating software on the system 100 and/or by manually operating the controls of the user interface display area 410, as described in more detail below in reference to FIGS. 17A-17J.

To achieve the synchronized pump output, the controller 150 predicts when the heart's r-wave pulses 380 will occur and causes the pump to pump at the appropriate time during the ECG 414. To make this prediction, the controller 150 measures the length various r-wave pulses 380 from the electrical signals 379 and 381 provided from the electrodes 142 and 144, respectively. From these pulses, the controller 150 tracks the time that elapses from one pulse 380 to the next, and uses this information to calculate a running average of the length of time separating two sequential r-wave pulses. From this information, the controller 150 projects the time of the next r-wave (and from the projection determines the time prior to or after that projected r-wave when the pumping should start to achieve optimal output delivery) by adding the average time separating two sequential r-wave pulses to the time of the previous r-wave 380. Based on this running average of separation time between r-waves, the controller 150 has the option to adjust the time of pump output in relation to subsequent r-waves, as reflected in the movement of wave 385 to the left or the right along the ECG 414 as signified by the arrow 383 in FIG. 16. Adjusting the wave 385 thus allows the user to adjust and customize the timing of output by the pump 106 so as to optimize the filling of the heart. In addition, the pump 106 may also be adjusted to increase or decrease the pump stroke volume to customize the volume of fluid 108 provided by the pump 106, and this may be done either in concert with or independent of the r-wave synchronization.

It should be noted that although the subsystem 153 particularly synchronizes with the r-wave cycle 385, this need not be the case. In alternative illustrative embodiments, the subsystem 153 may pump in synchronicity with any available characteristic of the heart, including fluid pressures into or out of a particular chamber or vessel. Also, the subsystem 153 may be programmed to pump in any arbitrary pattern, whether periodic or not.

Referring back to FIG. 11, the data management subsystem 151 receives and stores data and system information from the various other subsystems. The data and other information may be downloaded to a portable memory device and organized within a database, as desired by an operator. The stored data and information can be accessed by an operator and displayed through the operator interface subsystem 146.

Figure 17A:
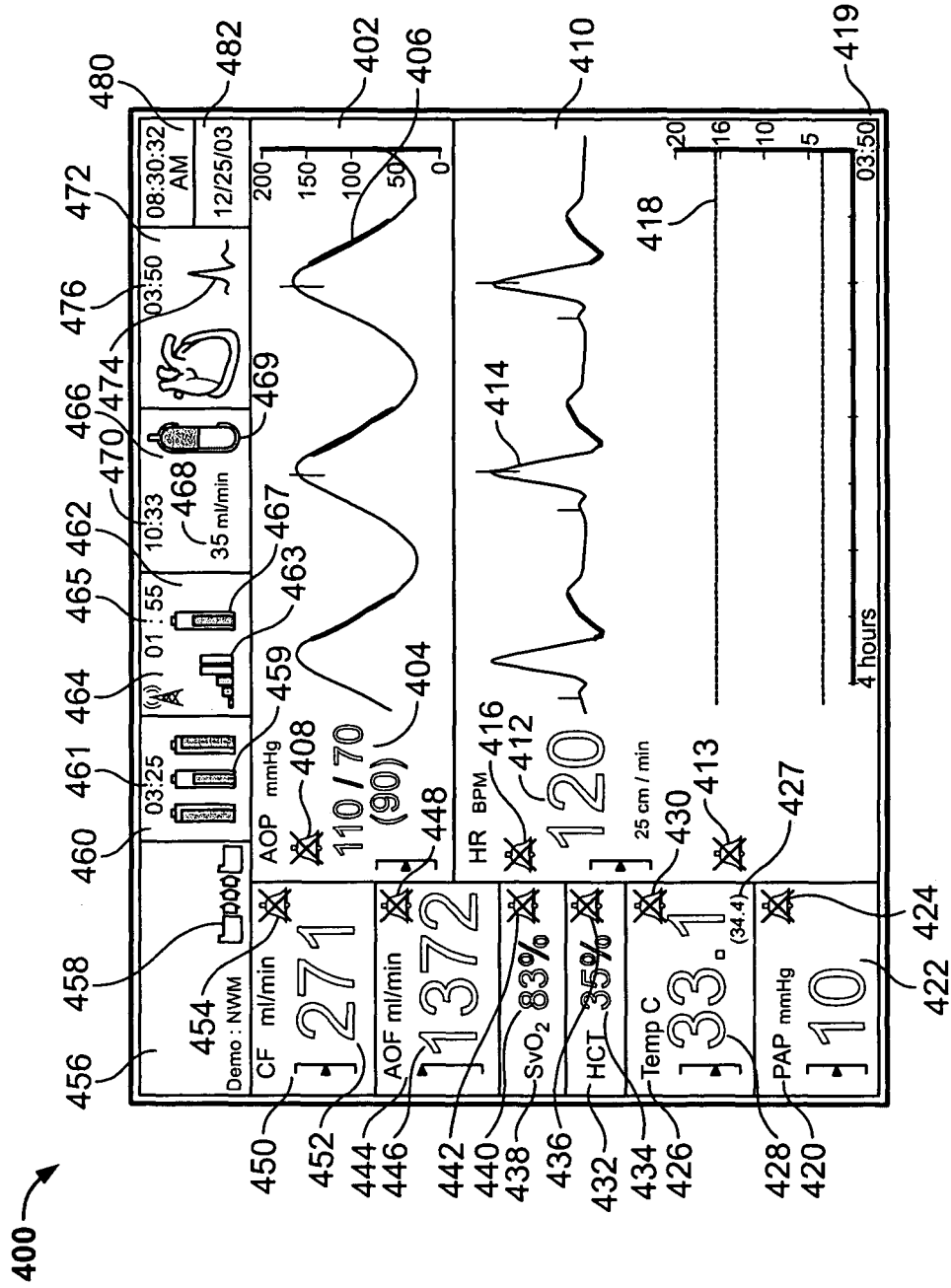
FIGS. 17A-17J depict exemplary display screens of the type that may be employed with an operator interface according to an illustrative embodiment of the invention.

Turning now to the operator interface subsystem 146, FIGS. 17A-17J show various illustrative display screens of the operator interface subsystem 146. The display screens of FIGS. 17A-17J enable the operator to receive information from and provide commands to the system 100. FIG. 17A depicts a top level "home page" display screen 400 according to an illustrative embodiment of the invention. From the display screen 400 an operator can access all of the data available from the data acquisition subsystem 147, and can provide any desired commands to the controller 150. As described in more detail in reference to FIGS. 17B-17J, the display screen 400 of FIG. 17A also allows the operator to access more detailed display screens for obtaining information, providing commands and setting operator selectable parameters.

With continued reference to FIG. 1, the display screen 400 includes a display area 402, which shows a number of numerical and graphical indications pertaining to the operation of the system 100. In particular, the display area 402 includes a numerical reading of the aorta output pressure (AOP) 404 of the perfusion fluid 108 exiting the aorta interface 162 on the organ chamber assembly 104, a wave form depiction 406 of the aortic fluid pressure (AOP) 404, and an AOP alarm image 408 indicating whether the fluid pressure 404 is too high or too low (the alarm 408 is shown as "off" in FIG. 17A). The display screen 400 also includes a display area 410 having a numerical indication 412 of the rate at which the heart 102 is beating, an ECG 414 of the heart 102, a heart rate (HR) alarm image 416 indicating whether the HR 412 exceeds or falls below operator set thresholds, and a time log 418 indicating how long the system 100 has been running, including priming time (discussed in further detail below with reference to FIG. 29A). A numerical display 419 shows the amount of time for which the system 100 has been supporting the heart 102. The indicator alarm 413 indicates when an operator preset time limit is exceeded.

The display screen 400 includes a number of additional display areas 420, 424, 432, 438, 444, 450, 456, 460, 462, 466, 472, 480, and 482. The display area 420 shows a numerical reading of the pulmonary artery pressure (PAP) 422. The PAP 422 is an indication of the pressure of the perfusion fluid 108 flowing from the heart's pulmonary artery 164, as measured by the pressure sensor 130. The display area 420 also provides a PAP alarm indicator 424, which signals when the PAP 422 is outside an operator preset range. The display area 426 indicates the temperature (Temp) 428 of the perfusion fluid 108 as it exits the heater 110. The display area 426 also includes a Temp alarm indicator 430, which signals in response to the Temp 428 being outside of an operator preset range. The upper limit of the operator preset range is shown at 427. The display area 432 shows a numerical reading of the hematocrit (HCT) 434 of the perfusion fluid 108, and an HCT alarm indicator 436 for signaling the operator if the HCT 434 falls below an operator preset threshold. The display area 438 shows the oxygen saturation ($SvO_2$) 440 of the perfusion fluid 108. The display area 438 also includes a $SvO_2$ alarm 442 for indicating if the $SvO_2$ 440 of the perfusion fluid 108 falls below an operator preset threshold. The display area 444 indicates the aorta output flow rate (AOF) 446 of the perfusion fluid 108 as it flows out of the aorta 158. The AOF 446 is measured by the flow rate sensor 134. The AOF alarm 448 indicates whether the flow rate 446 falls outside of an operator preset range. The display area 450 shows the organ chamber flow rate (CF) 452. The CF 452 is an indication of the flow rate of the perfusion fluid 108 as it exits the organ chamber 104, as measured by the flow rate sensor 136. The display area 450 also includes a CF alarm 454, which signals in response to the CF 454 falling outside of an operator preset range. The display area 456 includes a graphic 458 for indicating when a file transfer to the memory card is occurring.

The display area 460 shows a graphical representation 459 of the degree to which each of the batteries 352a-352c (described above with reference to FIG. 14) is charged. The display area 460 also provides a numerical indication 461 of the amount of time remaining for which the batteries 352a-352c can continue to run the system 100 in a current mode of operation. The display area 462 identifies whether the operator interface module 146 is operating in a wireless 464 fashion, along with a graphical representation 463 of the strength of the wireless connection between the operator interface module 146 and the remainder of the system 100. The display area 462 also provides graphical indication 467 of the charge remaining in the operator interface module battery 368 (described above with reference to FIG. 14) and a numerical indication 465 of the amount of time remaining for which the operator interface module battery 368 can support it in a wireless mode of operation. The display area 466 indicates the flow rate 468 of oxygen from the gas flow chamber 176. It also provides a graphical indication 469 of how full an onboard oxygen tank is, and a numerical indication 470 of the amount of time remaining before the onboard oxygen tank runs out. The display area 472 shows the heart rate of the heart 102, and the amount of time 476 for which the heart 102 has been cannulated onto the system 100. This field is duplicative of the field 419 mentioned above. The display areas 480 and 482 show the current time and date, respectively, of operation of the system 100.

Figure 17B:
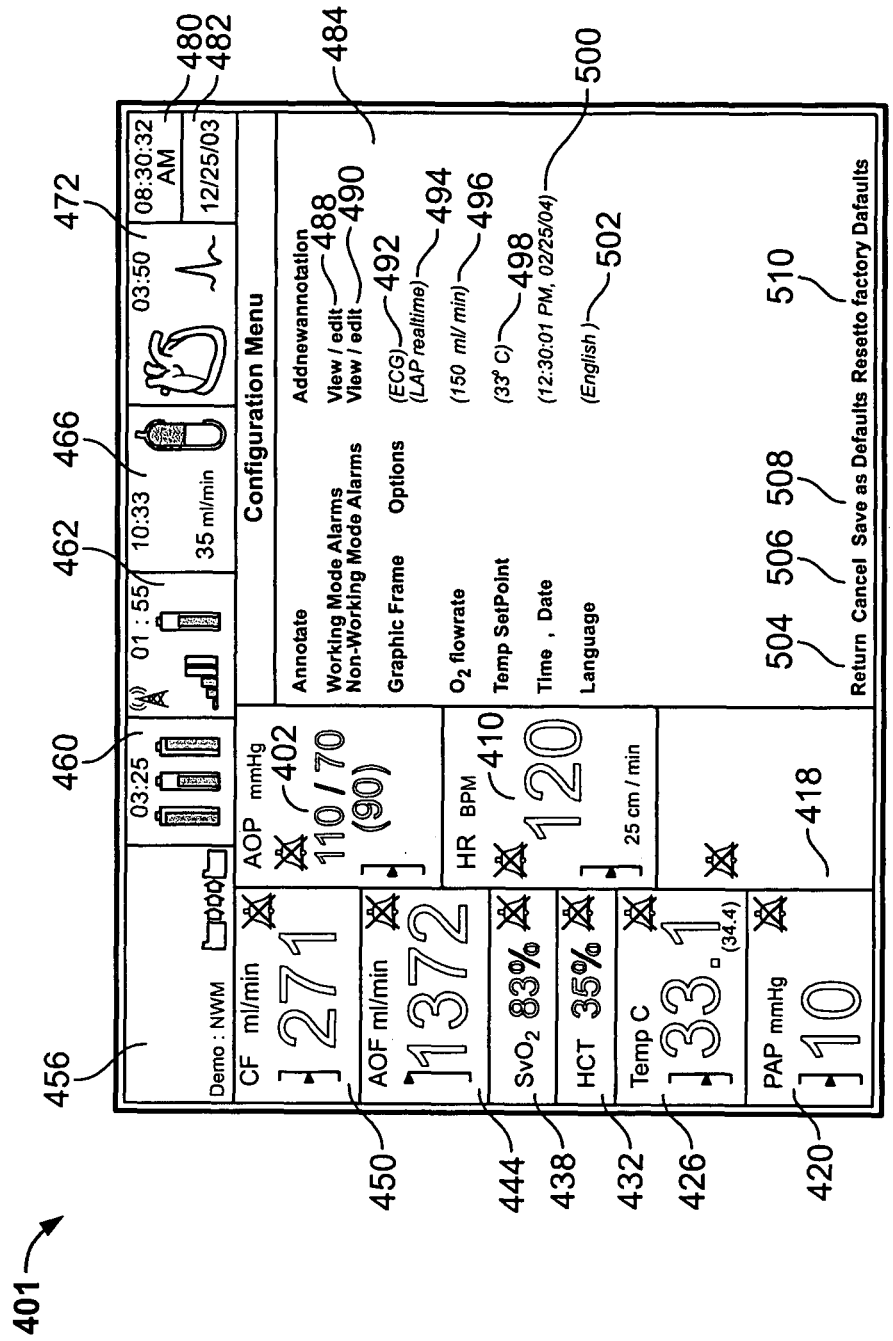
Figure 18A:
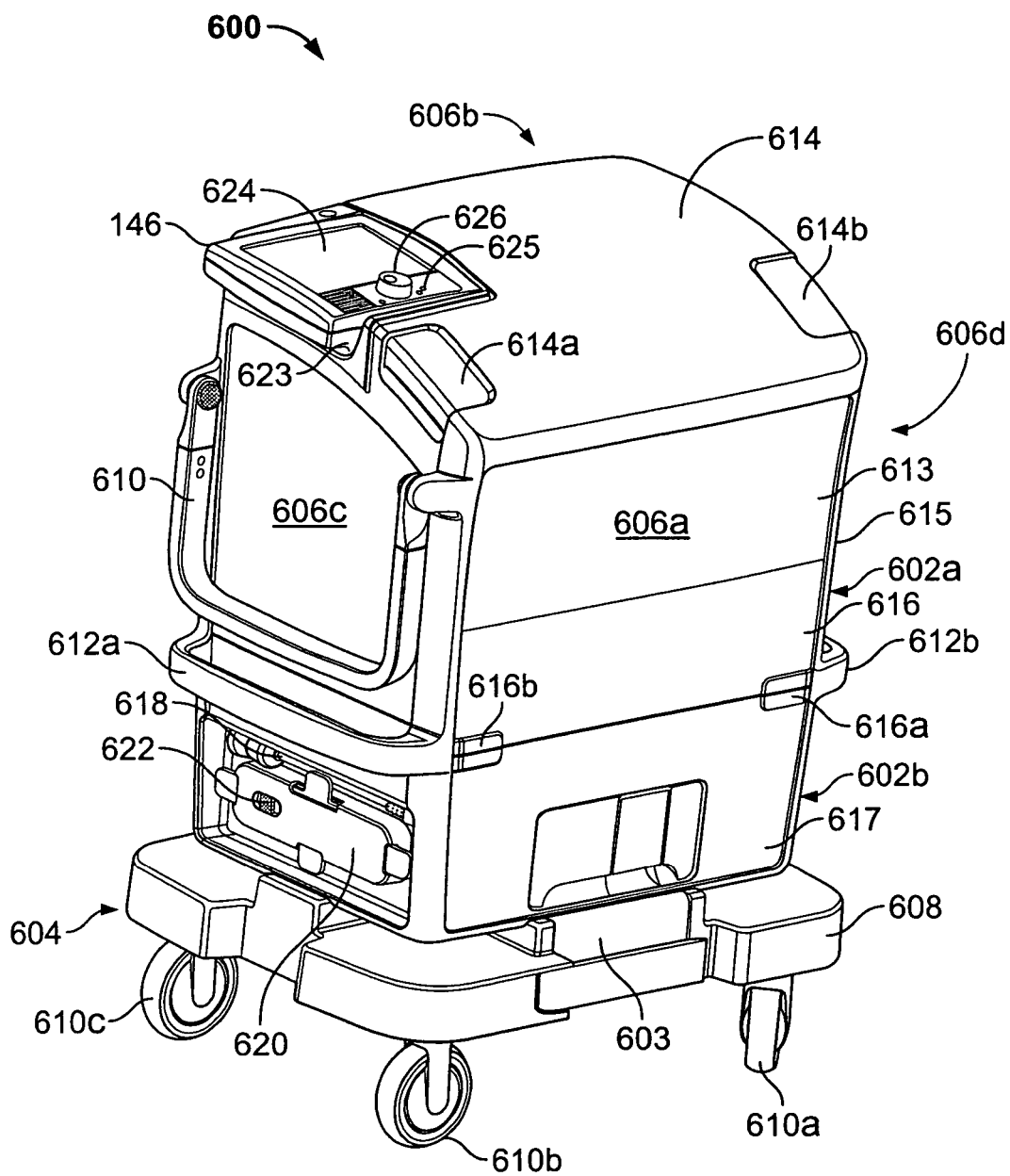
FIGS. 18A and 18B show an exemplary implementation of the system of FIG. 1 according to an illustrative embodiment of the invention.

Actuating a dial (or mouse, or other control device), such as the dial 626 shown in FIG. 18A, on the operator interface 146 opens a configuration menu 484, such as shown in the display screen 401 of FIG. 17B. As shown, accessing the configuration menu 484 covers the display areas 402 and 410 so they no longer show the graphical depictions of the pressure 406 and the heart rate 414, but continue to display critical alpha/numeric information. As also shown, all other display areas remain unchanged. This enables an operator to adjust operation of the system 100 while continuing to monitor critical information. According to one feature, the configuration menu 484 allows the operator to pre-program desired operational parameters for the system 100. Using the display screen 401, the operator can view/edit working and diastolic (or retrograde) mode alarms by selecting the fields 488 and 490, respectively. The operator can set particular ECG and LAP graphical options by selecting the fields 492 and 494. Additionally, the operator can set oxygen flow rate and perfusion fluid temperature by selecting the fields 496 and 498, respectively. Selecting the field 500 enables the operator to set the time and date, while selecting the field 502 enables the operator to select the language in which information is displayed. At the bottom of the display field 484, the operator has the option to return 504 to the display screen 400, cancel 506 any changes made to operational settings, save 508 the changes as new defaults, or reset 510 the operational settings to factory defaults.

Figure 17C:
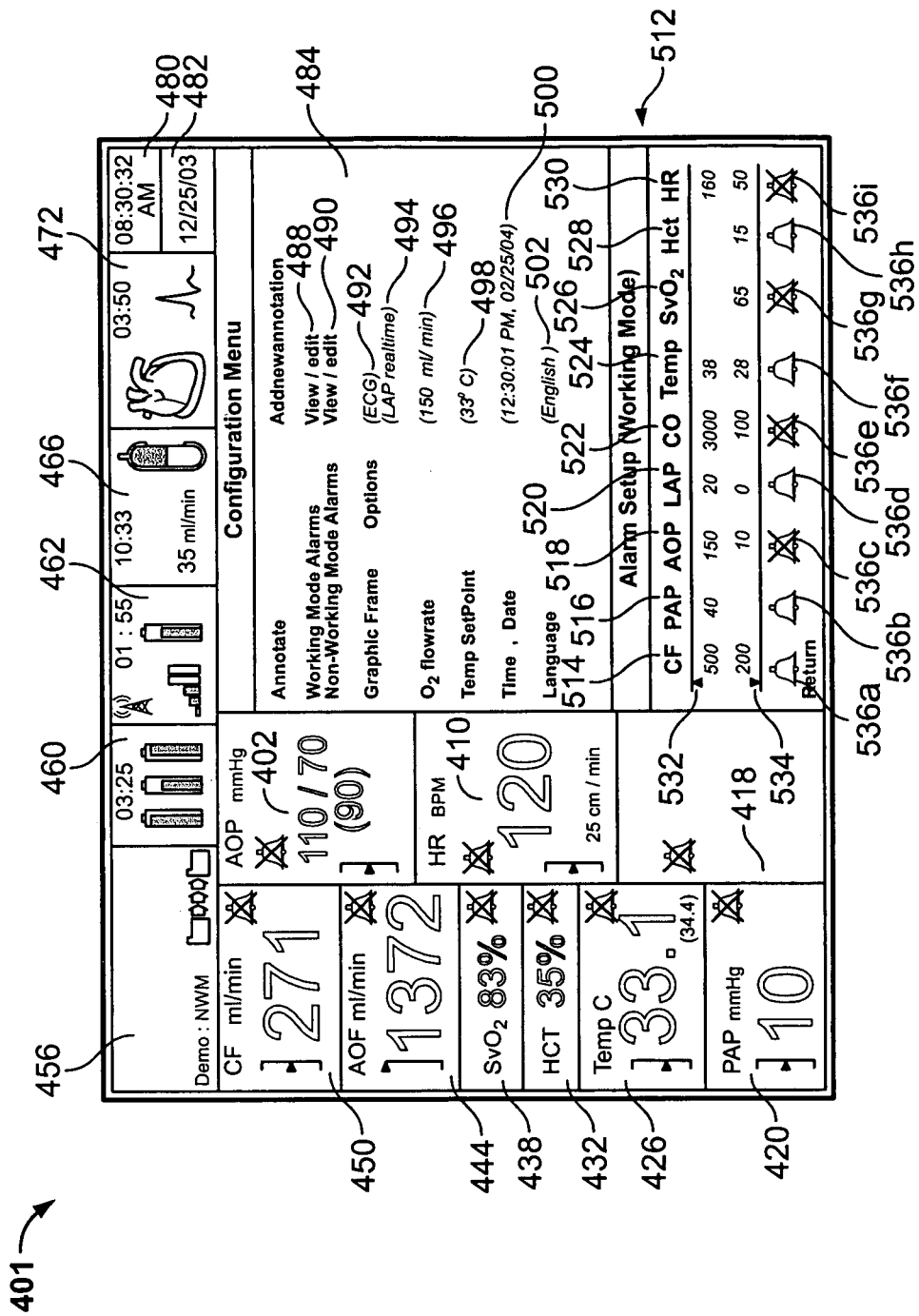
Figure 17D:
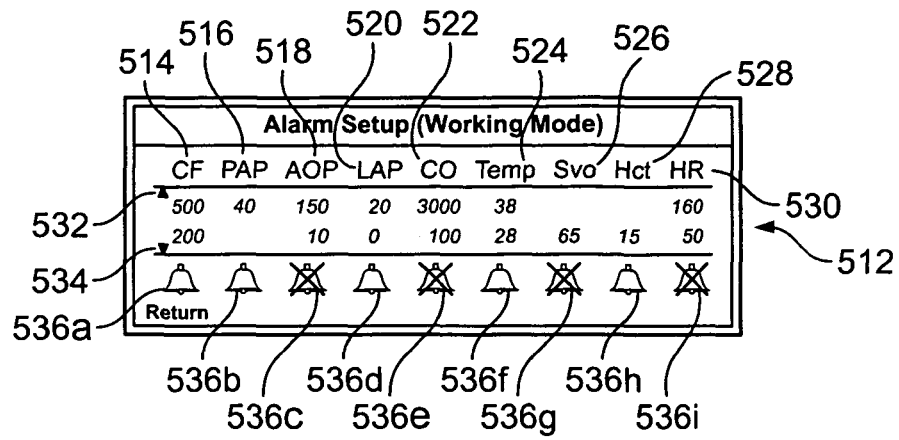

Referring to FIGS. 17C-17D, selecting the view/edit working mode alarms field 488 causes the working mode alarm dialog 512 of FIG. 17D to open within the display field 484 of FIG. 17C. The working mode dialog 512 displays the parameters associated with normal flow mode (described above with reference to FIGS. 1 and 3) and includes a field for setting numerical thresholds for each of the normal flow mode alarms. More specifically, the dialog 512 includes: CF alarm field 514; PAP alarm field 516; AOP alarm field 518; LAP alarm field 520; perfusion fluid Temp alarm field 524; $SvO_2$ alarm field 526; HCT alarm field 528; and HR alarm field 530. By selecting a particular alarm field and actuating the up 532 and/or down 534 arrows, a operator can adjust the acceptable upper and/or lower thresholds for each of the parameters associated with each of the alarms. The dialog 512 also includes alarm graphics 536a-536i, each of which being associated with a particular normal flow mode alarm. The operator can enable/disable any of the above normal flow mode alarms by selecting the associated alarm graphic 536a-536i. Any changes made using the dialog 512 are reflected in corresponding fields in the display screen 400 of FIG. 17A.

Figure 17E:
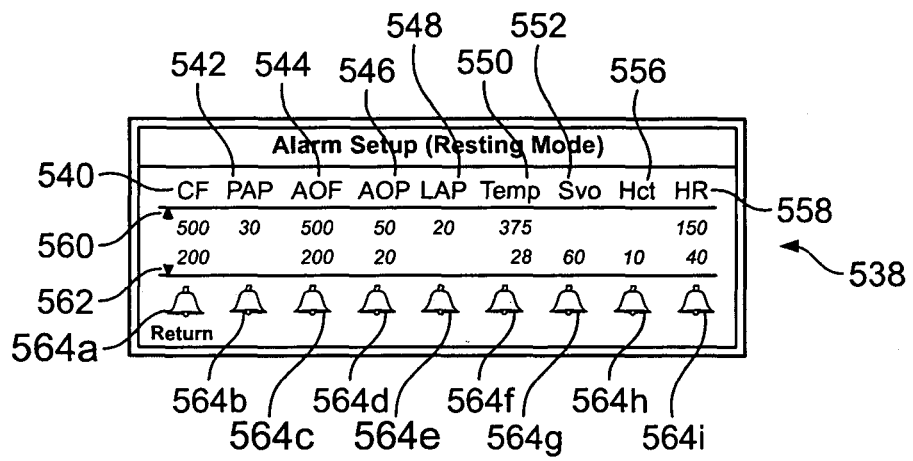
Figure 17F:
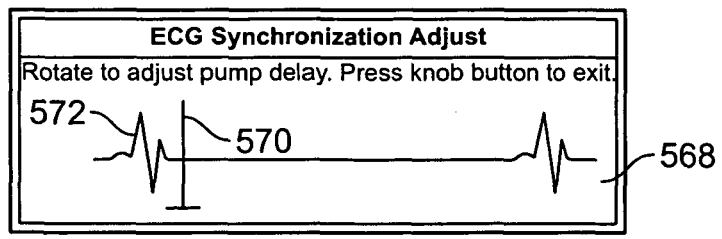
Figure 17G:
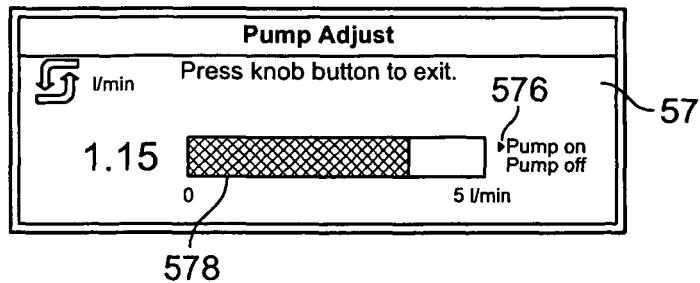
Figure 17H:
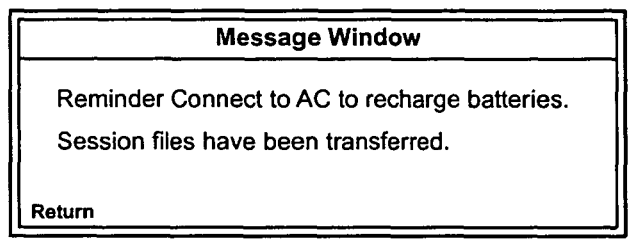
Figure 17I:
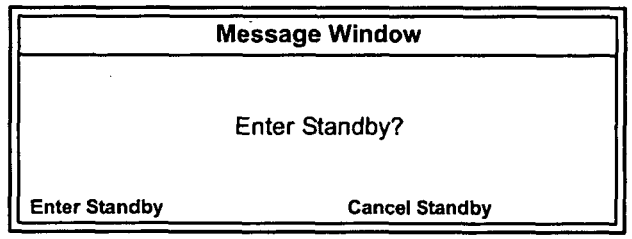
Figure 17J:
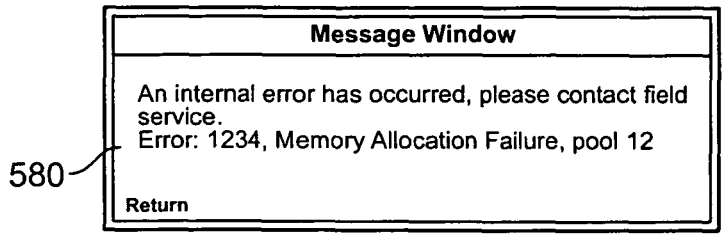

Referring to FIGS. 17A, 17B and 17E, selecting the view/edit non-working mode alarms field 490 causes the resting mode alarm dialog 538 of FIG. 17E to open within the display field 484 of FIG. 17C. The resting mode dialog 538 displays the parameters associated with retrograde flow mode (described above with reference to FIGS. 1 and 4) and includes a field for setting numerical thresholds for each of the retrograde flow mode alarms. According to the illustrative embodiment, the available alarms for the normal and retrograde flow modes are similar, but not necessarily the same. Additionally, even for those that are the same, the thresholds may differ. Accordingly, the invention enables the operator to select different alarms and/or different thresholds for each flow mode of operation. More specifically, the dialog 538 includes: CF alarm field 540; PAP alarm field 542; AOF alarm field 544; AOP alarm field 546; LAP alarm field 548; perfusion fluid Temp alarm field 550; $SvO_2$ alarm field 552; HCT alarm field 556; and HR alarm field 558. By selecting a particular alarm field and actuating the up 560 and/or down 562 arrows, an operator can adjust the acceptable numerical upper and/or lower thresholds for each of the parameters associated with each of the alarms. The dialog 538 also includes alarm graphics 564a-564i, each of which being associated with a particular normal flow mode alarm. The operator can enable/disable any of the above normal flow mode alarms by selecting the associated alarm graphic 564a-564i. As is the case of the dialog 512, any changes made using the dialog 538 are reflected in corresponding fields in the display screen 400 of FIG. 17A. In one implementation, the system 100 may be configured to automatically switch between sets of alarm limits for a given flow mode upon changing the flow mode.

Referring to FIGS. 17A, 17B, 17F and 17G, the operator interface 146 also provides graphical mechanisms for adjusting various parameters. For example, as noted above in reference to FIG. 16, one advantage of the user display area 402 is that it allows the operator to monitor (and adjust) the pumping of the subsystem 153. Display area 410 identifies the ECG waveform 414 of the heart 102, and display 402 shows in wave form 406 the pressure of fluid flowing through the aorta. In these two displays the operator can monitor the effect of the pumping profile on the heart's EGC 414, which allows the user to adjust the stroke volume of the pumping subsystem 153, to adjust the rate of the pumping subsystem 153 (and thus the flow-rate of the fluid 108 being pumped through the system 100), to manually impose, or adjust a time of, firing of the subsystem (e.g., by imposing a fixed delay between the r-wave 380 and the beginning of the pumping cycle), or to automatically program the pumping subsystem 153 to pump at a pre-determined time along the heart's ECG waveform 414, as needed to properly fill the heart according to whether the heart is being perfused in retrograde or normal mode. These pumping adjustments may be made by use of the various graphical frames of the operator interface 146. By way of example, in response to a operator selecting the ECG graphic frame option 492 located in the display field 484 of the display screen 401, the operator interface 146 displays the dialog 568 of FIG. 17F. The dialog 568 shows a graphical representation 572 of the ECG 414 along with a cursor 570. The position of the cursor 570 indicates the point at which the pumping subsystem 153 will initiate an output pumping stroke (i.e., the portion of the pumping cycle at which the pump motor 106 will push perfusion fluid 108 to the heart 102) relative to the ECG 414 of the heart 102. By rotating a mechanical knob 626 (shown in FIGS. 18A and 18B) on the operator interface 146, the operator moves the position of the cursor 570 to adjust when the pumping subsystem 153 will initiate the output pumping stroke relative to the r-wave pulse 380. As described above with regard to FIGS. 15 and 16, the pumping subsystem 153 receives an r-wave signal 380 from the ECG sensors 142 and 144. The pumping subsystem 153 uses the r-wave signal 380 along with the pumping adjustment information from the cursor 570 to synchronize perfusion fluid pumping with the beating of the heart 102. In another example, in response to the operator pressing the pump adjust button 625, the operator interface 146 displays the dialog 574 of FIG. 17G. From the dialog 574, the operator can select the pointer 576 and rotate the knob 626 to turn the pump motor 106 on and off. Additionally, the operator can select the bar graphic 578 and rotate the knob 626 to adjust the volume of fluid being pumped, which is displayed in liters/minute.

The operator interface 146 also provides a plurality of warning/reminder messages. By way of example, in FIG. 17H, the operator interface 146 displays a message to remind the operator to connect to AC power to recharge the batteries. This message appears, for example, in response to the controller 150 detecting an impending low battery condition. The operator interface 146 displays the message of FIG. 17I to confirm that the user wishes to enter standby mode and to remind the operator to insert a portable memory device, such as magnetic or optical disk, a portable disk drive, a flash memory card or other suitable memory device, to download and store information regarding a particular use of the system 100. The operator interface 146 displays the error messages, such as the error message of FIG. 17J, in response to an identifiable fault occurring. The error messages of FIG. 17J include, for example, error information 580 to aid a service technician in diagnosing and/or repairing the fault.

Figure 18B:
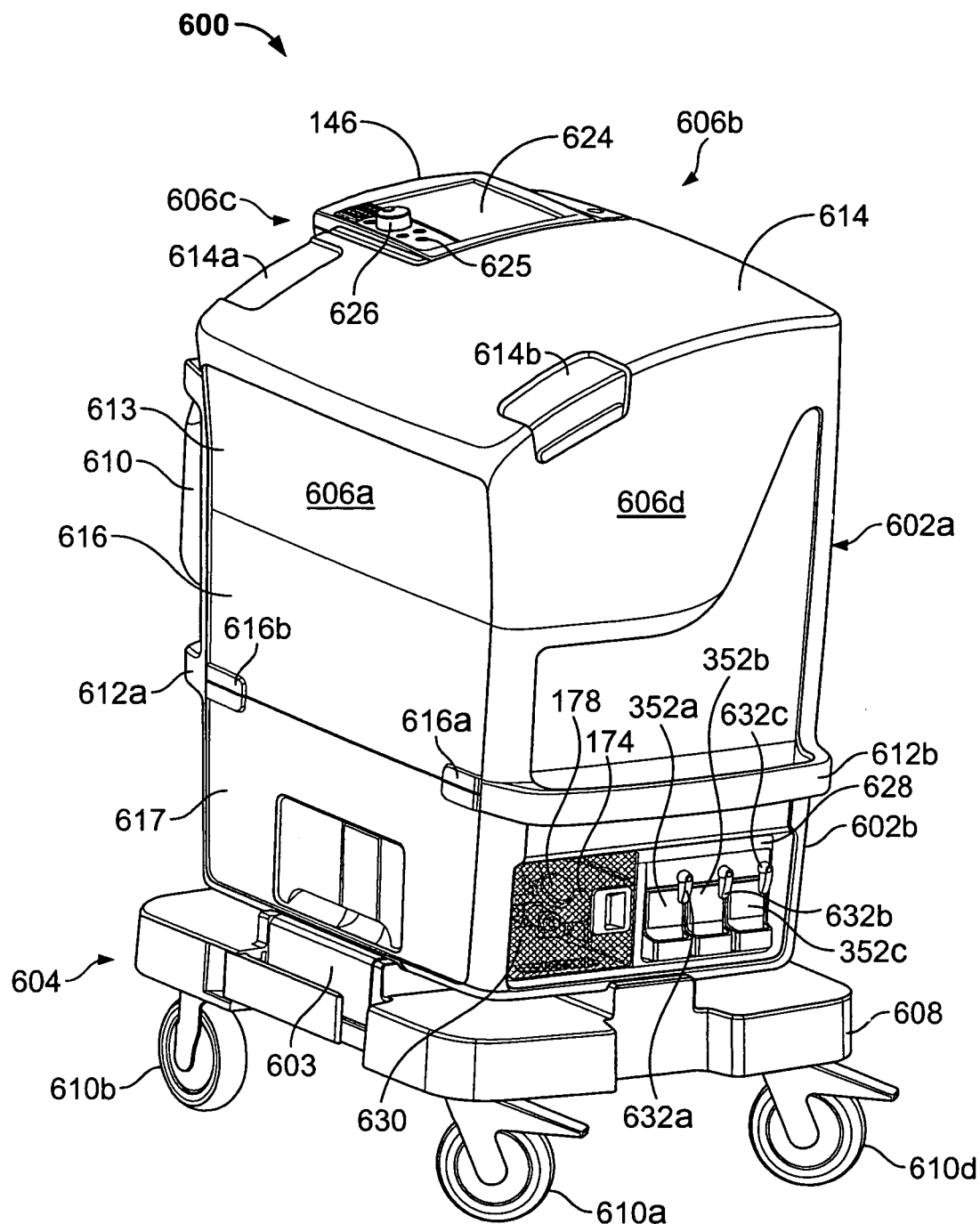

Having described an illustrative control systems and methods for achieving operation of the system 100, illustrative mechanical features of the system 100 will now be discussed, along with an illustrative division of components between the single use disposable module 634 and multiple use module 650 units. More particularly, FIGS. 18A-18B show a mechanical implementation 600 of the system of FIG. 1, according to an illustrative embodiment of the invention. As shown, the illustrative implementation 600 includes a housing 602 and a cart 604. The housing 602 conceptually divides into upper 602a and lower 602b housing sections, and includes front 606a, rear 606b, left 606c, and right 606d sides. The cart 604 includes a platform 608 and wheels 610a-610d for transporting the system 600 from place to place. A latch 603 secures the housing 602 to the cart 604. To further aid in portability, the system 600 also includes a handle 610 hinge mounted to the upper section 602a of the left side 606c of the housing 602, along with two rigidly mounted handles 612a and 612b mounted on the lower section 602b of the left 606c and right 606d sides of the housing 602.

The housing 602 further includes a removable top 614, and a front panel 615 having an upper panel 613, and a mid panel 616 hinged to a lower panel 617 by hinges 616a and 616b. The top 614 includes handles 614a and 614b for aiding with removal. In the illustrated embodiment, the upper panel 613 is screwed, bolted or otherwise adjoined to the top 614, such that removal of the top 614 also removes panel 613.

As shown in FIG. 18A, the system 600 includes an AC power cable 618, along with a frame 620 for securing the power cable 618, both located on the lower section 602b of the left side 606c of the housing 602. A software reset switch 622, also located on the lower section 602b of the left side 602c, enables an operator to restart the system software and electronics.

As shown in FIGS. 18A and 18B, the implementation 600 also includes the operator interface module 146, along with a cradle 623 for holding the operator interface module 146. The operator interface module 146 includes a display 624 for displaying information to an operator, for example, by way of the display screens of FIGS. 17A-17J. As mentioned above, the operator interface module 146 also includes a rotatable and depressible knob 626 for selecting between the various parameters and display screens of FIGS. 17A-17J. The knob 626 may also be used to set parameters for automatic control of the system 100, as well as to provide manual control over the operation of the system 100. For example, the knob 626 may be used to provide instructions to the controller 150 to increase perfusion fluid flow rates, gas flow rates, etc. As also discussed above with regard to FIGS. 1, 14 and 17A-17J, the operator interface module 146 includes its own battery 368 and may be removed from the cradle 623 and used in a wireless mode. While in the cradle 623, power connections enable the operator interface module 146 to be charged. As shown, the operator interface module also includes control buttons 625 for controlling the pump, silencing or disabling alarms, entering or exiting standby mode, entering or adjusting ECG synchronization mode, and starting the perfusion clock, which initiates the display of data obtained during organ care.

As shown in FIG. 18B, the illustrative implementation 600 also includes a battery compartment 628 and an oxygen tank bay 630, both located on the lower section 602b of the right side 606d of the housing 602. As shown, the battery compartment 628 houses the three system batteries 352a-352c, described above with regard to FIG. 14. According to one feature, the battery compartment 626 includes three battery locks 632a-632c. As described above with respect to FIG. 14, the battery locks 632a-632c interoperate mechanically so that only one of the three batteries 352a-352c may be removed at any given time.

The disposable module 634 and the multiple use unit 650 are constructed of material that is durable yet light-weight. In some illustrative embodiments, polycarbonate plastic is used to form one or more of the components of the units 634 and 650. To further reduce the weight, the chassis 635 and the multiple use module chassis 602 are formed from low weight materials such as, for example, carbon fiber epoxy composites, polycarbonate ABS-plastic blend, glass reinforced nylon, acetal, straight ABS, aluminum or magnesium. According to one illustrative embodiment, the weight of the entire system 600 is less than about 85 pounds, including the multiple use module, heart, batteries, gas tank, and priming, nutritional, preservative and perfusion fluids, and less than about 50 pounds, excluding such items. According to another illustrative embodiment, the weight of the disposable module 634 is less than about 12 pounds, excluding any solutions. According to a further illustrative embodiment, the multiple use module 650, excluding all fluids, batteries 352a-352c and oxygen supply 172, weighs less than about 50 pounds.

Figure 19A:
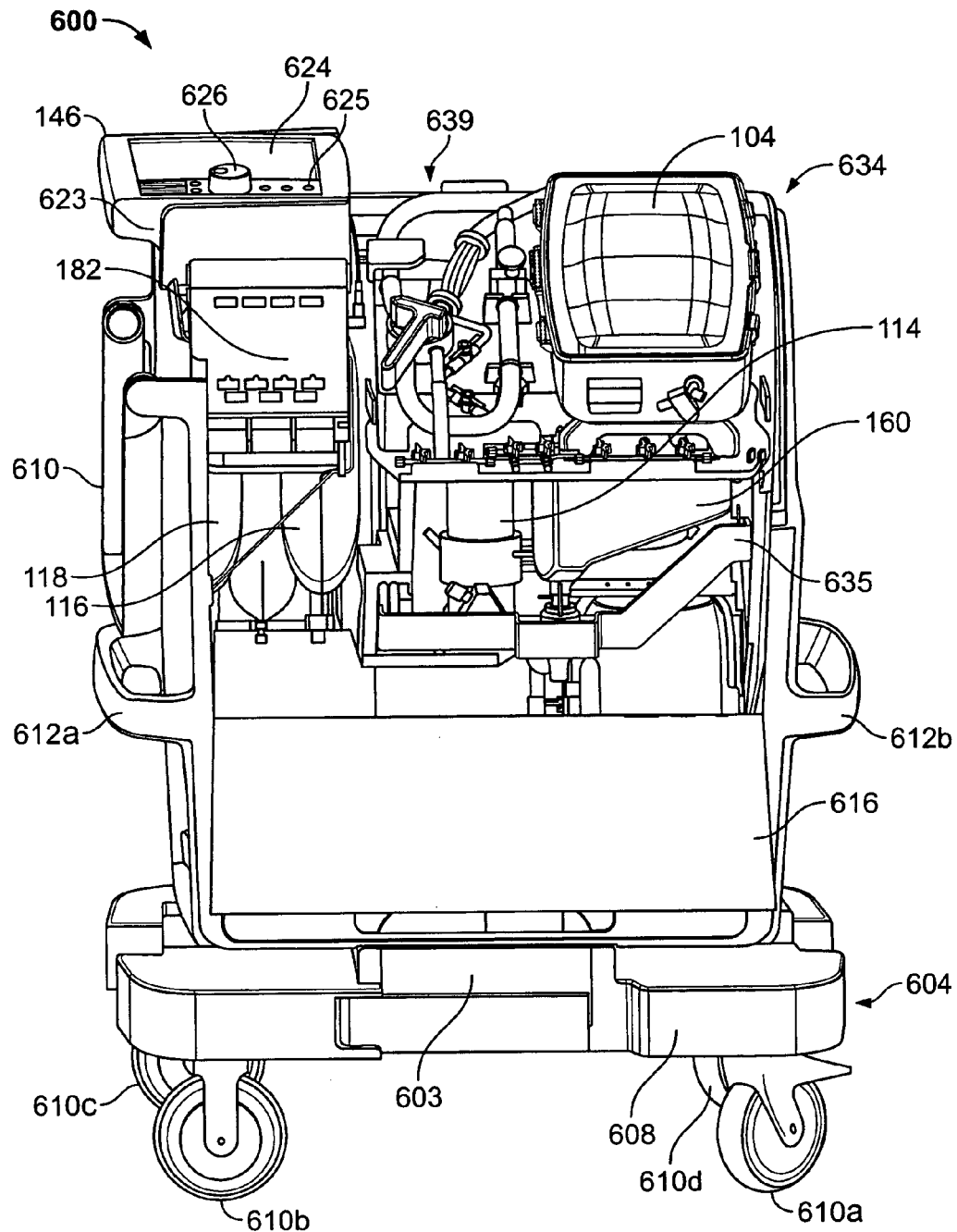
FIGS. 19A-19C show various views of the system of FIGS. 18A and 18B with its top off and front panel open according to an illustrative embodiment of the invention.
Figure 19B:
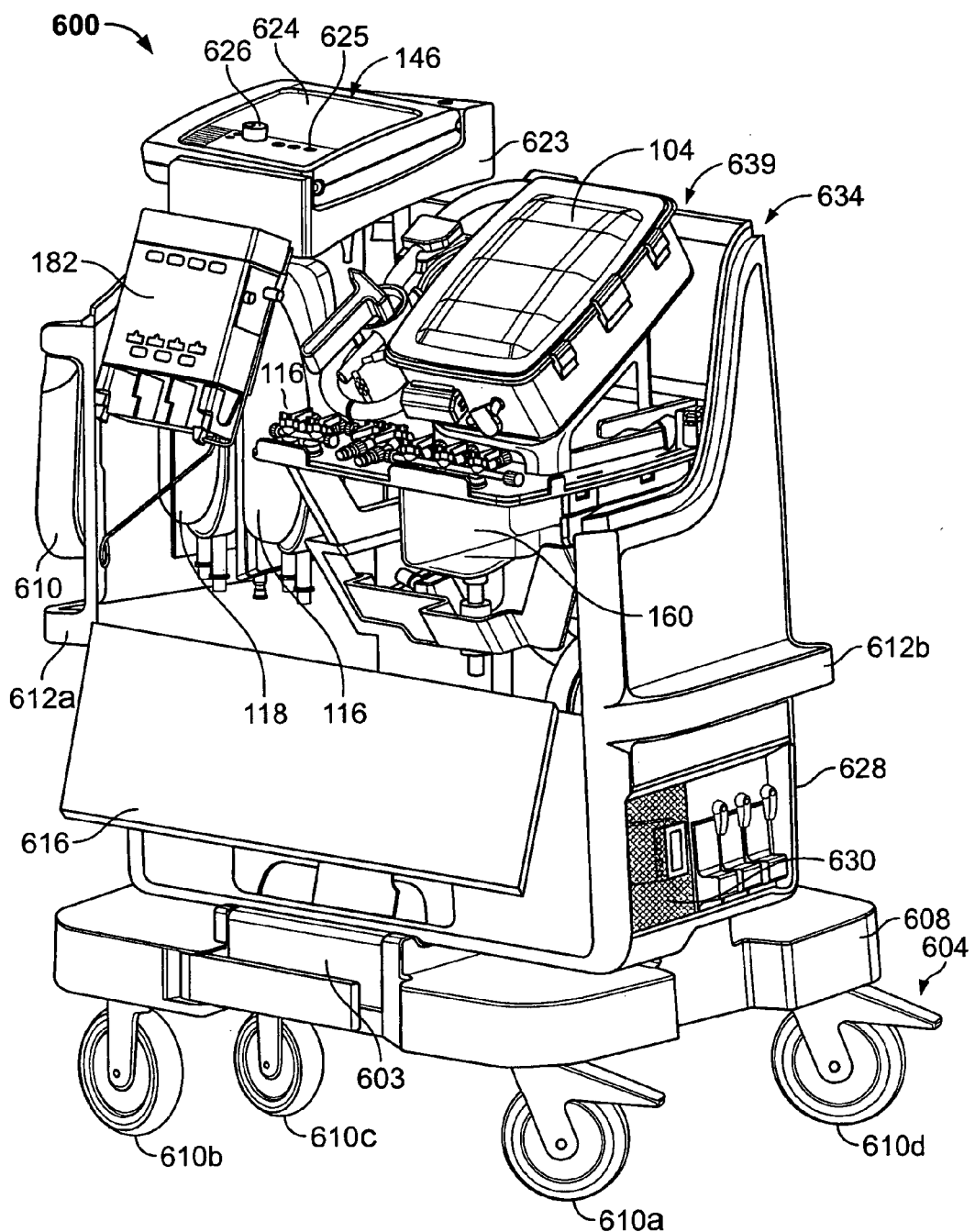
Figure 19C:
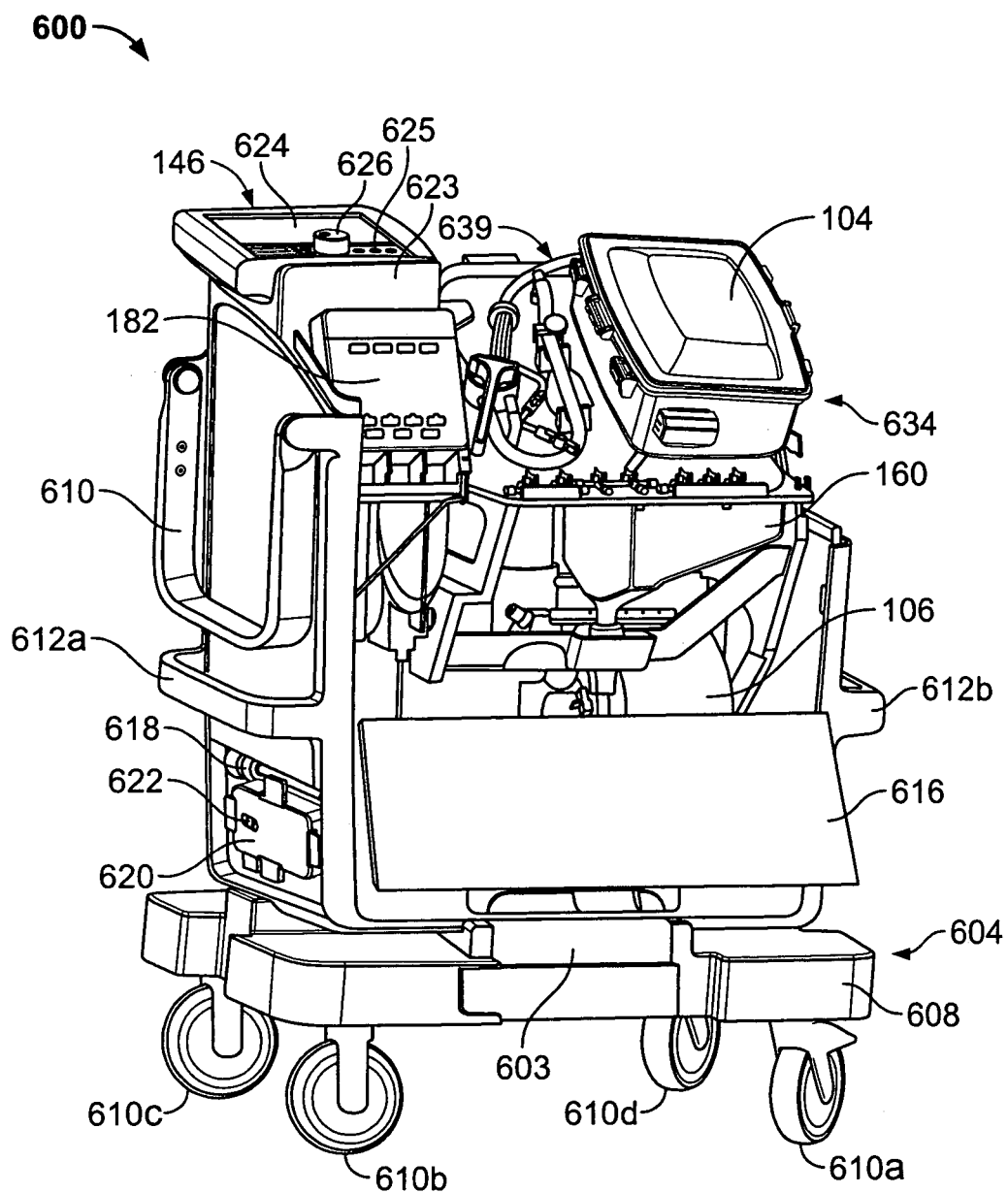

With continued reference to FIGS. 19A-19C, various views are shown of the implementation 600 of FIGS. 18A and 18B with the top 614 and upper front panel 613 removed and the front mid panel 616 open, according to an illustrative embodiment of the invention. With reference to FIGS. 19A-19C, the system 100 is structured as a single use disposable module 634 (shown and described in detail below with reference to FIGS. 24A-25C) and a multiple use module 650 (shown without the single use module in FIG. 20). As discussed in further detail below, according to one feature of the illustrative embodiment, all of the blood contacting components of the system 100 are included in the single use disposable module 634 so that after a use, the entire single use module 634 may be discarded, a new module 634 installed, and the system 100 available for use again within a very brief amount of time.

According to the illustrative embodiment, the single use module 634 includes a chassis 635 for supporting all of the components of the single use module 634. As described in more detail with regard to FIGS. 24A-25C, the components of the single use module 634 include the organ chamber assembly 104, described above in detail with respect to FIGS. 5A-5F, the perfusion fluid reservoir 160, the oxygenator 114, the perfusion fluid pump interface 300, and all of the various fluid flow conduits and peripheral monitoring components 633.

As shown in FIGS. 19A-20A, with the top 614 removed and the front panel 616 open, an operator has easy access to many of the components of the disposable 634 and multiple use 650 modules. For example, the operator may install, remove and view the levels of the nutrient 116 and preservative 118 supplies of the nutritional subsystem 115. The operator may also control operation of the nutrient 116 and preservative 118 infusion pump 182. The operator may also cannulate an organ, such as the heart 102, into the organ chamber assembly 104. As described in detail below with reference to FIGS. 21A-21C, this configuration also provides the operator with sufficient access to install and/or remove the single use module 634 to/from the multiple use module 650.

FIG. 20A shows a front perspective view of the multiple use module 650 with the single use module 634 removed. As shown, the multiple use module 650 includes: the cart 604; the lower section 602b of the housing 602, along with all of the components externally mounted to it, along with those contained therein (described in further detail below, with reference to FIGS. 21A-21C and 23A-23C); the upper section 602a of the housing 602 and all of the components externally mounted to it, including the top cover 614, the handles 610, 612a, and 612b, and the front panel 616; the operator interface module 146; and the perfusion fluid pump motor assembly 106. As described in detail below with reference to FIGS. 21A-21C, the multiple use module 650 also includes a bracket assembly 638 for receiving and locking into place the single use module 534.

Figure 22A:
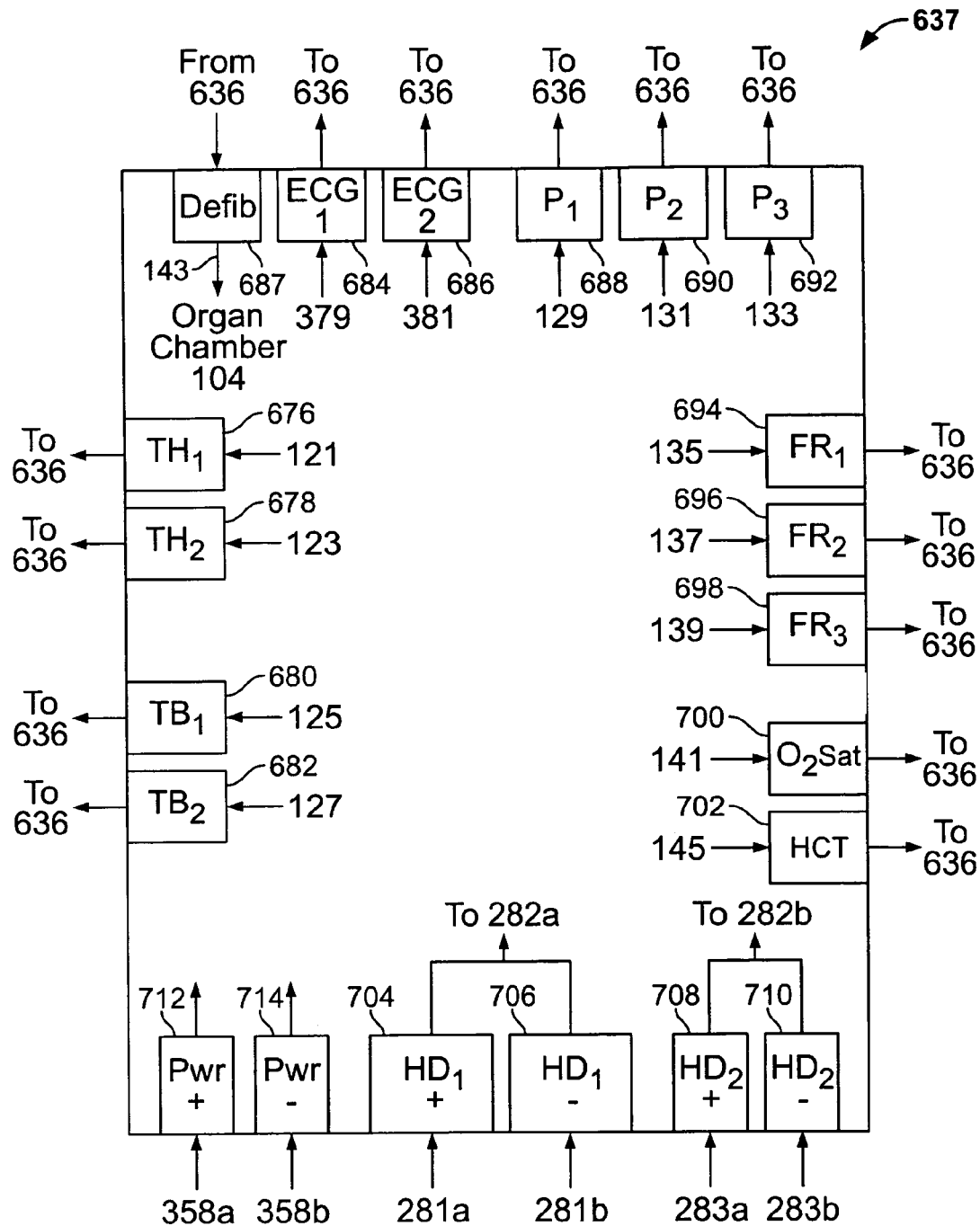
FIGS. 22A-22C show exemplary mechanisms for automatically making electro-optical interconnections between the single use disposable module and the multiple use module during the installation of FIGS. 21B and 21C.

As shown in FIG. 20A and described in further detail below with reference to FIGS. 22A-22C, the multiple use module 650 also includes a front-end interface circuit board 636 for interfacing with a front-end circuit board (shown in FIG. 24D at 637) of the disposable module 634. As also described in detail with reference to FIGS. 22A-22C, power and drive signal connections between the multiple use module 650 and the disposable module 634 are made by way of corresponding electromechanical connectors 640 and 647 on the front end interface circuit board 636 and the front end circuit board 637, respectively. By way of example, the front-end circuit board 637 receives power for the disposable module 634 from the front-end interface circuit board 636 via the electromechanical connectors 640 and 647. The front end circuit board 637 also receives drive signals for various components (e.g., the heater assembly 110, and the oxygenator 114) from the controller 150 via the front-end interface circuit board 636 and the electromechanical connectors 640 and 647. The front-end circuit board 637 and the front-end interface circuit board 636 exchange control and data signals (e.g., between the controller 150 and the disposable module 134) by way of optical connectors (shown in FIG. 22B at 648). As described in more detail with reference to FIGS. 22A-22F, the connector configuration employed between the front-end 637 and front-end interface 636 circuit boards ensures that critical power and data interconnections between the single and multiple use modules 634 and 650, respectively, continue to operate even during transport over rough terrain, such as may be experienced during organ transport.

As shown in FIG. 20A, according to another feature, the upper section 602a of the housing 602 includes a fluid tight basin 652, which is configured to capture any perfusion fluid 108 and/or nutritional 116 and/or preservative 118 solution that may inadvertently leak. The basin 652 also prevents any leaked fluid 108 or solution 116/118 from passing into the lower section 602b of the housing 602. In this way, the basin 652 shields the electronic components of the system 100 from any such leaked fluid 108 or solution 116/118. Shielded components include, for example, the power board 720 shown in and discussed in further detail below with reference to FIGS. 23C and 23D. The basin 652 includes a section 658, which extends over and shields the perfusion fluid pump 106 from any inadvertently leaked fluid. According to another feature, the basin 652 is sized to accommodate the entire volume of perfusion fluid 108 (including the maintenance solutions 116/118) contained within the system 100 at any particular time.

Figure 20B:
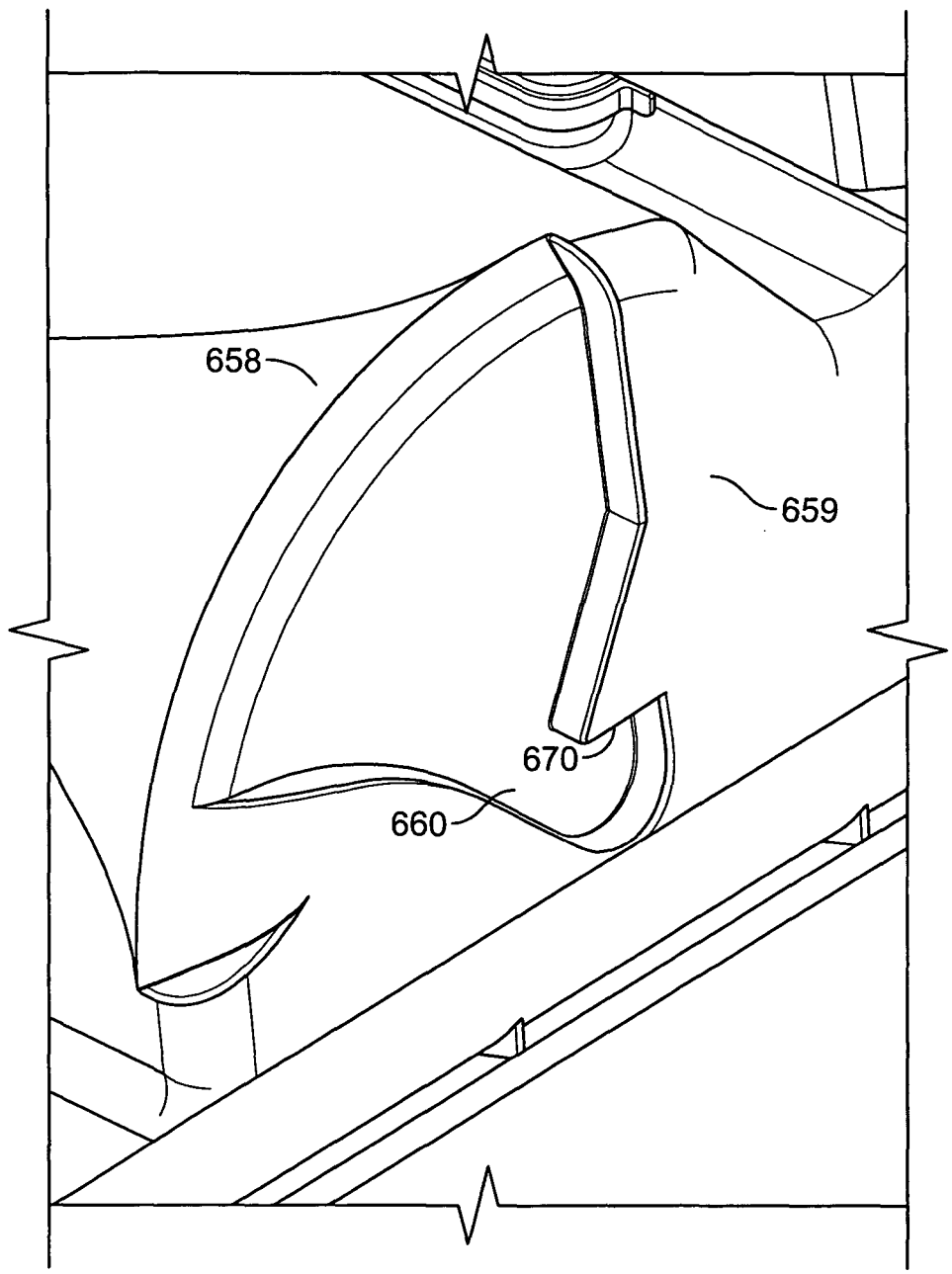
FIG. 20B is a side view of a slot formed in a basin of the multiple use module of FIG. 20A for engaging with a corresponding projection in the single use disposable module.

Referring also to FIG. 20B, according to a further feature of the illustrative embodiment, an outer side 659 of the pump covering portion 658 of the basin 652 includes a slot 660. As described in further detail below with reference to FIGS. 21A-21C and 24A, the slot 660 engages with a projection 662 on the single use module 634 during installation of the single use module 634 into the multiple use module 650.

Figure 21A:
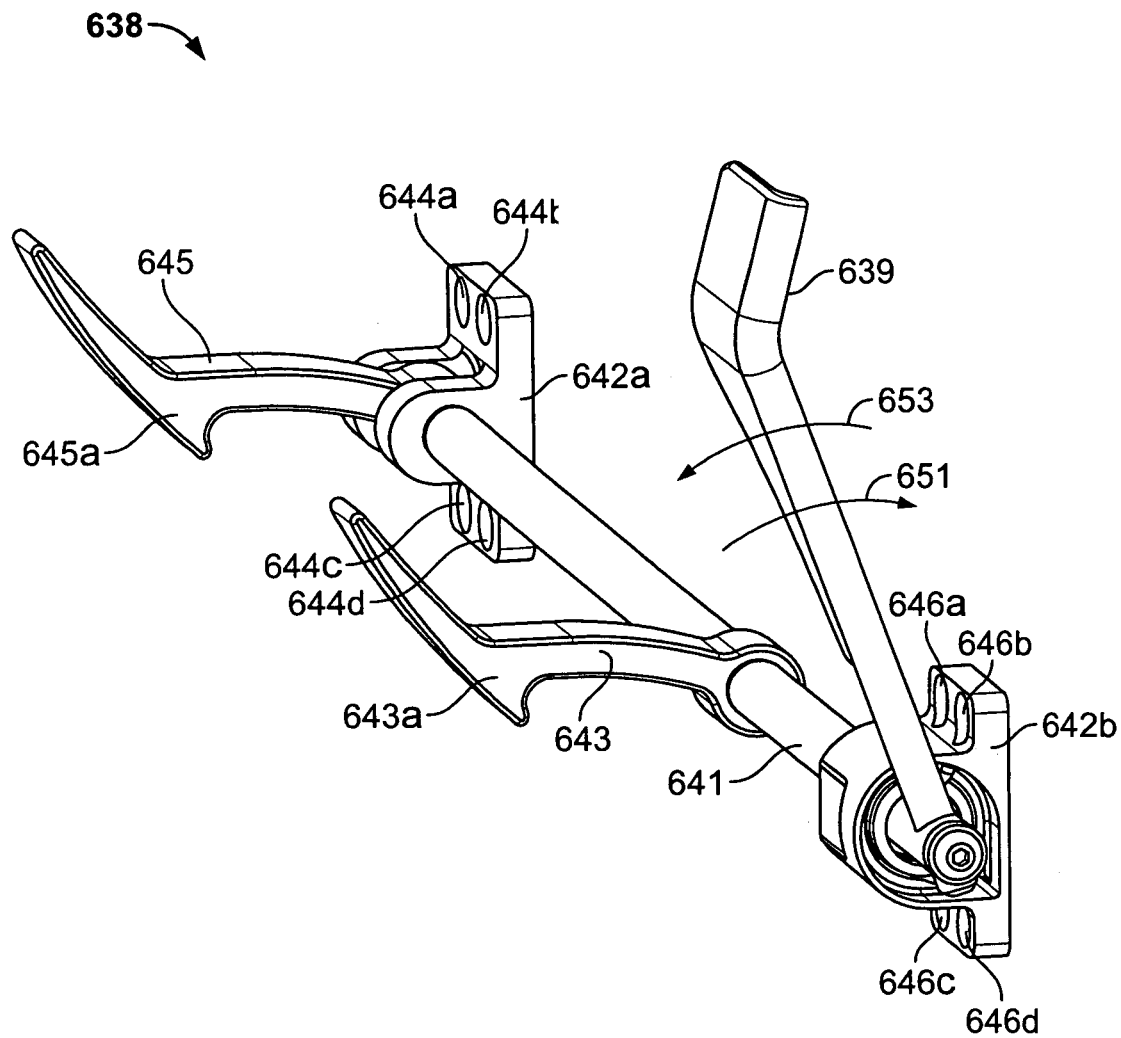
FIG. 21A shows a mounting bracket for receiving and locking into place the single use disposable module within the multiple use module of FIG. 20A.
Figure 21B:
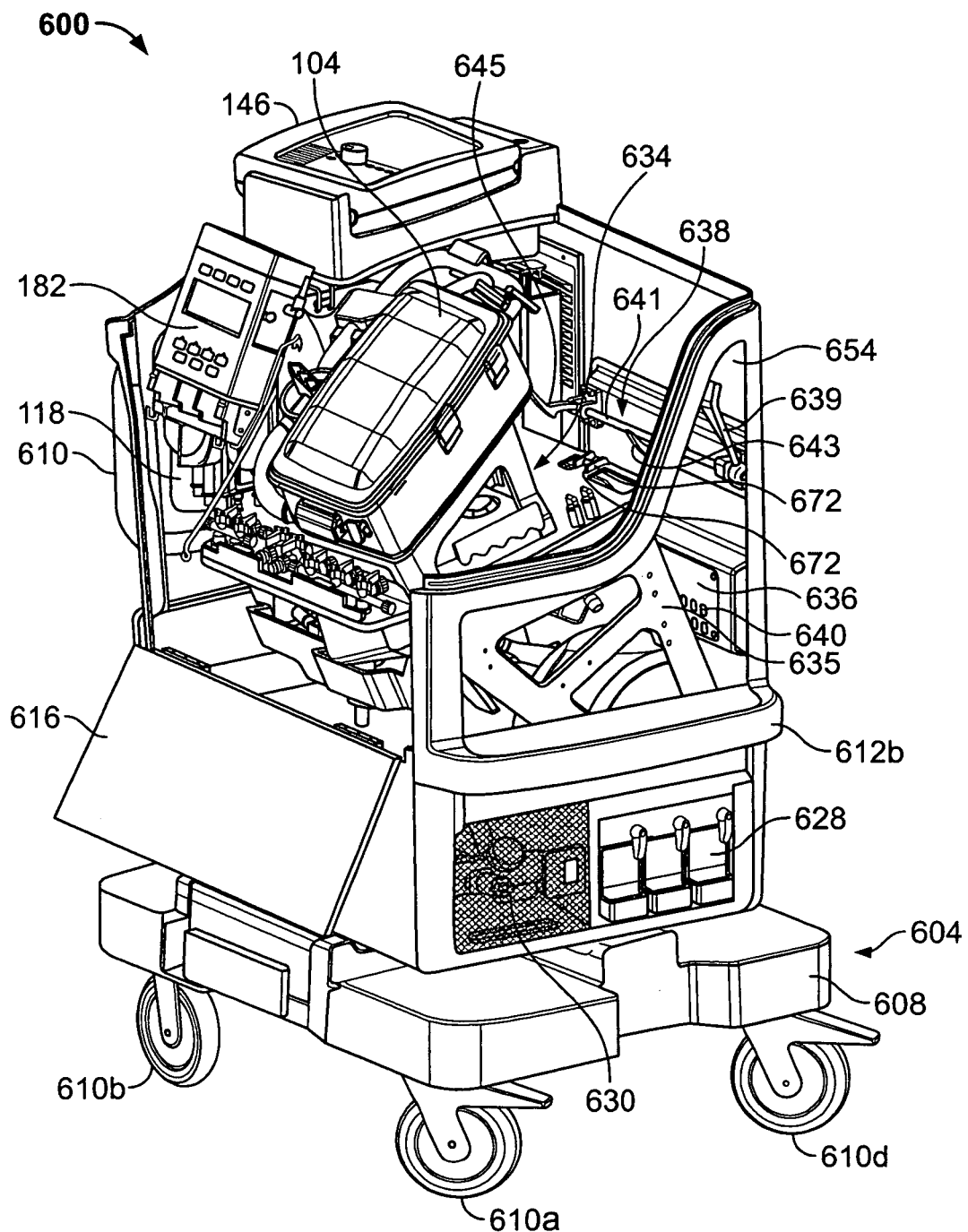
FIGS. 21B and 21C show installation of the single use disposable module into the multiple use module using the mounting bracket of FIG. 21A according to an illustrative embodiment of the invention.
Figure 21C:
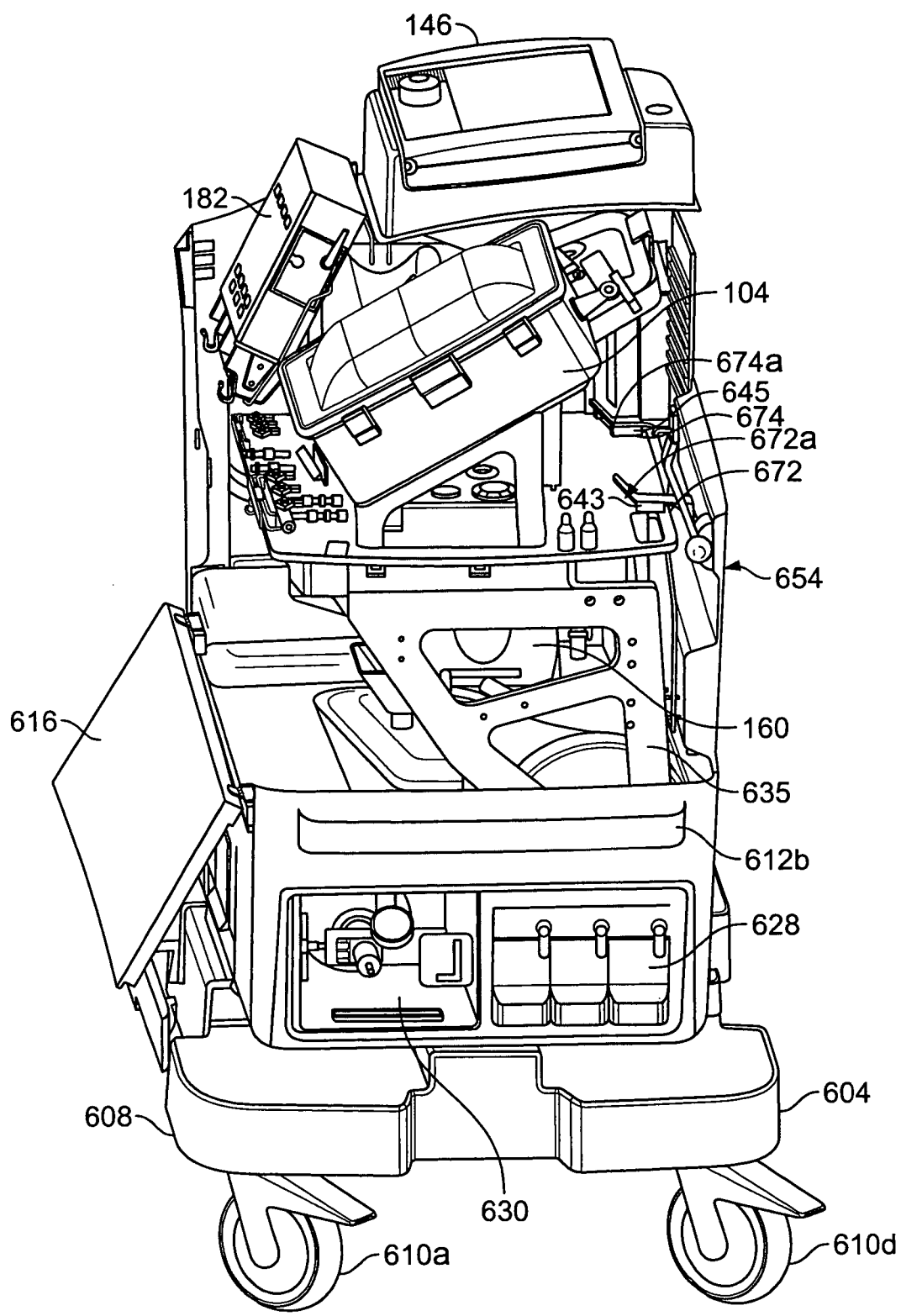

Turning now to the installation of the single use module 634 into the multiple use module 650, FIG. 21A shows a detailed view of the above-mentioned bracket assembly 638 located on the multiple use module 650 for receiving and locking into place the single use module 634. FIG. 21B shows a side perspective view of the single use module 634 being installed onto the bracket assembly 638 and into the multiple use module 650, and FIG. 21C shows a side view of the single use module 634 installed within the multiple use module 650. With reference to FIGS. 21A and 21B, the bracket assembly 638 includes two mounting brackets 642a and 642b, which mount to an internal side of a back panel 654 of the upper housing section 602a via mounting holes 644a-644d and 646a-646d, respectively. A cross bar 641 extends between and rotatably attaches to the mounting brackets 642a and 642b. Locking arms 643 and 645 are spaced apart along and radially extend from the cross bar 641. Each locking arm 643 and 645 includes a respective downward extending locking projection 643a and 645b. A lever 639 attaches to and extends radially upward from the cross bar 641. Actuating the lever 639 in the direction of the arrow 651 rotates the locking arms 643 and 645 toward the back 606b of the housing 602. Actuating the lever 639 in the direction of the arrow 653 rotates the locking arms 643 and 645 toward the front 606a of the housing 602.

Figure 24A:
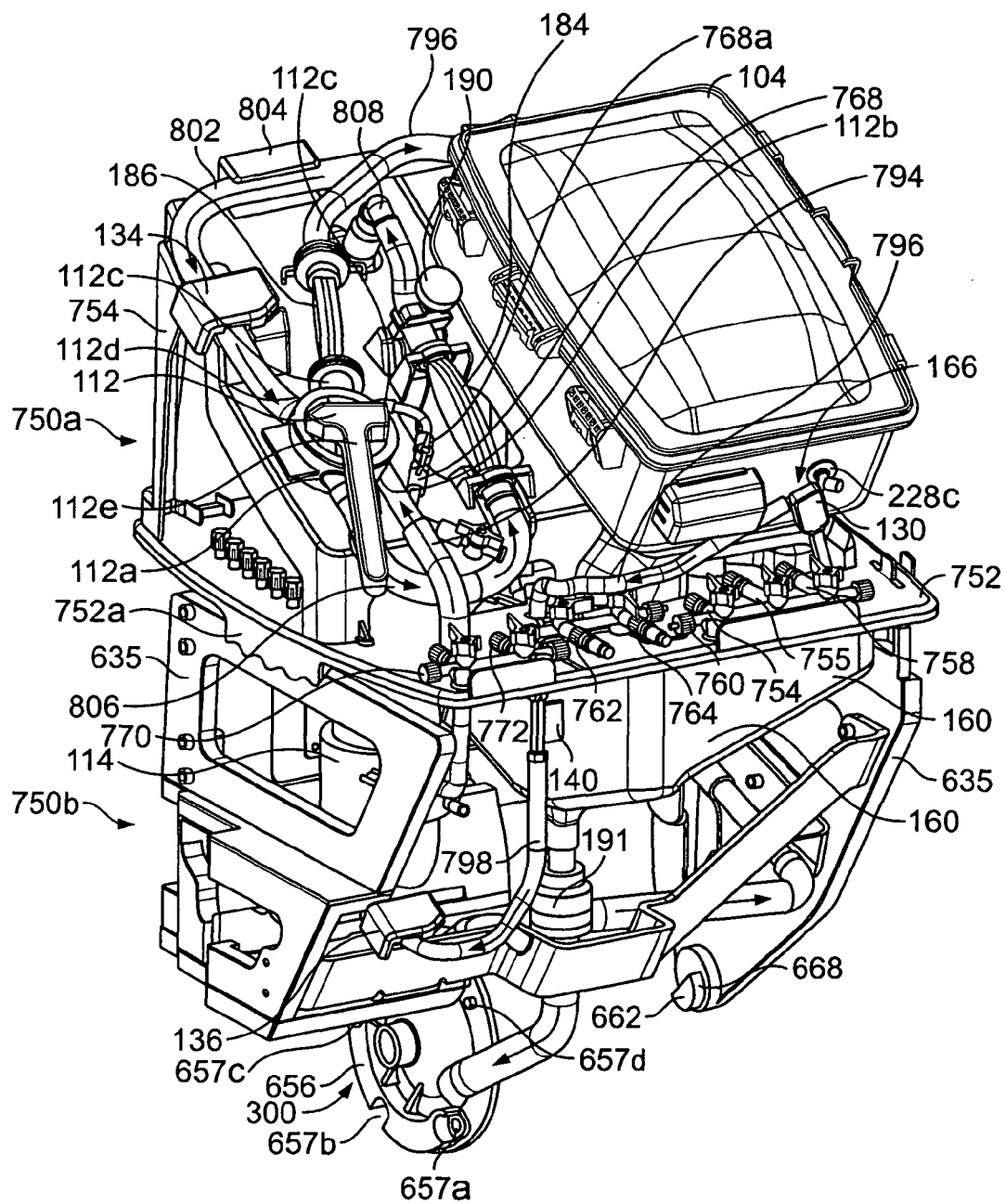
FIGS. 24A-24E show various top perspective views of a single use disposable module according to an illustrative embodiment of the invention.

As described above with respect to FIG. 10, the perfusion pump interface assembly 300 includes four projecting heat staking points 321a-321d. As shown in FIG. 24A, during assembly, the projections 321a-321d are aligned with corresponding apertures 657a-657d and heat staked through the apertures 657a-657d into the projections 321a-321d to rigidly mount the outer side 304 of the pump interface assembly 300 onto the C-shaped bracket 656 of the single use module chassis 635.

With reference to FIGS. 10, 20B, 21A, 21B and 24A, during installation, in a first step, the single use module 634 is lowered into the multiple use module 650 while tilting the single use module 634 forward (shown in FIG. 21B). This process slides the projection 662 of FIG. 24A into the slot 660 of FIG. 20B. As shown in FIG. 10, it also positions the flange 328 of the pump interface assembly 300 within the docking port 342 of the perfusion pump assembly 106, and the tapered projections 323a and 323b of the pump interface assembly 300 on the clockwise side of corresponding ones of the features 344a and 344b of the pump assembly bracket 346. In a second step, the single use module 634 is rotated backwards until locking arm cradles 672 and 674 of the single use module chassis 635 engage projections 643 and 645 of spring-loaded locking arm 638, forcing the projections 643 and 645 to rotate upward (direction 651), until locking projections 643a and 645a clear the height of the locking arm cradles 672 and 674, at which point the springs cause the locking arm 638 to rotate downward (direction 653), allowing locking projections 643a and 645a to releasably lock with locking arm cradles 672 and 674 of the disposable module chassis 635. This motion causes the curved surface of 668 of the disposable module chassis projection 662 of FIG. 24A to rotate and engage with a flat side 670 of the basin slot 660 of FIG. 20B. Lever 639 can be used to rotate the locking arm 638 upwards (direction 651) to release the single use module 635.

As shown in FIG. 10, this motion also causes the pump interface assembly 300 to rotate in a counterclockwise direction relative to the pump assembly 106 to slide the flange 328 into the slot 332 of the docking port 342, and at the same time, to slide the tapered projections 323a and 323b under the respective bracket features 344a and 344b. As the tapered projections 323a and 323b slide under the respective bracket features 344a and 344b, the inner surfaces of the bracket features 344a and 344b engage with the tapered outer surfaces of the tapered projections 323a and 323b to draw the inner side 306 of the pump interface assembly 300 toward the pump driver 334 to form the fluid tight seal between the pump interface assembly 300 and the pump assembly 106. The lever 639 may lock in place to hold the disposable module 634 securely within the multiple use module 650.

As mentioned briefly above with reference to FIG. 20A, interlocking the single use module 374 into the multiple use module 650 forms both electrical and optical interconnections between the front end interface circuit board 636 on the multiple use module 650 and the front end circuit board 637 on the single use module 634. The electrical and optical connections enable the multiple use module 650 to power, control and collect information from the single module 634. FIG. 22A is a conceptual drawing showing various optical couplers and electromechanical connectors on the front end circuit board 637 of the single-use disposable module 634 used to communicate with corresponding optical couplers and electromechanical connectors on the front end interface circuit board 636 of the multiple use module 650. Since this correspondence is one for one, the various optical couplers and electromechanical connectors are described only with reference to the front end circuit board 637, rather than also depicting the front end circuit board 650.

According to the illustrative embodiment, the front end circuit board 637 receives signals from the front end interface circuit board 636 via both optical couplers and electromechanical connectors. For example, the front end circuit board 637 receives power 358 (also shown in FIG. 14) from the front end interface circuit board 636 via the electromechanical connectors 712 and 714. The front end circuit board 637 the power to the components of the single use module 634, such as the various sensors and transducers of the single use module 634. Optionally, the front end circuit board 637 converts the power to suitable levels prior to distribution. The front end interface circuit board 636 also provides the heater drive signals 281a and 281b of FIG. 13 to the applicable connections 282a on the heater 246 of FIG. 6E via the electromechanical connectors 704 and 706. Similarly, the electromechanical connectors 708 and 710 couple the heater drive signals 283a and 283b of FIG. 13 to the applicable connections in 282b of the heater 248. The front-end circuit board 637 may receive a defibrillation command from the front end interface circuit board 636 via the electromechanical connector 687. In response, the front end circuit board 637 generates the defibrillation signal 143 having suitable current and voltage levels, and as shown in FIG. 5E, couples the signal 143 to the organ chamber assembly 104 via the electrical interface connections 235a-235b.

In another illustrative embodiment, the defibrillation command can be provided from an external source (not shown), rather than through the circuit board 636. As an example, and with reference to FIG. 5E and FIG. 1, an external defibrillation device can be plugged into the electrical coupler 613 shown in FIG. 24E, which is connected to the electrical interface connections 235a-235b. The external defibrillation device sends a defibrillation signal 143 through the coupler 613 and the interface connections 235a and 235b to electrodes 142 and 144. The electrodes 142 and 144 then deliver the signal 143 to the heart 102. This alternative embodiment allows the user to provide defibrillation (and pacing) without passing the signal 143 through the circuit boards 618, 636, and 637. An exemplary external defibrillation device may include the Zoll M-Series Portable Defibrillator.

According to the illustrative embodiment, the front end circuit board 637 receives signals from temperature, pressure, fluid flow-rate, oxygentation/hematocrit and ECG sensors, amplifies the signals, converts the signals to a digital format and provides them to the front-end interface circuit board 636 by way of optical couplers. For example, the front end circuit board 637 provides the temperature signal 121 from the sensor 120 on the heater plate 250 (shown in FIGS. 6A and 13) to the front end interface circuit board 636 by way of the optical coupler 676. Similarly, the front end circuit board 637 provides the temperature signal 123 from the sensor 122 on the heater plate 252 (shown in FIGS. 6A and 13) to the front end interface circuit board 636 by way of the optical coupler 678. The front end circuit board 637 also provides the perfusion fluid temperature signals 125 and 127 from the thermistor sensor 124 (shown in FIGS. 6A and 13) to the front end interface circuit board 636 via respective optical couplers 680 and 682. Perfusion fluid pressure signals 129, 131 and 133 are provided from respective pressure transducers 126, 128 and 130 to the front end interface circuit board 636 via respective optical couplers 688, 690 and 692. The front end circuit board 637 also provides perfusion fluid flow rate signals 135, 137 and 139 from respective flow rate sensors 134, 136 and 138 to the front end interface circuit board 636 by way of respective optical couplers 694, 696 and 698. Additionally, the front end circuit board 637 provides the oxygen saturation 141 and hematocrit 145 signals from the oxygen saturation sensor 140 to the front end interface circuit board 636 by way of respective optical couplers 700 and 702.

In other illustrative embodiments, one or more of the foregoing sensors are wired directly to the main system board 718 (described below with reference to FIG. 23D) for processing and analysis, thus by-passing the front-end interface board 636 and front-end board 637 altogether. Such embodiments may be desirable where the user prefers to re-use one or more of the sensors prior to disposal. In one such example, the flow rate sensors 134, 136 and 138 and the oxygen and hematocrit sensor 140 are electrically coupled directly to the system main board 718 through electrical coupler 611 shown in FIG. 23C, thus by-passing any connection with the circuit boards 636 and 637.

As described above with respect to FIGS. 11-16, the controller 150 employs the signals provided to the front end interface circuit board 636, along with other signals, to transmit data and otherwise control operation of the system 100. As described with respect to FIGS. 17A-17J, the controller 150 also displays sensor information, and may display to the operator various alarms relating to the sensor information by way of the operator interface module 146.

Figure 22B:
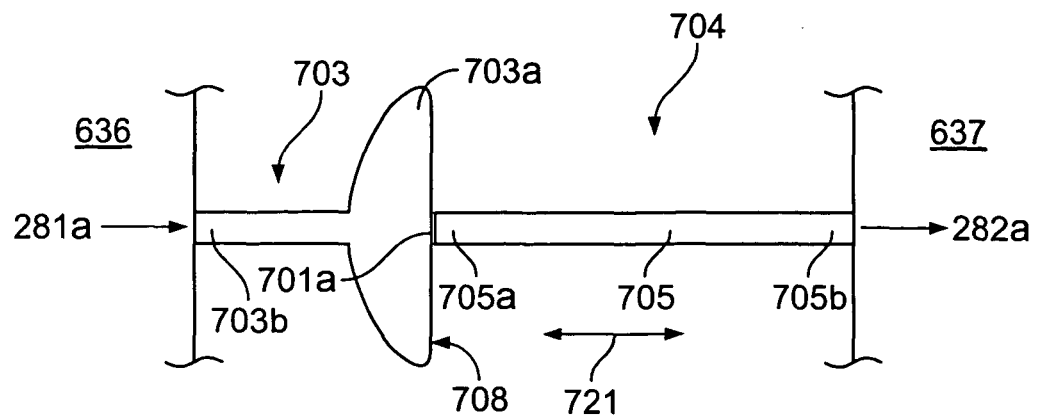
Figure 22C:
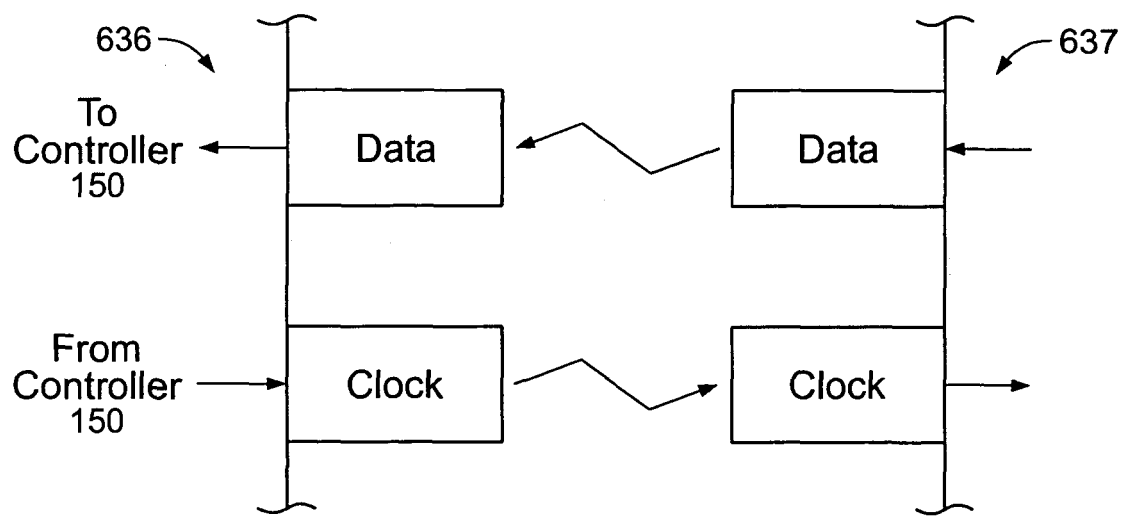

FIG. 22B illustrates the operation of an exemplary electromechanical connector pair of the type employed for the electrical interconnections between the circuit boards 636 and 637. Similarly, FIG. 22C illustrates the operation of an optical coupler pair of the type employed for the optically coupled interconnections between the circuit boards 636 and 637. One advantage of both the electrical connectors and optical couplers employed is that they ensure connection integrity, even when the system 100 is being transported over rough terrain, for example, such as being wheeled along a tarmac at an airport, being transported in an aircraft during bad weather conditions, or being transported in an ambulance over rough roadways. Additionally, the optical couplers electrically isolate the temperature, pressure and ECG sensors from the rest of the system 100, which prevents a defibrillation signal from damaging the system 100. The power for the front end board 637 is isolated in a DC power supply located on the front end interface board 636.

As shown in FIG. 22B, the electromechanical connectors, such as the connector 704, include a portion, such as the portion 703, located on the front end interface circuit board 636 and a portion, such as the portion 705, located on the front end circuit board 637. The portion 703 includes an enlarged head 703a mounted on a substantially straight and rigid stem 703b. The head 703 includes an outwardly facing substantially flat surface 708. The portion 705 includes a substantially straight and rigid pin 705 including an end 705a for contacting the surface 708 and a spring-loaded end 705b. Pin 705 can move axially in and out as shown by the directional arrow 721 while still maintaining electrical contact with the surface 708 of the enlarged head 703a. This feature enables the single use module 634 to maintain electrical contact with the multiple use module 650 even when experiencing mechanical disturbances associated with transport over rough terrain. An advantage of the flat surface 708 is that it allows for easy cleaning of the interior surface of the multiple use module 650. According to the illustrative embodiment, the system 100 employs a connector for the electrical interconnection between the single use disposable 634 and multiple use 650 modules. An exemplary connector is part no. 101342 made by Interconnect Devices. However, any suitable connector may be used.

Optical couplers, such as the optical couplers 684 and 687 of the front end circuit board 637, are used and include corresponding counterparts, such as the optical couplers 683 and 685 of the front end interface circuit board 636. The optical transmitters and optical receiver portions of the optical couplers may be located on either circuit board 636 or 637. For example, in the case of the ECG signal 379, the optical transmitter 684 is located on the circuit board 637 for receiving the electrical signal 379 and optically coupling it to the optical receiver 683 on the circuit board 636. In the case where the defibrillator signal is transmitted through the circuit boards 636 and 637 (rather than directly to the main board 718), the optical transmitter 685 on the circuit board 636 optically couples the signal to the optical receiver 687 on the circuit board 637.

As in the case of the electromechanical connectors employed, allowable tolerance in the optical alignment between the optical transmitters and corresponding optical receivers enables the circuit boards 636 and 637 to remain in optical communication even during transport over rough terrain. According to the illustrative embodiment, the system 100 uses optical couplers made under part nos. SFH485P and/or SFH203PFA by Osram. However, any suitable coupler may be used.

The couplers and connectors facilitate the transmission of data within the system 100. The front-end interface circuit board 636 and the front-end board 637 transmit data pertaining to the system 100 in a paced fashion. As shown in FIG. 22C, circuit board 636 transmits to the front-end board 637 a clock signal that is synchronized to the clock on the controller 150. The front-end circuit board 637 receives this clock signal and uses it to synchronize its transmission of system data (such as temperatures, pressures, ECG, r-wave detection, or other desired information) with the clock cycle of the controller 150. This data is digitized by a processor on the front-end circuit board 637 according to the clock signal and a pre-set sequence of data type and source address (i.e. type and location of the sensor providing the data). The front-end interface circuit board 636 receives the data from the front-end board 637 and transmits the data set to the main board 618 for use by the controller 150 in evaluation, display, and system control, as described above with reference to FIGS. 11, 12 and 14. Additional optical couplers can be added between the multiple use module and single use module for transmission of control data from the multiple use module to the single use module, such data including heater control signals or pump control signals.

Figure 23A:
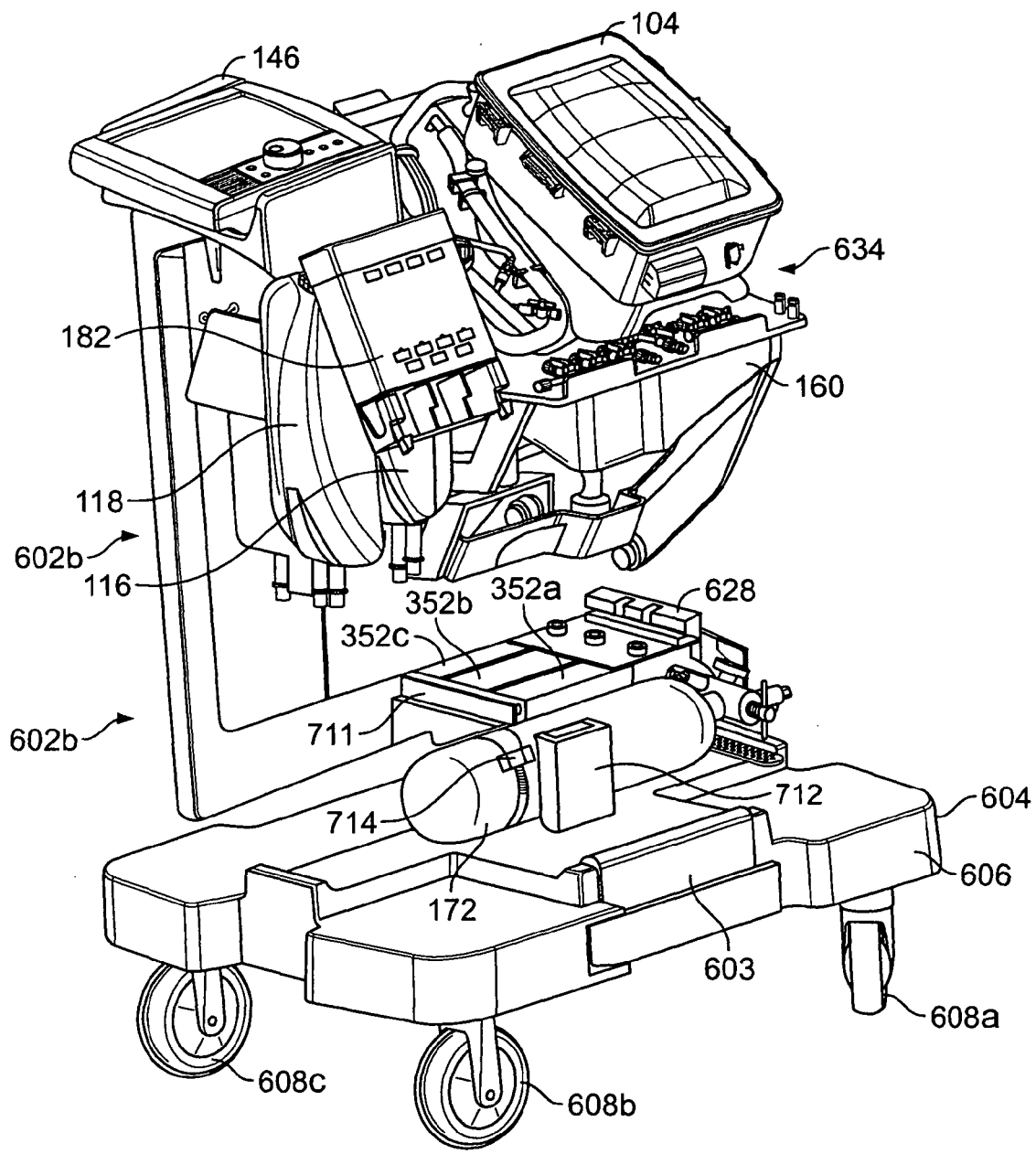
FIGS. 23A-23C show various views of the system of FIGS. 18A and 18B with all of the external walls removed according to an illustrative embodiment of the invention.
Figure 23B:
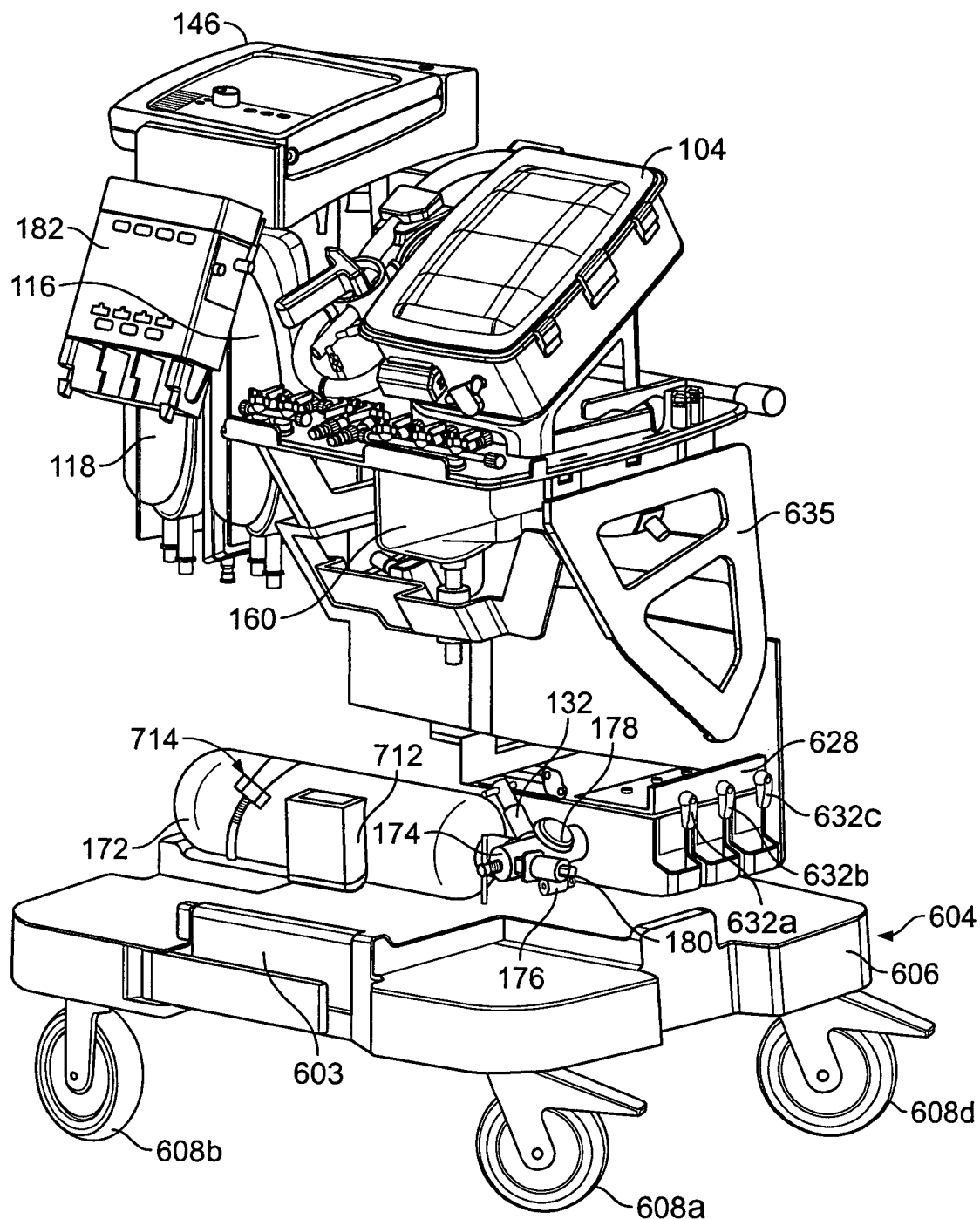

Having described the mechanical, electrical and optical interconnections between the single use module 634 and the multiple use module 650, additional components of the multiple use module 650 will now be discussed with respect to FIGS. 23A-23D, followed by a description of the mechanical arrangement of the components of the single use module 634 with respect to FIGS. 24A-28C. As shown in FIGS. 23A-23D, with the walls of the housing 602 removed, in addition to those components previously discussed, the multiple use module 650 includes an on-board gas supply 172, located in the lower section 602b of the housing 602. The gas supply 172 is depicted in FIGS. 23A-23D as a tank, positioned within the gas tank bay 630 by a support structure 712, which abuts the tank 172. Optionally, the gas supply 172 may be further secured within the gas tank bay 630 by a strap and buckle assembly 714 or other suitable mechanism. With particular reference to FIG. 23B and as described above with reference to FIG. 1, the gas supply 172 provides gas to the system 100 through the gas regulator 174 and the gas flow chamber 176. The gas pressure sensor 132 measures the gas pressure in the gas supply 172, and the gas pressure gauge 178 provides a visual indication of the fullness of the gas supply 172. Additionally, an electrical connection between the controller 150 and the gas flow chamber 176 enables the controller 150 to regulate automatically the gas flow into the oxygenator 114.

Figure 23C:
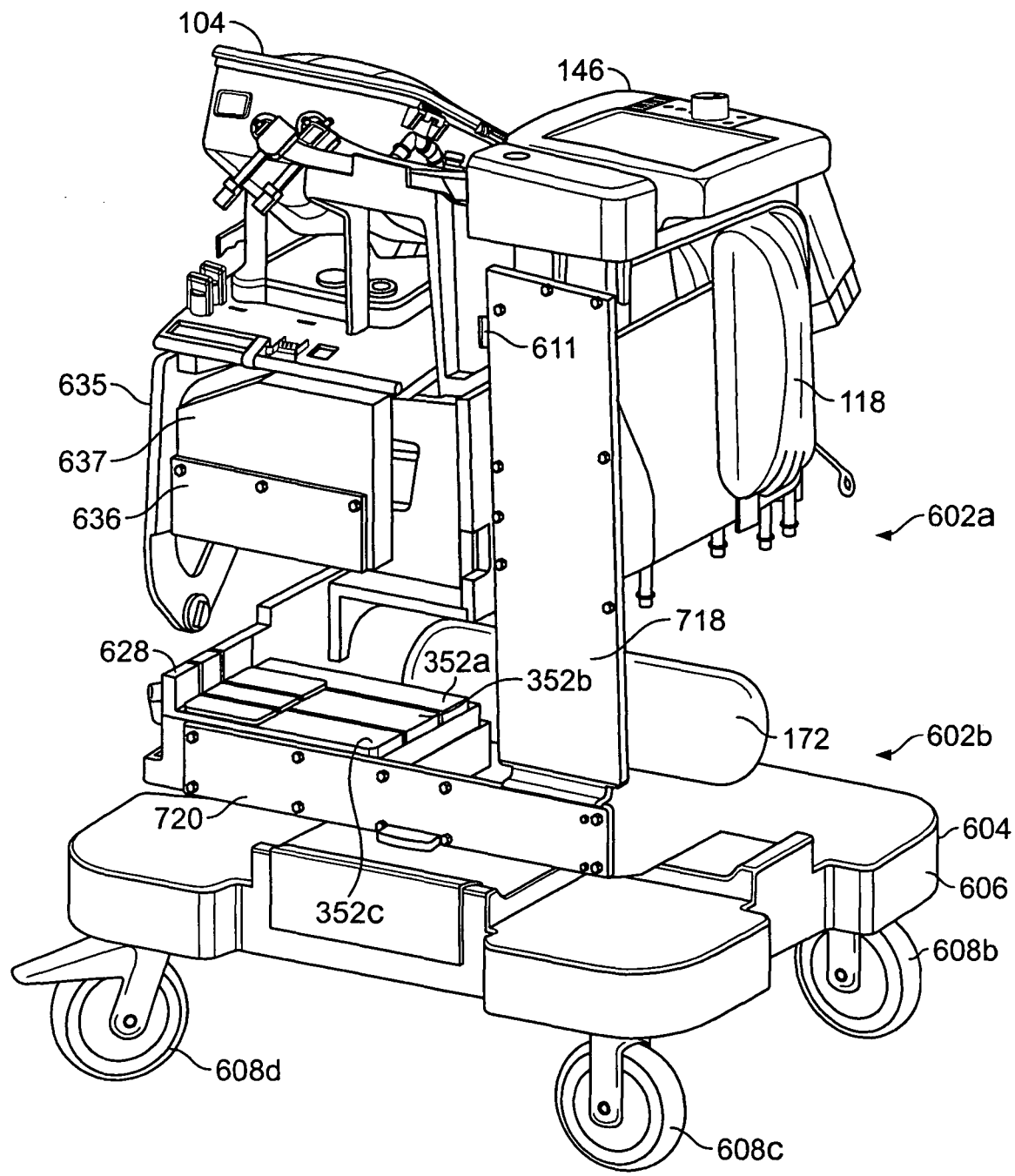

As shown most clearly in FIG. 23C, the battery bay 628 houses the batteries 352a-352c. As noted above with reference to FIG. 14, a lock-out mechanism is used to prevent more than one of the batteries 352a-352c from being removed from the battery bay 628 at a given time while the system 100 is operating.

Figure 23D:
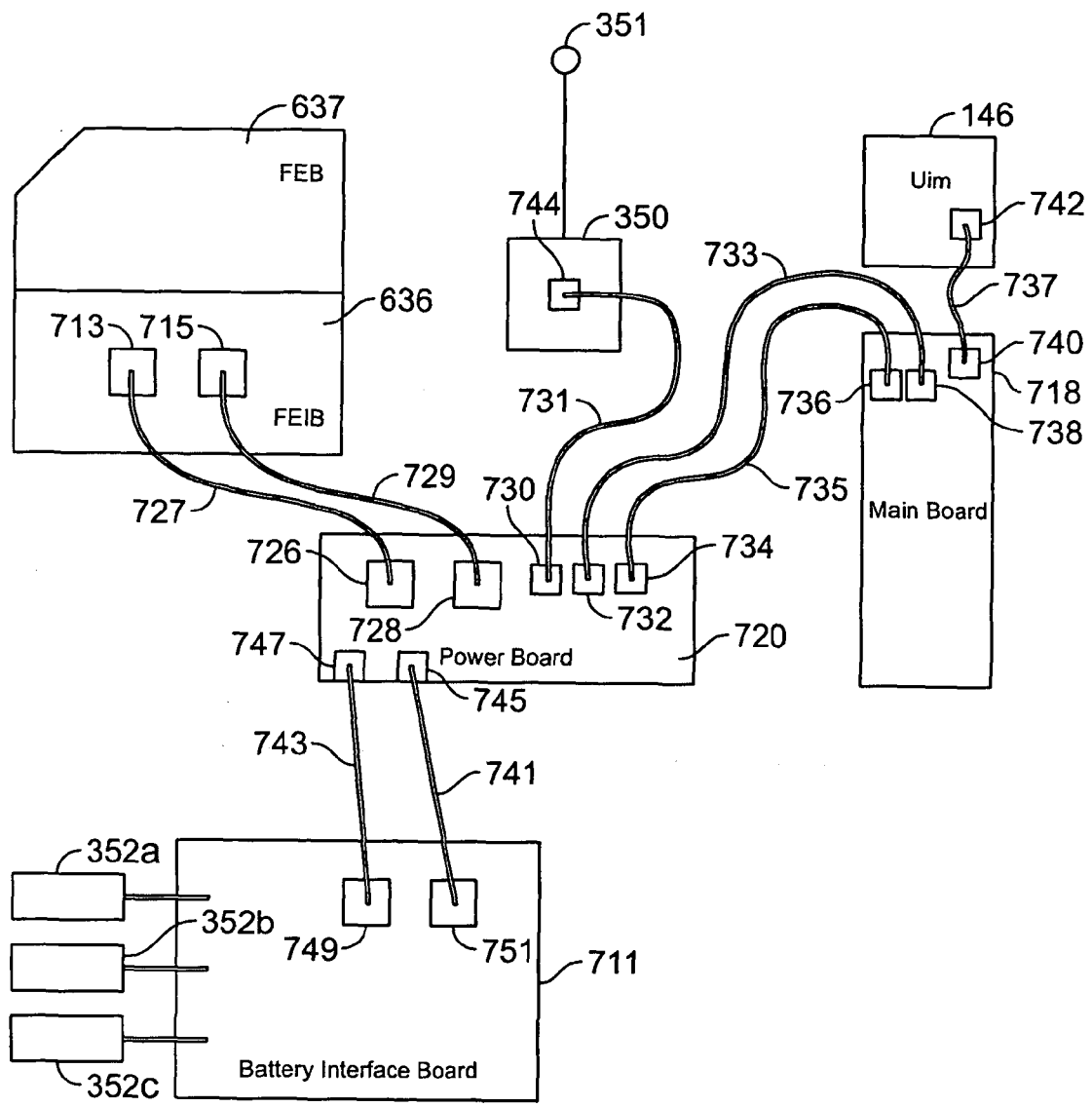
FIG. 23D is a conceptual diagram showing interconnections between the circuit boards of FIGS. 23A-23C according to an illustrative embodiment of the invention.

As discussed above, the system 100 includes a plurality of interconnected circuit boards for facilitating power distribution and data transmission to, from and within the system 100. Particularly, as discussed above with reference to FIGS. 22A-22E and as shown in FIG. 23C, the multiple use module 650 includes a front end interface circuit board 636, which optically and electromechanically couples to the front end circuit board 637 of the single use module 650. As also shown in FIG. 23C, the system 100 further includes a main board 718, a power circuit board 720, and a battery interface board 711 located on the multiple use module 650. The main board 718 is configured to allow the system 100 to be fault tolerant, in that if a fault arises in the operation of a given circuit board (as shown in FIG. 23D), the main board 718 saves pumping and heating parameters in non-volatile memory. When the system 100 reboots, it can re-capture and continue to perform according to such parameters.

Referring to the conceptual drawing of FIG. 23D, cabling 731 brings power (such as AC power 351) from a power source 350 to the power circuit board 720 by way of connectors 744 and 730. The power supply 350 converts the AC power to DC power and distributes the DC power as described above with reference to the power subsystem of FIG. 14. Referring also to FIGS. 14 and 22A, the power circuit board 720 couples DC power and a data signal 358 via respective cables 727 and 729 from the connectors 726 and 728 to corresponding connectors 713 and 715 on the front end interface circuit board 636. Cable 729 carries both power and a data signal to the front end interface board 636. Cable 727 carries power to the heater 110 via the front-end interface board 636. The connectors 713 and 715 interfit with corresponding connectors 712 and 714 (described above with respect to FIG. 22A) on the front end circuit board 637 on the single use module 634 to provide power to the single use module 634.

As shown in FIG. 23D, the power circuit board 720 also provides DC power 358 and a data signal from the connectors 732 and 734, respectively, on the power circuit board 720 to corresponding connectors 736 and 738 on the main circuit board 718 by way of the cables 733 and 735. Referring also to FIGS. 14 and 19A, the cable 737 couples DC power 358 and a data signal from a connector 740 on the main circuit board 718 to the operator interface module 146 by way of a connector 742 on the operator interface module cradle 623. The power circuit board 720 also provides DC power 358 and a data signal from connectors 745 and 747 via cables 741 and 743 to connectors 749 and 751 on a battery interface board 711. Cable 741 carries the DC power signal and cable 743 carries the data signal. Battery interface board 711 distributes DC power and data to batteries 352a, 352b and 352c. Batteries 352a, 352b and 352c contain electronic circuits that allow them to communicate with each other to monitor the respective charges, as described above in reference to FIG. 14, so that the controller 150 can monitor and control the charging and discharging of the batteries 352a-352c.

According to some illustrative embodiments, the controller 150 is located on the main circuit board 718 and performs all control and processing required by the system 100. However, in other illustrative embodiments, the controller 150 is distributed, locating some processing functionality on the front end interface circuit board 636, some on the power circuit board 720, and/or some in the operator interface module 146. Suitable cabling is provided between the various circuit boards, depending on whether and the degree to which the controller 150 is distributed within the system 100.

As described above with reference to FIGS. 19A-19C and 23A-23C, the system 100 mechanically divides into the single use disposable module 634 and the multiple use module 650. As also described above, according to the illustrative embodiment, the single use module 634 includes all or substantially all of the perfusion fluid 108 contacting elements/assemblies of the system 100, along with various peripheral components, flow conduits, sensors and support electronics for operating the blood contacting components. As discussed above with reference to FIGS. 22A and 23D, according to the illustrative embodiment, the module 634 does not include a processor, instead relying on the controller 150, which may, for example, be distributed between the front end interface circuit board 636, the power circuit board 720, the operator interface module 146, and the main circuit board 718, for control. However, in other illustrative embodiments, the single use module 634 may include its own controller/processor, for example, on the front end circuit board 637.

Referring to FIGS. 24A-28C, the single use module 634 will next be described in terms of the components included therein. After that, exemplary forward and retrograde flow modes are traced through the described components.

Figure 24B:
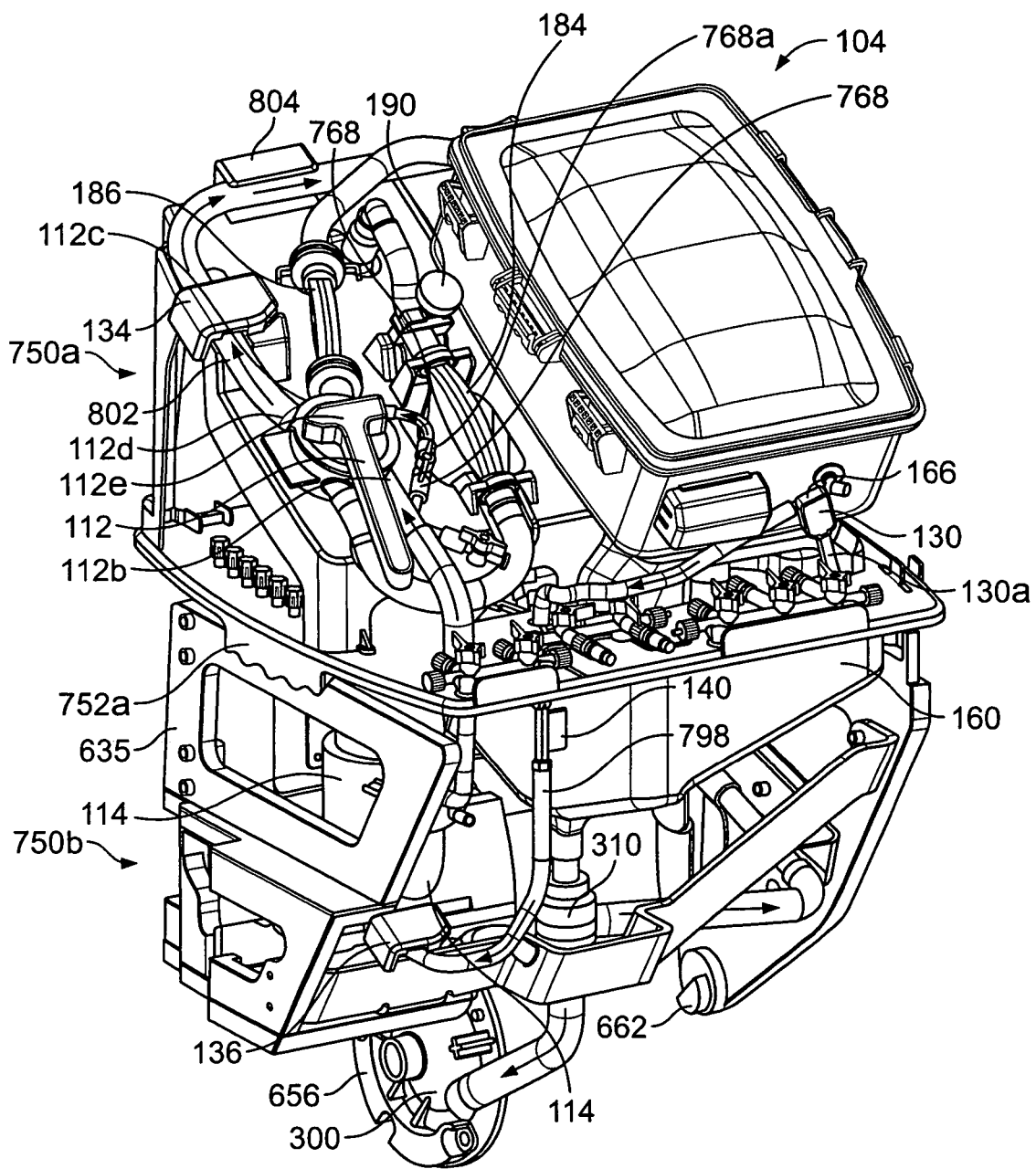
Figure 24C:
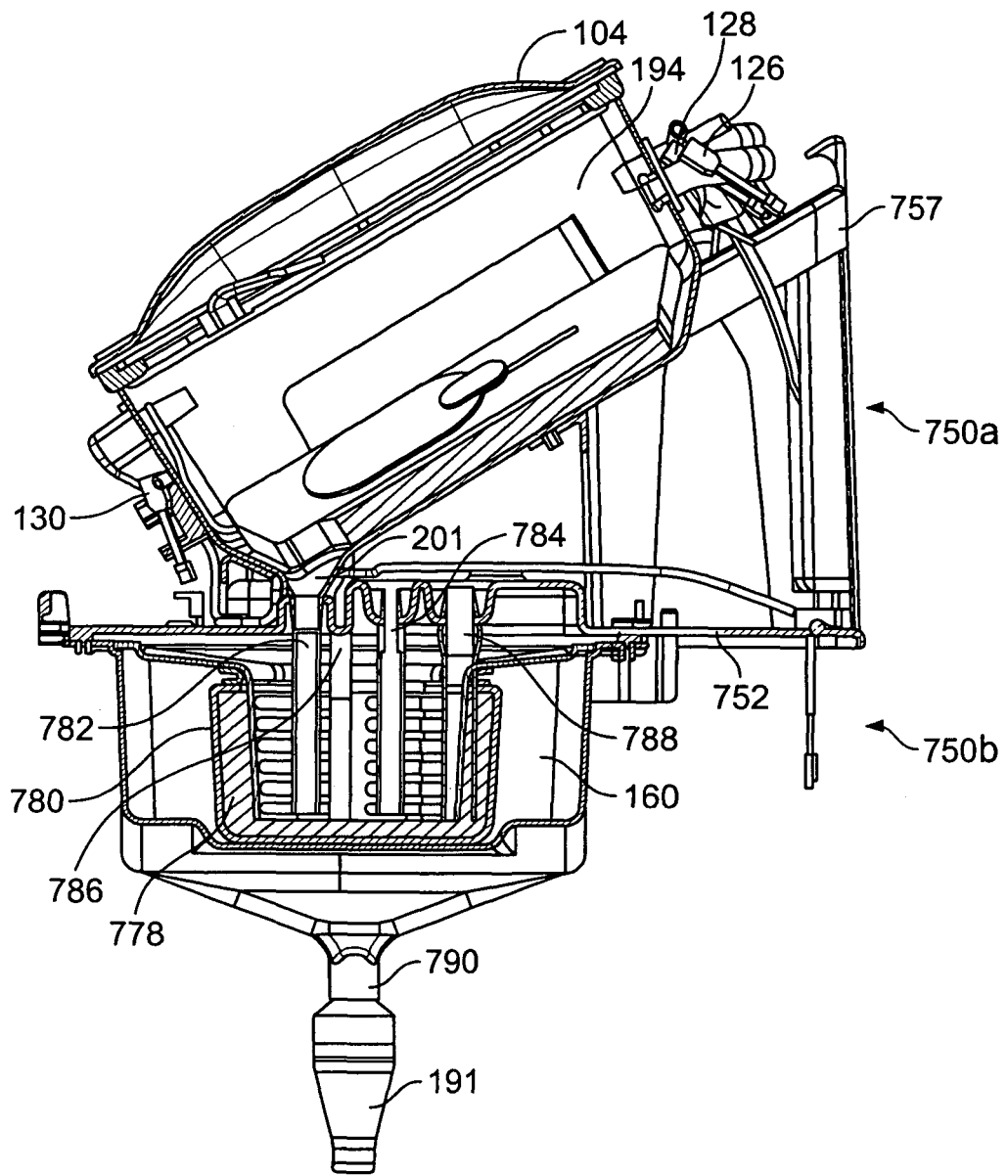
Figure 24D:
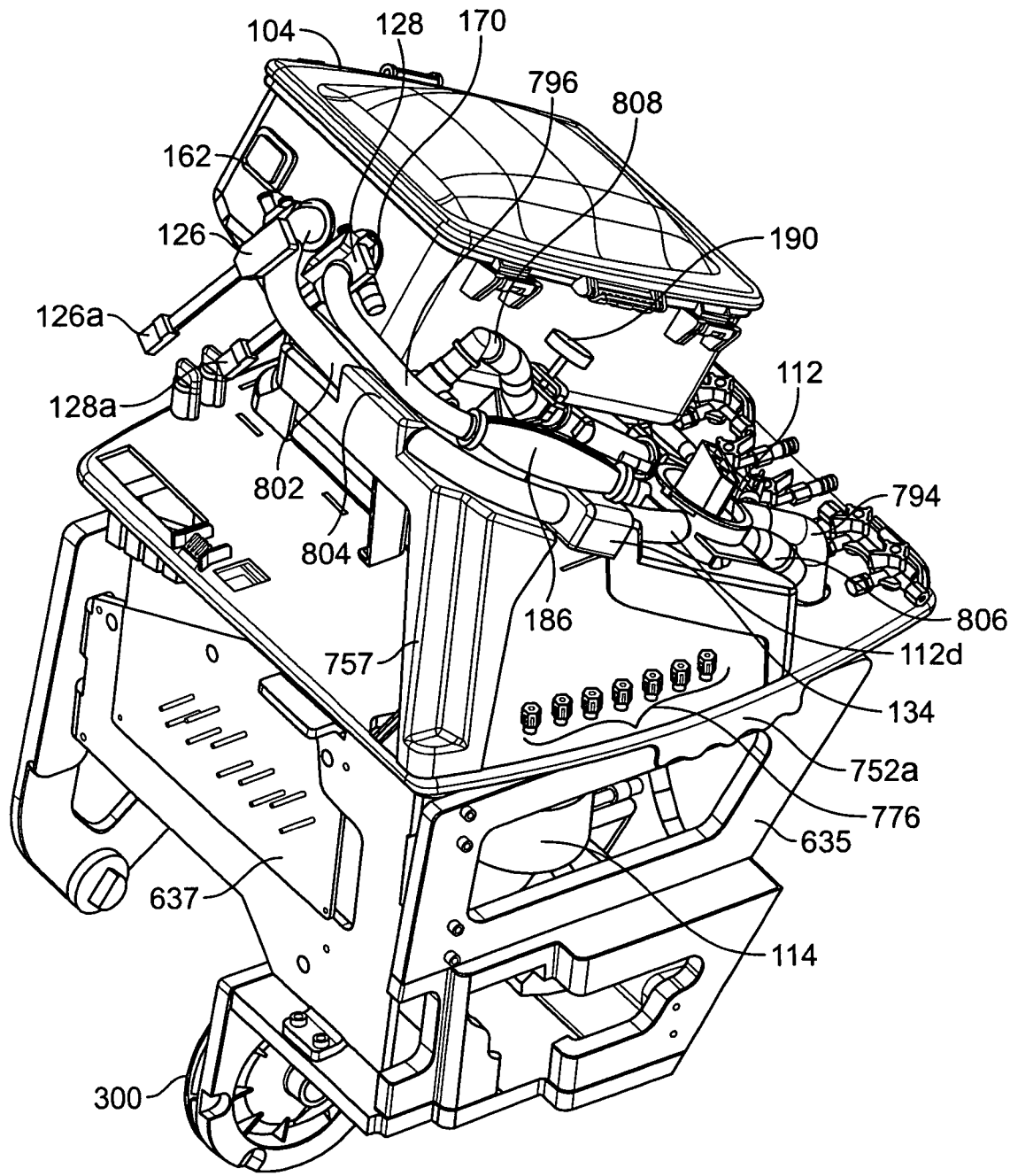
Figure 25A:
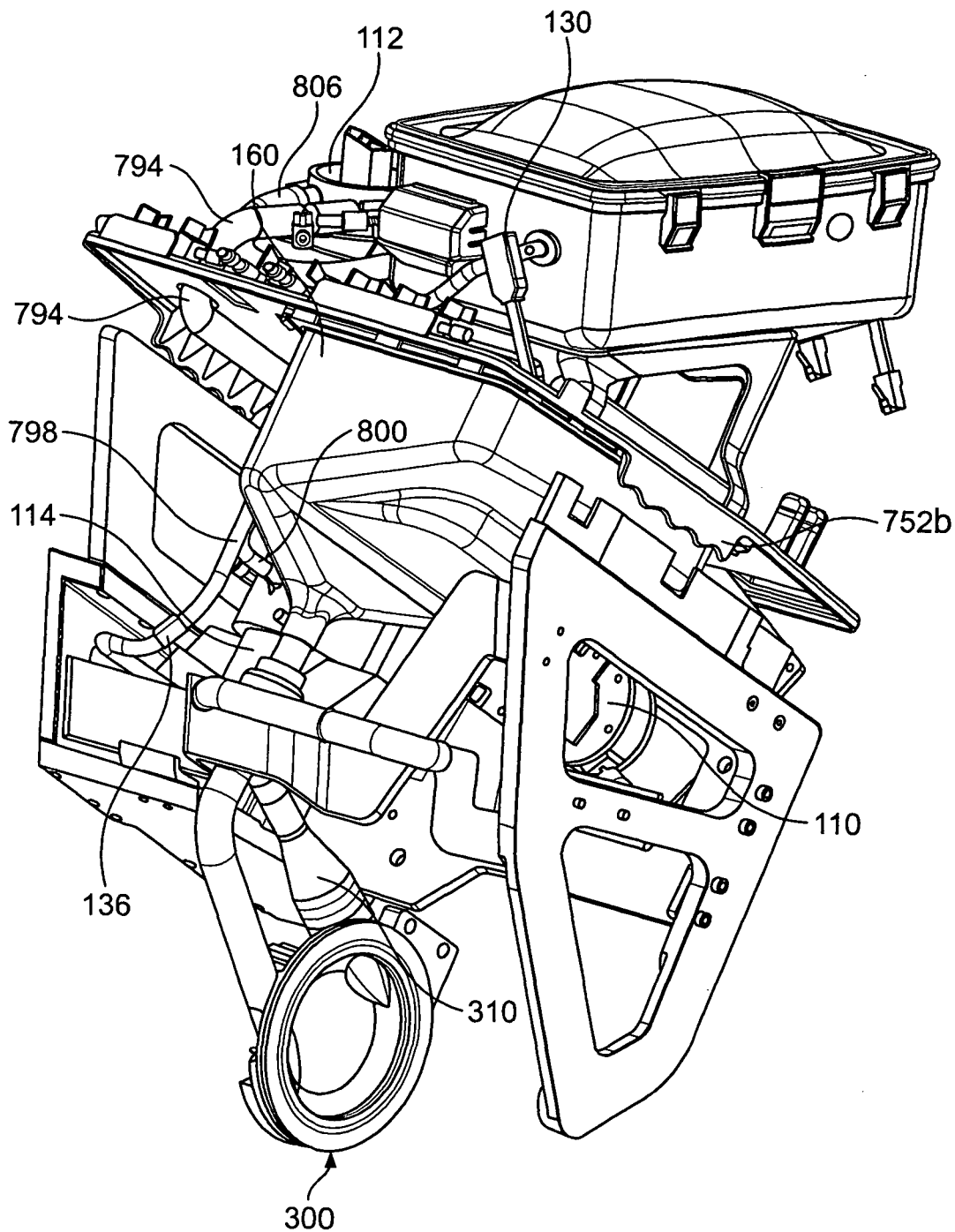
FIGS. 25A-25C show various bottom perspective views of the illustrative single use disposable module of FIGS. 24A-24D.
Figure 25B:
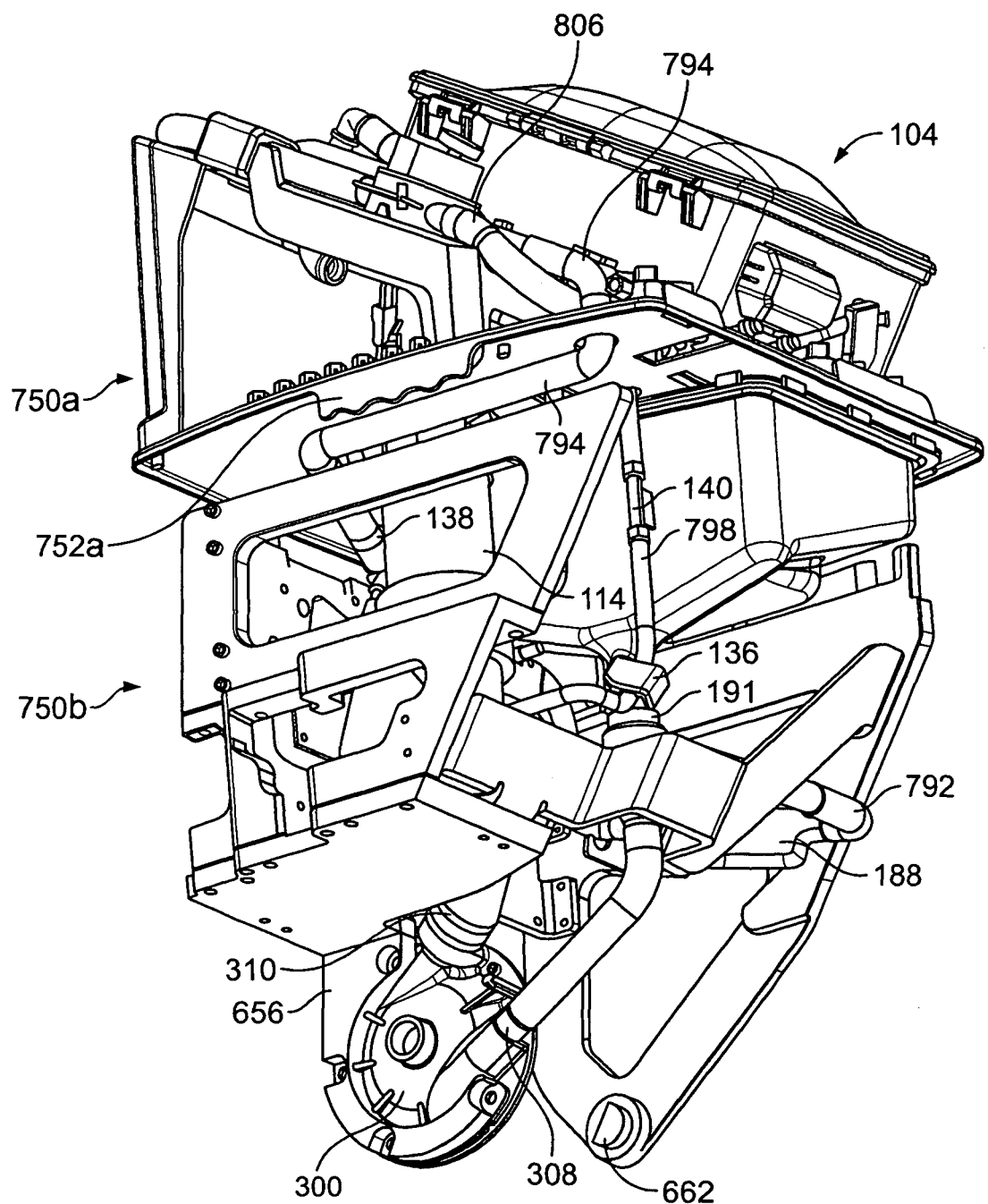
Figure 25C:
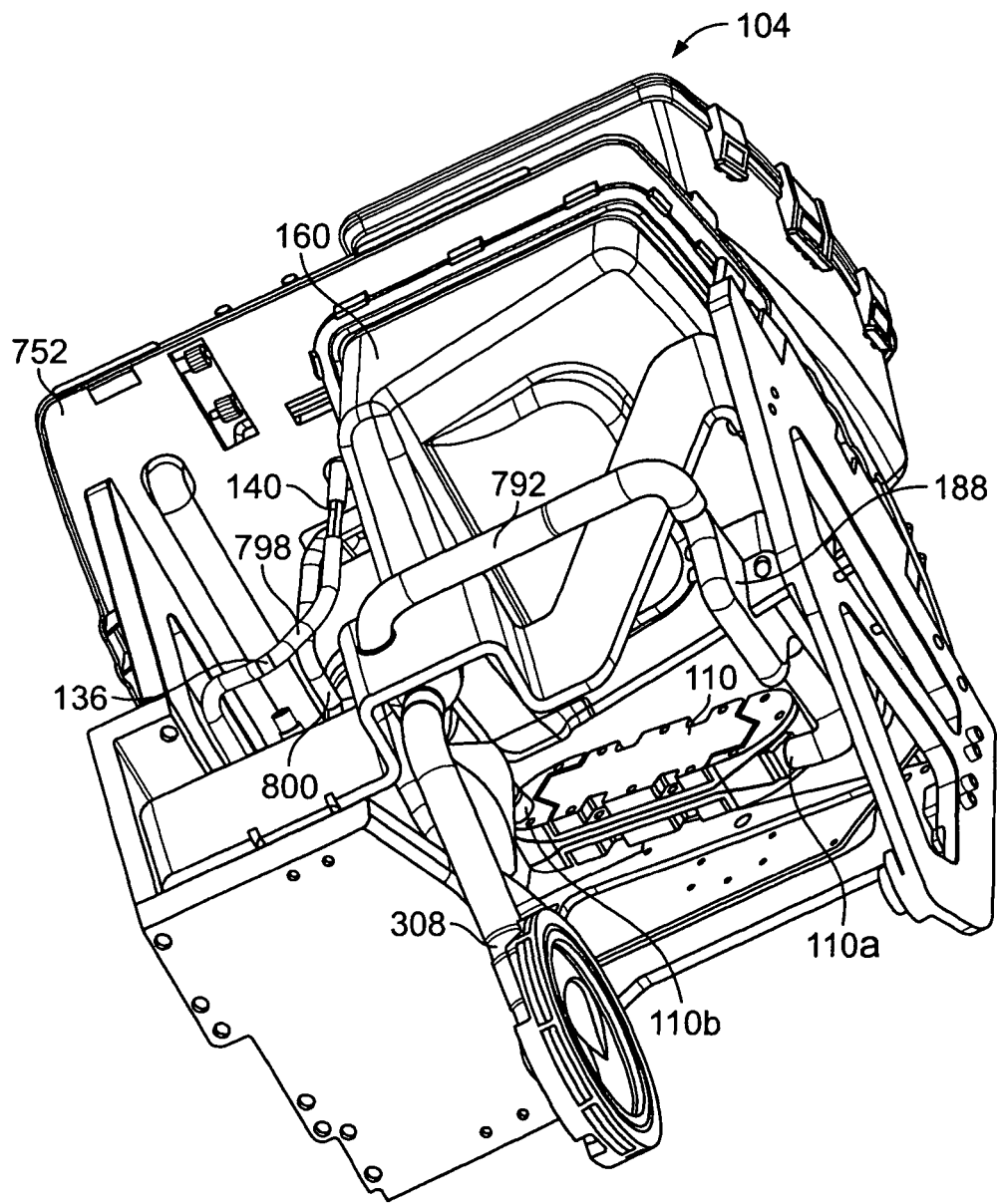

Referring first to FIG. 24A, the disposable module 634 includes a chassis 635 having upper 750a and lower 750b sections. The upper section 750a includes a platform 752 for supporting various components. The lower section 750b supports the platform 752 and includes structures for pivotably connecting with the multiple use module 650. More particularly, the lower chassis section 750b includes the C-shaped mount 656 for rigidly mounting the perfusion fluid pump interface assembly 300, and the projection 662 for sliding into and snap fitting with the slot 660 of FIG. 20B. The lower chassis section 750b also provides structures for mounting the oxygenator 114. As shown in FIGS. 25A and 25C, the lower section 750b further includes structures for mounting the heater assembly 110. Additionally, the reservoir 160 mounts to the underside of the platform 725 and extends into the lower chassis section 750b. Various sensors, such as the $O_2$ saturation and hematocrit sensor 140 (shown in FIG. 24A and described in detail below with reference to FIGS. 28A-28C), the flow rate sensor 136 (shown in FIG. 24A), the flow rate sensor 138 (shown in FIG. 25B), are located within and/or mount to the lower chassis section 750b. The flow pressure compliance chamber 188 (shown in FIG. 25B) is also located in the lower chassis section 750b. As shown in FIG. 24D, the lower chassis section 750b also mounts the front end circuit board 637. Conduits located in the lower chassis section 750b are described in further detail below with reference to the normal and retrograde flow paths through the single use module 634.

Referring to FIGS. 24A-25C, and as mentioned above, the upper chassis section 750a includes the platform 752. The platform 752 includes handles 752a and 752b formed therein to assist in installing and removing the single use module 634 from the multiple use module 650. Alternatively, such handles can be located on the platform 757 to allow for easier accessibility during installation of the single use module into the multiple use module. As shown most clearly in FIG. 24C, an angled platform 757 mounts onto the platform 752. The organ chamber assembly 104 mounts to the angled platform 757. According to the illustrative embodiment, with the single use module 634 installed within the multiple use module 650, the platform 757 is angled at about 10° to about 80° relative to horizontal, to provide an optimal angle of operation for the heart 102 when placed within the organ chamber assembly 104. In some illustrative embodiments, the platform 757 is angled at about 20° to about 60°, or about 30° to about 50° relative to horizontal. The flow mode selector valve 112, the flow rate sensor 134, and the perfusion fluid flow pressure compliance chambers 184 and 186 also mount onto the angled platform 757.

Figure 24E:
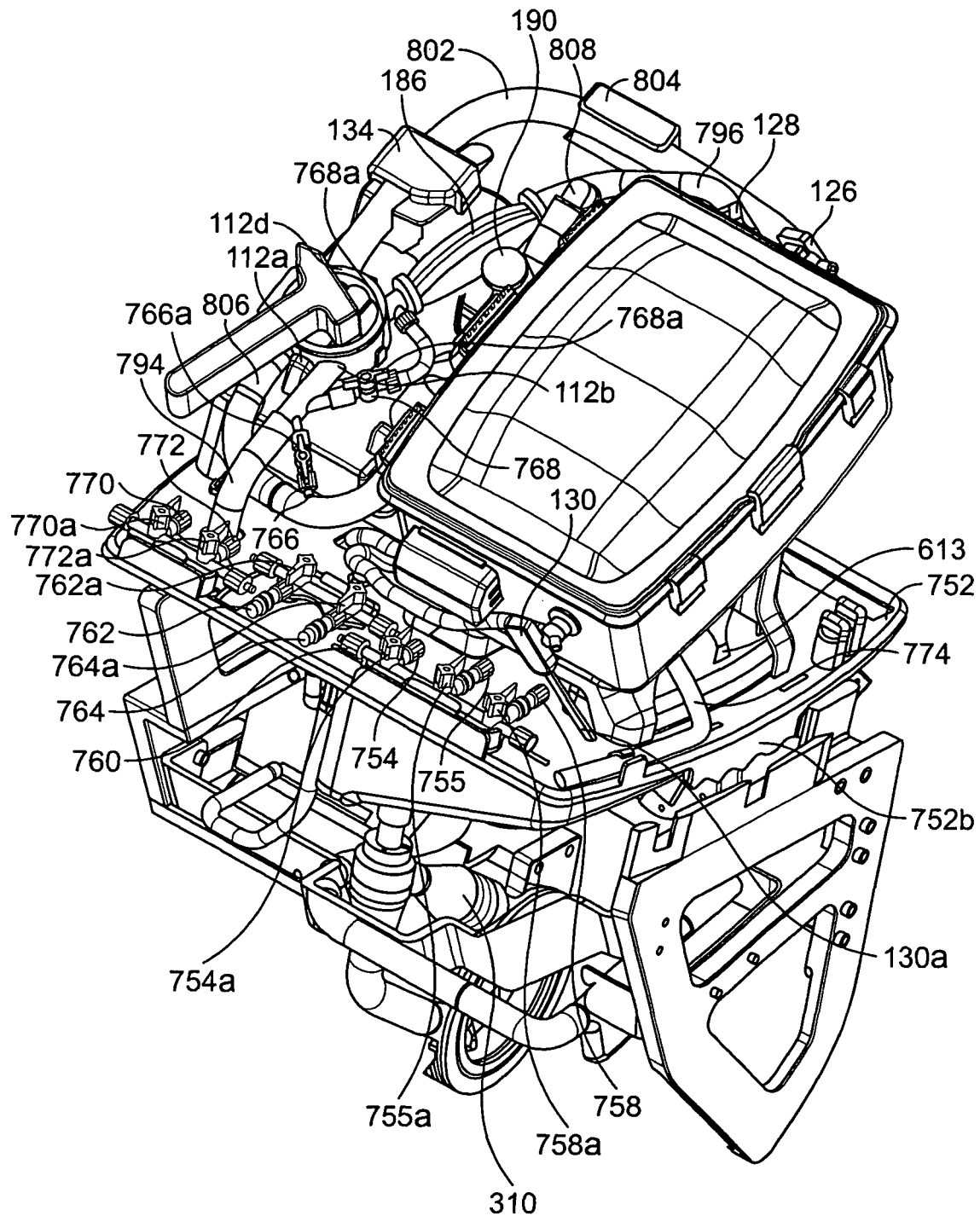

Referring to FIG. 24E, several fluid ports mount to the platform 752. For example, a fluid sampling port 754 enables an operator to sample the flow into and/or out of the aorta 158 via the cannulation interface 162 on the organ chamber assembly 104. A fluid sampling port 755 enables the operator to sample the flow into the left atrium 152 via the interface 170 on the organ chamber assembly 104. Additionally, a fluid port 758 enables the operator to sample the coronary flow out of the pulmonary artery 164 via the pulmonary artery interface 166 on the organ chamber 104. According to the illustrative embodiment, the operator turns the a respective valve 754a, 755a or 758a to obtain flow from the sampling ports 754, 755 and 758. Flow from the particular port selected is provided at a single common outlet 764. According to one feature, only flow from the left most port selected is provided at the outlet 764. By way of example, if the operator opens both ports 755 and 758, only flow from port 755 is provided at the outlet 764. In this way, system 100 reduces the likelihood of an operator mixing samples from multiple ports.

The single use module 634 also includes a general injection port 762, operable with the valve 762a, for enabling the operator to inject medication into the perfusion fluid 108, for example, via the reservoir 160. Both the sampling 764 and injection 762 ports mount to the platform 752. Also located on the upper chassis section 750a is an infusion port 766, operable with the valve 766a, for flowing the nutritional 116 and preservative 118 fluids into the perfusion fluid 108. The upper chassis section 750a also includes a tube 774 for loading the exsanguinated blood from the donor into the reservoir 160. As shown in FIG. 24D, the single use module 634 also includes non-vented caps 776 for replacing vented caps on selected fluid ports that are used while running a sterilization gas through the single use module 634 during sterilization. Preferably, such sterilization takes place prior to packaging the single use module 634 for sale.

The upper chassis section 750a also includes the flow clamp 190 for regulating back pressure applied to the left atrium 152 when the heart 102 is cannulated and operating in normal flow mode in the organ chamber assembly 104. The upper chassis section 750a further includes a trickle valve 768. The trickle valve 768 may be opened and closed with the handle 768a to regulate a small fluid flow to the left atrium 152 to moisten the left atrium 152 during retrograde flow mode. The upper chassis section 750a also includes ports 770 for infusion of additional solutions and 772 for purging the oxygenator 114, operable with respective valves 770a and 772a.

As shown most clearly in FIGS. 24A and 24D, the upper chassis section 750 further includes the flow pressure probes 126, 128 and 130. As described above with reference to FIG. 1, the probe 126 measures the pressure of the perfusion fluid 108 flowing into/out of the aorta 158. The probe 128 measures the pressure of the perfusion fluid 108 flowing into the left atrium 152 through the pulmonary vein 168. The probe 130 measures the pressure of the perfusion fluid 108 flowing out of the pulmonary artery 164. Each probe includes a respective connector 126a, 128a and 130a (shown shortened for clarity) for coupling a respective signal 129, 131, and 133 to the front end circuit board 637.

Referring particularly to the single use module 654 cross-sectional side view of FIG. 24C, the reservoir 160 includes several components. More specifically, the reservoir 160 includes four inlets: 782, 784, 786 and 788. The inlet 782 transfers perfusion fluid 108 from the drain 201 of the organ chamber 194 into the reservoir 160. The inlet 784 receives exsanguinated blood from the tube 774. The inlet 786 receives oxygenated perfusion fluid 108 from the oxygenator 114, and the inlet 788 receives perfusion fluid 108 out of the aorta 158 via the back pressure clamp 190. The reservoir 160 also has an outlet 790, which provides the perfusion fluid to the one way inlet valve 191. The reservoir 160 further includes a defoamer 778 and a filter 780. The defoamer 778 removes bubbles out of the perfusion fluid 108 as it enters the reservoir 160. According to the illustrative embodiment, the defoamer is made of porous polyurethane foam with an anti-foam coating. The filter 780 is a polyester felt, which filters debris, blood particles, emboli, and air bubbles out of the perfusion fluid as it enters the reservoir 160.

As mentioned above in the summary, the $O_2$ saturation and hematocrit sensor 140 employed in the single use module 634 includes important advantages over prior art approaches. FIGS. 28A-28C depict an illustrative embodiment of the $O_2$ saturation and hematocrit sensor 140 of the invention. As shown in FIG. 28A, the sensor 140 includes an in-line cuvette shaped section of tube 812 connected to the conduit 798, which has at least one optically clear window through which an infrared sensor can provide infrared light. Exemplary sensors used in the in-line cuvette-shaped tube 812 are those made by Datamed, BL0P4. As shown in the cross-sectional view of FIG. 28B, the cuvette 812 is a one-piece molded part having connectors 801a and 801b. The connectors 801a and 801b are configured to adjoin to connecting receptacles 803a and 803b, respectively, of conduit ends 798a and 798b. This interconnection between cuvette 812 and conduit ends 798a and 798b is configured so as to provide a substantially constant cross-sectional flow area inside conduit 798 and cuvette 812. The configuration thereby reduces, and in some embodiments substantially removes, discontinuities at the interfaces 814a and 814b between the cuvette 812 and the conduit 798. Reduction/removal of the discontinuities enables the blood based perfusion fluid 108 to flow through the cuvette with reduced lysing of red blood cells and reduced turbulence, which enables a more accurate reading of perfusion fluid oxygen levels. This also reduces damage to the perfusion fluid 108 by the system 100, which ultimately reduces damage done to the heart 102 while being perfused by the system 100.

According to the illustrative embodiment, the cuvette 812 is formed from a light transmissive material, such as any suitable light transmissive glass or polymer. As shown in FIG. 28A, the sensor 140 also includes an optical transceiver 816 for directing light waves at perfusion fluid 108 passing through the cuvette 812 and for measuring light transmission and/or light reflectance to determine the amount of oxygen in the perfusion fluid 108. As illustrated in FIG. 28C, in some embodiments a light transmitter is located on one side of the cuvette 812 and a detector for measuring light transmission through the perfusion fluid 108 is located on an opposite side of the cuvette 812. FIG. 28C depicts a top cross-sectional view of the cuvette 812 and the transceiver 816. The transceiver 816 fits around cuvette 812 such that transceiver interior flat surfaces 811 and 813 mate against cuvette flat surfaces 821 and 823, respectively, while the interior convex surface 815 of transceiver 816 mates with the cuvette 812 convex surface 819. In operation, when uv light is transmitted from the transceiver 816, it travels from flat surface 811 through the fluid 108 inside cuvette 812, and is received by flat surface 813. The flat surface 813 may be configured with a detector for measuring the light transmission through the fluid 108.

Figure 26A:
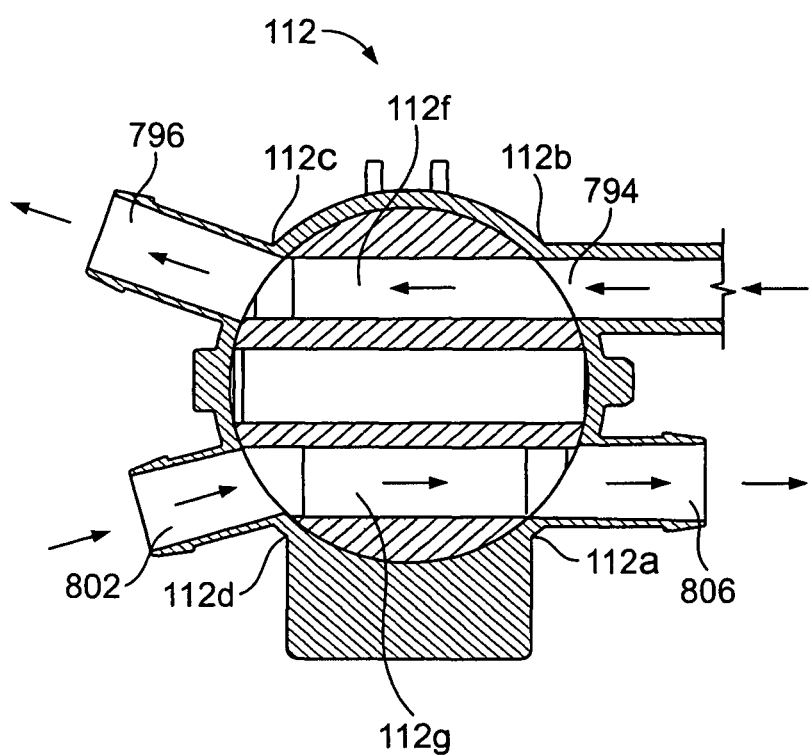
FIGS. 26A and 26B depict the operation of a flow mode selector valve according to an illustrative embodiment of the invention.
Figure 26B:
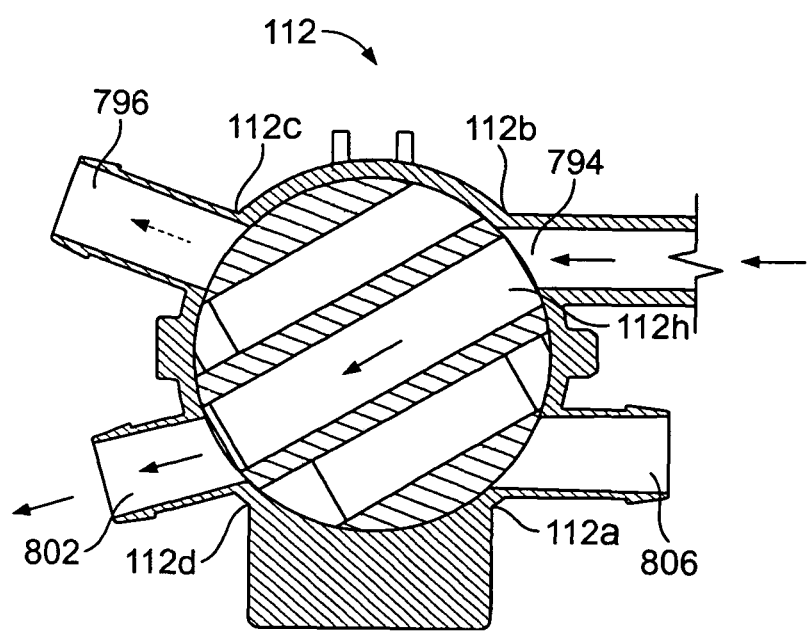

The fluid flow path through the single use module 634 in both normal and retrograde flow modes will now be described with reference to FIGS. 24A-24D and FIG. 25A. As described above with reference to FIGS. 1-4, the system 100 can maintain the heart 102 in two modes of operation; a normal flow mode, shown in FIG. 3, and a retrograde flow mode shown in FIG. 4. As mentioned above with regard to FIG. 1, to change between normal and retrograde flow modes, the system 100 provides the flow mode selector valve 112, shown in detail in FIGS. 26A and 26B. To operate in normal flow mode, the operator sets the flow mode selector valve handle 112e to the position indicated in FIG. 24A. This has the effect of aligning the flow paths through the selector valve 112 as shown in FIG. 26A. Specifically, in normal flow mode, fluid can flow into port 112b, through the flow channel 112f and out the port 112c. Additionally, fluid can flow into port 112d, through the flow channel 112g and out the port 112a. To operate in retrograde flow mode, the operator sets the flow mode selector valve handle 112e to the position indicated in FIG. 24B. This has the effect of aligning the flow paths through the selector valve 112 as shown in FIG. 26B. Specifically, in retrograde flow mode, fluid can flow into port 112b, through the flow channel 112h and out the port 112d.

Referring to FIG. 24A, in normal flow mode, the reservoir 160 provides the perfusion fluid 108 to the one way inlet valve 191 of the perfusion pump interface assembly 300. Referring to FIG. 25A, the perfusion pump 106 pumps the perfusion fluid 108 out the outlet valve 310. Referring to FIG. 25C, the perfusion fluid 108 then flows through the conduit 792 and the compliance chamber 188 and into the inlet 110a of the heater assembly 110. The heater assembly 110 heats the perfusion fluid 108 and then flows it out the heater outlet 110b. Referring to FIG. 24A, the heated perfusion fluid 108 flows from the heater outlet 110b in the lower chassis section 750b through the chassis plate 752 and into the port 112b of the mode select valve 112 via the conduit 794. Referring also to FIG. 24D, the perfusion fluid 108 flows out the mode valve port 112c, through the compliance chamber 186, the conduit 796, and the pressure sensor 128 into the pulmonary vein cannulation interface 170 on the organ chamber assembly 104.

Referring to FIG. 24A, in normal flow mode, the heart 102 pumps the perfusion fluid 108 out the pulmonary artery 164 through the pulmonary artery interface 166 and the pressure sensor 130. The conduit 796 then flows the perfusion fluid 108 from the pulmonary artery interface 166 through the plate 752 and through the O₂ saturation and hematocrit sensor 140. Referring also to FIGS. 25A and 25C, the conduit 798 then flows the perfusion fluid 108 from the sensor 140 through the flow-rate sensor 136 into the oxygenator 114. The conduit 800 flows the perfusion fluid 108 from the oxygenator 114 back into the reservoir 160 by way of the reservoir inlet 786.

Referring to FIGS. 24A, 24D and 24E, in normal flow mode, the heart 102 also pumps the perfusion fluid 108 out of the aorta 158 through the aorta interface 162 and the pressure sensor 126. The conduit 802 flows the perfusion fluid 108 from the pressure sensor 126 through the flow rate sensor 134 and back into the port 112d on the flow mode selector valve 112. A clamp 804 holds the conduit 802 in place. A conduit 806 flows the perfusion fluid 108 out the port 112a from the flow mode selector valve 112 through the compliance chamber 184 and the back pressure adjustment clamp 190. As mentioned above, the clamp 190 may be adjusted to restrict flow through the conduit 806 to adjust the back pressure seen by the aorta 158 during normal flow mode to more realistically simulate normal physiologic conditions. The compliance chamber 184, which can expand and contract as perfusion fluid 108 is pumped into and out of it, interoperates with the clamp 190 to dampen flow pressure spikes to further improve simulation of near-normal physiologic conditions. The after-load clamp 190 is configured to closely emulate systemic vascular resistance of the human body which affects aortic pressure, left atrial pressure, and coronary flow. A conduit 808 returns the perfusion fluid 108 into the reservoir 160 by way of the reservoir inlet 788.

In retrograde flow mode, the flow mode selector valve 112 is positioned as shown in FIG. 24B. Referring to FIG. 24B, the reservoir 160 provides the perfusion fluid 108 to the inlet valve 191. As shown in FIG. 25A, the perfusion pump 106 pumps the perfusion fluid 108 out the outlet valve 310. As shown in FIG. 25C, the perfusion fluid 108 then flows through the conduit 792 and the compliance chamber 188 and into the inlet 110a of the heater assembly 110. The heater assembly 110 heats the perfusion fluid 108 and then flows it out the heater outlet 110b. Referring to FIG. 24B, the heated perfusion fluid 108 flows from the heater outlet 110b in the lower chassis section 750b through the chassis plate 752 and into the input 112b of the mode select valve 112 via the conduit 794. Referring also to FIG. 24D, the perfusion fluid 108 flows out the mode valve outlet 112d, into the conduit 802, through the flow rate sensor 134, the pressure sensor 126 and into the aorta 158 via the aorta interface 162. The perfusion fluid 108 then flows through the coronary sinus 155 and the rest of the coronary vasculature.

Referring to FIG. 24B, in retrograde flow mode, the heart 102 pumps the perfusion fluid 108 out of the pulmonary artery 164 and through the pulmonary artery interface 166 and the pressure sensor 130. The conduit 796 then flows the perfusion fluid from the pulmonary artery interface 166 through the plate 752 and into the O₂ saturation and hematocrit sensor 140. Referring also to FIGS. 25A and 25C, the conduit 798 then flows the perfusion fluid 108 from the sensor 140 through the flow rate sensor 136 into the oxygenator 114. The conduit 800 flows the perfusion fluid 108 from the oxygenator 114 back into the reservoir 160 by way of the reservoir inlet 786. In retrograde flow mode, substantially no perfusion fluid is pumped into or out of the left atrium 152 via the pulmonary vein 168 and the pulmonary vein interface 170, with the exception of a small amount of perfusion fluid diverted by the trickle valve 768 from the conduit 794 around the flow mode selector valve 112 into the compliance chamber 186. As mentioned above, the trickle flow provides sufficient perfusion fluid 108 to keep the left atrium 152 moistened during retrograde flow.

As described above, the illustrative embodiment of the system 100 has one or more sensors or probes for measuring fluid flow and pressure. The probes and/or sensors may be obtained from standard commercial sources. The flow rate sensors 134, 136 and 138 are conventional, ultrasonic flow sensors, such as those available from Transonic Systems Inc., Ithaca, N.Y. The fluid pressure probes 126, 128 and 130 may be conventional, strain gauge pressure sensors available from MSI or G.E. Thermometrics. Alternatively, a pre-calibrated pressure transducer chip can be embedded into organ chamber connectors and wired to a data collection site such as the front end board 637.

Figure 29A:
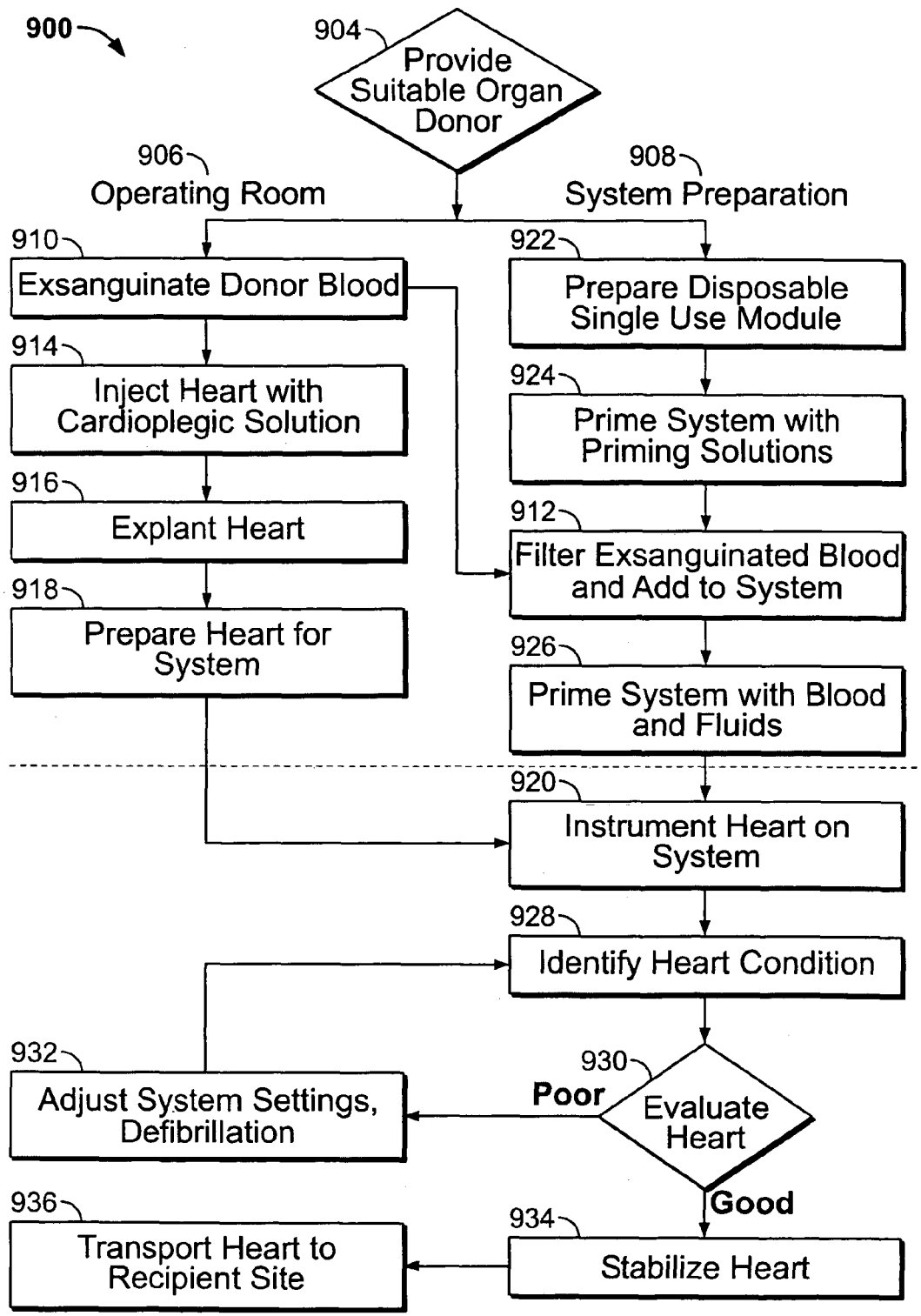
FIG. 29A is a flow diagram depicting a donor-side process for removing an organ from a donor and placing it into the organ care system of FIG. 1 according to an illustrative embodiment of the invention.
Figure 29B:
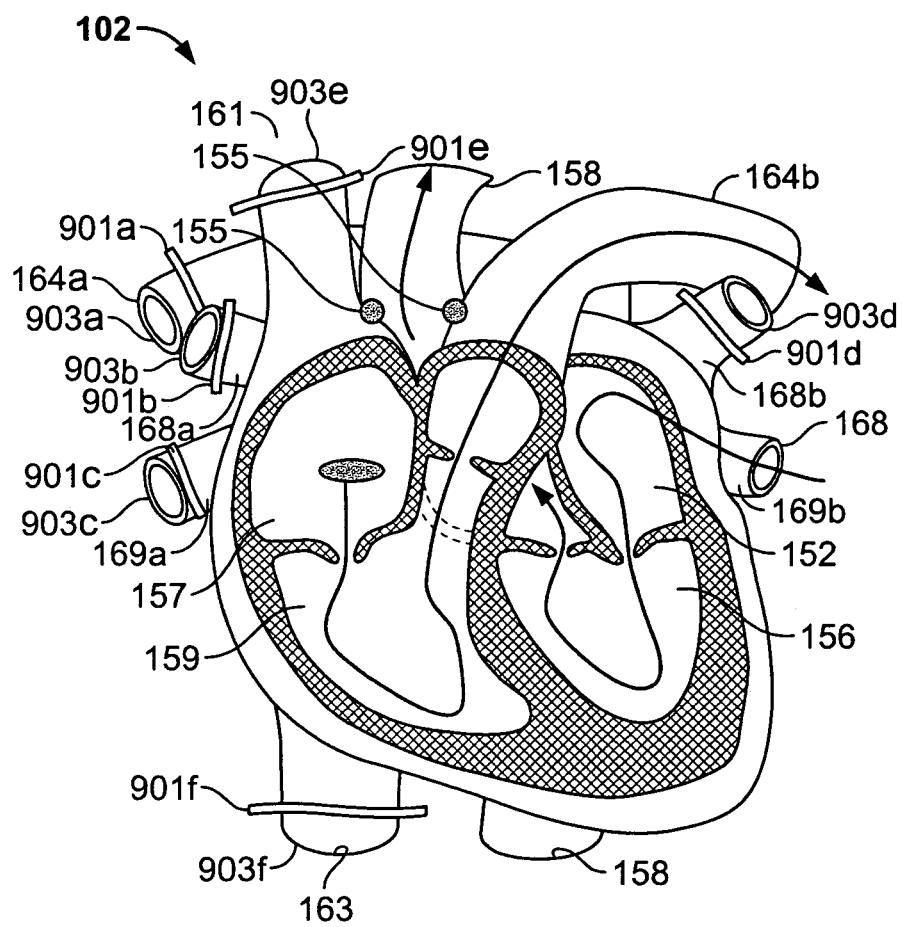
FIG. 29B is a diagram depicting a harvested heart with suture and cannulation sites according to an illustrative embodiment of the invention.
Figure 30:
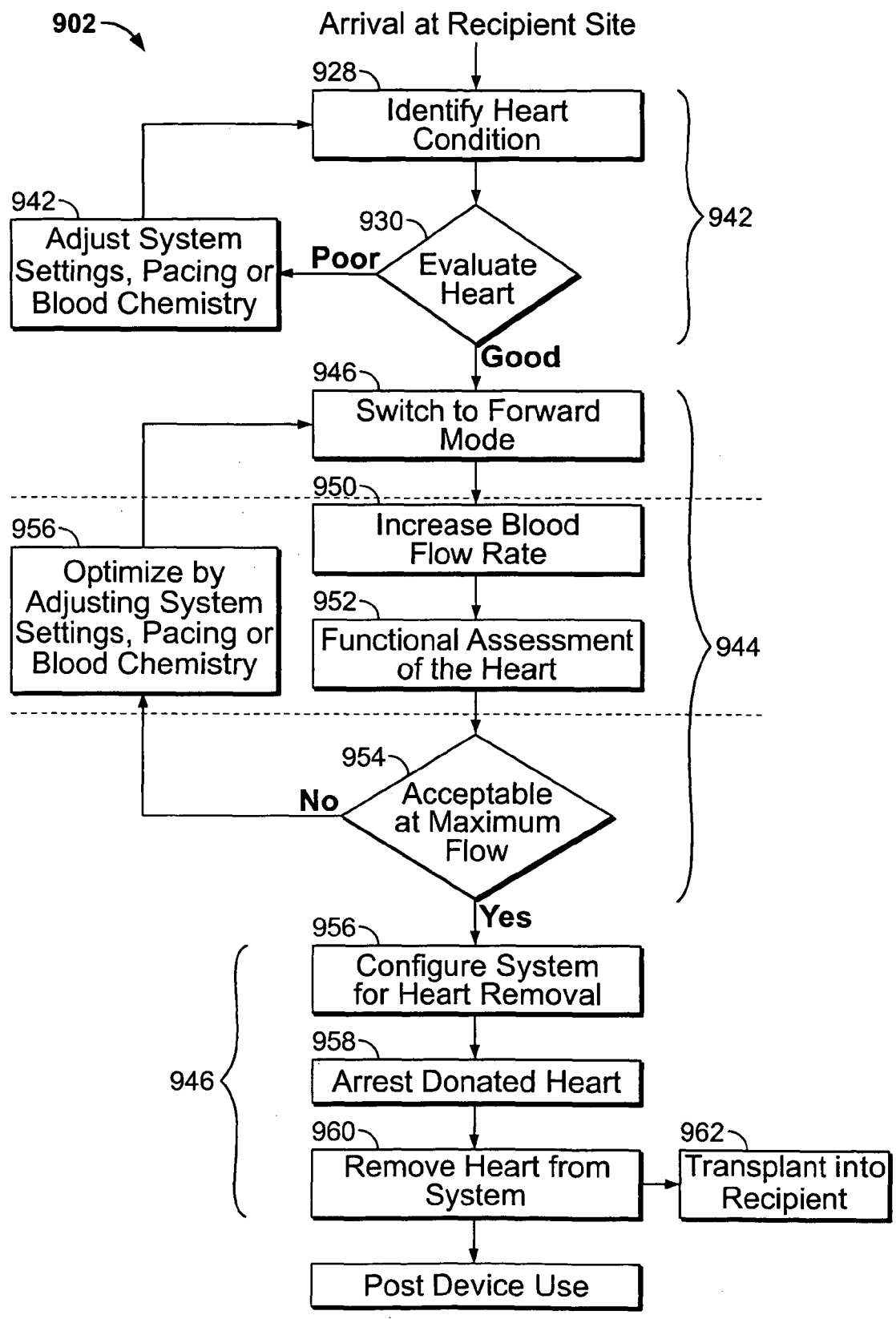
FIG. 30 is a flow diagram depicting a recipient-side process for removing an organ from the organ care system of FIG. 1 and transplanting it into a recipient according to an illustrative embodiment of the invention.

Having described the electrical and mechanical components and functionality of illustrative embodiments of the system 100 and certain modes of operation thereof, the system 100 will next be described with reference to the illustrative organ harvest and transplant procedures of FIGS. 29A and 29B. More particularly, FIG. 29A is a flow diagram 900 depicting exemplary methodologies for harvesting the donor heart 102 and cannulating it into the system 100 at a donor location. FIG. 29B depicts particular points of care for handling the heart 102 in preparation for cannulation, and FIG. 30 is a flow diagram 902 of exemplary methodologies for removing the donor organ 102 from the system 100 and transplanting it into a patient at a recipient site.

As shown in FIG. 29A, the process of obtaining and preparing the heart 102 for cannulation and transport begins by providing a suitable organ donor 904. The organ donor is brought to a donor location, whereupon the process of receiving and preparing the donor heart 102 for cannulation and transport proceeds down two intersecting pathways 906 and 908. The pathway 906 principally involves preparing the donor heart 102 for transplant, while the pathway 908 principally involves preparing the system 100 to receive the donor heart 102 and then transporting the heart 102 via system 100 to the recipient site.

With particular reference to FIG. 29A, the first pathway 906 includes exsanguinating the donor 910, arresting the donor heart 914, explanting the heart 916, and preparing the heart 102 for cannulation 918 into the system 100. In particular, in the exsanguination step 910, the donor's blood is removed and set aside so it can be used to perfuse the heart 102 during preservation on the system 100. This step is performed by inserting a catheter into either the arterial or venous vasculature of the donor to allow the donor's blood to flow out of the donor and be collected into a blood collection bag. The donor's blood is allowed to flow out until the necessary amount of blood is collected, typically 1.0-2.5 liters, whereupon the catheter is removed. The blood extracted through exsanguination is then filtered and added to a fluid reservoir 160 of the system 100 in preparation for use with the system 100. Alternatively, the blood can be exsanguinated from the donor and filtered for leukocytes and platelets in a single step that uses an apparatus having a filter integrated with the cannula and blood collection bag. An example of such a filter is a Pall BC2B filter. After the donor's blood is exsanguinated, the donor heart 102 is injected in step 914 with a cardioplegic solution to temporarily halt beating in preparation for harvesting the heart 102.

After the heart 102 is arrested, the heart 102 is explanted 916 from the donor and prepared 918 for loading onto the system 100. In general, the steps of explanting the heart 916 and preparing for loading 918 involve severing the connections between the vasculature of the heart 102 and the interior chest cavity of the donor, suturing various of the severed connections, then lifting the heart 102 from the chest cavity.

More particularly, as shown in FIG. 29B, the right and left pulmonary arteries 164a and 164b are severed, and the right pulmonary artery 164a is tied-off by a surgical thread 901a or other suitable mechanism. The tying prevents fluid from flowing through the severed end 903a of the left pulmonary artery 164a. As described above with reference to FIGS. 24A-24B, the left pulmonary artery 164b remains unsutured to allow it to be cannulated to the organ chamber assembly 104, thereby allowing perfusion fluid 108 to flow through the left pulmonary artery 164b, through the pulmonary artery cannulation interface 170, and back to the reservoir 160. The left pulmonary veins 168b and 169b and the right pulmonary veins 168a and 169a are also severed, and all except a single pulmonary vein 169b are tied off with surgical thread 901b, 901c, and 901d, respectively. This prevents fluid from flowing through the severed ends 903b and 903c of the right pulmonary veins 168a and 169a, or through the severed end 903d of the left pulmonary vein 168b, but allows the untied pulmonary vein to be cannulated to the organ chamber assembly 104 through the pulmonary vein interface 170. As described above with reference to FIGS. 24A-24B, this arrangement allows the perfusion fluid 108 to flow through the right pulmonary artery 164b, through the pulmonary artery interface 166, and back to the oxygenator 114. Alternatively, blood can be expelled from the right ventricle via cannulating the pulmonary arterial trunk. The pulmonary arterial trunk is not shown but includes the segment of pulmonary artery 164 between the branches 164a and 164b of the pulmonary artery 164 and the right ventricle 159. The superior vena cava 161 is also severed and, once the heart is connected to the system 100 and begins beating, is tied with thread 901e to prevent fluid from flowing through its end 903e. The inferior vena cava 163 is similarly severed and tied with thread 901f or oversewn to prevent fluid from flowing through its end 903f. The aorta 158 is also severed (in the illustrated embodiment at a point downstream from the coronary sinus 155) but is not tied off, allowing it to be cannulated to the organ chamber assembly 104. In one embodiment, the aorta 158 is cannulated to an aortic connector, which can be easily attached to the aorta interface 170.

With continued reference to the flow chart of FIG. 29A, after the heart vasculature is severed and appropriately tied, the heart 102 is then loaded onto the system 100 by inserting it into the organ chamber assembly 104 and cannulating the aorta 158, left pulmonary artery 164b, and a pulmonary vein 169b to the appropriate points in the organ chamber assembly 104.

Often, hearts obtained from donors who have also donated their lungs are missing part or all of the left atrium 152. In this situation, the heart 102 can still be instrumented and perfused in the retrograde mode by cannulating the aorta 158 and either the right pulmonary artery 164a or pulmonary artery trunk (not shown, but described above), and allowing any remaining left atrium 152 portion to remain open during the preservation period.

With continued reference to FIG. 29A, during the preparation of the heart via path 906, the system 100 is prepared through the steps of path 908 so it is primed and waiting to receive the heart 102 for cannulation and transport as soon as the heart 102 is prepared. By quickly transferring the heart 102 from the donor to the system 100, and subsequently perfusing the heart 102 with the perfusion fluid 108, a medical operator can minimize the amount of time the heart 102 is deprived of oxygen and other nutrients, and thus reduce ischemia and other ill effects that arise during current organ care techniques. In certain embodiments, the amount of time between infusing the heart 102 with cardioplegic solution and beginning flow of the perfusion fluid 108 through the heart 102 via the system 100 is less than about 15 minutes. In other illustrative embodiments, the between-time is less than about ½ hour, less than about 1 hour, less than about 2 hours, or even less than about 3 hours. Similarly, the time between transplanting the heart into an organ care system 100 and bringing the heart 102 to a near physiological temperature (e.g., between about 34° C. and about 37° C.) occurs within a brief period of time so as to reduce ischemia within the heart tissues. In some illustrative embodiments, the period of time is less than about 5 minutes, while in other applications it may be less than about ½ hour, less than about 1 hour, less than about 2 hours, or even less than about 3 hours. According to some illustrative embodiments, the heart can be transferred directly from the donor to the system 100, without the use of cardioplegia, and in such applications the time to beginning the flow of warm perfusion fluid 108 and/or time to the heart reaching near physiologic temperature is similarly less than about 5 minutes, less than about ½ hour, less than about 1 hour, less than about 2 hours, or even less than about 3 hours. In one implementation, the donor heart is not arrested prior to removal from the donor, and is instrumented onto the system 100 while the heart 102 is still beating.

As shown in FIG. 29A, the system 100 is prepared in pathway 908 through a series of steps, which include preparing the single use module 634 (step 922), priming the system 100 with priming solution (step 924), filtering the blood from the donor and adding it to the system 100 reservoir 160 (step 912), and connecting the heart 102 into the system 100 (step 904). In particular, the step 922 of preparing the single use module 634 includes assembling the disposable single use module 634. Suitable assemblies are shown, for example, in FIGS. 24A-24D, FIGS. 25A-25C, and FIG. 26. After the module 634 is assembled, or provided in the appropriate assembly, it is then inserted into multiple use module 650 through the process described above with reference to FIGS. 21A-21C.

In step 924, the loaded system 100 is primed with priming solution, as described in more particular detail below with reference to Table 1. According to one feature, to aid in priming, the system 100 provides an organ bypass conduit 810 shown installed into the organ chamber assembly 104 in FIG. 27A. As depicted, the bypass conduit includes three segments 810a-810c. Segment 810a attaches to the pulmonary artery cannulation interface 170. The segment 810b attaches to the aorta cannulation interface 810b, and the segment 810c attaches to the pulmonary vein cannulation interface 166. Using the bypass conduit 810 so attached/cannulated into the organ chamber assembly 104, an operator can cause the system 100 to circulate the perfusion fluid 108 through all of the paths used during actual operation. This enables the system 100 to be thoroughly tested and primed prior to cannulating the heart 102 into place.

In the next step 912, blood from the donor is filtered and added to the reservoir 160. The filtering process helps reduce the inflammatory process through the complete or partial removal of leukocytes and platelets. Additionally, the donor blood is mixed with one or more nutritional 116 and/or preservative 118 solutions to form the perfusion fluid 108. In step 926, the system 100 is primed with the perfusion fluid 108 by pumping it through the system 100 in the retrograde flow mode, as described above in reference to FIG. 24B, and with the bypass conduit 810 in place. As the perfusion fluid 108 circulates through the system 100 in priming step 926, it is warmed to the desired temperature as it passes through heater assembly 110. The desired temperature range and heating applications are described above in reference to FIGS. 6A through 6E, and in respect to FIG. 13. In step 920, after the system 100 is primed with the perfusion fluid 108, the bypass conduit 810 is removed, and the heart 102 is instrumented, as described above and shown in FIG. 27B, onto the system 100.

After the heart 102 is instrumented onto the system 100, the pump 104 is activated and the flow mode valve 112 is positioned in retrograde flow mode (described above with reference to FIGS. 1 and 4) to pump the perfusion fluid 108 in retrograde flow mode through the aorta into the vasculature of the heart 102. The pumping of the warm, oxygen and nutrient enriched perfusion fluid 108 through the heart 102 allows the heart 102 to function ex vivo in a near normal physiologic state. In particular, the warm perfusion fluid 108 warms the heart 102 as it perfuses through it, which may cause the heart 102 to resume beating in its natural fashion. In some instances, it is desirable to assist the heart 102 in resuming its beating, which may be done by providing hand massage or a defibrillation signal 143 (shown in FIG. 22E) to the heart 102. This may be done as described above with reference to the organ chamber assembly of FIGS. 5A-5F and operator interface 146 of FIGS. 17A-17J.

Figure 27A:
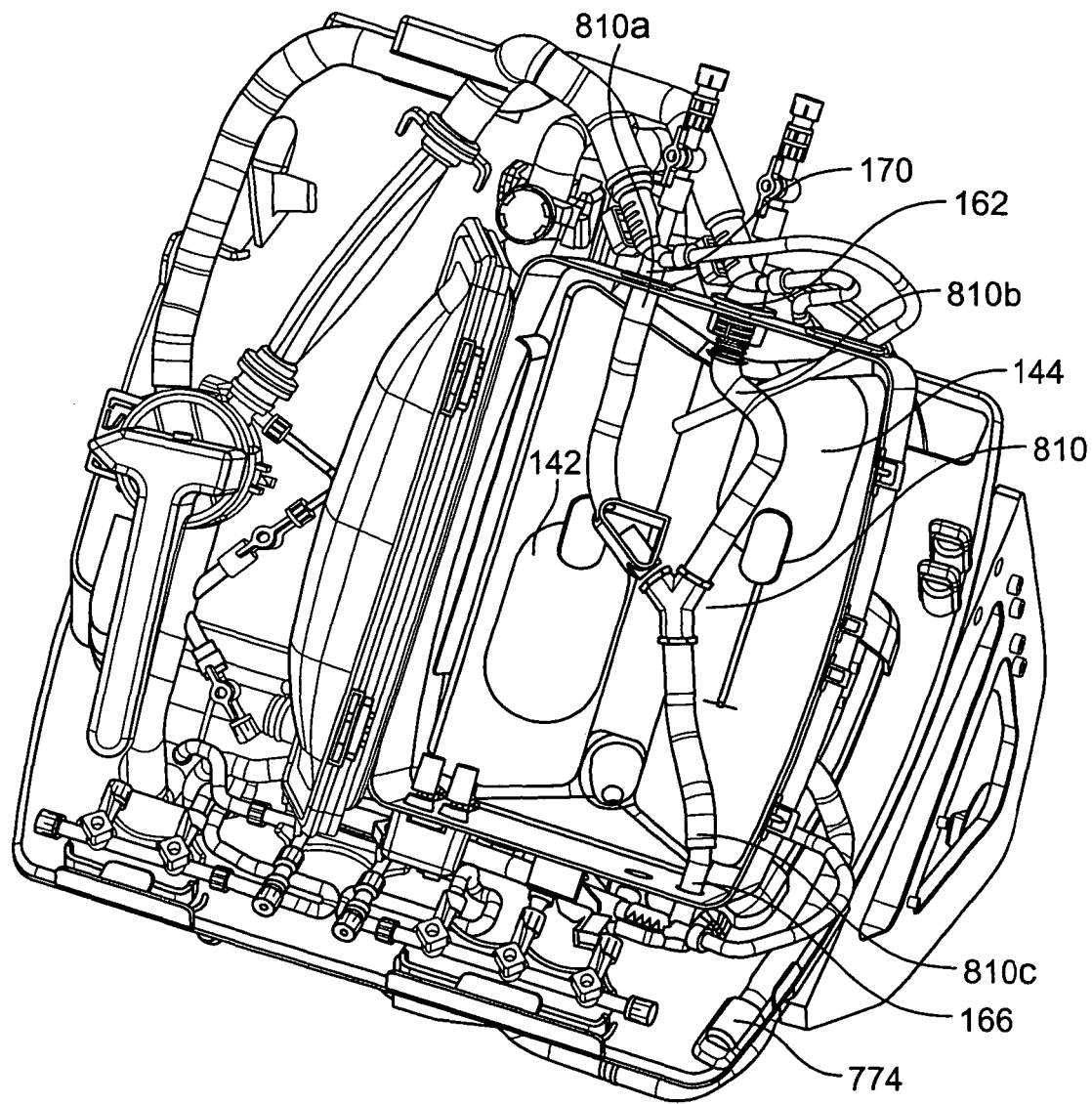
FIGS. 27A and 27B show various top views of the single use disposable module of FIGS. 19A-19C with the top off of illustrative organ chamber.
Figure 27B:
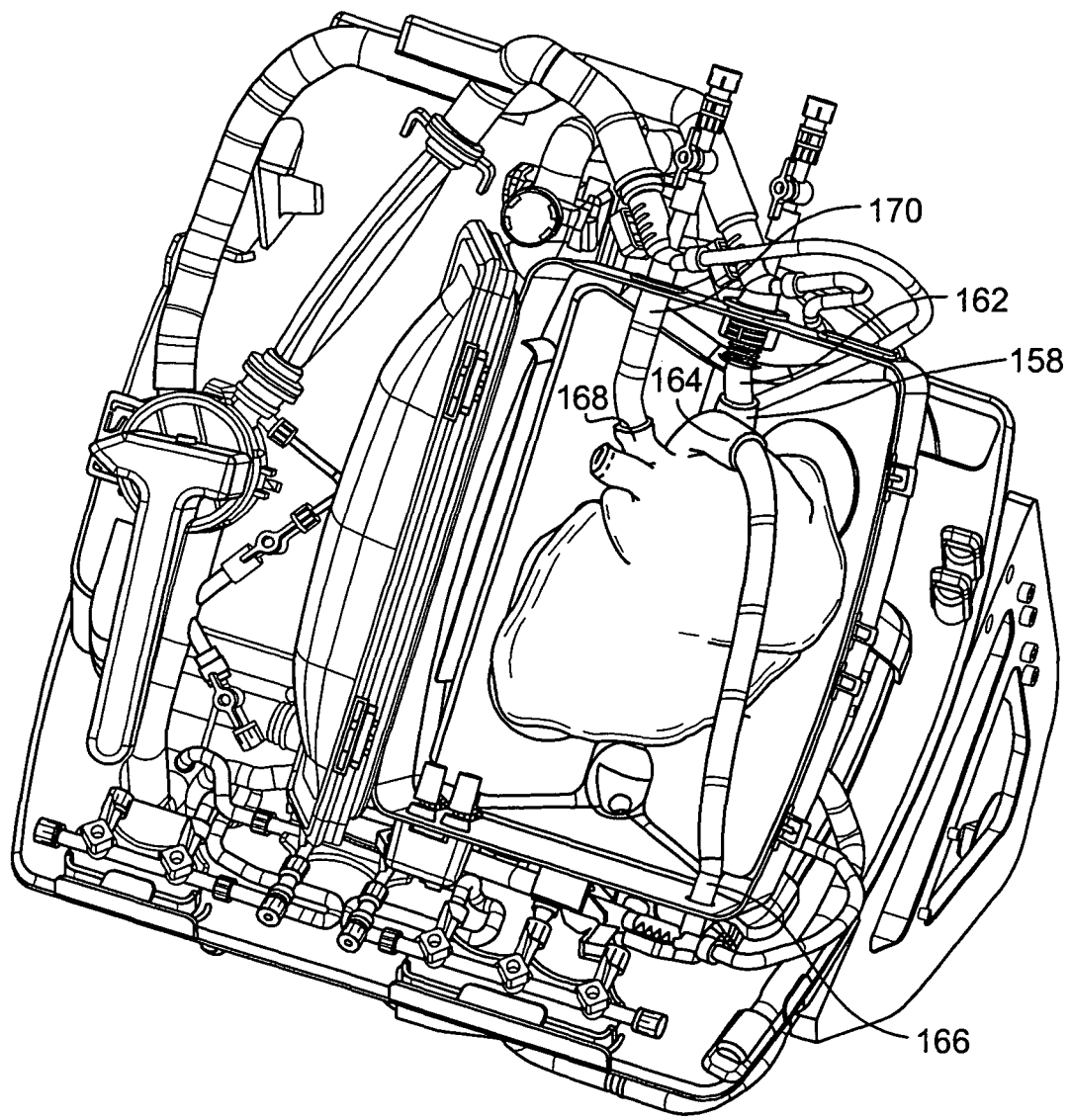

After the heart is instrumented onto the system 100 at step 920, subsequent steps 928 and 930 allow the operator to test the heart 102 and the system 100, and to evaluate their respective conditions. Illustratively, step 928 involves evaluating ECG signals 379 and 381 from the sensors 142 and 144 (positioned as shown in FIG. 27A), respectively, as well as hematocrit 145 and oxygen saturation 141 levels of the perfusion fluid 108 from the sensor 140. As further described in reference to FIG. 12 and FIGS. 17A-17I, the operator can also monitor the fluid flows, pressures, and temperatures of the system 100 while the heart 102 is cannulated. As described above with reference to FIGS. 5E and 5F, the testing step 928 may also include having the operator touch/examine the heart 102 by lifting an outer lid 196 of the organ chamber 104 and touching/examining the heart 102 indirectly through the flexible membrane 198b. During the evaluation step 930, based on the data and other information obtained during testing 928, the operator determines whether and how to adjust the system 100 properties (e.g., fluid flows, pressures, and temperatures), and whether to provide additional defibrillation, or other needed modes of treatment to the heart 102. The operator makes any such adjustments in step 932, then repeats steps 928 and 930 to re-test and re-evaluate the heart 102 and the system 100. In certain embodiments, the operator may also opt to perform surgical, therapeutic or other procedures on the heart 102 during the adjustment step 932. For example, the operator can conduct an evaluation of the physiological fitness of the heart, such as for example, performing an ultrasound or other imaging test, performing an echocardiogram or diagnostic test on the heart, measuring arterial blood gas levels and other evaluative tests.

In another application, during or after step 932, the system 100 allows a medical operator to evaluate the organ for compatibility with an intended recipient after explantation but prior to implantation into the donor. For example, the operator can perform a Human Leukocyte Antigen (HLA) matching test on the organ while the organ is cannulated to the system 100. Such tests may require 12 hours or longer and are performed to ensure compatibility of the organ with the intended recipient. The preservation of an organ using the system 100 described above may allow for preservation times in excess of the time needed to complete an HLA match, potentially resulting in improved post-transplant outcomes. In the HLA matching test example, the HLA test can be performed on the heart while a preservation solution is pumping into the heart.

According to a further illustrative embodiment, after the heart is functioning as determined by the step 932, the operator can perform surgery on the heart or provide therapeutic or other treatment, such as immunosuppressive treatments, chemotherapy, genetic testing and therapies, or irradiation therapy. Because the system 100 allows the heart 102 to be perfused under near physiological temperature, fluid flow rate, and oxygen saturation levels, the heart 102 can be maintained after the adjustment step 932 for a long period of time (e.g., for a period of at least 3 days or more, greater than at least 1 week, at least 3 weeks, or a month or more) to allow for repeated evaluation and treatment.

According to the illustrative embodiment, the testing 928, evaluation 930 and adjustment 932 steps may be conducted with the system 100 operating in retrograde flow mode, or may be conducted with the system 100 operating in normal flow mode. In normal flow mode, the operator can test the function of the heart 102 under normal or near normal physiologic blood flow conditions. Based on the evaluation 930, the settings of the system 100 may be adjusted in step 932, if necessary, to modify the flow, heating and/or other characteristics to stabilize the heart 102 in step 934 in preparation for transport to the recipient site in step 936. After the heart 102 and the system 100 is tested and evaluated to ensure appropriate performance, the system 100 with the loaded heart 102 is transported to the recipient site at step 936.

Referring now to FIG. 30, the first phase 942 of the transplant process involves repeating the testing 928 and evaluation 930 steps undertaken just prior to leaving the donor site 936. If the function and characteristics of the heart 102 are not acceptable, the system 100 can be adjusted 942 as appropriate, for example, to provide appropriate fluid oxygenation or nutritional levels, or to increase or decrease the appropriate fluid temperature. As noted above, surgical and/or other therapeutic/remedial procedures may be performed on the heart 102, along with the testing 928 and evaluation 930. According to the illustrative embodiment, testing at the recipient site may be performed in retrograde flow mode, normal flow mode, or a combination of both.

At step 946, after testing is complete, the system 100 is placed in normal/forward flow mode. In certain embodiments, this step 946 is not initiated until the left atrium 152 and pulmonary vein 164 are cannulated, there is adequate operating volume in the system, the heart exhibits stable electrical activity, the ABG and electrolytes are within acceptable ranges, SvO2 is >80%, and blood temperature is between about 34° C. and about 36° C. The step 946 is may be accomplished by slowing and/or stopping the retrograde pumping of the system 100, then restarting the pumping in forward mode. In certain embodiments, prior to restarting in forward mode, the user opens the aortic sampling port 754a, releases the pressure control clamp 190 by turning it counter-clockwise, then increases the flow rate of pump 106 to about 1.0 L/min, sets the flow control valve 112 to normal/forward flow, and increases the flow rate of pump 106 to about 2.0 L/min to allow the blood 102 to displace air in the perfusate lines (e.g., 802) of the system 100 and pass through the left side of the heart 102 and down the reservoir return line 808. The user then closes the aortic sampling port 754a.

The flow rate of the perfusion fluid 108 emitted from the pump 106 is then increased at step 950 to a level of the clinician's choosing (typically between about 1 L/min to about 5 L/min) to approximate the physiologic flow rate provided by the heart 102 while functioning in normal beating mode. The heart 102 and the system 100 are again tested at step 952 in a similar fashion to that described above with respect to steps 928 and 930. The clinician may also choose to perform any other tests or evaluations on the heart, for example echocardiogram, electrolyte measurements, cardiac enzyme measurements, metabolyte measurements, intravascular ultrasound evaluation, pressure-volume loop evaluation, and Millar pressure evaluation.

In the third phase 946 at the recipient site, the heart 102 is prepared for implantation into the recipient. This phase includes the step 956 of powering down the pump 106 to stop the flow of perfusion fluid 108. Next, in step 958, the heart 102 is arrested, for example by injecting it with cardioplegic solution in a similar fashion to what is done in step 914 at the donor site. In step 960, the heart 102 is de-cannulated and removed from the organ chamber assembly 106. In step 962, the heart 102 is transplanted into the recipient patient by first removing the sutures 901a-901f, then inserting the heart 102 into the recipient's chest cavity, and suturing the various heart vesicles (e.g., 158, 164a, 164b, 168a, 168b, 169a, 169b, and 903a-903f) to their appropriate mating vesicles within the recipient.

While external devices and methods have been described to defibrillate the heart, deliver pacing signals to the heart, and perform blood chemistry analyses from samples taken from the perfusion fluid, it may also be beneficial to integrate these features into the portable system. Such features include defibrillation, pacing, diagnostic ECG sensing, and blood chemistry analyses.

As described above, the system 100 employs a priming solution, and also employs a perfusion fluid 108 that combines a nutritional supplement 116 solution and a preservative solution 118 with a blood product or synthetic blood product to form the perfusion fluid 108. The priming, supplement 116, and preservative 118 solutions are described next.

According to certain embodiments, solutions with particular solutes and concentrations are selected and proportioned to enable the organ to function at physiologic or near physiologic conditions. For example, such conditions include maintaining organ function at or near a physiological temperature and/or preserving an organ in a state that permits normal cellular metabolism, such as protein synthesis.

In certain embodiments solutions are formed from compositions by combining components with a fluid, from more concentrated solutions by dilution, or from more dilute solutions by concentration. In exemplary embodiments, suitable solutions include an energy source, one or more stimulants to assist the organ in continuing its normal physiologic function prior to and during transplantation, and one or more amino acids selected and proportioned so that the organ continues its cellular metabolism during perfusion. Cellular metabolism includes, for example conducting protein synthesis while functioning during perfusion. Some illustrative solutions are aqueous based, while other illustrative solutions are non-aqueous, for example organic solvent-based, ionic-liquid-based, or fatty-acid-based.

The solutions may include one or more energy-rich components to assist the organ in conducting its normal physiologic function. These components may include energy rich materials that are metabolizable, and/or components of such materials that an organ can use to synthesize energy sources during perfusion. Exemplary sources of energy-rich molecules include, for example, one or more carbohydrates. Examples of carbohydrates include monosaccharides, disaccharides, oligosaccharides, polysaccharides, or combinations thereof, or precursors or metabolites thereof. While not meant to be limiting, examples of monosaccharides suitable for the solutions include octoses; heptoses; hexoses, such as fructose, allose, altrose, glucose, mannose, gulose, idose, galactose, and talose; pentoses such as ribose, arabinose, xylose, and lyxose; tetroses such as erythrose and threose; and trioses such as glyceraldehyde. While not meant to be limiting, examples of disaccharides suitable for the solutions include (+)-maltose (4-O-(α-D-glucopyranosyl)-α-D-glucopyranose), (+)-cellobiose (4-O-(β-D-glucopyranosyl)-D-glucopyranose), (+)-lactose (4-O-(β-D-galactopyranosyl)-β-D-glucopyranose), sucrose (2-O-(α-D-glucopyranosyl)-β-D-fructofuranoside). While not meant to be limiting, examples of polysaccharides suitable for the solutions include cellulose, starch, amylose, amylopectin, sulfomucopolysaccharides (such as dermatane sulfate, chondroitin sulfate, sulodexide, mesoglycans, heparan sulfates, idosanes, heparins and heparinoids), and glycogen. In some embodiments, monossacharides, disaccharides, and polysaccharides of both aldoses, ketoses, or a combination thereof are used. One or more isomers, including enantiomers, diastereomers, and/or tautomers of monossacharides, disaccharides, and/or polysaccharides, including those described and not described herein, may be employed in the solutions described herein. In some embodiments, one or more monossacharides, disaccharides, and/or polysaccharides may have been chemically modified, for example, by derivatization and/or protection (with protecting groups) of one or more functional groups. In certain embodiments, carbohydrates, such as dextrose or other forms of glucose are preferred.

Other possible energy sources include adenosine triphosphate (ATP), co-enzyme A, pyruvate, flavin adenine dinucleotide (FAD), thiamine pyrophosphate chloride (co-carboxylase), β-nicotinamide adenine dinucleotide (NAD), β-nicotinamide adenine dinucleotide phosphate (NADPH), and phosphate derivatives of nucleosides, i.e. nucleotides, including mono-, di-, and tri-phosphates (e.g., UTP, GTP, GDF, and UDP), coenzymes, or other bio-molecules having similar cellular metabolic functions, and/or metabolites or precursors thereof. For example, phosphate derivatives of adenosine, guanosine, thymidine (5-Me-uridine), cytidine, and uridine, as well as other naturally and chemically modified nucleosides are contemplated.

In certain embodiments, one or more carbohydrates is provided along with a phosphate source, such as a nucleotide. The carbohydrate helps enable the organ to produce ATP or other energy sources during perfusion. The phosphate source may be provided directly through ATP, ADP, AMP or other sources. In other illustrative embodiments, a phosphate is provided through a phosphate salt, such as glycerophosphate, sodium phosphate or other phosphate ions. A phosphate may include any form thereof in any ionic state, including protonated forms and forms with one or more counter ions.

The solutions may include one or more organ stimulants for assisting the organ's normal physiologic function during perfusion. In some illustrative embodiments, where the transplanted organ is a heart, cardio stimulants are provided to enable the heart to continue functioning (e.g., continue beating) during perfusion and transplantation. Such stimulants may include, for example, catecholamines, such as epinephrine and/or norepinephrine, which facilitate beating of the heart. Other cardio stimulants may be used, such as certain forms of peptides and/or polypeptides (e.g., vasopressin, Anthropleurin-A and Anthropleurin-B), and/or β1/β2-adrenoreceptor blocking agents (such as CGP 12177), buplinarol, pindolol, alprenolol, and cardiac glycosides. One or more natural products may also be used, such as digitalis (digoxin), palustrin, and/or ferulic acid. Stimulants such as those mentioned above can be included with the solutions or added at the point of use by the user.

In some instances, additional components are provided to assist the organ in conducting its metabolism during perfusion. These components include, for example, forms or derivatives of adenine and/or adenosine, which may be used for ATP synthesis, for maintaining endothelial function, and/ or for attenuating ischemia and/or reperfusion injury. According to certain implementations, a magnesium ion source is provided with a phosphate, and in certain embodiments, with adenosine to further enhance ATP synthesis within the cells of the perfused organ.

Solutions described herein may include one or more amino acids, preferably a plurality of amino acids, to support protein synthesis by the organ's cells. Suitable amino acids include, for example, any of the naturally-occurring amino acids. The amino acids may be, in various enantiomeric or diastereomeric forms. For example, solutions may employ either D- or L-amino acids, or a combination thereof, i.e. solutions enantioenriched in more of the D- or L-isomer or racemic solutions. Suitable amino acids may also be non-naturally occurring or modified amino acids, such as citrulline, orniithine, homocystein, homoserine, β-amino acids such as β-alanine, amino-caproic acid, or combinations thereof.

Certain exemplary solutions include some but not all naturally-occurring amino acids. In some embodiments, solutions include essential amino acids. For example, a solution may be prepared with one or more or all of the following amino-acids:

|  |
|---|
| Glycine |
| Alanine |
| Arginine |
| Aspartic Acid |
| Glutamic Acid |
| Histidine |
| Isoleucine |
| Leucine |
| Methionine |
| Phenylalanine |
| Proline |
| Serine |
| Thereonine |
| Tryptophan |
| Tyrosine |
| Valine |
| Lysine acetate |

In certain embodiments, non-essential and/or semi-essential amino acids are not included in the solutions. For example, in some embodiments, asparagine, glutamine, and/ or cysteine are not included. In other embodiments, the solution contains one or more non-essential and/or semi-essential amino acids. Accordingly, in other embodiments, asparagine, glutamine, and/or cysteine are included.

The solutions may also contain electrolytes, particularly calcium ions for facilitating enzymatic reactions, cardiac contractility, and/or coagulation within the organ. Other electrolytes may be used, such as sodium, potassium, chloride, sulfate, magnesium and other inorganic and organic charged species, or combinations thereof. It should be noted that any component provided hereunder may be provided, where valence and stability permit, in an ionic form, in a protonated or unprotonated form, in salt or free base form, or as ionic or covalent substituents in combination with other components that hydrolyze and make the component available in aqueous solutions, as suitable and appropriate.

In certain embodiments, the solutions contain buffering components. For example, suitable buffer systems include 2-morpholinoethanesulfonic acid monohydrate (MES), cacodylic acid, $H_2CO_3/NaHCO_3$ ($pK_{a1}$), citric acid ($pK_{a3}$), bis(2-hydroxyethyl)-imino-tris-(hydroxymethyl)-methane (Bis-Tris), N-carbamoylmethylimidino acetic acid (ADA), 3-bis[tris(hydroxymethyl)methylamino]propane (Bis-Tris Propane) ($pK_{a1}$), piperazine-1,4-bis(2-ethanesulfonic acid) (PIPES), N-(2-Acetamido)-2-aminoethanesulfonic acid (ACES), imidazole, N,N-bis(2-hydroxyethyl)-2-aminoethanesulfonic acid (BES), 3-(N-morpholino)propanesulphonic acid (MOPS), $NaH_2PO_4/Na_2HPO_4$ ($pK_{a2}$), N-tris(hydroxymethyl)methyl-2-aminoethanesulfonic acid (TES), N-(2-hydroxyethyl)-piperazine-N'-2-ethanesulfonic acid (HEPES), N-(2-hydroxyethyl)piperazine-N'-(2-hydroxypropanesulfonic acid) (HEPPSO), triethanolamine, N-[tris(hydroxymethyl)methyl]glycine (Tricine), tris hydroxymethylaminoethane (Tris), glycineamide, N,N-bis(2-hydroxyethyl) glycine (Bicine), glycylglycine ($pK_{a2}$), N-tris (hydroxymethyl)methyl-3-aminopropanesulfonic acid (TAPS), or a combination thereof. In some embodiments, the solutions contain sodium bicarbonate, potassium phosphate, or TRIS buffer.

The solutions may include other components to help maintain the organ and protect it against ischemia, reperfusion injury and other ill effects during perfusion. In certain exemplary embodiments these components may include hormones (e.g., insulin), vitamins (e.g., an adult multi-vitamin, such as multi-vitamin MVI-Adult), and/or steroids (e.g., dexamethasone and SoluMedrol).

In another aspect, a blood product is provided with the solution to support the organ during metabolism. Exemplary suitable blood products may include whole blood, and/or one or more components thereof such as blood serum, plasma, albumin, and red blood cells. In embodiments where whole blood is used, the blood may be passed through a leukocyte and platelet depleting filter to reduce pyrogens, antibodies and/or other items that may cause inflammation in the organ. Thus, in some embodiments, the solution employs whole blood that has been at least partially depleted of leukocytes and/or whole blood that has been at least partially depleted of platelets.

The solutions are preferably provided at a physiological temperature and maintained thereabout throughout perfusion and recirculation. As used herein, "physiological temperature" is referred to as temperatures between about 25° C. and about 37° C., for example, between about 30° C. and about 37° C., such as between about 34° C. and about 37° C.

Table 1 sets forth components that are used in an exemplary aqueous priming solution. The component amounts in Table 1 are relative to each other and to the amount of aqueous solvent employed in the solution (about 500 mL in the exemplary embodiment) and may be scaled as appropriate. In certain embodiments, the quantity of aqueous solvent varies ± about 10%.

TABLE 1

Composition of Exemplary Priming Solution (about 500 mL aqueous solution)

| Component | Amount | Specification |
|---|---|---|
| Mannitol | 12.5 g | ± about 10% |
| Sodium Chloride | 4.8 g | ± about 10% |
| Potassium Chloride | 185 mg | ± about 10% |
| Magnesium Sulfate heptahydrate | 185 mg | ± about 10% |
| Sodium Glycerophosphate | 900 mg | ± about 10% |

The exemplary priming solution is added to the system 100 through priming step 924, as more fully described with reference to FIG. 29A.

With regard to the nutritional supplement solution 116, in certain embodiments it includes one or more carbohydrates and may also include a phosphate source. The nutritional supplement solution 116 is typically maintained at a pH of about 5.0 to about 6.5, for example about 5.5 to about 6.0.

Table 2 sets forth components that are used in an exemplary nutritional supplement solution 116. In some embodiments, the nutritional solution 116 further includes sodium glycerol phosphate. The amount of components in Table 2 is relative to the amount of aqueous solvent employed in the solution 116 (about 500 mL) and may be scaled as appropriate. In some embodiments, the quantity of aqueous solvent varies ± about 10%.

TABLE 2

Components of Exemplary Nutritional Solution (about 500 mL)

| Component | Amount | Specification |
|---|---|---|
| Dextrose | 40 g | ± about 10% |

In certain embodiments the nutritional solution 116 includes one or more carbohydrates and may also include a phosphate source. The nutritional solution 116 is typically maintained at a pH of about 5.0 to about 6.5, for example of about 5.5 to about 6.0.

The preservation solution 118 may include one or more preservatives. In an exemplary embodiment, one or more cardio stimulants are included for assisting normal physiologic function of the heart 102 during perfusion and transplantation. Such stimulants may include, for example, catecholamines, such as epinephrine and/or norepinephrine, which facilitate beating of the heart.

Other components may be added to the preservation solution 118, including, for example, adenosine, magnesium, phosphate, calcium, and/or sources thereof. In some instances, additional components are provided to assist the organ in conducting its metabolism during perfusion. These components include, for example, forms of adenosine, which may be used for ATP synthesis, for maintaining endothelial function, and/or for attenuating ischemia and/or reperfusion injury. Components may also include other nucleosides, such as guanosine, thymidine (5-Me-uridine), cytidine, and uridine, as well as other naturally and chemically modified-nucleosides including nucleotides thereof. According to some implementations, a magnesium ion source is provided with a phosphate source, and in certain embodiments, with adenosine to further enhance ATP synthesis within the cells of the perfused organ. A plurality of amino acids may also be added to support protein synthesis by the heart's 102 cells. Applicable amino acids may include, for example, any of the naturally-occurring amino acids, as well as those mentioned above.

Table 3 sets forth components that may be used in a solution 118 for preserving an organ as described herein. The solution 118 may include one or more of the components described in Table 3.

TABLE 3

| Component | Exemplary Concentration Ranges in Preservative Solution |
|---|---|
| Alanine | about 1 mg/L-about 10 g/L |
| Arginine | about 1 mg/L-about 10 g/L |
| Asparagine | about 1 mg/L-about 10 g/L |

TABLE 3-continued

| Component | Exemplary Concentration Ranges in Preservative Solution |
|---|---|
| Aspartic Acid | about 1 mg/L-about 10 g/L |
| Cysteine | about 1 mg/L-about 10 g/L |
| Cystine | about 1 mg/L-about 10 g/L |
| Glutamic Acid | about 1 mg/L-about 10 g/L |
| Glutamine | about 1 mg/L-about 10 g/L |
| Glycine | about 1 mg/L-about 10 g/L |
| Histidine | about 1 mg/L-about 10 g/L |
| Hydroxyproline | about 1 mg/L-about 10 g/L |
| Isoleucine | about 1 mg/L-about 10 g/L |
| Leucine | about 1 mg/L-about 10 g/L |
| Lysine | about 1 mg/L-about 10 g/L |
| Methionine | about 1 mg/L-about 10 g/L |
| Phenylalanine | about 1 mg/L-about 10 g/L |
| Proline | about 1 mg/L-about 10 g/L |
| Serine | about 1 mg/L-about 10 g/L |
| Threonine | about 1 mg/L-about 10 g/L |
| Tryptophan | about 1 mg/L-about 10 g/L |
| Tyrosine | about 1 mg/L-about 10 g/L |
| Valine | about 1 mg/L-about 10 g/L |
| Adenine | about 1 mg/L-about 10 g/L |
| ATP | about 10 ug/L-about 100 g/L |
| Adenylic Acid | about 10 ug/L-about 100 g/L |
| ADP | about 10 ug/L-about 100 g/L |
| AMP | about 10 ug/L-about 100 g/L |
| Ascorbic Acid | about 1 ug/L-about 10 g/L |
| D-Biotin | about 1 ug/L-about 10 g/L |
| Vitamin D-12 | about 1 ug/L-about 10 g/L |
| Cholesterol | about 1 ug/L-about 10 g/L |
| Dextrose (Glucose) | about 1 g/L-about 150 g/L |
| Multi-vitamin Adult | about 1 mg/L-about 20 mg/L or 1 unit vial |
| Epinephrine | about 1 ug/L-about 1 g/L |
| Folic Acid | about 1 ug/L-about 10 g/L |
| Glutathione | about 1 ug/L-about 10 g/L |
| Guanine | about 1 ug/L-about 10 g/L |
| Inositol | about 1 g/L-about 100 g/L |
| Riboflavin | about 1 ug/L-about 10 g/L |
| Ribose | about 1 ug/L-about 10 g/L |
| Thiamine | about 1 mg/L-about 10 g/L |
| Uracil | about 1 mg/L-about 10 g/L |
| Calcium Chloride | about 1 mg/L-about 100 g/L |
| NaHCO$_3$ | about 1 mg/L-about 100 g/L |
| Magnesium sulfate | about 1 mg/L-about 100 g/L |
| Potassium chloride | about 1 mg/L-about 100 g/L |
| Sodium glycerophosphate | about 1 mg/L-about 100 g/L |
| Sodium Chloride | about 1 mg/L-about 100 g/L |
| Sodium Phosphate | about 1 mg/L-about 100 g/L |
| Insulin | about 1 IU-about 150 IU |
| Serum albumin | about 1 g/L-about 100 g/L |
| Pyruvate | about 1 mg/L-about 100 g/L |
| Coenzyme A | about 1 ug/L-about 10 g/L |
| Serum | about 1 ml/L-about 100 ml/L |
| Heparin | about 500 U/L-about 1500 U/L |
| Solumedrol | about 200 mg/L-about 500 mg/L |
| Dexamethasone | about 1 mg/L-about 1 g/L |
| FAD | about 1 ug/L-about 10 g/L |
| NADP | about 1 ug/L-about 10 g/L |
| adenosine | about 1 mg/L-about 10 g/L |
| guanosine | about 1 mg/L-about 10 g/L |
| GTP | about 10 ug/L-about 100 g/L |
| GDP | about 10 ug/L-about 100 g/L |
| GMP | about 10 ug/L-about 100 g/L |

Table 4 sets forth components that are used in an exemplary preservative solution 118. The amounts provided in Table 4 describe preferred amounts relative to other components in the table and may be scaled to provide compositions of sufficient quantity. In some embodiments, the amounts listed in Table 4 can vary by ± about 10% and still be used in the solutions described herein.

TABLE 4

Components of Exemplary Preservative Solution

| Component | Amount |
|---|---|
| Adenosine | About 675 mg-About 825 mg |
| Calcium Chloride dihydrate | About 2100 mg-About 2600 mg |
| Glycine | About 315 mg-About 385 mg |
| L-Alanine | About 150 mg-About 200 mg |
| L-Arginine | About 600 mg-About 800 mg |
| L-Aspartic Acid | About 220 mg-About 270 mg |
| L-Glutamic Acid | About 230 mg-About 290 mg |
| L-Histidine | About 200 mg-About 250 mg |
| L-Isoleucine | About 100 mg-about 130 mg |
| L-Leucine | About 300 mg-About 380 mg |
| L-Methionine | About 50 mg-About 65 mg |
| L-Phenylalanine | About 45 mg-About 60 mg |
| L-Proline | About 110 mg-About 140 mg |
| L-Serine | About 80 mg-About 105 mg |
| L-Thereonine | About 60 mg-About 80 mg |
| L-Tryptophan | About 30 mg-About 40 mg |
| L-Tyrosine | About 80 mg-About 110 mg |
| L-Valine | About 150 mg-About 190 mg |
| Lysine Acetate | About 200 mg-About 250 mg |
| Magnesium Sulfate Heptahydrate | About 350 mg-About 450 mg |
| Potassium Chloride | About 15 mg-About 25 mg |
| Sodium Chloride | About 1500 mg-About 2000 mg |
| Dextrose | About 25 gm-About 120 gm |
| Epinephrine | About 0.25 mg-About 1.0 mg |
| Insulin | About 75 Units-About 150 Units |
| MVI-Adult | 1 unit vial |
| SoluMedrol | about 200 mg-500 mg |
| Sodium Bicarbonate | About 10-25 mEq |

In the exemplary embodiment of a solution 118, the components in Table 4 are combined in the relative amounts listed therein per about 1 L of aqueous fluid to form the solution 118. In some embodiments, the components in Table 4 are combined in the relative amounts listed therein per about 500 mL of aqueous fluid and then combined with the solution 116, also about 500 mL, to provide a maintenance solution 116/118 of about 1 L of aqueous fluid. In some embodiments the quantity of aqueous fluid in solutions 116, 118, and/or 116/118 can vary ± about 10%. The pH of the solution 118 may be adjusted to be between about 7.0 and about 8.0, for example about 7.3 and about 7.6. The solution 118 may be sterilized, for example by autoclaving, to provide for improved purity.

Table 5 sets forth another exemplary preservative solution 118, comprising a tissue culture media-having the components identified in Table 5 and combined with an aqueous fluid, which may be used in the perfusion fluid 108 as described herein. The amounts of components listed in Table 5 are relative to each other and to the quantity of aqueous solution used. In some embodiments, about 500 mL of aqueous fluid is used. In other embodiments about 1 L of aqueous fluid is used. For example, combination of about 500 mL of preservative solution 118 with 500 mL of nutritional solution 116 affords a maintenance solution 116/118 of about 1 L. In some embodiments, the quantity of aqueous solution can vary ± about 10%. The component amounts and the quantity of aqueous solution may be scaled as appropriate for use. The pH of the preservative solution 118, in this embodiment, may be adjusted to be about 7.0 to about 8.0, for example about 7.3 to about 7.6.

TABLE 5

Composition of Another Exemplary Preservative Solution
(about 500 mL aqueous solution)

| Tissue Culture Component | Amount | Specification |
|---|---|---|
| Adenosine | 750 mg | ± about 10% |
| Calcium Chloride dihydrate | 2400 mg | ± about 10% |
| Glycine | 350 mg | ± about 10% |
| L-Alanine | 174 mg | ± about 10% |
| L-Arginine | 700 mg | ± about 10% |
| L-Aspartic Acid | 245 mg | ± about 10% |
| L-Glutamic Acid | 258 mg | ± about 10% |
| L-Histidine | 225 mg | ± about 10% |
| L-Isoleucine | 115.5 mg | ± about 10% |
| L-Leucine | 343 mg | ± about 10% |
| L-Methionine | 59 mg | ± about 10% |
| L-Phenylalanine | 52 mg | ± about 10% |
| L-Proline | 126 mg | ± about 10% |
| L-Serine | 93 mg | ± about 10% |
| L-Thereonine | 70 mg | ± about 10% |
| L-Tryptophan | 35 mg | ± about 10% |
| L-Tyrosine | 92 mg | ± about 10% |
| L-Valine | 171.5 mg | ± about 10% |
| Lysine Acetate | 225 mg | ± about 10% |
| Magnesium Sulfate Heptahydrate | 400 mg | ± about 10% |
| Potassium Chloride | 20 mg | ± about 10% |
| Sodium Chloride | 1750 mg | ± about 10% |

Since amino acids are the building blocks of proteins, the unique characteristics of each amino acid impart certain important properties on a protein such as the ability to provide structure and to catalyze biochemical reactions. The selection and concentrations of the amino acids provided in the preservative solutions provide support of normal physiologic functions such as metabolism of sugars to provide energy, regulation of protein metabolism, transport of minerals, synthesis of nucleic acids (DNA and RNA), regulation of blood sugar and support of electrical activity, in addition to providing protein structure. Additionally, the concentrations of specific amino acids found in the preservative solutions can be used to predictably stabilize the pH of the maintenance solution 116/118 and perfusion fluid 108.

Certain embodiments of the preservative solution 118 include epinephrine and a plurality of amino acids. In certain embodiments, the preservative solution 118 includes electrolytes, such as calcium and magnesium.

In one embodiment, a maintenance solution 116/118 is made from the combination of the preservative solution 118, including one or more amino acids, and the nutritional solution 116, including one or more carbohydrates, such as glucose or dextrose. The maintenance solution 116/118 may also have additives, such as those described herein, administered at the point of use just prior to infusion into the organ perfusion system. For example, additional additives that can be included with the solution or added at the point of use by the user include hormones and steroids, such as dexamethasone and insulin, as well as vitamins, such as an adult multivitamin, for example adult multivitamins for infusion, such as MVI-Adult. Additional small molecules and large bio-molecules may also be included with the solution or added at the point of use by the user at port 762, for example, therapeutics and/or components typically associated with blood or blood plasma, such as albumin.

In some embodiments, therapeutics that may be included in the compositions, solutions, and systems described herein include hormones, such as thyroid hormones, for example $T_3$ and/or $T_4$ thyroid hormones. Further therapeutics that may be included include drugs such as anti-arrhythmic drugs, for example, for heart therapy, and beta blockers. For instance, in certain embodiments, one or more thyroid hormones, one or more anti-arrhythmic drugs, and one or more beta blockers are added to the nutritional solution 116, the preservative solution 118, and/or the maintenance solutions 116/118 either before or during perfusion of the organ. The above therapeutics may also be added directly to the system, for example, to the perfusion fluid 108, before or during perfusion of the organ.

With further reference to Table 4, certain components used in the exemplary preservation solution 118 are molecules, such as small organic molecules or large bio-molecules, that would be inactivated, for example through decomposition or denaturing, if passed through sterilization. According to the system 100, the inactivatable components of the solution 118 may be prepared separately from the remaining components of the solution 118. The separate preparation involves separately purifying each component through known techniques. The remaining components of the solution 118 are sterilized, for example through an autoclave, then combined with the biological components.

Table 6 lists certain biological components that may be separately purified and added to the solutions described herein after sterilization, according to this two-step process. These additional or supplemental components may be added to solutions 118, 116, 116/118, the priming solution or a combination thereof individually, in various combinations, all at once as a composition, or as a combined solution. For example, in certain embodiments, the epinephrine, insulin, and MVI-Adult, listed in Table 6, are added to the maintenance solution 116/118. In another example, the SoluMedrol and the sodium bicarbonate, listed in Table 6, are added to the priming solution. The additional components may also be combined in one or more combinations or all together and placed in solution before being added to solutions 116, 118, 116/118, and/or the priming solution. In some embodiments, the additional components are added directly to the perfusion fluid 108 through port 762. The component amounts listed in Table 6 are relative to each other and/or to the amounts of components listed in one or more of Tables 1-5 as well as the amount of aqueous solution used in preparing solutions 116, 118, 116/118, and/or the priming solution and may be scaled as appropriate for the amount of solution required.

TABLE 6

Exemplary Biological Components Added Prior to Use

| Component | Amount | Type | Specification |
|---|---|---|---|
| Epinephrine | About 0.50 mg | Catecholamine Hormone | ± about 10% |
| Insulin | about 100 Units | Hormone | ± about 10% |
| MVI-Adult | 1 mL unit vial | Vitamin | ± about 10% |
| SoluMedrol | About 250 mg | Steroid | ± about 10% |
| Sodium Bicarbonate | About 20 mEq | Buffer | ± about 10% |

In one embodiment, a composition for use in a maintenance solution 116/118 is provided comprising one or more carbohydrates, one or more organ stimulants, and a plurality of amino acids that do not include asparagine, glutamine, or cysteine. The composition may also include other substances, such as those used in solutions described herein.

In another embodiment, a system for perfusing an organ, such as a heart, is provided comprising an organ and a substantially cell-free composition, comprising one or more carbohydrates, one or more organ stimulants, and a plurality of amino acids that do not include asparagine, glutamine, or cysteine. Substantially cell-free includes systems that are substantially free from cellular matter; in particular, systems that are not derived from cells. For example, substantially cell-free includes compositions and solutions prepared from non-cellular sources.

In another aspect, the solutions 116 and 118 may be provided in the form of a kit that includes one or more organ maintenance solutions. An exemplary maintenance solution may include components identified above in one or more fluid solutions for use in an organ perfusion fluid 108. In certain embodiments, the maintenance solution 116/118 may include multiple solutions, such as a preservation solution 118 and a nutritional solution 116 and/or a supplemental composition or solution, or may include dry components that may be regenerated in a fluid to form one or more solutions 116/118. The kit may also comprise components from the solutions 116 and/or 118 in one or more concentrated solutions which, on dilution, provide a preservation, nutritional, and/or supplemental solution as described herein. The kit may also include a priming solution. In an exemplary embodiment, the maintenance solution includes a preservation solution 118 and a nutritional solution 116 such as those described above, and a priming solution such as that described above.

In certain embodiments, the kit is provided in a single package, wherein the kit includes one or more solutions (or components necessary to formulate the one or more solutions by mixing with an appropriate fluid), and instructions for sterilization, flow and temperature control during perfusion and use and other information necessary or appropriate to apply the kit to organ perfusion. In certain embodiments, a kit is provided with only a single solution 116, 118 and/or 116/118 (or set of dry components for use in a solution upon mixing with an appropriate fluid), and the single solution 116, 118 and/or 116/118 (or set of dry components) is provided along with a set of instructions and other information or materials necessary or useful to operate the solution 116, 118 and/or 116/118 in the system 100.

In another aspect, the systems, solutions and methods may be used to deliver therapeutics to an organ during perfusion. For example, one or more of the solutions and/or systems described above may include one or more drugs, biologics, gene therapy vectors, or other therapeutics which are delivered to the organ during perfusion. Suitable exemplary therapeutics may include drugs, biologics, or both. Suitable drugs may include, for example, anti fungals, anti-microbials or anti-biotics, anti-inflamatories, anti-proliferatives, anti-virals, steroids, retinoids, NSAIDs, vitamin D3 and vitamin D3 analogs, calcium channel blockers, complement neutralizers, ACE inhibitors, immuno-suppressants, and other drugs. Suitable biologics may include proteins; suitable biologics may also include vectors loaded with one or more genes for gene therapy application.

For example, suitable steroids include but are not limited to androgenic and estrogenic steroid hormones, androgen receptor antagonists and 5-α-reductase inhibitors, and corticosteroids. Specific examples include but are not limited to alclometasone, clobetasol, fluocinolone, fluocortolone, diflucortolone, fluticasone, halcinonide, mometasone, prednisone, prednisolone, methylprednisolone, triamcinolone, betamethasone, and dexamethasone, and various esters and acetonides thereof.

Suitable retinoids include but are not limited to retinol, retinal, isotretinoin, acitretin, adapalene, tazarotene, and bexarotene.

Suitable NSAIDs include but are not limited to naproxen, suprofen, ketoprofen, ibuprofen, flurbiprofen, diclofenac, indomethacin, celecoxib, and rofecoxib.

Suitable vitamin D3 analogues include but are not limited to doxercalciferol, seocalcitol, calcipotriene, tacalcitol, calcitriol, ergocalciferol, and calcifediol.

Suitable anti-viral agents include but are not limited to trifluridine, cidofovir, acyclovir, penciclovir, famciclovir, valcyclovir, gancyclovir, and docosanol.

Suitable human carbonic anhydrase inhibitors include but are not limited to methazoliamide, acetazolamide, and dorzolamide.

Suitable anti-proliferative agents include but are not limited to 5-FU, taxol, daunorubicin, and mitomycin.

Suitable antibiotic (antimicrobial) agents include but are not limited to bacitracin, chlorhexidine, chlorhexidine digluconate, ciprofloxacin, clindamycin, erythromycin, gentamicin, lomefloxacin, metronidazole, minocycline, moxifloxacin, mupirocin, neomycin, ofloxacin, polymyxin B, rifampicin, ruflozacin, tetracycline, tobramycin, triclosan, and vancomycin. The antiviral and antibacterial prodrugs described herein may be used to treat appropriately responsive systemic infections.

In certain embodiments, a solution system for use in a perfusion fluid 108, comprising a first chamber containing a first solution, such as a preservation solution 118, that includes one or more cardio stimulants and a plurality of amino acids that do not include asparagine, glutamine, or cysteine, and a second chamber, containing a second solution, such as a nutritional solution 116, that includes one or more carbohydrates, such as dextrose. The system may also include a sterilization system for sterilizing the first solution and the second solution prior to using the solutions to perfuse a heart. In some embodiments, one or more of the solutions 118 and 116 includes one or more therapeutics. In some embodiments the solution system includes a third chamber comprising a priming solution, such as is described above, which may have one or more carbohydrates. In certain embodiments, the first solution 118 includes epinephrine, adenosine, insulin, one or more immuno-suppressants, a multi-vitamin, and/or one or more electrolytes.

Figure 31:
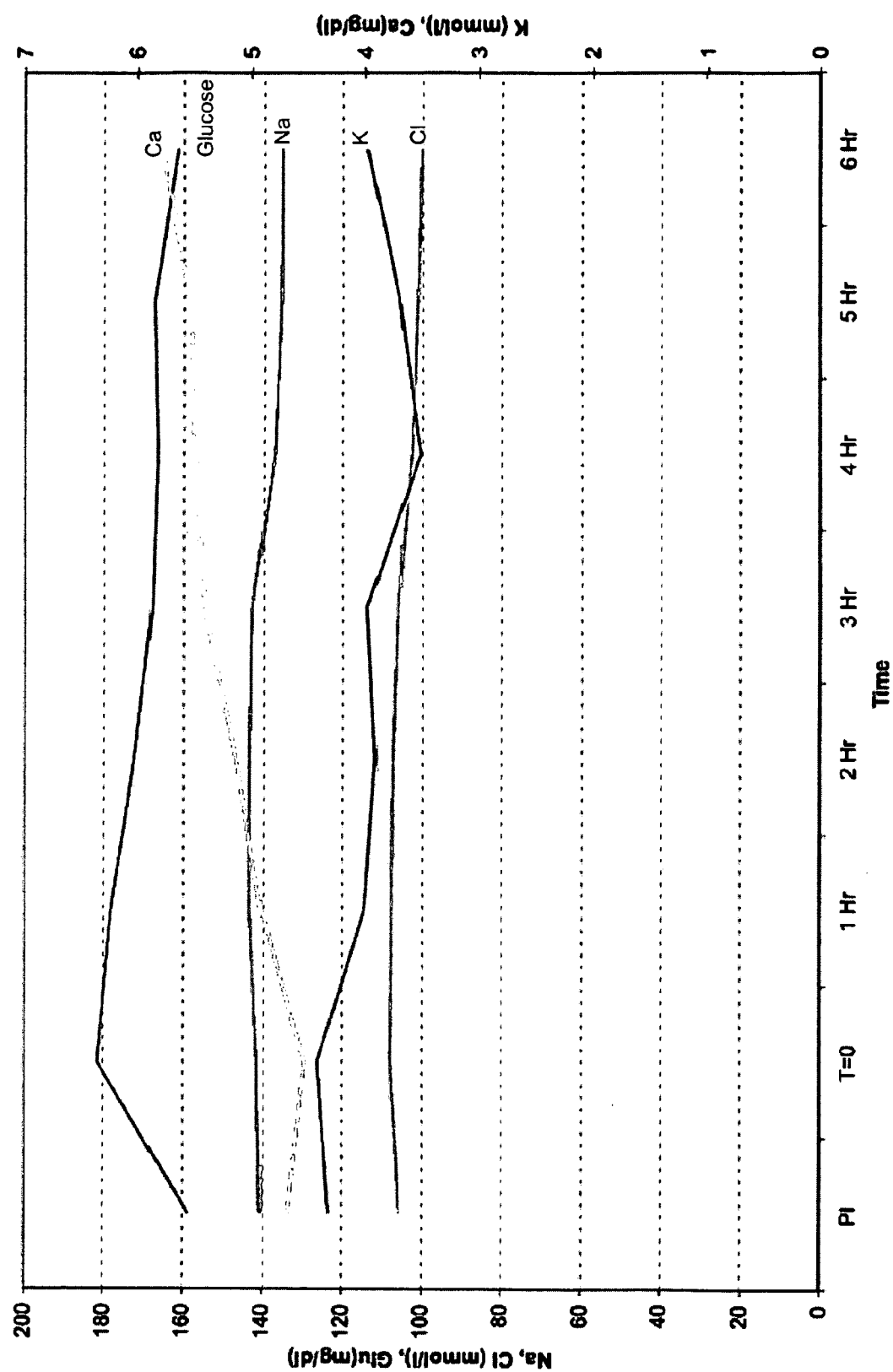
FIG. 31 depicts a chart demonstrating electrolyte stability for an organ under going perfusion in forward mode according to an embodiment of the invention.

Certain experimental data are available to describe certain embodiments of the solutions described herein and their use in organ perfusion. Certain data are set for in FIGS. 31-33. FIG. 31 depicts a chart demonstrating electrolyte stability for an organ under going perfusion in forward mode according to an embodiment of the system 100. In the embodiment associated with FIG. 31, the organ is a heart 102 wherein perfusion is conducted in forward mode (as described above) by pumping perfusion fluid 108 containing solution 116/118 to the let atria 152 and out of the aorta 158. The rate of perfusion is approximately 30 mL/hr. As can be seen from FIG. 31, the levels of various electrolytes: sodium, potassium, calcium, and chloride ions, as well as dissolved glucose, remain at stable levels throughout the course of perfusion, from before the organ is cannulated to the perfusion system 100 to six hours after cannulation within the system 100.

Figure 32:
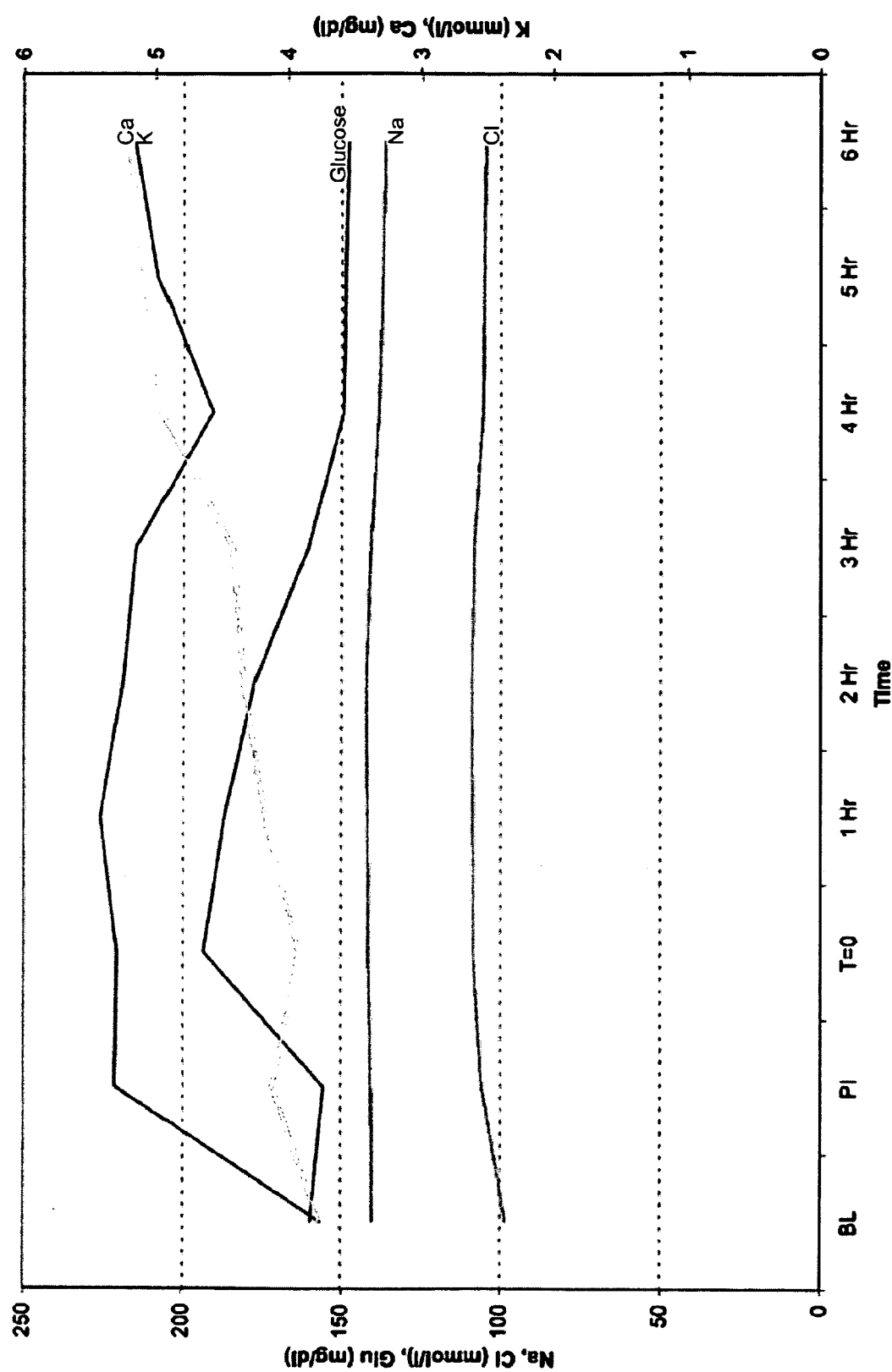
FIG. 32 depicts a chart demonstrating electrolyte stability for an organ under going perfusion in retrograde mode according to another an embodiment of the invention.

FIG. 32 depicts a chart demonstrating electrolyte stability for an organ under going retrograde perfusion according to another embodiment of the system 100. In the embodiment associated with FIG. 32, the organ is a heart wherein perfusion occurs by pumping the perfusion fluid 108 containing the solution 116/118 into the aorta 158 and through the coronary sinus 155. The rate of perfusion is approximately 30 mL/hr. As can be seen from FIG. 32, the levels of various electrolytes: sodium, potassium, calcium, and chloride ions, as well as dissolved glucose, remain at stable levels throughout the course of perfusion, from before the organ is cannulated to the perfusion system 100 to six hours after cannulation. FIG. 32 also demonstrates that the levels of the electrolytes and glucose remain at levels similar to those for the base line (BL) normal physiological state for the organ.

Figure 33:
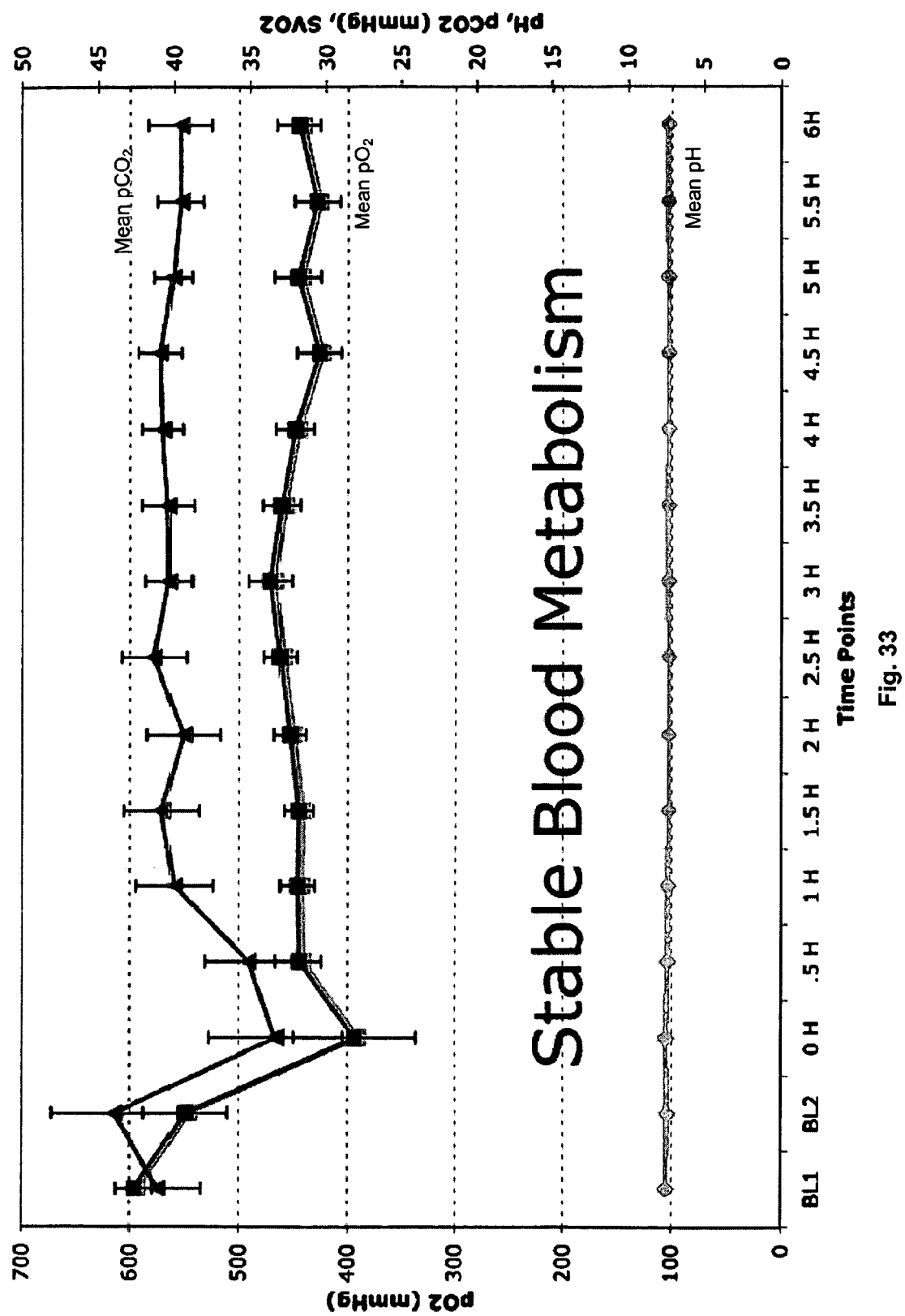
FIG. 33 depicts a chart demonstrating the arterial blood gas profile for an organ under going perfusion according to an embodiment of the invention.

FIG. 33 depicts a chart demonstrating the arterial blood gas profile for an organ under going perfusion according to another embodiment of the invention. As can be seen from FIG. 33, the levels of various blood gasses: carbon dioxide and oxygen, and pH remain at stable levels throughout the six hour course of perfusion. FIG. 33 also demonstrates that the levels of carbon dioxide, oxygen, and pH remain at levels similar to those for two base line (BL) measurements for the normal physiological state for the organ. FIGS. 31-33 demonstrate the ability of the present systems and methods to maintain an organ under stable physiological or near physiological conditions.

It is to be understood that while the invention has been described in conjunction with the various illustrative embodiments, the forgoing description is intended to illustrate and not limit the scope of the invention, which is defined by the scope of the appended claims. For example, a variety of systems and/or methods may be implemented based on the disclosure and still fall within the scope of the invention. Other aspects, advantages, and modifications are within the scope of the following claims. All references cited herein are incorporated by reference in their entirety and made part of this application.

What is claimed is:

1. A single use disposable module for a heart preservation system, the single use disposable module comprising:
   a chassis,
   a perfusion circuit for circulating perfusion fluid, said perfusion circuit including a pump interface having a housing in fluid tight interconnection with a surface that is movable with respect to the housing to translate pumping force from a pump driver to the perfusion fluid, and
   an organ chamber assembly mounted to the chassis for containing a heart during perfusion, the organ chamber assembly including a first conduit for connecting the perfusion circuit to an aorta of the heart and a second conduit for connecting the perfusion circuit to a pulmonary vein of the heart, wherein the pump interface is mounted to the chassis and separably aligns with the pump driver by at least a first flange projecting from the pump interface that is sized to interlock with a corresponding slot on the pump driver;
   and wherein the pump interface includes at least a tapered projection that is sized to interlock with a corresponding bracket on the pump driver to form a fluid tight seal between the pump interface and the pump driver.

2. The single use module of claim 1 wherein the organ chamber assembly includes a third conduit for connecting the perfusion circuit to a pulmonary artery of the heart.

3. The single use module of claim 1 comprising a reservoir for containing the perfusion fluid and in fluid communication with the organ chamber assembly and the perfusion circuit, said reservoir being mounted to the chassis.

4. The single use module of claim 1 comprising a flow select valve for selecting between pumping the perfusion fluid to the first conduit and pumping the perfusion fluid to the second conduit.

5. The single use module of claim 1 comprising a fluid heater for maintaining the perfusion fluid at a temperature between about 32° C. and about 37° C. where said perfusion fluid enters the organ chamber assembly.

6. The single use module of claim 5, wherein the fluid heater includes at least one heated plate in direct contact with the perfusion fluid.

7. The single use module of claim 6 including at least one temperature sensor for sensing a temperature of the heated plate.

8. The single use module of claim 5, wherein the fluid heater includes a pair of heated plates between which the perfusion fluid to be heated flows.

9. The single use module of claim 5 comprising a temperature sensor for sensing temperature of the perfusion fluid.

10. The single module of claim 9, wherein the temperature sensor senses the temperature of the perfusion fluid as it exits the fluid heater.

11. The single use module of claim 9, wherein the temperature sensor senses the temperature of the perfusion fluid as it enters the fluid heater.

12. The single use module of claim 5, wherein the fluid heater includes a heating element in contact with a plate, the plate being for direct contact with the perfusion fluid.

13. The single use module of claim 12 comprising a temperature sensor for sensing temperature of the heating element.

14. The single use module of claim 1 comprising an optical interface for communicating with a corresponding optical interface on a multiple use module when interlocked with the multiple use module.

15. The single use module of claim 1 comprising an oxygenator in fluid communication with the perfusion circuit for providing oxygen to the perfusion fluid.

16. The single use module of claim 1 comprising an oxygen sensor for determining an oxygen level in the perfusion fluid.

17. The single use module of claim 16, wherein the oxygen level includes an oxygen saturation level in the perfusion fluid.

18. The single use module of claim 16, wherein the oxygen sensor measures a hematocrit of the perfusion fluid.

19. The single use module of claim 16, wherein the oxygen sensor is positioned to measure the oxygen level of the perfusion fluid entering the heart.

20. The single use module of claim 16, wherein the oxygen sensor is positioned to measure the oxygen level of the perfusion fluid leaving the heart.

21. The single use module of claim 16, wherein the oxygen sensor includes an in-line cuvette through which the perfusion fluid passes, an optical source for directing light at the perfusion fluid passing through the cuvette, and an optical sensor for measuring an optical quality of the perfusion fluid passing through the cuvette.

22. The single use module of claim 16, wherein the oxygen sensor includes a seamless in-line cuvette through which the perfusion fluid passes.

23. The single use module of claim 1 comprising a flow rate sensor for sensing a flow rate of the perfusion fluid entering the organ chamber assembly.

24. The single use module of claim 1 comprising a flow rate sensor for sensing a flow rate of the perfusion fluid leaving the organ chamber assembly.

25. The single use module of claim 5 comprising a compliance chamber located between the fluid heater and the organ chamber assembly, wherein said compliance chamber is in fluid communication with the perfusion circuit.

26. The single use module of claim 25, wherein the compliance chamber is located between the fluid heater and the second conduit.

27. The single use module of claim 25, wherein the compliance chamber is located between the fluid heater and the first conduit.

28. The single use module of claim 5 comprising a compliance chamber located between the pump interface and the fluid heater, wherein said compliance chamber is in fluid communication with the perfusion circuit.

29. The single use module of claim 1 comprising a sampling port for sampling fluids from the organ chamber assembly.

30. The single use module of claim 1 comprising a plurality of ports for sampling fluids from the organ chamber assembly, interlocked such that sampling fluid from a first of the plurality of ports prohibits simultaneously sampling fluids from a second port of the plurality.

31. The single use module of claim 1 comprising one or more processors for collecting information from one or more sensors on the single use module.

32. The single use module of claim 31 comprising an optical interface for providing the information from the one or more sensors to a multiple use module.

33. The single use module of claim 1, wherein the pump interface mounts to the chassis and includes features for interlocking with mating features on a pump driver for forming fluid sealing interconnection between the pump interface and the pump driver.

34. The single use module of claim 1 comprising axially extending protuberances on the pump interface, the protuberances abutting one or more surfaces on a multiple use module to compress the pump interface toward the pump driver such that the pump interface is aligned to receive a pump driver head.

35. The single use module of claim 1, wherein the organ chamber assembly includes a first hinged cover for covering the organ chamber assembly, the first hinged cover including an outer frame and a flexible pliant membrane disposed on the outer frame.

36. The single use module of claim 35, wherein the flexible pliant membrane is sized and shaped for extending into the organ chamber assembly.

37. The single use module of claim 1, wherein the organ chamber assembly includes a second hinged cover for covering the first hinged cover.

38. The single use module of claim 37, wherein the second hinged cover is substantially rigid.

39. The single use module of claim 1, wherein the organ chamber assembly includes a pad assembly for supporting the heart, the pad assembly including at least one electrode for providing electrical stimulation to the heart.

40. The single use module of claim 39, wherein the at least one electrode is sized, shaped and positioned on the pad assembly to provide sutureless interconnection with the heart.

41. The single use module of claim 1, wherein the organ chamber assembly includes a pad assembly for supporting a heart the pad assembly including at least one sensor for monitoring electrical signals from the heart.

42. The single use module of claim 41, wherein the at least one sensor is sized, shaped and positioned in the pad assembly to provide sutureless interconnection with the heart.

43. The single use module of claim 41, wherein the signals include an r-wave for the heart.

44. The single use module of claim 1, wherein the organ chamber assembly includes a resealable membrane for automatically resealing subsequent to being pierced.

45. The single use module of claim 2, wherein the perfusion circuit includes a bypass tube for providing a three way connection between the first conduit, the second-conduit, and the third conduit.

46. The single use module of claim 4 comprising a trickle line for providing a small flow of perfusion fluid to the first conduit when the second conduit is selected on the flow select valve.

47. The single use module of claim 1 comprising an infusion port for injecting chemical solutions into the perfusion fluid.

48. A single use module for a heart preservation system, the single use module comprising,
- a chassis,
- a perfusion circuit for circulating perfusion fluid, said perfusion circuit including a pump interface having a housing in fluid tight interconnection with a surface that is movable with respect to the housing to translate pumping force from a pump driver to the perfusion fluid, and
- an organ chamber assembly mounted to the chassis for containing a heart during perfusion, the organ chamber assembly including an aorta conduit for connecting the perfusion circuit to an aorta of the heart and a pulmonary vein conduit for connecting the perfusion circuit to a pulmonary vein of the heart,
- a reservoir mounted to the chassis, said reservoir being in fluid communication with the organ chamber assembly and the perfusion circuit for containing perfusion fluid for the heart,
- a heater for maintaining the perfusion fluid at a temperature between about 32° C. and about 37° C. where said perfusion fluid enters the organ chamber assembly
- wherein the pump interface is mounted to the chassis and separably aligns with the pump driver by at least a first flange projecting from the pump interface that is sized to interlock with a corresponding slot on the pump driver.

49. A single use smart module for a heart preservation system, the single use module comprising,
- a chassis,
- a perfusion circuit for circulating perfusion fluid, said perfusion circuit including a pump interface having a housing in fluid tight interconnection with a surface that is movable with respect to the housing to translate pumping force from a pump driver to the perfusion fluid, and
- an organ chamber assembly mounted to the chassis for containing a heart during perfusion, the organ chamber assembly including an aorta conduit for connecting the independent perfusion circuit to an aorta of the heart and a pulmonary vein conduit for connecting the independent perfusion circuit to a pulmonary vein of the heart,
- a reservoir mounted to the chassis, said reservoir being in fluid communication with the organ chamber assembly and the perfusion circuit for containing perfusion fluid for the heart,
- a processor for monitoring and controlling, at least in part, operation of the perfusion circuit, organ chamber assembly, reservoir, and pump interface,
- wherein the pump interface is mounted to the chassis and includes an interlocking connection that separably aligns with a corresponding interlocking connection on the pump driver to form a fluid tight seal between the pump interface and the pump driver.

50. The single use module of claim 1, including a circuit board and an electromechanical connector protruding from the circuit board, said electromechanical connector being capable of providing an electrical interconnection between the circuit board and an interface circuit board.

51. The single use module of claim 50, wherein the electromechanical connector is a substantially straight and rigid pin.

52. The single use module of claim 51, wherein the substantially straight and rigid pin can move axially in and out.

53. The single use module of claim 52, wherein the substantially straight and rigid pin includes a spring.

54. The single use module of claim 52, wherein the substantially straight and rigid pin includes a spring loaded end.

55. A single use disposable module for a heart preservation system, the single use disposable module comprising:
- a chassis,
- a perfusion circuit for circulating perfusion fluid,
- an organ chamber assembly mounted to the chassis for containing a heart during perfusion, the organ chamber assembly including a first conduit for connecting the perfusion circuit to an aorta of the heart and a second conduit for connecting the perfusion circuit to a pulmonary vein of the heart, and
- a pump interface mounted to the chassis, said pump interface consisting essentially of a an inlet, an outlet, and a housing including at least a tapered projection that is sized to interlock with a corresponding bracket to form a fluid tight interconnection with a surface that is movable with respect to the housing.

56. The single use disposable module of claim 55, including a circuit board and an electromechanical connector protruding from the circuit board, said electromechanical connector being capable of providing an electrical interconnection between the circuit board and an interface circuit board.

57. The single use module of claim 56, wherein the electromechanical connector is a substantially straight and rigid pin.

58. The single use module of claim 57, wherein the substantially straight and rigid pin can move axially in and out.

59. The single use module of claim 58, wherein the substantially straight and rigid pin includes a spring.

60. The single use module of claim 58, wherein the substantially straight and rigid pin includes a spring loaded end.

61. The single use module of claim 57, wherein the electromechanical connector is a rigid pin that includes a spring, whereby said rigid pin contacts a head of the interface circuit board.

62. A single use disposable module for use with a multiple use module of a heart preservation system, the single use disposable module comprising:
- a chassis,
- a perfusion circuit for circulating perfusion fluid,
- an organ chamber assembly mounted to the chassis for containing a heart during perfusion, the organ chamber assembly including a first conduit for connecting the perfusion circuit to an aorta of the heart and a second conduit for connecting the perfusion circuit to a pulmonary vein of the heart,
- a circuit board, and
- an electromechanical connector protruding from the circuit board that is configured to move axially with respect to the circuit board, said electromechanical connector being capable of providing an electrical interconnection between the circuit board and an electromechanical contact on an interface circuit board in the multiple use module.

63. The single use module of claim 62, wherein the electromechanical connector is a substantially straight and rigid pin.

64. The single use module of claim 63, wherein the substantially straight and rigid pin includes a spring.

65. The single use module of claim 63, wherein the substantially straight and rigid pin includes a spring loaded end.

* * * * *